United States Patent
Gilmore et al.

(10) Patent No.: US 12,172,995 B2
(45) Date of Patent: Dec. 24, 2024

(54) SUBSTITUTED INDOLE AND INDAZOLE COMPOUNDS

(71) Applicant: BRISTOL-MYERS SQUIBB COMPANY, Princeton, NJ (US)

(72) Inventors: John L. Gilmore, Yardley, PA (US); Shoshana L. Posy, Highland Park, NJ (US); Alaric J. Dyckman, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 913 days.

(21) Appl. No.: 17/287,612

(22) PCT Filed: Oct. 22, 2019

(86) PCT No.: PCT/US2019/057311
§ 371 (c)(1),
(2) Date: Apr. 22, 2021

(87) PCT Pub. No.: WO2020/086503
PCT Pub. Date: Apr. 30, 2020

(65) Prior Publication Data
US 2021/0403468 A1    Dec. 30, 2021

Related U.S. Application Data

(60) Provisional application No. 62/749,828, filed on Oct. 24, 2018.

(51) Int. Cl.
| | | |
|---|---|---|
| C07D 471/04 | (2006.01) | |
| A61K 31/437 | (2006.01) | |
| A61K 31/4545 | (2006.01) | |
| A61K 31/5377 | (2006.01) | |
| A61P 37/00 | (2006.01) | |
| C07D 401/14 | (2006.01) | |
| C07D 491/107 | (2006.01) | |
| C07D 495/10 | (2006.01) | |
| C07D 519/00 | (2006.01) | |

(52) U.S. Cl.
CPC ......... *C07D 471/04* (2013.01); *C07D 401/14* (2013.01); *C07D 519/00* (2013.01)

(58) Field of Classification Search
CPC .. C07D 471/04; C07D 401/14; C07D 519/00; C07D 491/107; C07D 495/10; A61P 37/00; A61K 31/437; A61K 31/4545; A61K 31/5377
See application file for complete search history.

(56) References Cited

U.S. PATENT DOCUMENTS

| | | |
|---|---|---|
| 6,187,777 B1 | 2/2001 | Norman et al. |
| 6,306,874 B1 | 10/2001 | Fraley et al. |
| 6,867,200 B1 | 3/2005 | Allen et al. |
| 7,410,975 B2 | 8/2008 | Lipford et al. |
| 8,138,187 B2 | 3/2012 | Zemolka et al. |
| 8,354,400 B2 | 1/2013 | Zheng et al. |
| 9,126,996 B2 | 9/2015 | Lipford et al. |
| 9,126,999 B2 | 9/2015 | Bolvin et al. |
| 9,241,991 B2 | 1/2016 | Ji et al. |
| 9,353,115 B2 | 5/2016 | Lipford et al. |
| 9,376,398 B2 | 6/2016 | Hori et al. |
| 9,428,495 B2 | 8/2016 | Carlson et al. |
| 9,643,967 B2 | 5/2017 | Koul et al. |
| 2004/0014802 A1 | 1/2004 | Dutruc-Rosset et al. |
| 2006/0235037 A1 | 10/2006 | Purandare et al. |
| 2010/0160314 A1 | 6/2010 | Lipford et al. |
| 2010/0197657 A1 | 8/2010 | Chang et al. |
| 2011/0015219 A1 | 1/2011 | Trawick et al. |
| 2011/0071150 A1 | 3/2011 | Alam et al. |
| 2011/0105427 A1 | 5/2011 | Daun et al. |

(Continued)

FOREIGN PATENT DOCUMENTS

| | | |
|---|---|---|
| EP | 2738172 A1 | 6/2014 |
| WO | 03051847 A1 | 6/2003 |

(Continued)

OTHER PUBLICATIONS

Turner, L. D., "Identification of an indazole-based pharmacophore for the inhibition of FGFR kinases using fragment-led de novo design." ACS medicinal chemistry letters 8.12 (2017): 1264-1268.*
Bobko, et al., "Synthesis of 2,5-disubstituted-3-cyanoindoles", Tetrahedron Letters, 2012, vol. 53, pp. 200-202.
International Preliminary Report, PCT/US2019/057311, Oct. 22, 2019, 7 pgs.
Kawai, T. and Shizuo Akira, "The Role of Pattern-Recognition Receptors in Innate Immunity: Update on Toll-like Receptors", Nature Immunol. 11, 373-384 (2011).
Kutchukian, Peter S. et al., "Chemistry Informer Libraries: a chemoinformatics enabled approach to evaluate and advance synthetic methods", Chemical Science, 2016, vol. 7, No. 4, pp. 2604-2613.

(Continued)

*Primary Examiner* — John M Mauro
(74) *Attorney, Agent, or Firm* — Gary Greenblatt

(57) ABSTRACT

Disclosed are compounds of Formula (I) N-oxides, or salts thereof, wherein X is $CR_1$ or N; and G, A, $R_1$; and n are defined herein. Also disclosed are methods of using such compounds as inhibitors of signaling through Toll-like receptor 7, or 8, or 9, and pharmaceutical compositions comprising such compounds. These compounds are useful in treating inflammatory and autoimmune diseases.

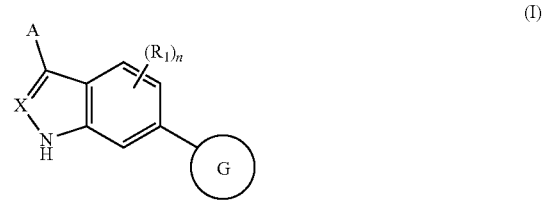

(I)

9 Claims, No Drawings

(56) References Cited

U.S. PATENT DOCUMENTS

| | | |
|---|---|---|
| 2011/0183967 A1 | 7/2011 | Zheng et al. |
| 2011/0275631 A1 | 11/2011 | Abeywardane et al. |
| 2013/0045986 A1 | 2/2013 | Nagarathnam et al. |
| 2013/0324547 A1 | 12/2013 | Boivin et al. |
| 2014/0066432 A1 | 3/2014 | Howbert et al. |
| 2014/0088085 A1 | 3/2014 | Burgess et al. |
| 2014/0242121 A1 | 8/2014 | Lipford et al. |
| 2015/0214490 A1 | 7/2015 | Kim et al. |
| 2015/0231142 A1 | 8/2015 | Van Goor et al. |
| 2017/0008885 A1 | 1/2017 | Koul et al. |
| 2017/0273983 A1 | 9/2017 | Ding et al. |
| 2018/0000790 A1 | 1/2018 | Dyckman et al. |

FOREIGN PATENT DOCUMENTS

| | | |
|---|---|---|
| WO | 03057696 A1 | 7/2003 |
| WO | 03074047 A1 | 9/2003 |
| WO | 2006113458 A1 | 10/2006 |
| WO | 2007000241 A1 | 1/2007 |
| WO | 2007115306 A2 | 10/2007 |
| WO | 2008065198 A1 | 6/2008 |
| WO | 2008152471 A1 | 12/2008 |
| WO | 2009030996 A1 | 3/2009 |
| WO | 2010003133 A2 | 1/2010 |
| WO | 2010149769 A1 | 12/2010 |
| WO | 2013010904 A1 | 1/2013 |
| WO | 2013181579 A2 | 12/2013 |
| WO | 2015088045 A1 | 6/2015 |
| WO | 2016029077 A1 | 2/2016 |
| WO | 2016075224 A1 | 5/2016 |
| WO | 2018005586 A1 | 1/2018 |
| WO | 2018026620 A1 | 2/2018 |
| WO | 2018049089 A1 | 3/2018 |
| WO | 2019126113 A1 | 6/2019 |

OTHER PUBLICATIONS

Lamphier, M. et al., "Novel Small Molecule Inhibitors of TLR7 and TLR9: Mechanism of Action and Efficacy in Vivo", Mol Pharmacol, 2014, vol. 85, pp. 429-440.

Patra, Mahesh Chandra and Sangdun Choi, "Recent Progress in the Development of Toll-like Receptor (TLR) antagonists", Exp. Opin. on Therapeutic Patents, 2016, vol. 26:6, pp. 719-730.

Roy, et al., "Design and development of benzoxazole derivatives with toll-like receptor 9 antagonism", Eur J Med Chem, 2017, vol. 134, pp. 334-347.

Sims, J. E. and Dirk E. Smith, "The IL-1 Family: Regulators of Immunity", Nature Rev. Immunol. 2010, vol. 10, pp. 89-102.

Witherington, Jason, etl., "6-Heteroaryl-pyrazolo[3,4-b]pyridines: Potent and Selective Inhibitors of Glycogen Synthase Kinase-3 (GSK-3)", Bioorganic & Medicinal Chemistry Letters, 2003, 13, pp. 3059-3062.

Fukuda, et al., "Discovery of D379182026: A potent orally active hepcidin pmduction inhibitor", Bioorganic & Medicinal Chemistry Letters, 2017, vol. 27, pp. 3716-3722.

* cited by examiner

SUBSTITUTED INDOLE AND INDAZOLE COMPOUNDS

CROSS-REFERENCE TO RELATED APPLICATIONS

This application is a national phase application under 35 U.S.C. § 371 of International Patent Application No. PCT/US2019/057311, filed Oct. 22, 2019, which claims priority to U.S. Provisional Application Ser. 62/749,828, filed Oct. 24, 2018, the contents of which are specifically incorporated fully herein by reference.

DESCRIPTION

The present invention generally relates to substituted indole and indazole compounds useful as inhibitors of signaling through Toll-like receptor 7, 8, or 9 (TLR7, TLR8, TLR9) or combinations thereof. Provided herein are substituted indole compounds, compositions comprising such compounds, and methods of their use. The invention further pertains to pharmaceutical compositions containing at least one compound according to the invention that are useful for the treatment of conditions related to TLR modulation, such as inflammatory and autoimmune diseases, and methods of inhibiting the activity of TLRs in a mammal.

Toll/IL-1 receptor family members are important regulators of inflammation and host resistance. The Toll-like receptor family recognizes molecular patterns derived from infectious organisms including bacteria, fungi, parasites, and viruses (reviewed in Kawai, T. et al., *Nature Immunol.*, 11:373-384 (2010)). Ligand binding to the receptor induces dimerization and recruitment of adaptor molecules to a conserved cytoplasmic motif in the receptor termed the Toll/IL-1 receptor (TIR) domain with the exception of TLR3, all TLRs recruit the adaptor molecule MyD88. The IL-1 receptor family also contains a cytoplasmic TIR motif and recruits MyD88 upon ligand binding (reviewed in Sims, J. E. et al., *Nature Rev. Immunol.*, 10:89-102 (2010)).

Toll-like receptors (TLRs) are a family of evolutionarily conserved, transmembrane innate immune receptors that participate in the first-line defense. As pattern recognition receptors, the TLRs protect against foreign molecules, activated by pathogen associated molecular patterns (PAMPs), or from damaged tissue, activated by danger associated molecular patterns (DAMPs). A total of 13 TLR family members have been identified, 10 in human, that span either the cell surface or the endosomal compartment. TLR7/8/9 are among the set that are endosomally located and respond to single-stranded RNA (TLR7 and TLR8) or unmethylated single-stranded DNA containing cytosine-phosphate-guanine (CpG) motifs (TLR9).

Activation of TLR7/8/9 can initiate a variety of inflammatory responses (cytokine production, B cell activation and IgG production, Type I interferon response). In the case of autoimmune disorders, the aberrant sustained activation of TLR7/8/9 leads to worsening of disease states. Whereas overexpression of TLR7 in mice has been shown to exacerbate autoimmune disease, knockout of TLR7 in mice was found to be protective against disease in lupus-prone MRL/lpr mice. Dual knockout of TLR7 and 9 showed further enhanced protection.

As numerous conditions may benefit by treatment involving modulation of cytokines, IFN production and B cell activity, it is immediately apparent that new compounds capable of modulating TLR7 and/or TLR8 and/or TLR9 and methods of using these compounds could provide substantial therapeutic benefits to a wide variety of patients.

The present invention relates to a new class of indole and indazole compounds found to be effective inhibitors of signaling through TLR7/8/9. These compounds are provided to be useful as pharmaceuticals with desirable stability, bioavailability, therapeutic index, and toxicity values that are important to their drugability.

SUMMARY OF THE INVENTION

The present invention provides compounds of Formula (I) that are useful as inhibitors of signaling through Toll-like receptor 7, 8, or 9 and are useful for the treatment of proliferative diseases, allergic diseases, autoimmune diseases and inflammatory diseases, or stereoisomers, N-oxides, tautomers, pharmaceutically acceptable salts, solvates or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for inhibition of Toll-like receptor 7, 8, or 9 comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating proliferative, metabolic, allergic, autoimmune and inflammatory diseases, comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method of treating a disease or disorder associated with Toll-like receptor 7, 8, or 9 activity, the method comprising administering to a mammal in need thereof, at least one of the compounds of Formula (I) or salts, solvates, and prodrugs thereof.

The present invention also provides processes and intermediates for making the compounds of Formula (I) including salts, solvates, and prodrugs thereof.

The present invention also provides at least one of the compounds of Formula (I) or salts, solvates, and prodrugs thereof, for use in therapy.

The present invention also provides the use of at least one of the compounds of Formula (I) or salts, solvates, and prodrugs thereof, for the manufacture of a medicament for the treatment of prophylaxis of Toll-like receptor 7, 8, or 9 related conditions, such as allergic disease, autoimmune diseases, inflammatory diseases, and proliferative diseases.

The compound of Formula (I) and compositions comprising the compounds of Formula (I) may be used in treating, preventing, or curing various Toll-like receptor 7, 8, or 9 related conditions. Pharmaceutical compositions comprising these compounds are useful for treating, preventing, or slowing the progression of diseases or disorders in a variety of therapeutic areas, such as allergic disease, autoimmune diseases, inflammatory diseases, and proliferative diseases.

These and other features of the invention will be set forth in expanded form as the disclosure continues.

DETAILED DESCRIPTION

The first aspect of the present invention provides at least one compound of Formula (I):

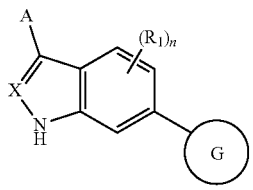
(I)
N-oxide, or a salt thereof, wherein:
X is CR₁ or N;
each R₁ is independently H, F, Cl, —CN, C$_{1-3}$ alkyl, C$_{1-2}$ fluoroalkyl, —OCH₃, or —S(O)—₂(C$_{1-3}$ alkyl);
G is:
(i)
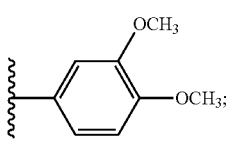
(ii)
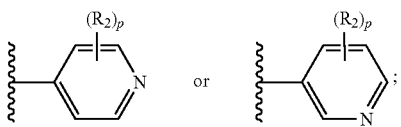
(iii)
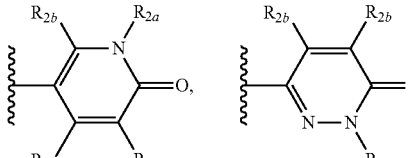
(iv) a 9-membered heterocyclic ring selected from:
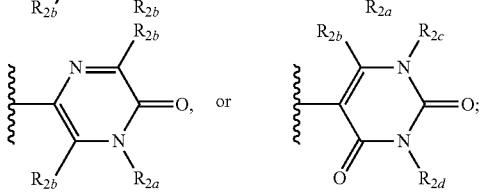
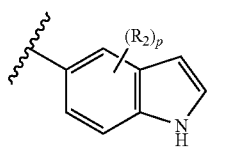
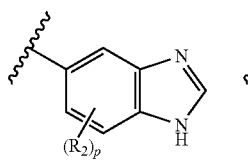
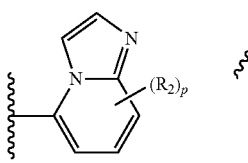
-continued
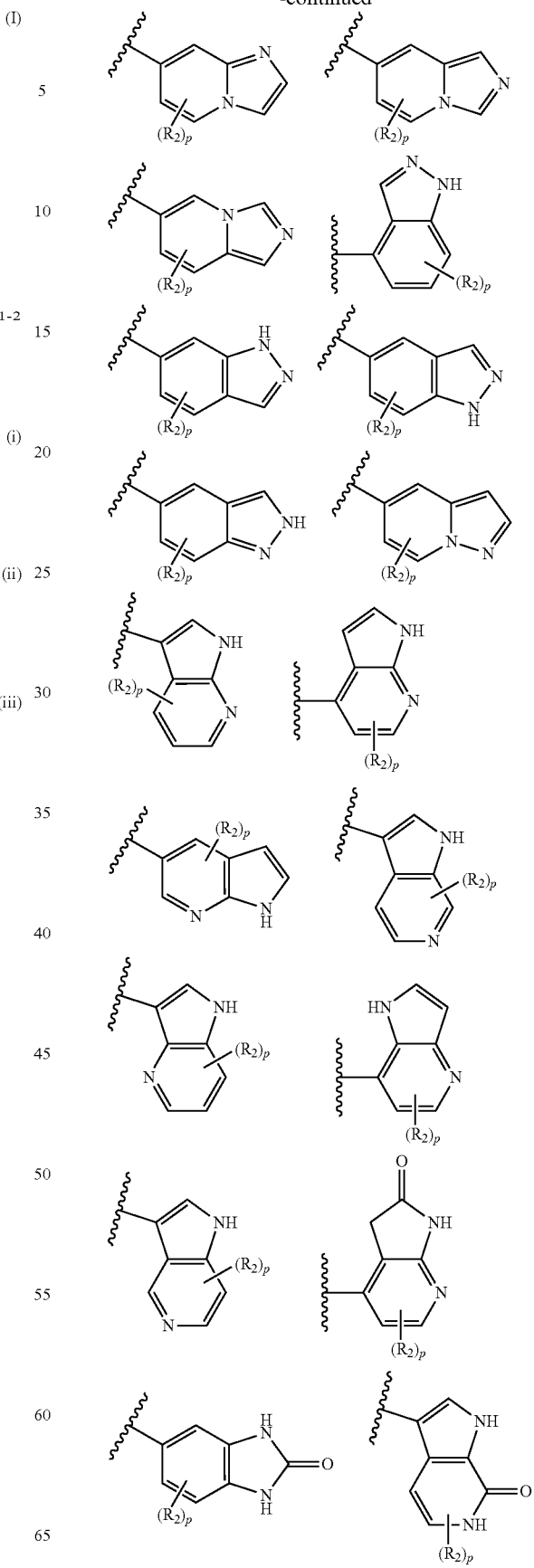

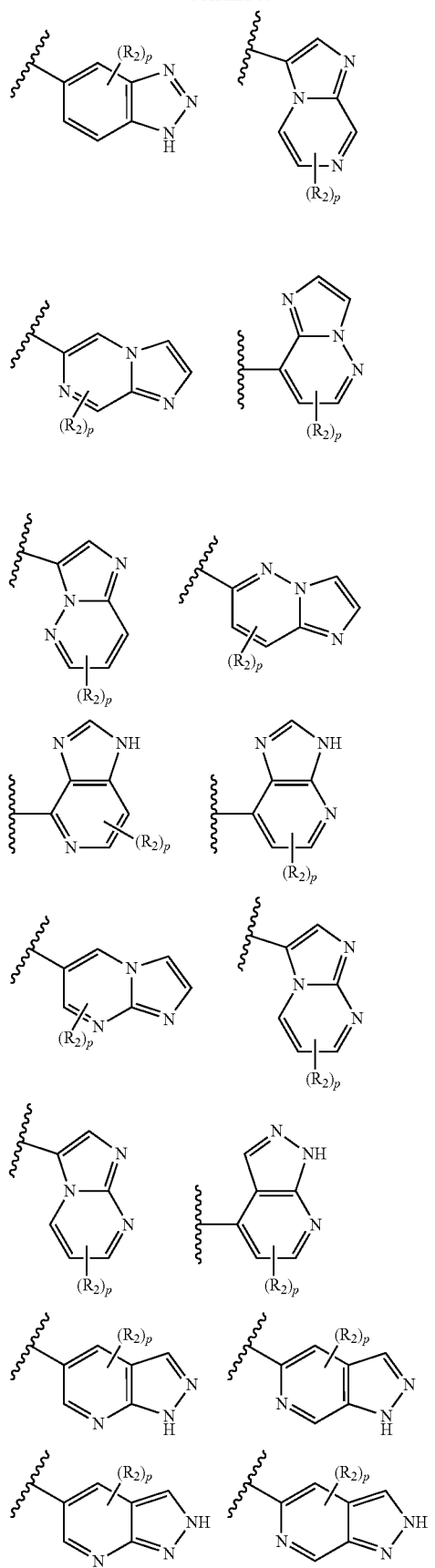
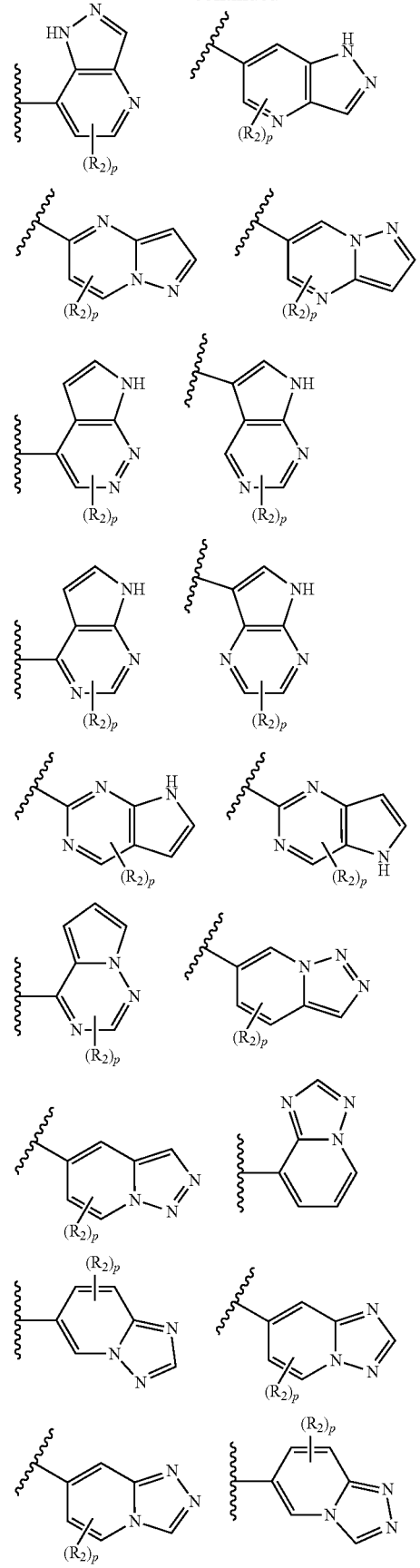

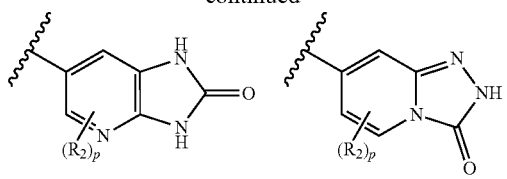
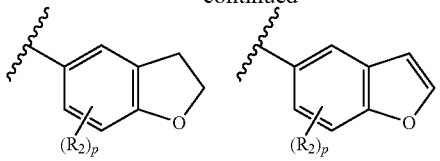
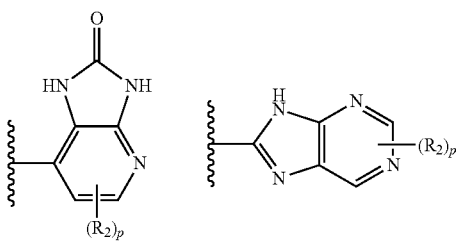
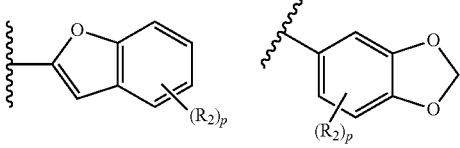
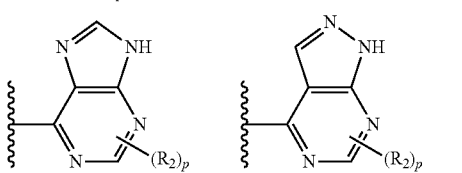
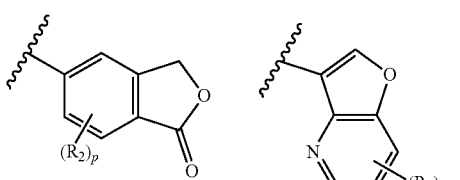
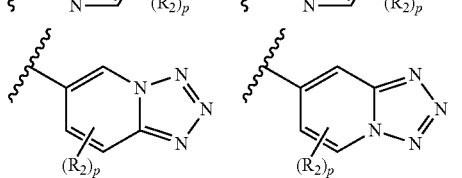
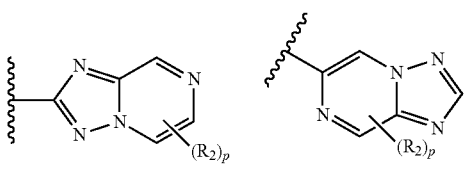
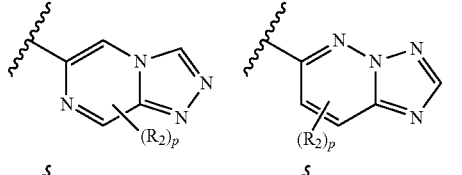
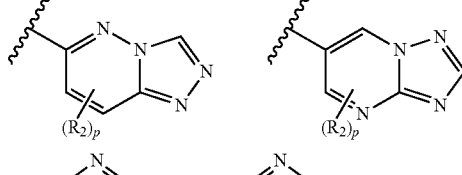
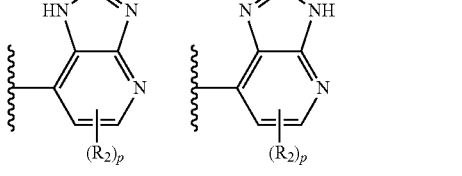
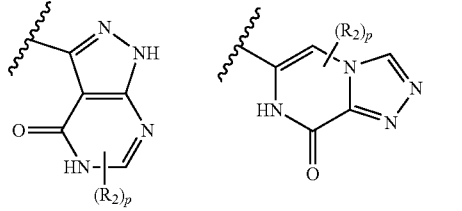
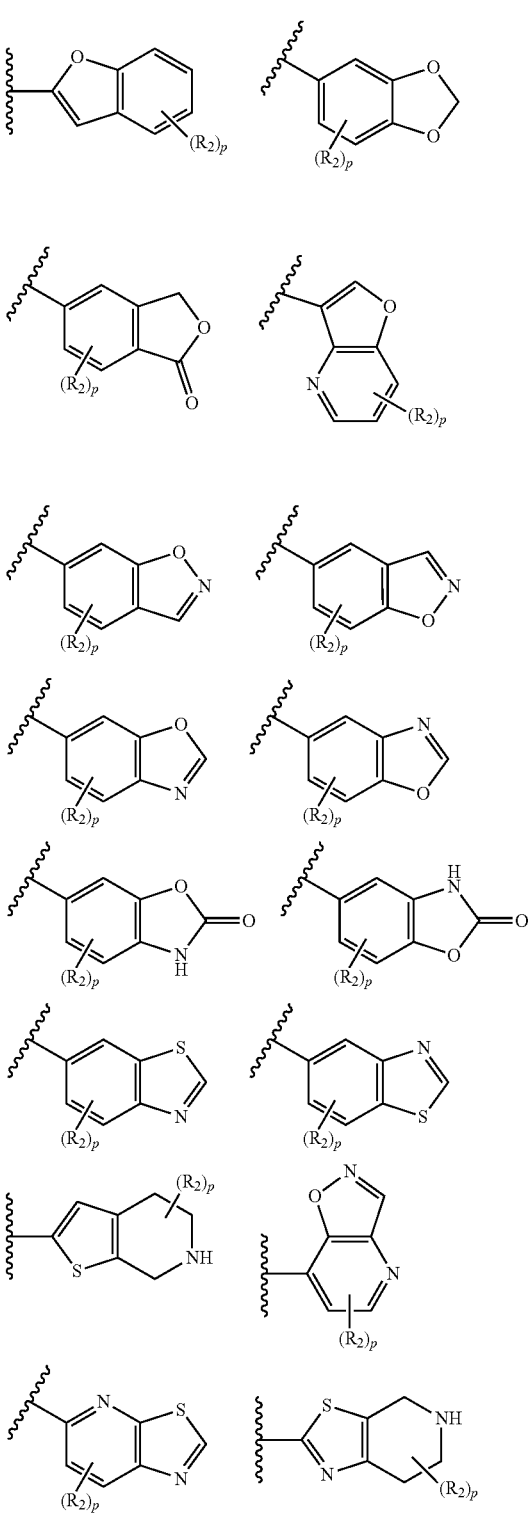

-continued

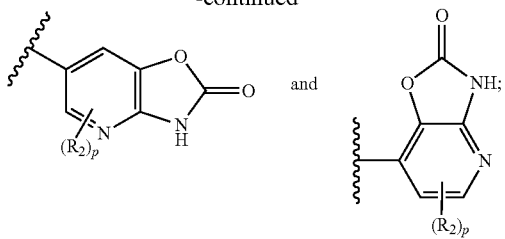

and or (v) 10-membered heterocyclic ring selected from:

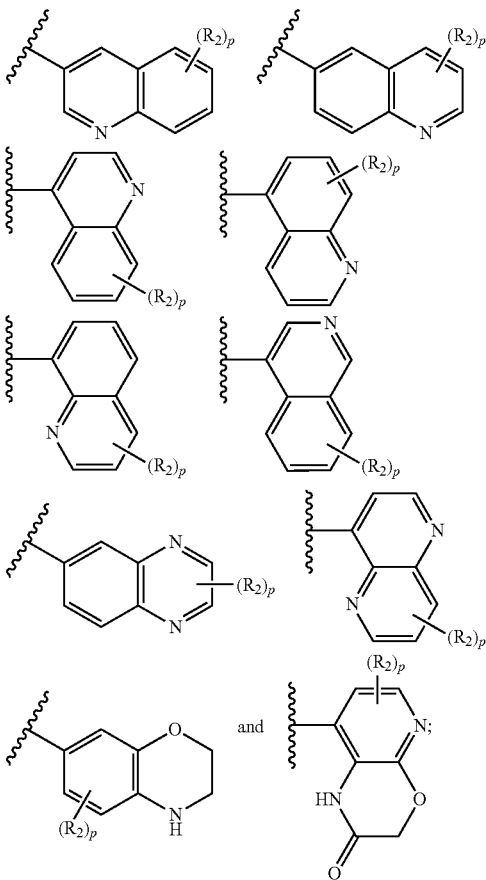

and each $R_2$ is independently halo, —CN, —OH, —NO$_2$, $C_{1-4}$ alkyl, $C_{1-2}$ fluoroalkyl, $C_{1-2}$ cyanoalkyl, $C_{1-3}$ hydroxyalkyl, $C_{1-3}$ aminoalkyl, —O(CH$_2$)$_{1-2}$OH, —(CH$_2$)$_{0-4}$O(C$_{1-4}$ alkyl), $C_{1-3}$ fluoroalkoxy, —(CH$_2$)$_{1-4}$O(C$_{1-3}$ alkyl), —O(CH$_2$)$_{1-2}$OC(O)(C$_{1-3}$ alkyl), —O(CH$_2$)$_{1-2}$NR$_x$R$_x$, —C(O)O(C$_{1-3}$ alkyl), —(CH$_2$)$_{0-2}$C(O)NR$_y$R$_y$, —C(O)NR$_x$(C$_{1-5}$ hydroxyalkyl), —C(O)NR$_x$(C$_{2-6}$ alkoxyalkyl), —C(O)NR$_x$(C$_{3-6}$ cycloalkyl), —NR$_y$R$_y$, —NR$_y$(C$_{1-3}$ fluoroalkyl), —NR$_y$(C$_{1-4}$ hydroxyalkyl), —NR$_x$CH$_2$(phenyl), —NR$_x$S(O)$_2$(C$_{3-6}$ cycloalkyl), —NR$_x$C(O)(C$_{1-3}$ alkyl), —NR$_x$CH$_2$(C$_{3-6}$ cycloalkyl), —(CH$_2$)$_{0-2}$S(O)$_2$(C$_{1-3}$ alkyl), —(CH$_2$)$_{0-2}$(C$_{3-6}$ cycloalkyl), —(CH$_2$)$_{0-2}$(phenyl), morpholinyl, dioxothiomorpholinyl, dimethyl pyrazolyl, methylpiperidinyl, methylpiperazinyl, amino-oxadiazolyl, imidazolyl, pyrimidinyl, triazolyl, or —C(O)(thiazolyl);

$R_{2a}$ is $C_{1-6}$ alkyl, $C_{1-3}$ fluoroalkyl, $C_{1-6}$ hydroxyalkyl, $C_{1-3}$ aminoalkyl, —(CH$_2$)$_{0-4}$O(C$_{1-3}$ alkyl), $C_{3-6}$ cycloalkyl, —(CH$_2$)$_{1-3}$C(O)NR$_y$R$_y$, —CH$_2$(C$_{3-6}$ cycloalkyl), —CH$_2$(phenyl), tetrahydrofuranyl, tetrahydropyranyl, or phenyl;

each $R_{2b}$ is independently H, halo, —CN, —NR$_x$R$_x$, $C_{1-6}$ alkyl, $C_{1-3}$ fluoroalkyl, $C_{1-3}$ hydroxyalkyl, $C_{1-3}$ fluoroalkoxy, —(CH$_2$)$_{0-2}$O(C$_{1-3}$ alkyl), —(CH$_2$)$_{0-3}$C(O)NR$_y$R$_x$, —(CH$_2$)$_{1-3}$(C$_{3-6}$ cycloalkyl), —C(O)O(C$_{1-3}$ alkyl), —C(O)NR$_x$(C$_{1-3}$ alkyl), —CR$_x$=CR$_x$R$_x$, or —CR$_x$=CH(C$_{3-6}$ cycloalkyl);

$R_{2c}$ is $R_{2a}$ or $R_{2b}$;

$R_{2d}$ is $R_{2a}$ or $R_{2b}$; provided that one of $R_{2c}$ and $R_{2d}$ is $R_{2a}$, and the other of $R_{2c}$ and $R_{2}$ is $R_{2b}$;

A is:

(i) H, —NR$_y$R$_y$, or —OCH$_2$CH$_2$NR$_y$R$_y$;

(ii) —CR$_x$R$_x$R$_3$, —CH$_2$CH$_2$NR$_x$R$_3$, —C(O)NR$_x$R$_3$, —NR$_x$R$_3$, —NR$_x$CH$_2$CH$_2$R$_3$, —OR$_3$, or —NR$_x$C(O)R$_3$; or (iii) R$_3$;

$R_3$ is $C_{3-6}$ cycloalkyl, azetidinyl, morpholinyl, piperazinyl, piperidinyl, or pyrrolidinyl, each substituted with zero to 2 $R_{3a}$;

each $R_{3a}$ is independently $C_{1-6}$ alkyl, $C_{1-6}$ cyanoalkyl, $C_{1-6}$ fluoroalkyl, $C_{1-6}$ hydroxyalkyl, —CH$_2$C(O)NR$_y$R$_y$, —C(O)(CH$_2$)$_{1-3}$NR$_y$R$_y$, —NR$_y$R$_y$, —(CH$_2$)$_{1-3}$S(O)$_2$(C$_{1-3}$ alkyl), —(CH$_2$)$_{1-3}$NR$_x$S(O)$_2$(C$_{1-3}$ alkyl), —NR$_x$(CH$_2$)$_{1-2}$C(O)NR$_y$R$_y$, —NR$_x$(CH$_2$)$_{1-3}$S(O)$_2$(C$_{1-3}$ alkyl), —NR$_x$(C$_{3-6}$ cycloalkyl), —NR$_x$(oxetanyl), —CH$_2$(methyltriazolyl), morpholinyl, oxetanyl, pyrrolidinyl, fluoropyrrolidinyl, hydroxy-methylpyrrolidinyl, tetrahydropyranyl, 1-oxa-6-azaspiro[3.3]heptanyl, 2-oxa-6-azaspiro[3.3]heptanyl, 2-oxa-6-azaspiro[3.4]octanyl, 6-oxa-2-azaspiro[3.4]octanyl, 2,2-dioxo-2-thia-6-azaspiro[3.3]heptanyl, 2-oxa-7-azaspiro[4.4]nonanyl, or azetidinyl substituted with zero to 3 substituents independently selected from F, Cl, —OH, —CN, $C_{1-3}$ alkyl, $C_{1-3}$ hydroxyalkyl, $C_{1-3}$ fluoroalkyl, and $C_{1-3}$ alkoxy;

each $R_x$ is independently H or —CH$_3$;

each $R_y$ is independently H or $C_{1-6}$ alkyl;

n is zero, 1, or 2; and p is zero, 1, or 2.

One embodiment provides a compound of Formula (I), N-oxide, or a salt thereof wherein X is N; and A, G, R$_1$, and n are defined in the first aspect. The compounds of this embodiment have the structure of Formula (Ia):

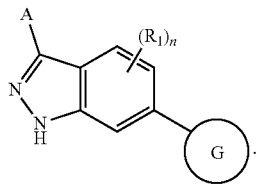

(Ia)

Included in this embodiment are compounds in which A is: (i) —OCH$_2$CH$_2$NR$_y$R$_y$; (ii) —CR$_x$R$_x$R$_3$, —CH$_2$CH$_2$NR$_x$R$_3$, —C(O)NR$_x$R$_3$, —NR$_x$R$_3$, —NR$_x$CH$_2$CH$_2$R$_3$, —OR$_3$, or —NR$_x$C(O)R$_3$; or (iii) R$_3$; wherein R$_3$, R$_x$, and R$_y$ are defined in the first aspect. Also included in this embodiment are compounds in which A is —CR$_x$R$_x$R$_3$, —CH$_2$CH$_2$NR$_x$R$_3$, —C(O)NR$_x$R$_3$, —NR$_x$R$_3$, —NR$_x$CH$_2$CH$_2$R$_3$, —OR$_3$, —NR$_x$C(O)R$_3$, or R$_3$. Additionally, included in this embodiment are compounds in which G is:

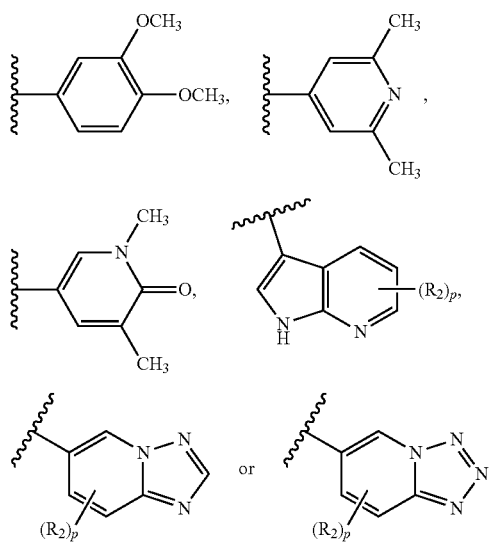

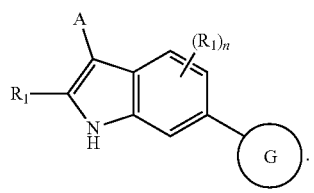

One embodiment provides a compound of Formula (I), N-oxide, or a salt thereof wherein X is $CR_1$; and A, G, $R_1$, and n are defined in the first aspect. The compounds of this embodiment have the structure of Formula (Ib):

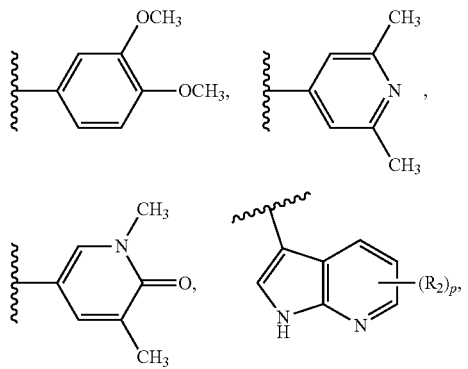

(Ib)

Included in this embodiment are compounds in which A is: (i) —$OCH_2CH_2NR_yR_3$; (ii) —$CR_xR_xR_3$, —$CH_2CH_2NR_xR_3$, —$C(O)NR_xR_3$, —$NR_xR_3$, —$NR_xCH_2CH_2R_3$, —$OR_3$, or —$NR_xC(O)R_3$; or (iii) $R_3$; wherein $R_3$, $R_x$, and $R_y$ are defined in the first aspect. Also included in this embodiment are compounds in which A is —$CR_xR_xR_3$, —$CH_2CH_2NR_xR_3$, —$C(O)NR_xR_3$, —$NR_xR_3$, —$NR_xCH_2CH_2R_3$, —$OR_3$, —$NR_xC(O)R_3$, or $R_3$. Additionally, included in this embodiment are compounds in which G is:

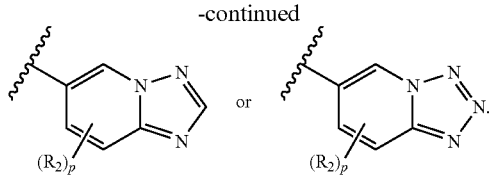

One embodiment provides a compound of Formula (I), N-oxide, or a salt thereof wherein:

X is $CR_1$ or N;

each $R_1$ is independently H, F, Cl, —CN, $C_{1-3}$ alkyl, $C_{1-2}$ fluoroalkyl, —$OCH_3$, or —$S(O)$—$_2(C_{1-2}$ alkyl);

G is:

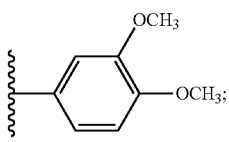
(i)

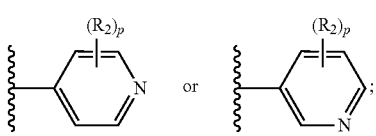
(ii)

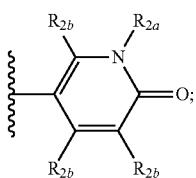
(iii)

or (iv) a 9-membered heterocyclic ring selected from:

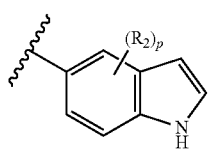 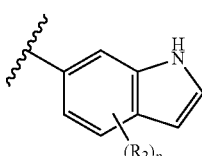

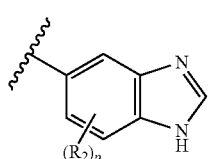 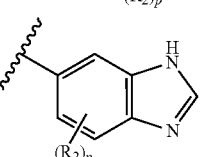

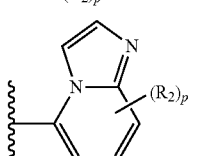 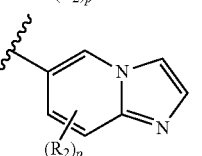

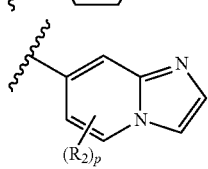 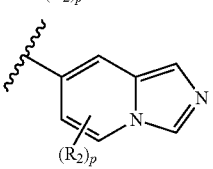

-continued
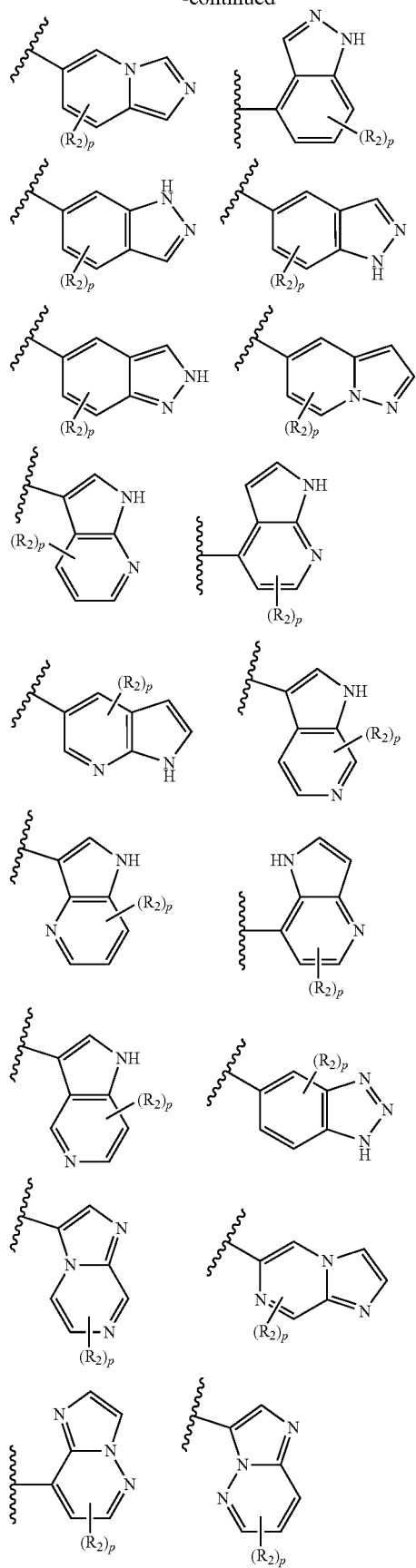
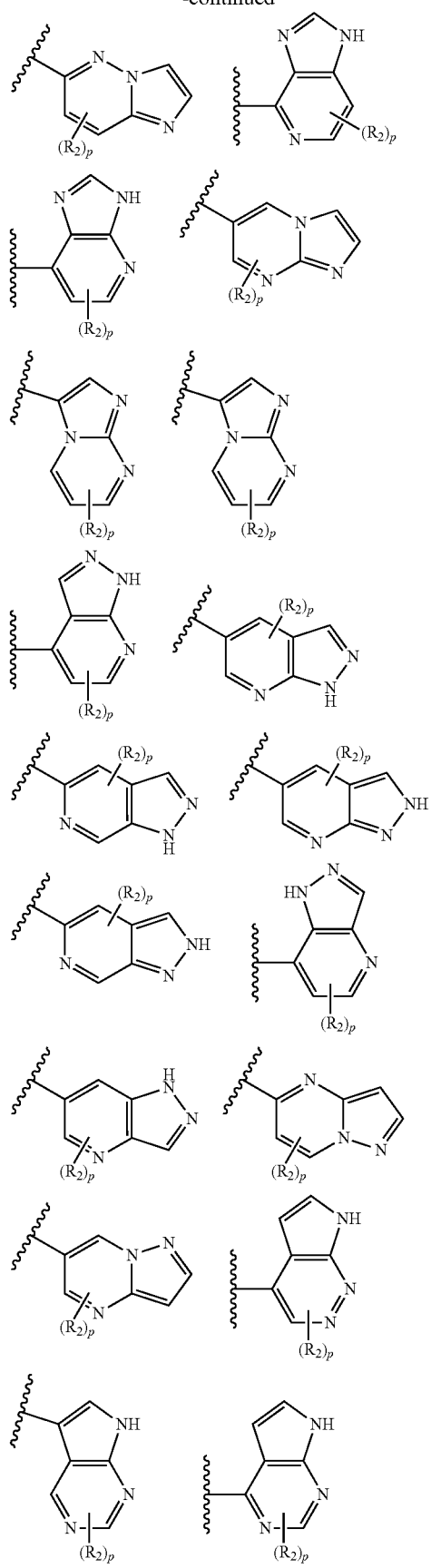

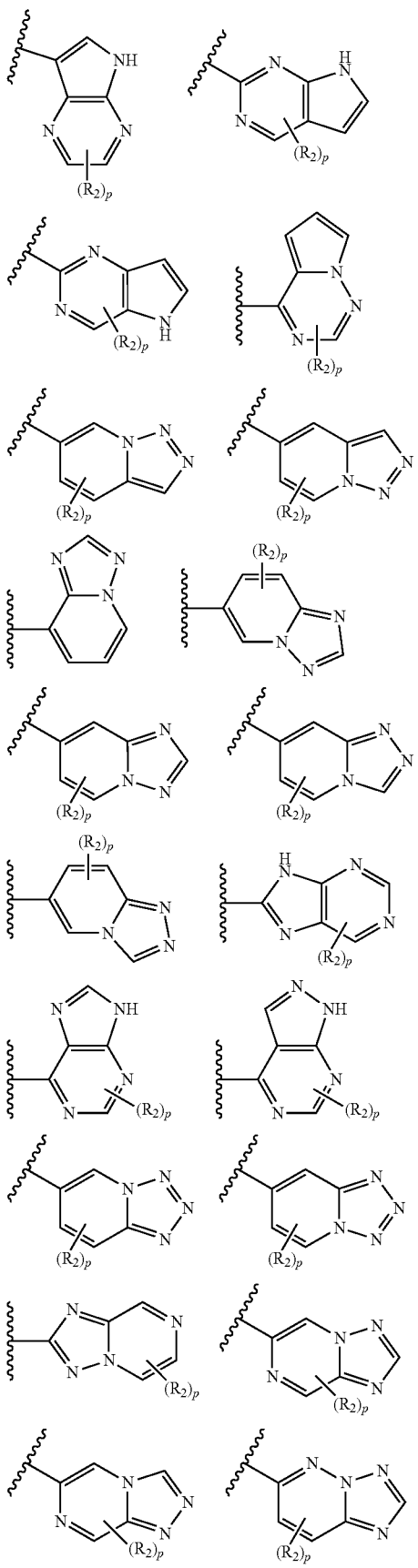
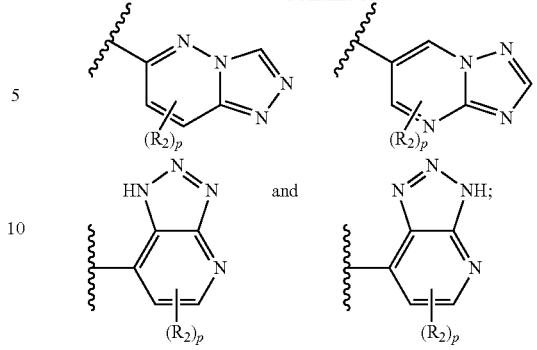

each $R_2$ is independently F, Cl, —CN, —OH, $C_{1-3}$ alkyl, $C_{1-2}$ fluoroalkyl, $C_{1-2}$ cyanoalkyl, $C_{1-3}$ hydroxyalkyl, $C_{1-2}$ aminoalkyl, —$(CH_2)_{0-2}O(C_{1-3}$ alkyl), $C_{3-6}$ cycloalkyl, —$NR_xR_x$, —$(CH_2)_{0-2}C(O)NR_xR_x$, —$(CH_2)_{0-2}S(O)_2(C_{1-3}$ alkyl), —$CH_2(C_{3-6}$ cycloalkyl), —$CH_2$(phenyl), phenyl, pyrimidinyl, or triazolyl; $R_{2a}$ is $C_{1-4}$ alkyl, $C_{1-2}$ fluoroalkyl, $C_{1-4}$ hydroxyalkyl, —$(CH_2)_{1-3}OCH_3$, $C_{3-6}$ cycloalkyl, —$CH_2C(O)NR_xR_x$, —$CH_2(C_{3-6}$ cycloalkyl), —$CH_2$(phenyl), tetrahydrofuranyl, or phenyl; each $R_{2b}$ is independently H, F, Cl, —CN, —$NR_xR_x$, $C_{1-6}$ alkyl, $C_{1-2}$ fluoroalkyl, $C_{1-3}$ hydroxyalkyl, —$(CH_2)_{0-2}O(C_{1-2}$ alkyl), —$(CH_2)_{0-2}C(O)NR_xR_x$, —$(CH_2)_{1-3}$(cyclopropyl), —$C(O)O(C_{1-2}$ alkyl), or —$C(O)NR_x(C_{1-3}$ alkyl); A is: (i) —$OCH_2CH_2NR_xR_x$; (ii) —$CR_xR_xR_3$, —$CH_2CH_2NR_xR_3$, —$C(O)NR_xR_3$, —$NR_xR_3$, —$NR_xCH_2CH_2R_3$, —$OR_3$, or —$NR_xC(O)R_3$; or (iii) $R_3$; and each $R_{3a}$ is independently $C_{1-4}$ alkyl, $C_{1-3}$ cyanoalkyl, $C_{1-3}$ fluoroalkyl, $C_{1-4}$ hydroxyalkyl, —$CH_2C(O)NR_xR_x$, —$C(O)(CH_2)_{1-3}NR_xR_x$, —$NR_yR_y$, —$(CH_2)_{1-2}S(O)_2(C_{1-2}$ alkyl), —$(CH_2)_{1-2}NR_xS(O)_2(C_{1-2}$ alkyl), —$NR_xCH_2C(O)NR_yR_y$, —$NR_xCH_2CH_2S(O)_2(C_{1-2}$ alkyl), —$NR_x(C_{3-6}$ cycloalkyl), —$NR_x$(oxetanyl), —$CH_2$(methyltriazolyl), morpholinyl, oxetanyl, pyrrolidinyl, fluoropyrrolidinyl, hydroxy-methylpyrrolidinyl, tetrahydropyranyl, 1-oxa-6-azaspiro[3.3]heptanyl, 2-oxa-6-azaspiro[3.3]heptanyl, 2-oxa-6-azaspiro[3,4]octanyl, 6-oxa-2-azaspiro[3,4]octanyl, 2,2-dioxo-2-thia-6-azaspiro[3.3]heptanyl, 2-oxa-7-azaspiro[4.4]nonanyl, or azetidinyl substituted with zero to 3 substituents independently selected from F, Cl, —OH, —CN, $C_{1-2}$ alkyl, $C_{1-2}$ hydroxyalkyl, $C_{1-2}$ fluoroalkyl, and $C_{1-3}$ alkoxy.

One embodiment provides a compound of Formula (I), N-oxide, or a salt thereof wherein:
X is $CR_1$ or N;
each $R_3$ is independently H, —$CH_3$, —$CH_2CH_3$, —$CH(CH_3)_2$, —$OCH_3$, or —$S(O)_2CH_3$;
G is:

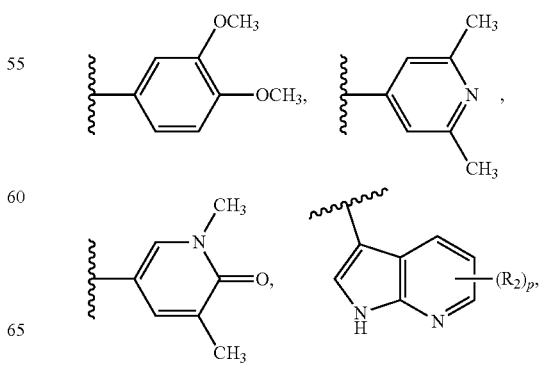

-continued

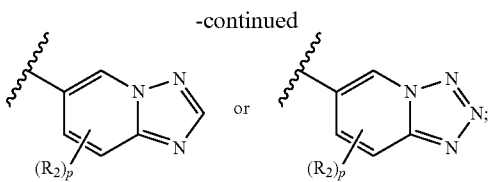

each R$_2$ is independently —CN, —CH$_3$, —OCH$_3$, or pyrimidinyl;
A is:
(i) H, —NH$_2$, or —OCH$_2$CH$_2$N(CH$_3$)$_2$;
(ii) —CH$_2$R$_3$, —CH$_2$CH$_2$NHR$_3$, —C(O)NHR$_3$, —NHR$_3$, —NHCH$_2$CH$_2$R$_3$, —OR$_3$, or —NHC(O)R$_3$; or
(iii) R$_3$;
R$_3$ is azetidinyl, cyclobutyl, cyclohexyl, piperazinyl, piperidinyl, or pyrrolidinyl, each substituted with zero to 1 R$_{3a}$; R$_{3a}$ is —CH$_3$, —CH$_2$CH$_2$CH$_3$, —CH(CH$_3$)$_2$, —CH$_2$CN, —CH$_2$CH$_2$CN, —CH$_2$CH$_2$CF$_3$, —CH$_2$C(CH$_3$)$_2$OH, —CH$_2$C(O)NH$_2$, —CH$_2$C(O)N(CH$_3$)$_2$, —C(O)CH$_2$N(CH$_3$)$_2$, —C(O)CH$_2$CH$_2$N(CH$_3$)$_2$, —C(O)CH$_2$CH$_2$CH$_2$N(CH$_3$)$_2$, —NH(CH$_3$), —N(CH$_3$)$_2$, —NH(CH(CH$_3$)$_2$), —CH$_2$CH$_2$S(O)$_2$CH$_3$, —CH$_2$CH$_2$NHS(O)$_2$CH$_3$, —NHCH$_2$C(O)N(CH$_3$)$_2$, —NHCH$_2$CH$_2$S(O)$_2$CH$_3$, —NH(cyclopropyl), —NH(oxetanyl), —N(CH$_3$)(oxetanyl), —CH$_2$(methyltriazolyl), morpholinyl, oxetanyl, pyrrolidinyl, fluoropyrrolidinyl, hydroxy-methylpyrrolidinyl, tetrahydropyranyl, 1-oxa-6-azaspiro[3.3]heptanyl, 2-oxa-6-azaspiro[3.3]heptanyl, 2-oxa-6-azaspiro[3.4]octanyl, 6-oxa-2-azaspiro[3.4]octanyl, 2,2-dioxo-2-thia-6-azaspiro[3.3]heptanyl, 2-oxa-7-azaspiro[4.4]nonanyl, or azetidinyl substituted with zero to 2 substituents independently selected from F, —OH, —CH$_3$, —CH$_2$OH, —OCH$_3$, —OCH$_2$CH$_3$, and —OCH(CH$_3$)$_2$; n is zero or 1; and p is zero, 1, or 2. Included in this embodiment are compounds in which X is CR$_1$. Also included in this embodiment are compounds in which X is N.

One embodiment provides a compound of Formula (I), N-oxide, or a salt thereof wherein:
X is CH or N;
each R$_1$ is independently H, —CH$_3$, —CH$_2$CH$_3$, —CH(CH$_3$)$_2$, —OCH$_3$, or —S(O)$_2$CH$_3$;
G is:

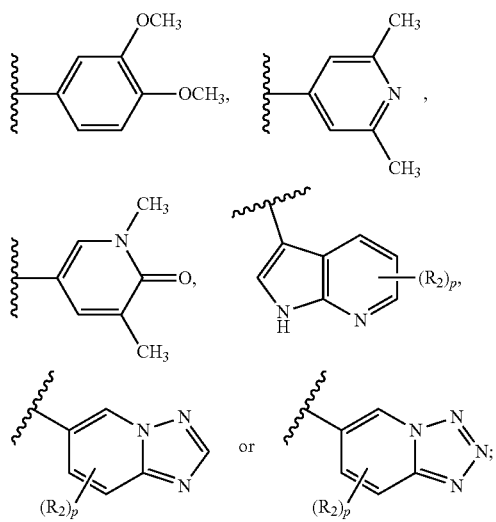

each R$_2$ is independently —CN, —CH$_3$, —OCH$_3$, or pyrimidinyl; A is: (i) —OCH$_2$CH$_2$N(CH$_3$)$_2$; (ii) —CH$_2$R$_3$, —CH$_2$CH$_2$NHR$_3$, —C(O)NHR$_3$, —NHR$_3$, —NHCH$_2$CH$_2$R$_3$, —OR$_3$, or —NHC(O)R$_3$; or (iii) R$_3$; R$_3$ is azetidinyl, cyclobutyl, cyclohexyl, piperazinyl, piperidinyl, or pyrrolidinyl, each substituted with zero to 1 R$_{3a}$; R$_{3a}$ is —CH$_3$, —CH$_2$CH$_2$CH$_3$, —CH(CH$_3$)$_2$, —CH$_2$CN, —CH$_2$CH$_2$CN, —CH$_2$CH$_2$CF$_3$, —CH$_2$C(CH$_3$)$_2$OH, —CH$_2$C(O)NH$_2$, —CH$_2$C(O)N(CH$_3$)$_2$, —C(O)CH$_2$N(CH$_3$)$_2$, —C(O)CH$_2$CH$_2$N(CH$_3$)$_2$, —C(O)CH$_2$CH$_2$CH$_2$N(CH$_3$)$_2$, —NH(CH$_3$), —N(CH$_3$)$_2$, —NH(CH(CH$_3$)$_2$), —CH$_2$CH$_2$S(O)$_2$CH$_3$, —CH$_2$CH$_2$NHS(O)$_2$CH$_3$, —NHCH$_2$C(O)N(CH$_3$)$_2$, —NH(CH$_2$CH$_2$S(O)$_2$CH$_3$), —NH(cyclopropyl), —NH(oxetanyl), —N(CH$_3$)(oxetanyl), —CH$_2$(methyltriazolyl), morpholinyl, oxetanyl, pyrrolidinyl, fluoropyrrolidinyl, hydroxy-methylpyrrolidinyl, tetrahydropyranyl, 1-oxa-6-azaspiro[3.3]heptanyl, 2-oxa-6-azaspiro[3.3]heptanyl, 2-oxa-6-azaspiro[3.4]octanyl, 6-oxa-2-azaspiro[3.4]octanyl, 2,2-dioxo-2-thia-6-azaspiro[3.3]heptanyl, 2-oxa-7-azaspiro[4.4]nonanyl, or azetidinyl substituted with zero to 2 substituents independently selected from F, —OH, —CH$_3$, —CH$_2$OH, —OCH$_3$, —OCH$_2$CH$_3$, and —OCH(CH$_3$)$_2$; n is zero or 1; and p is zero, 1, or 2. Included in this embodiment are compounds in which X is CH. Also included in this embodiment are compounds in which X is N.

One embodiment provides a compound of Formula (I), N-oxide, or a salt thereof wherein:
X is CH or N;
G is:

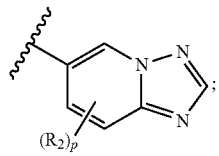

R$_2$ is —CH$_3$ or —OCH$_3$; A is: —OR$_3$ or R$_3$; R$_3$ is cyclobutyl, cyclohexyl, piperazinyl, piperidinyl, or pyrrolidinyl, each substituted with zero to 1 R$_{3a}$; R$_{3a}$ is C$_{1-6}$ alkyl, C$_{1-6}$ cyanoalkyl, C$_{1-6}$ fluoroalkyl, C$_{1-6}$ hydroxyalkyl, —CH$_2$C(O)NR$_x$R$_y$, —C(O)(CH$_2$)$_{1-3}$NR$_y$R$_y$, —NR$_y$R$_y$, —(CH$_2$)$_{1-3}$S(O)$_2$(C$_{1-3}$ alkyl), —(CH$_2$)$_{1-3}$NR$_x$S(O)$_2$(C$_{1-3}$ alkyl), —NR$_x$(CH$_2$)$_{1-2}$C(O)NR$_y$R$_y$, —NR$_x$(CH$_2$)$_{1-3}$S(O)$_2$(C$_{1-3}$ alkyl), —NR$_x$(C$_{3-6}$ cycloalkyl), —NR$_x$(oxetanyl), —CH$_2$(methyltriazolyl), morpholinyl, oxetanyl, pyrrolidinyl, fluoropyrrolidinyl, hydroxy-methylpyrrolidinyl, tetrahydropyranyl, 1-oxa-6-azaspiro[3.3]heptanyl, 2-oxa-6-azaspiro[3.3]heptanyl, 2-oxa-6-azaspiro[3.4]octanyl, 6-oxa-2-azaspiro[3.4]octanyl, 2,2-dioxo-2-thia-6-azaspiro[3.3]heptanyl, 2-oxa-7-azaspiro[4.4]nonanyl, or azetidinyl substituted with zero to 3 substituents independently selected from F, Cl, —OH, —CN, C$_{1-3}$ alkyl, C$_{1-3}$ hydroxyalkyl, C$_{1-3}$ fluoroalkyl, and C$_{1-3}$ alkoxy; each R$_x$ is independently H or —CH$_3$; each R$_y$ is independently H or C$_{1-6}$ alkyl; n is zero or 1; and p is zero or 1. Included in this embodiment are compounds in which R$_{3a}$ is C$_{1-4}$ alkyl, C$_{1-3}$ cyanoalkyl, C$_{1-3}$ fluoroalkyl, C$_{1-4}$ hydroxyalkyl, —CH$_2$C(O)NR$_x$R$_x$, —C(O)(CH$_2$)$_{1-3}$NR$_x$R$_x$, —NR$_y$R$_y$, —(CH$_2$)$_{1-2}$S(O)$_2$(C$_{1-2}$ alkyl), —(CH$_2$)$_{1-2}$NR$_x$S(O)$_2$(C$_{1-2}$ alkyl), —NR$_x$CH$_2$C(O)NR$_y$R$_y$, —NR$_x$CH$_2$CH$_2$S(O)$_2$(C$_{1-2}$ alkyl), —NR$_x$(C$_{3-6}$ cycloalkyl), —NR$_x$(oxetanyl), —CH$_2$(methyltriazolyl), morpholinyl, oxetanyl, pyrrolidinyl, fluoropyrrolidinyl, hydroxy-methylpyrrolidinyl, tetrahydropyranyl, 1-oxa-6-azaspiro[3.3]heptanyl, 2-oxa-6-azaspiro[3.3]heptanyl, 2-oxa-6-azaspiro[3.4]octanyl, 6-oxa-2-azaspiro[3.4]octanyl, 2,2-dioxo-2-thia-6-azaspiro[3.3]heptanyl, 2-oxa-7-azaspiro[4.4]nonanyl, or azetidinyl substituted with zero to 3 substituents independently selected from F, Cl, —OH, —CN, $C_{1-2}$ alkyl, $C_{1-2}$ hydroxyalkyl, $C_{1-2}$ fluoroalkyl, and $C_{1-3}$ alkoxy. Also included in this embodiment are compounds in which $R_{3a}$ is —CH$_3$, —CH$_2$CH$_2$CH$_3$, —CH(CH$_3$)$_2$, —CH$_2$CN, —CH$_2$CH$_2$CN, —CH$_2$CH$_2$CF$_3$, —CH$_2$C(CH$_3$)$_2$OH, —CH$_2$C(O)NH$_2$, —CH$_2$C(O)N(CH$_3$)$_2$, —C(O)CH$_2$N(CH$_3$)$_2$, —C(O)CH$_2$CH$_2$N(CH$_3$)$_2$, —C(O)CH$_2$CH$_2$CH$_2$N(CH$_3$)$_2$, —NH(CH$_3$), —N(CH$_3$)$_2$, —NH(CH(CH$_3$)$_2$), —CH$_2$CH$_2$S(O)$_2$CH$_3$, —CH$_2$CH$_2$NHS(O)$_2$CH$_3$, —NHCH$_2$C(O)N(CH$_3$)$_2$, —NHCH$_2$CH$_2$S(O)$_2$CH$_3$, —NH(cyclopropyl), —NH(oxetanyl), —N(CH$_3$)(oxetanyl), —CH$_2$(methyltriazolyl), morpholinyl, oxetanyl, pyrrolidinyl, fluoropyrrolidinyl, hydroxy-methylpyrrolidinyl, tetrahydropyranyl, 1-oxa-6-azaspiro[3.3]heptanyl, 2-oxa-6-azaspiro[3.3]heptanyl, 2-oxa-6-azaspiro[3.4]octanyl, 6-oxa-2-azaspiro[3.4]octanyl, 2,2-dioxo-2-thia-6-azaspiro[3.3]heptanyl, 2-oxa-7-azaspiro[4.4]nonanyl, or azetidinyl substituted with zero to 2 substituents independently selected from F, —OH, —CH$_3$, —CH$_2$OH, —OCH$_3$, —OCH$_2$CH$_3$, and —OCH(CH$_3$)$_2$.

One embodiment provides a compound of Formula (I), N-oxide, or a salt thereof wherein A is H or —NH$_2$; and X, G, $R_1$, n, and p are defined in the first aspect. Included in this embodiment are compounds in which A is H. Also included in this embodiment are compounds in which A is —NH$_2$.

One embodiment provides a compound of Formula (I), N-oxide, or a salt thereof wherein A is H, —NR$_y$R$_y$, or —OCH$_2$CH$_2$NR$_y$R$_y$; and X, G, $R_1$, $R_x$, $R_y$, n, and p are defined in the first aspect. Included in this embodiment are compounds in which A is H, —NR$_x$R$_x$, or —OCH$_2$CH$_2$NR$_x$R$_x$. Also included in this embodiment are compounds in which A is H, —NH$_2$, or —OCH$_2$CH$_2$N(CH$_3$)$_2$.

One embodiment provides a compound of Formula (I), N-oxide, or a salt thereof wherein A is —NR$_y$R$_y$ or —OCH$_2$CH$_2$NR$_y$R$_y$; and X, G, $R_1$, $R_x$, $R_y$, n, and p are defined in the first aspect. Included in this embodiment are compounds in which A is —NR$_x$R$_x$ or —OCH$_2$CH$_2$NR$_x$R$_x$. Also included in this embodiment are compounds in which A is —NH$_2$ or —OCH$_2$CH$_2$N(CH$_3$)$_2$.

One embodiment provides a compound of Formula (I), N-oxide, or a salt thereof wherein A is (i) H, —NR$_x$R$_x$, or —OCH$_2$CH$_2$NR$_x$R$_x$; (ii) —CR$_x$R$_x$R$_3$, —CH$_2$CH$_2$NR$_x$R$_3$, —C(O)NR$_x$R$_3$, —NR$_x$R$_3$, —NR$_x$CH$_2$CH$_2$R$_3$, —OR$_3$, or —NR$_x$C(O)R$_3$; or (iii) R$_3$; and X, G, $R_1$, R$_3$, $R_x$, n, and p are defined in the first aspect. Included in this embodiment are compounds in which A is: (i) H, —NH$_2$, or —OCH$_2$CH$_2$N(CH$_3$)$_2$; (ii) —CH$_2$R$_3$, —CH$_2$CH$_2$NHR$_3$, —C(O)NHR$_3$, —NHR$_3$, —NHCH$_2$CH$_2$R$_3$, —OR$_3$, or —NHC(O)R$_3$; or (iii) R$_3$. Also included in this embodiment are compounds in which A is: (i) —OCH$_2$CH$_2$N(CH$_3$)$_2$; (ii) —CH$_2$R$_3$, —CH$_2$CH$_2$NHR$_3$, —C(O)NHR$_3$, —NHR$_3$, —NHCH$_2$CH$_2$R$_3$, —OR$_3$, or —NHC(O)R$_3$; or (iii) R$_3$.

One embodiment provides a compound of Formula (I), N-oxide, or a salt thereof wherein A is (i) —OCH$_2$CH$_2$NR$_y$R$_y$; (ii) —CR$_x$R$_x$R$_3$, —CH$_2$CH$_2$NR$_x$R$_3$, —C(O)NR$_x$R$_3$, —NR$_x$R$_3$, —NR$_x$CH$_2$CH$_2$R$_3$, —OR$_3$, or —NR$_x$C(O)R$_3$; or (iii) R$_3$; and X, G, $R_1$, R$_3$, $R_x$, $R_y$, n, and p are defined in the first aspect. Included in this embodiment are compounds in which A is —CR$_x$R$_x$R$_3$, —CH$_2$CH$_2$NR$_x$R$_3$, —C(O)NR$_x$R$_3$, —NR$_x$R$_3$, —NR$_x$CH$_2$CH$_2$R$_3$, —OR$_3$, —NR$_x$C(O)R$_3$, or R$_3$. Also included in this embodiment are compounds in which A is: —CH$_2$R$_3$, —CH$_2$CH$_2$NHR$_3$, —C(O)NHR$_3$, —NHR$_3$, —NHCH$_2$CH$_2$R$_3$, —OR$_3$, —NHC(O)R$_3$, or R$_3$.

One embodiment provides a compound of Formula (I), N-oxide, or a salt thereof wherein A is —CR$_x$R$_x$R$_3$, —CH$_2$CH$_2$NR$_x$R$_3$, —C(O)NR$_x$R$_3$, —NR$_x$R$_3$, —NR$_x$CH$_2$CH$_2$R$_3$, —OR$_3$, or —NR$_x$C(O)R$_3$; and X, G, $R_1$, R$_3$, $R_x$, n, and p are defined in the first aspect. Included in this embodiment are compounds in which A is —CH$_2$R$_3$, —CH$_2$CH$_2$NHR$_3$, —C(O)NHR$_3$, —NHR$_3$, —NHCH$_2$CH$_2$R$_3$, —OR$_3$, or —NHC(O)R$_3$. Also included in this embodiment are compounds in which R$_3$ is azetidinyl, cyclobutyl, cyclohexyl, piperazinyl, piperidinyl, or pyrrolidinyl, each substituted with zero to 1 $R_{3a}$; and $R_{3a}$ is —CH$_3$, —CH$_2$CH$_2$CH$_3$, —CH(CH$_3$)$_2$, —CH$_2$CN, —CH$_2$CH$_2$CN, —CH$_2$CH$_2$CF$_3$, —CH$_2$C(CH$_3$)$_2$OH, —CH$_2$C(O)NH$_2$, —CH$_2$C(O)N(CH$_3$)$_2$, —C(O)CH$_2$N(CH$_3$)$_2$, —C(O)CH$_2$CH$_2$N(CH$_3$)$_2$, —C(O)CH$_2$CH$_2$CH$_2$N(CH$_3$)$_2$, —NH(CH$_3$), —N(CH$_3$)$_2$, —NH(CH(CH$_3$)$_2$), —CH$_2$CH$_2$S(O)$_2$CH$_3$, —CH$_2$CH$_2$NHS(O)$_2$CH$_3$, —NHCH$_2$C(O)N(CH$_3$)$_2$, —NHCH$_2$CH$_2$S(O)$_2$CH$_3$, —NH(cyclopropyl), —NH(oxetanyl), —N(CH$_3$)(oxetanyl), —CH$_2$(methyltriazolyl), morpholinyl, oxetanyl, pyrrolidinyl, fluoropyrrolidinyl, hydroxy-methylpyrrolidinyl, tetrahydropyranyl, 1-oxa-6-azaspiro[3.3]heptanyl, 2-oxa-6-azaspiro[3.3]heptanyl, 2-oxa-6-azaspiro[3.4]octanyl, 6-oxa-2-azaspiro[3.4]octanyl, 2,2-dioxo-2-thia-6-azaspiro[3.3]heptanyl, 2-oxa-7-azaspiro[4.4]nonanyl, or azetidinyl substituted with zero to 2 substituents independently selected from F, —OH, —CH$_3$, —CH$_2$OH, —OCH$_3$, —OCH$_2$CH$_3$, and —OCH(CH$_3$)$_2$. Additionally, included in this embodiment are compounds in which A is —C(O)NH(piperidinyl), —CH$_2$(piperidinyl), —CH$_2$CH$_2$NH(piperidinyl), —NHCH$_2$CH$_2$(pyrrolidinyl), —NH(piperidinyl), —NHC(O)(piperidinyl), —O(cyclohexyl), or —O(piperidinyl), wherein each of said cyclohexyl, piperidinyl, and pyrrolidinyl is substituted with zero to 1 $R_{3a}$; and $R_{3a}$ is defined in the first aspect.

One embodiment provides a compound of Formula (I), N-oxide, or a salt thereof wherein A is R$_3$; and X, G, $R_1$, R$_3$, n, and p are defined in the first aspect. Included in this embodiment are compounds in which R$_3$ is azetidinyl, cyclobutyl, cyclohexyl, piperazinyl, piperidinyl, or pyrrolidinyl, each substituted with zero to 1 $R_{3a}$; and $R_{3a}$ is —CH$_3$, —CH$_2$CH$_2$CH$_3$, —CH(CH$_3$)$_2$, —CH$_2$CN, —CH$_2$CH$_2$CN, —CH$_2$CH$_2$CF$_3$, —CH$_2$C(CH$_3$)$_2$OH, —CH$_2$C(O)NH$_2$, —CH$_2$C(O)N(CH$_3$)$_2$, —C(O)CH$_2$N(CH$_3$)$_2$, —C(O)CH$_2$CH$_2$N(CH$_3$)$_2$, —C(O)CH$_2$CH$_2$CH$_2$N(CH$_3$)$_2$, —NH(CH$_3$), —N(CH$_3$)$_2$, —NH(CH(CH$_3$)$_2$), —CH$_2$CH$_2$S(O)$_2$CH$_3$, —CH$_2$CH$_2$NHS(O)$_2$CH$_3$, —NHCH$_2$C(O)N(CH$_3$)$_2$, —NHCH$_2$CH$_2$S(O)$_2$CH$_3$, —NH(cyclopropyl), —NH(oxetanyl), —N(CH$_3$)(oxetanyl), —CH$_2$(methyltriazolyl), morpholinyl, oxetanyl, pyrrolidinyl, fluoropyrrolidinyl, hydroxy-methylpyrrolidinyl, tetrahydropyranyl, 1-oxa-6-azaspiro[3.3]heptanyl, 2-oxa-6-azaspiro[3.3]heptanyl, 2-oxa-6-azaspiro[3.4]octanyl, 6-oxa-2-azaspiro[3.4]octanyl, 2,2-dioxo-2-thia-6-azaspiro[3.3]heptanyl, 2-oxa-7-azaspiro[4.4]nonanyl, or azetidinyl substituted with zero to 2 substituents independently selected from F, —OH, —CH$_3$, —CH$_2$OH, —OCH$_3$, —OCH$_2$CH$_3$, and —OCH(CH$_3$)$_2$.

One embodiment provides a compound of Formula (I), N-oxide, or a salt thereof wherein each $R_1$ is independently H, F, Cl, —CN, $C_{1-3}$ alkyl, —CH$_2$F, —CHF$_2$, —CF$_3$, —OCH$_3$, or —S(O)$_2$CH$_3$; and X, A, G, n, and p are defined in the first aspect. Included in this embodiment are compound in which each $R_1$ is independently H, —$CH_3$, —$CH_2CH_3$, —$CH(CH_3)_2$, —$CF_3$, —$OCH_3$, or —$S(O)_2CH_3$. Also included in this embodiment are compounds in which each $R_1$ is independently H, —$CH_3$, —$CH_2CH_3$, —$CH(CH_3)_2$, or —$OCH_3$.

One embodiment provides a compound of Formula (I), N-oxide, or a salt thereof wherein each $R_2$ is independently F, Cl, —CN, —OH, $C_{1-3}$ alkyl, $C_{1-2}$ fluoroalkyl, $C_{1-2}$ cyanoalkyl, $C_{1-3}$ hydroxyalkyl, $C_{1-2}$ aminoalkyl, —$(CH_2)_{0-2}$O($C_{1-3}$ alkyl), $C_{3-6}$ cycloalkyl, —$NR_xR_x$, —$(CH_2)_{0-2}$C(O)$NR_xR_x$, —$(CH_2)_{0-2}$S(O)$_2$($C_{1-3}$ alkyl), —$CH_2(C_{3-6}$ cycloalkyl), —$CH_2$(phenyl), phenyl, pyrimidinyl, or triazolyl; and X, A, G, $R_x$, n, and p are defined in the first aspect. Included in this embodiment are compounds in which each $R_2$ is independently F, Cl, —CN, —OH, $C_{1-2}$ alkyl, $C_{1-2}$ fluoroalkyl, $C_{1-2}$ cyanoalkyl, $C_{1-2}$ hydroxyalkyl, —O($C_{1-3}$ alkyl), $C_{3-6}$ cycloalkyl, phenyl, pyrimidinyl, or triazolyl. Also, included in this embodiment are compounds in which each $R_2$ is independently —CN, —$CH_3$, —$OCH_3$, or pyrimidinyl.

One embodiment provides a compound of Formula (I), N-oxide, or a salt thereof wherein $R_3$ is $C_{4-6}$ cycloalkyl, azetidinyl, morpholinyl, piperazinyl, piperidinyl, or pyrrolidinyl, each substituted with zero to 2 $R_{3a}$; each $R_{3a}$ is independently $C_{1-6}$ alkyl, $C_{1-6}$ cyanoalkyl, $C_{1-6}$ fluoroalkyl, $C_{1-6}$ hydroxyalkyl, —$CH_2C(O)NR_yR_y$, —$C(O)(CH_2)_{1-3}NR_yR_y$, —$NR_yR_y$, —$(CH_2)_{1-3}S(O)_2$($C_{1-3}$ alkyl), —$(CH_2)_{1-3}NR_xS(O)_2$($C_{1-3}$ alkyl), —$NR_x(CH_2)_{1-2}C(O)NR_yR_y$, —$NR_x(CH_2)_{1-3}S(O)_2$($C_{1-3}$ alkyl), —$NR_x(C_{3-6}$ cycloalkyl), —$NR_x$(oxetanyl), —$CH_2$(methyltriazolyl), morpholinyl, oxetanyl, pyrrolidinyl, fluoropyrrolidinyl, hydroxy-methylpyrrolidinyl, tetrahydropyranyl, 1-oxa-6-azaspiro[3.3]heptanyl, 2-oxa-6-azaspiro[3.3]heptanyl, 2-oxa-6-azaspiro[3.4]octanyl, 6-oxa-2-azaspiro[3.4]octanyl, 2,2-dioxo-2-thia-6-azaspiro[3.3]heptanyl, 2-oxa-7-azaspiro[4.4]nonanyl, or azetidinyl substituted with zero to 3 substituents independently selected from F, Cl, —OH, —CN, $C_{1-3}$ alkyl, $C_{1-3}$ hydroxyalkyl, $C_{1-3}$ fluoroalkyl, and $C_{1-3}$ alkoxy; and X, A, G, $R_1$, $R_x$, $R_y$, n, and p are defined in the first aspect. Included in this embodiment are compounds in which $R_3$ is azetidinyl, cyclobutyl, cyclohexyl, piperazinyl, piperidinyl, or pyrrolidinyl, each substituted with zero to 1 $R_{3a}$; and $R_{3a}$ is —$CH_3$, —$CH_2CH_2CH_3$, —$CH(CH_3)_2$, —$CH_2CN$, —$CH_2CH_2CN$, —$CH_2CH_2CF_3$, —$CH_2C(CH_3)_2OH$, —$CH_2C(O)NH_2$, —$CH_2C(O)N(CH_3)_2$, —$C(O)CH_2N(CH_3)_2$, —$C(O)CH_2CH_2N(CH_3)_2$, —$C(O)CH_2CH_2CH_2N(CH_3)_2$, —$NH(CH_3)$, —$N(CH_3)_2$, —$NH(CH(CH_3)_2)$, —$CH_2CH_2S(O)_2CH_3$, —$CH_2CH_2NHS(O)_2CH_3$, —$NHCH_2C(O)N(CH_3)_2$, —$NHCH_2CH_2S(O)_2CH_3$, —NH(cyclopropyl), —NH(oxetanyl), —$N(CH_3)$(oxetanyl), —$CH_2$(methyltriazolyl), morpholinyl, oxetanyl, pyrrolidinyl, fluoropyrrolidinyl, hydroxy-methylpyrrolidinyl, tetrahydropyranyl, 1-oxa-6-azaspiro[3.3]heptanyl, 2-oxa-6-azaspiro[3.3]heptanyl, 2-oxa-6-azaspiro[3.4]octanyl, 6-oxa-2-azaspiro[3.4]octanyl, 2,2-dioxo-2-thia-6-azaspiro[3.3]heptanyl, 2-oxa-7-azaspiro[4.4]nonanyl, or azetidinyl substituted with zero to 2 substituents independently selected from F, —OH, —$CH_3$, —$CH_2OH$, —$OCH_3$, —$OCH_2CH_3$, and —$OCH(CH_3)_2$. Also, included in this embodiment are compounds in which $R_3$ is azetidinyl, cyclobutyl, cyclohexyl, piperazinyl, piperidinyl, or pyrrolidinyl, each substituted with zero to 1 $R_{3a}$; and $R_{3a}$ is —$CH_3$, —$CH_2CH_2CH_3$, —$CH(CH_3)_2$, —$CH_2CN$, —$CH_2CH_2CN$, —$CH_2CH_2CF_3$, —$CH_2C(CH_3)_2OH$, —$CH_2C(O)NH_2$, —$CH_2C(O)N(CH_3)_2$, —$C(O)CH_2N(CH_3)_2$, —$C(O)CH_2CH_2N(CH_3)_2$, —$C(O)CH_2CH_2CH_2N(CH_3)_2$, —$NH(CH_3)$, —$N(CH_3)_2$, —$NH(CH(CH_3)_2)$, —$CH_2CH_2S(O)_2CH_3$, —$CH_2CH_2NHS(O)_2CH_3$, —$NHCH_2C(O)N(CH_3)_2$, —$NH(CH_2CH_2S(O)_2CH_3)$, —$NH$(cyclopropyl), —NH(oxetanyl), —$N(CH_3)$(oxetanyl), —$CH_2$(methyltriazolyl), morpholinyl, oxetanyl, pyrrolidinyl, fluoropyrrolidinyl, hydroxy-methylpyrrolidinyl, tetrahydropyranyl, 1-oxa-6-azaspiro[3.3]heptanyl, 2-oxa-6-azaspiro[3.3]heptanyl, 2-oxa-6-azaspiro[3.4]octanyl, 6-oxa-2-azaspiro[3.4]octanyl, 2,2-dioxo-2-thia-6-azaspiro[3.3]heptanyl, 2-oxa-7-azaspiro[4.4]nonanyl, or azetidinyl substituted with zero to 2 substituents independently selected from F, —OH, —$CH_3$, —$CH_2OH$, —$OCH_3$, —$OCH_2CH_3$, and —$OCH(CH_3)_2$. Additionally, included in this embodiment are compounds in which $R_3$ is cyclobutyl, cyclohexyl, piperazinyl, piperidinyl, or pyrrolidinyl, each substituted with zero to 1 $R_{3a}$; and $R_{3a}$ is —$CH_3$, —$CH_2CH_2CH_3$, —$CH(CH_3)_2$, —$CH_2CN$, —$CH_2CH_2CN$, —$CH_2CH_2CF_3$, —$CH_2C(CH_3)_2OH$, —$CH_2C(O)NH_2$, —$CH_2C(O)N(CH_3)_2$, —$C(O)CH_2N(CH_3)_2$, —$C(O)CH_2CH_2N(CH_3)_2$, —$C(O)CH_2CH_2CH_2N(CH_3)_2$, —NH($CH_3$), —$N(CH_3)_2$, —$NH(CH(CH_3)_2)$, —$CH_2CH_2S(O)_2CH_3$, —$CH_2CH_2NHS(O)_2CH_3$, —$NHCH_2C(O)N(CH_3)_2$, —$NH(CH_2CH_2S(O)_2CH_3)$, —NH(cyclopropyl), —NH(oxetanyl), —$N(CH_3)$(oxetanyl), —$CH_2$(methyltriazolyl), morpholinyl, oxetanyl, pyrrolidinyl, fluoropyrrolidinyl, hydroxy-methylpyrrolidinyl, tetrahydropyranyl, 1-oxa-6-azaspiro[3.3]heptanyl, 2-oxa-6-azaspiro[3.3]heptanyl, 2-oxa-6-azaspiro[3.4]octanyl, 6-oxa-2-azaspiro[3.4]octanyl, 2,2-dioxo-2-thia-6-azaspiro[3.3]heptanyl, 2-oxa-7-azaspiro[4.4]nonanyl, or azetidinyl substituted with zero to 2 substituents independently selected from F, —OH, —$CH_3$, —$CH_2OH$, —$OCH_3$, —$OCH_2CH_3$, and —$OCH(CH_3)_2$.

One embodiment provides a compound of Formula (I), N-oxide, or a salt thereof wherein X is CH or N; n is zero, 1, or 2; and A, G, $R_1$, and p are defined in the first aspect. Included in this embodiment are compounds in which n is zero or 1. Also included in this embodiment are compounds in which n is zero. Additionally, included in this embodiment are compounds in which n is 1.

One embodiment provides a compound of Formula (I), N-oxide, or a salt thereof wherein n is zero or 1; and X, A, G, $R_1$, and p are defined in the first aspect. Included in this embodiment are compounds in which n is zero. Also included in this embodiment are compounds in which n is 1.

One embodiment provides a compound of Formula (I), N-oxide, or a salt thereof wherein p is zero or 1; and X, A, G, $R_1$, and n are defined in the first aspect. Included in this embodiment are compounds in which p is zero. Also included in this embodiment are compounds in which p is 1.

One embodiment provides a compound of Formula (I), N-oxide, or a salt thereof wherein said compound is: 8-methyl-6-(5-methyl-3-(piperidin-4-yl)-1H-indol-6-yl)-[1,2,4]triazolo[1,5-a]pyridine (1); 8-methyl-6-(4-methyl-3-(piperidin-4-yl)-1H-indol-6-yl)-[1,2,4]triazolo[1,5-a]pyridine (2); N,N-dimethyl-4-(5-methyl-6-(8-methyl-[1,2,4]triazolo[1,5-a]pyridin-6-yl)-1H-indazol-3-yl)cyclohexan-1-amine (3-4); 2-(dimethylamino)-1-(3-(4-methyl-6-(8-methyl-[1,2,4]triazolo[1,5-a]pyridin-6-yl)-1H-indazol-3-yl)piperidin-1-yl)ethan-1-one (5); N,N-dimethyl-3-(5-methyl-6-(8-methyl-[1,2,4]triazolo[1,5-a]pyridin-6-yl)-1H-indazol-3-yl)cyclobutan-1-amine (6-7); 2-(4-(4-ethyl-6-(8-methyl-[1,2,4]triazolo[1,5-a]pyridin-6-yl)-1H-indazol-3-yl)piperidin-1-yl)-N,N-dimethylacetamide (8); 6-(5-isopropyl-3-(1-propylpiperidin-4-yl)-1H-indazol-6-yl)-8-methyl-[1,2,4]triazolo[1,5-a]pyridine (9); 8-methyl-6-(5-methyl-3-(piperidin-4-ylmethyl)-1H-indazol-6-yl)-[1,2,4]triazolo[1,5-a]pyridine (10); 8-methoxy-6-(3-(piperidin-4-yl)-1H-indol-6-yl)-[1,2,4]triazolo[1,5-a]pyridine (11); 8-methyl-6-

(3-(piperidin-4-yl)-1H-indol-6-yl)-[1,2,4]triazolo[1,5-a]pyridine (12); N-(2-(6-(8-methyl-[1,2,4]triazolo[1,5-a]pyridin-6-yl)-1H-indol-3-yl)ethyl)piperidin-4-amine (13); N,N-dimethyl-4-(6-(8-methyl-[1,2,4]triazolo[1,5-a]pyridin-6-yl)-1H-indol-3-yl)cyclohexan-1-amine (14); N,N-dimethyl-4-(6-(8-methyl-[1,2,4]triazolo[1,5-a]pyridin-6-yl)-1H-indol-3-yl) cyclohexan-1-amine (15); 8-methyl-6-(4-methyl-3-(piperidin-4-yl)-1H-indol-6-yl)-[1,2,4]triazolo[1,5-a]pyridine (16); 8-methyl-6-(3-(piperidin-4-yl)-1H-indazol-6-yl)-[1,2,4]triazolo[1,5-a]pyridine (17); 8-methyl-6-(5-methyl-3-(piperidin-4-yl)-1H-indazol-6-yl)-[1,2,4]triazolo[1,5-a]pyridine (18); 6-(5-methoxy-3-(piperidin-4-yl)-1H-indazol-6-yl)-8-methyl-[1,2,4]triazolo[1,5-a]pyridine (19); 2-(dimethylamino)-1-(4-(5-methyl-6-(8-methyl-[1,2,4]triazolo[1,5-a]pyridin-6-yl)-1H-indazol-3-yl)piperidin-1-yl)ethan-1-one (20); 8-methyl-6-(5-methyl-3-(1-(tetrahydro-2H-pyran-4-yl)piperidin-4-yl)-1H-indazol-6-yl)-[1,2,4]triazolo[1,5-a]pyridine (21); 8-methyl-6-(5-methyl-3-(1-propylpiperidin-4-yl)-1H-indazol-6-yl)-[1,2,4]triazolo[1,5-a]pyridine (22); N,N-dimethyl-2-(4-(5-methyl-6-(8-methyl-[1,2,4]triazolo[1,5-a]pyridin-6-yl)-1H-indazol-3-yl)piperidin-1-yl)acetamide (23); 8-methyl-6-(5-methyl-3-(piperidin-3-yl)-1H-indazol-6-yl)-[1,2,4]triazolo[1,5-a]pyridine (24); 1,3-dimethyl-5-(5-methyl-3-(piperidin-4-yl)-1H-indazol-6-yl)pyridin-2(1H)-one (25); 8-methyl-6-(5-methyl-3-(pyrrolidin-3-yl)-1H-indazol-6-yl)-[1,2,4]triazolo[1,5-a]pyridine (26); 8-methyl-6-(4-methyl-3-(piperidin-4-yl)-1H-indazol-6-yl)-[1,2,4]triazolo[1,5-a]pyridine (27); N,N-dimethyl-2-((4-(5-methyl-6-(8-methyl-[1,2,4]triazolo[1,5-a]pyridin-6-yl)-1H-indazol-3-yl)cyclohexyl)amino)acetamide (28); N,N-dimethyl-2-((4-(5-methyl-6-(8-methyl-[1,2,4]triazolo[1,5-a]pyridin-6-yl)-1H-indazol-3-yl)cyclohexyl)amino)acetamide (29); 4-(5-methyl-6-(8-methyl-[1,2,4]triazolo[1,5-a]pyridin-6-yl)-1H-indazol-3-yl)-N-(2-(methylsulfonyl)ethyl) cyclohexan-1-amine (30); 4-(5-methyl-6-(8-methyl-[1,2,4]triazolo[1,5-a]pyridin-6-yl)-1H-indazol-3-yl)-N-(2-(methylsulfonyl)ethyl)cyclohexan-1-amine (31); N-methyl-N-(4-(5-methyl-6-(8-methyl-[1,2,4]triazolo[1,5-a]pyridin-6-yl)-1H-indazol-3-yl)cyclohexyl)oxetan-3-amine (32); N-methyl-N-(4-(5-methyl-6-(8-methyl-[1,2,4]triazolo[1,5-a]pyridin-6-yl)-1H-indazol-3-yl)cyclohexyl)oxetan-3-amine (33); N-(4-(5-methyl-6-(8-methyl-[1,2,4]triazolo[1,5-a]pyridin-6-yl)-1H-indazol-3-yl)cyclohexyl)oxetan-3-amine (34); N-(4-(5-methyl-6-(8-methyl-[1,2,4]triazolo[1,5-a]pyridin-6-yl)-1H-indazol-3-yl)cyclohexyl)oxetan-3-amine (35); N-cyclopropyl-4-(5-methyl-6-(8-methyl-[1,2,4]triazolo[1,5-a]pyridin-6-yl)-1H-indazol-3-yl) cyclohexan-1-amine (36); N-cyclopropyl-4-(5-methyl-6-(8-methyl-[1,2,4]triazolo[1,5-a]pyridin-6-yl)-1H-indazol-3-yl)cyclohexan-1-amine (37); N-isopropyl-4-(5-methyl-6-(8-methyl-[1,2,4]triazolo[1,5-a]pyridin-6-yl)-1H-indazol-3-yl)cyclohexan-1-amine (38); N-isopropyl-4-(5-methyl-6-(8-methyl-[1,2,4]triazolo[1,5-a]pyridin-6-yl)-1H-indazol-3-yl) cyclohexan-1-amine (39); 2-(dimethylamino)-1-(3-(5-methyl-6-(8-methyl-[1,2,4]triazolo[1,5-a]pyridin-6-yl)-1H-indazol-3-yl)piperidin-1-yl)ethan-1-one (40); N,N-dimethyl-2-(3-(5-methyl-6-(8-methyl-[1,2,4]triazolo[1,5-a]pyridin-6-yl)-1H-indazol-3-yl)piperidin-1-yl) acetamide (41); 8-methyl-6-(5-methyl-3-(1-(oxetan-3-yl)piperidin-3-yl)-1H-indazol-6-yl)-[1,2,4] triazolo[1,5-a]pyridine (42); 8-methyl-6-(5-methyl-3-(1-(tetrahydro-2H-pyran-4-yl) piperidin-3-yl)-1H-indazol-6-yl)-[1,2,4]triazolo[1,5-a]pyridine (43); N-methyl-4-(5-methyl-6-(8-methyl-[1,2,4]triazolo[1,5-a]pyridin-6-yl)-1H-indazol-3-yl)cyclohexan-1-amine (44); 8-methoxy-6-(5-methyl-3-(piperidin-3-yl)-1H-indazol-6-yl)-[1,2,4]triazolo[1,5-a]pyridine (45); 1,3-dimethyl-5-(5-methyl-3-(piperidin-3-yl)-1H-indazol-6-yl)pyridin-2(1H)-one (46); 5-methyl-6-(1-methyl-1H-pyrrolo[2,3-b]pyridin-3-yl)-3-(piperidin-3-yl)-1H-indazole (47); 7,8-dimethyl-6-(5-methyl-3-(piperidin-3-yl)-1H-indazol-6-yl)-[1,2,4]triazolo[1,5-a]pyridine (48); 6-(3-(azetidin-3-yl)-5-methyl-1H-indazol-6-yl)-8-methyl-[1,2,4]triazolo[1,5-a]pyridine (49); 6-(2,6-dimethylpyridin-4-yl)-5-methyl-3-(piperidin-3-yl)-1H-indazole (50); 8-methyl-6-(4-methyl-3-(piperidin-3-yl)-1H-indazol-6-yl)-[1,2,4]triazolo[1,5-a]pyridine (51); 8-methyl-6-(5-methyl-3-(1-(tetrahydro-2H-pyran-4-yl)piperidin-3-yl)-1H-indazol-6-yl)-[1,2,4]triazolo[1,5-a]pyridine (52); N,N-dimethyl-2-(3-(5-methyl-6-(8-methyl-[1,2,4]triazolo[1,5-a]pyridin-6-yl)-1H-indazol-3-yl)piperidin-1-yl) acetamide (53); 2-(dimethylamino)-1-(3-(5-methyl-6-(8-methyl-[1,2,4]triazolo[1,5-a]pyridin-6-yl)-1H-indazol-3-yl)piperidin-1-yl)ethan-1-one (54); 8-methyl-6-(5-methyl-3-(1-(tetrahydro-2H-pyran-4-yl)piperidin-3-yl)-1H-indazol-6-yl)-[1,2,4]triazolo[1,5-a]pyridine (55); 2-(dimethylamino)-1-(3-(5-methyl-6-(8-methyl-[1,2,4]triazolo[1,5-a]pyridin-6-yl)-1H-indazol-3-yl)piperidin-1-yl)ethan-1-one (56); N,N-dimethyl-2-(3-(5-methyl-6-(8-methyl-[1,2,4]triazolo[1,5-a]pyridin-6-yl)-1H-indazol-3-yl)piperidin-1-yl)acetamide (57); 6-(5-methyl-3-(piperidin-3-yl)-1H-indazol-6-yl)-[1,2,4]triazolo[1,5-a] pyridine (58); N,N-dimethyl-2-(3-(4-methyl-6-(8-methyl-[1,2,4]triazolo[1,5-a]pyridin-6-yl)-1H-indazol-3-yl)piperidin-1-yl)acetamide (59); 8-methyl-6-(4-methyl-3-(1-(tetrahydro-2H-pyran-4-yl)piperidin-3-yl)-1H-indazol-6-yl)-[1,2,4]triazolo[1,5-a]pyridine (60); 8-methyl-6-(4-methyl-3-(1-methylpiperidin-3-yl)-1H-indazol-6-yl)-[1,2,4]triazolo[1,5-a]pyridine (61); 6-(3,4-dimethoxyphenyl)-5-methyl-3-(piperidin-3-yl)-1H-indazole (62); 8-methyl-6-(5-methyl-1H-indazol-6-yl)-[1,2,4]triazolo[1,5-a]pyridine (63); 8-methoxy-6-(5-methyl-1H-indazol-6-yl)-[1,2,4]triazolo[1,5-a]pyridine (64); 8-methyl-6-(4-methyl-1H-indazol-6-yl)-[1,2,4]triazolo[1,5-a]pyridine (65); 8-methoxy-6-(4-methyl-1H-indazol-6-yl)-[1,2,4]triazolo[1,5-a] pyridine (66); 2-methyl-1-(4-(5-methyl-6-(8-methyl-[1,2,4]triazolo[1,5-a]pyridin-6-yl)-1H-indazol-3-yl)piperidin-1-yl)propan-2-ol (67); 8-methyl-6-(5-methyl-3-(1-(2-(methylsulfonyl) ethyl)piperidin-4-yl)-1H-indazol-6-yl)-[1,2,4]triazolo[1,5-a]pyridine (68); N-(2-(4-(5-methyl-6-(8-methyl-[1,2,4]triazolo[1,5-a]pyridin-6-yl)-1H-indazol-3-yl)piperidin-1-yl)ethyl) methanesulfonamide (69); 2-(4-(5-methyl-6-(8-methyl-[1,2,4]triazolo[1,5-a]pyridin-6-yl)-1H-indazol-3-yl)piperidin-1-yl)acetamide (70); 2-(4-(5-methyl-6-(8-methyl-[1,2,4] triazolo[1,5-a]pyridin-6-yl)-1H-indazol-3-yl)piperidin-1-yl)acetonitrile (71); 3-(4-(5-methyl-6-(8-methyl-[1,2,4]triazolo[1,5-a]pyridin-6-yl)-1H-indazol-3-yl)piperidin-1-yl)propanenitrile (72); 8-methyl-6-(5-methyl-3-(1-(oxetan-3-yl)piperidin-4-yl)-1H-indazol-6-yl)-[1,2,4] triazolo[1,5-a]pyridine (73); 8-methyl-6-(5-methyl-3-(piperidin-4-yl)-1H-indazol-6-yl) tetrazolo[1,5-a]pyridine (74); 2-(dimethylamino)-1-(4-(4-methyl-6-(8-methyl-[1,2,4]triazolo[1,5-a]pyridin-6-yl)-1H-indazol-3-yl)piperidin-1-yl)ethan-1-one (75); N,N-dimethyl-2-(4-(4-methyl-6-(8-methyl-[1,2,4]triazolo[1,5-a]pyridin-6-yl)-1H-indazol-3-yl)piperidin-1-yl) acetamide (76); 2-methyl-1-(4-(4-methyl-6-(8-methyl-[1,2,4]triazolo[1,5-a]pyridin-6-yl)-1H-indazol-3-yl)piperidin-1-yl)propan-2-ol (77); 8-methyl-6-(4-methyl-3-(1-(tetrahydro-2H-pyran-4-yl)piperidin-4-yl)-1H-indazol-6-yl)-[1,2,4]triazolo[1,5-a]pyridine (78); 8-methyl-6-(4-methyl-3-(1-methylpiperidin-4-yl)-1H-indazol-6-yl)-[1,2,4]triazolo[1,5-a]pyridine (79); N,N-dimethyl-4-(4-methyl-6-(8-methyl-[1,2,4]triazolo[1,5-a]pyridin-6-yl)-1H-indazol-3-yl) cyclohexan-1-amine (80); N,N-dimethyl-4-(4-methyl-6-(8-methyl-[1,2,4]triazolo[1,5-a]pyridin-6-yl)-1H-indazol-3-yl)cyclohexan-1-amine (81);

6-(5-ethyl-3-(piperidin-4-yl)-1H-indazol-6-yl)-8-methyl-[1,2,4]triazolo[1,5-a]pyridine (82); 5,8-dimethyl-6-(5-methyl-3-(piperidin-4-yl)-1H-indazol-6-yl)-[1,2,4]triazolo[1,5-a]pyridine (83); 6-(5-methyl-3-(piperidin-4-yl)-1H-indazol-6-yl)-[1,2,4]triazolo[1,5-a]pyridine-8-carbonitrile (84); 6-(5-methyl-3-(piperidin-4-yl)-1H-indazol-6-yl)-8-(pyrimidin-5-yl)-[1,2,4]triazolo[1,5-a]pyridine (85); 6-(4-methoxy-3-(piperidin-4-yl)-1H-indazol-6-yl)-8-methyl-[1,2,4]triazolo[1,5-a]pyridine (86); 2-(dimethylamino)-1-(4-(5-ethyl-6-(8-methyl-[1,2,4]triazolo[1,5-a]pyridin-6-yl)-1H-indazol-3-yl)piperidin-1-yl)ethan-1-one (87); 6-(5-ethyl-3-(1-(tetrahydro-2H-pyran-4-yl)piperidin-4-yl)-1H-indazol-6-yl)-8-methyl-[1,2,4]triazolo[1,5-a]pyridine (88); 6-(5-ethyl-3-(1-(oxetan-3-yl)piperidin-4-yl)-1H-indazol-6-yl)-8-methyl-[1,2,4]triazolo[1,5-a]pyridine (89); 6-(5-ethyl-3-(1-isopropylpiperidin-4-yl)-1H-indazol-6-yl)-8-methyl-[1,2,4]triazolo[1,5-a]pyridine (90); 2-(4-(5-ethyl-6-(8-methyl-[1,2,4]triazolo[1,5-a]pyridin-6-yl)-1H-indazol-3-yl)piperidin-1-yl)-N,N-dimethylacetamide (91); 2-(4-(5-ethyl-6-(8-methyl-[1,2,4]triazolo[1,5-a]pyridin-6-yl)-1H-indazol-3-yl)piperidin-1-yl)acetamide (92); 4-(5-ethyl-6-(8-methyl-[1,2,4]triazolo[1,5-a]pyridin-6-yl)-1H-indazol-3-yl)-N,N-dimethylcyclohexan-1-amine (93-94); 2-((4-(5-ethyl-6-(8-methyl-[1,2,4]triazolo[1,5-a]pyridin-6-yl)-1H-indazol-3-yl)cyclohexyl)amino)-N,N-dimethylacetamide (95-96); N-cyclopropyl-4-(5-ethyl-6-(8-methyl-[1,2,4]triazolo[1,5-a]pyridin-6-yl)-1H-indazol-3-yl)cyclohexan-1-amine (97-98); 4-(5-ethyl-6-(8-methyl-[1,2,4]triazolo[1,5-a]pyridin-6-yl)-1H-indazol-3-yl)-N-(2-(methylsulfonyl)ethyl)cyclohexan-1-amine (99-100); 1-(4-(5-ethyl-6-(8-methyl-[1,2,4]triazolo[1,5-a]pyridin-6-yl)-1H-indazol-3-yl)piperidin-1-yl)-2-methylpropan-2-ol (101); 6-(5-isopropyl-3-(piperidin-4-yl)-1H-indazol-6-yl)-8-methyl-[1,2,4]triazolo[1,5-a]pyridine (102); 3-(dimethylamino)-1-(4-(5-ethyl-6-(8-methyl-[1,2,4]triazolo[1,5-a]pyridin-6-yl)-1H-indazol-3-yl)piperidin-1-yl)propan-1-one (103); 2-(4-(5-ethyl-6-(8-methyl-[1,2,4]triazolo[1,5-a]pyridin-6-yl)-1H-indazol-3-yl)piperidin-1-yl)acetonitrile (104); 6-(5-ethyl-3-(1-((1-methyl-1H-1,2,3-triazol-4-yl)methyl)piperidin-4-yl)-1H-indazol-6-yl)-8-methyl-[1,2,4]triazolo[1,5-a]pyridine (105); 3-(4-(5-ethyl-6-(8-methyl-[1,2,4]triazolo[1,5-a]pyridin-6-yl)-1H-indazol-3-yl)piperidin-1-yl)propanenitrile (106); 4-(dimethylamino)-1-(4-(5-ethyl-6-(8-methyl-[1,2,4]triazolo[1,5-a]pyridin-6-yl)-1H-indazol-3-yl)piperidin-1-yl)butan-1-one (107); 6-(5-ethyl-3-(1-(3,3,3-trifluoropropyl)piperidin-4-yl)-1H-indazol-6-yl)-8-methyl-[1,2,4]triazolo[1,5-a]pyridine (108); 6-(4-ethyl-3-(piperidin-4-yl)-1H-indazol-6-yl)-8-methyl-[1,2,4]triazolo[1,5-a]pyridine (109); 2-(dimethylamino)-1-(4-(4-ethyl-6-(8-methyl-[1,2,4]triazolo[1,5-a]pyridin-6-yl)-1H-indazol-3-yl)piperidin-1-yl)ethan-1-one (110); 2-(dimethylamino)-1-(4-(5-isopropyl-6-(8-methyl-[1,2,4]triazolo[1,5-a]pyridin-6-yl)-1H-indazol-3-yl)piperidin-1-yl)ethan-1-one (111); 2-(4-(5-isopropyl-6-(8-methyl-[1,2,4]triazolo[1,5-a]pyridin-6-yl)-1H-indazol-3-yl)piperidin-1-yl)-N,N-dimethylacetamide (112); 1-(4-(5-isopropyl-6-(8-methyl-[1,2,4]triazolo[1,5-a]pyridin-6-yl)-1H-indazol-3-yl)piperidin-1-yl)-2-methylpropan-2-ol (113); 4-(5-isopropyl-6-(8-methyl-[1,2,4]triazolo[1,5-a]pyridin-6-yl)-1H-indazol-3-yl)-N,N-dimethylcyclohexan-1-amine (114-115); 6-(5-isopropyl-3-(1-(tetrahydro-2H-pyran-4-yl)piperidin-4-yl)-1H-indazol-6-yl)-8-methyl-[1,2,4]triazolo[1,5-a]pyridine (116); 2-(dimethylamino)-1-(4-(5-isopropyl-6-(8-methoxy-[1,2,4]triazolo[1,5-a]pyridin-6-yl)-1H-indazol-3-yl)piperidin-1-yl)ethan-1-one (117); N-cyclopropyl-4-(5-isopropyl-6-(8-methyl-[1,2,4]triazolo[1,5-a]pyridin-6-yl)-1H-indazol-3-yl)cyclohexan-1-amine (118-119); 6-(5-isopropyl-3-(1-(oxetan-3-yl)piperidin-4-yl)-1H-indazol-6-yl)-8-methyl-[1,2,4]triazolo[1,5-a]pyridine (120); 3-(4-(5-isopropyl-6-(8-methyl-[1,2,4]triazolo[1,5-a]pyridin-6-yl)-1H-indazol-3-yl)piperidin-1-yl)propanenitrile (121); 3-(dimethylamino)-1-(4-(5-isopropyl-6-(8-methyl-[1,2,4]triazolo[1,5-a]pyridin-6-yl)-1H-indazol-3-yl)piperidin-1-yl)propan-1-one (122); 6-(5-isopropyl-3-(1-isopropylpiperidin-4-yl)-1H-indazol-6-yl)-8-methyl-[1,2,4]triazolo[1,5-a]pyridine (123); 2-((4-(5-isopropyl-6-(8-methyl-[1,2,4]triazolo[1,5-a]pyridin-6-yl)-1H-indazol-3-yl)cyclohexyl)amino)-N,N-dimethylacetamide (124-125); 4-(5-isopropyl-6-(8-methyl-[1,2,4]triazolo[1,5-a]pyridin-6-yl)-1H-indazol-3-yl)-N-(2-(methylsulfonyl)ethyl) cyclohexan-1-amine (126-127); 6-(4-(5-isopropyl-6-(8-methyl-[1,2,4]triazolo[1,5-a]pyridin-6-yl)-1H-indazol-3-yl)cyclohexyl)-2-oxa-6-azaspiro[3.3]heptane (128-129); 6-(5-isopropyl-3-(4-(pyrrolidin-1-yl)cyclohexyl)-1H-indazol-6-yl)-8-methyl-[1,2,4]triazolo[1,5-a]pyridine (130-131); 4-(4-(5-isopropyl-6-(8-methyl-[1,2,4]triazolo[1,5-a]pyridin-6-yl)-1H-indazol-3-yl)cyclohexyl)morpholine (132-133); 6-(3-(4-(3,3-difluoroazetidin-1-yl)cyclohexyl)-5-isopropyl-1H-indazol-6-yl)-8-methyl-[1,2,4]triazolo[1,5-a]pyridine (134-135); 6-(3-(4-(3,3-dimethylazetidin-1-yl)cyclohexyl)-5-isopropyl-1H-indazol-6-yl)-8-methyl-[1,2,4]triazolo[1,5-a]pyridine (136-137); 6-(3-(4-(azetidin-1-yl)cyclohexyl)-5-isopropyl-1H-indazol-6-yl)-8-methyl-[1,2,4]triazolo[1,5-a]pyridine (138-139); 4-(5-isopropyl-6-(8-methoxy-[1,2,4]triazolo[1,5-a]pyridin-6-yl)-1H-indazol-3-yl)-N,N-dimethylcyclohexan-1-amine (140-141); 6-(4-(5-isopropyl-6-(8-methyl-[1,2,4]triazolo[1,5-a]pyridin-6-yl)-1H-indazol-3-yl)cyclohexyl)-2-thia-6-azaspiro[3.3]heptane 2,2-dioxide (142-143); 6-(5-isopropyl-3-(4-(3-methoxyazetidin-1-yl)cyclohexyl)-1H-indazol-6-yl)-8-methyl-[1,2,4]triazolo[1,5-a]pyridine (144-145); (1-(4-(5-isopropyl-6-(8-methyl-[1,2,4]triazolo[1,5-a]pyridin-6-yl)-1H-indazol-3-yl)cyclohexyl)azetidine-3,3-diyl)dimethanol (146); 6-(5-isopropyl-3-(4-(3-methoxyazetidin-1-yl)cyclohexyl)-1H-indazol-6-yl)-8-methoxy-[1,2,4]triazolo[1,5-a]pyridine (147-148); 6-(3-(4-(3-ethoxyazetidin-1-yl)cyclohexyl)-5-isopropyl-1H-indazol-6-yl)-8-methyl-[1,2,4]triazolo[1,5-a]pyridine (149-150); 6-(3-(4-(3-fluoroazetidin-1-yl)cyclohexyl)-5-isopropyl-1H-indazol-6-yl)-8-methyl-[1,2,4]triazolo[1,5-a]pyridine (151-152); 1-(4-(5-isopropyl-6-(8-methyl-[1,2,4]triazolo[1,5-a]pyridin-6-yl)-1H-indazol-3-yl)cyclohexyl)-3-methylazetidin-3-ol (153-154); 6-(4-(5-isopropyl-6-(8-methyl-[1,2,4]triazolo[1,5-a]pyridin-6-yl)-1H-indazol-3-yl)cyclohexyl)-1-oxa-6-azaspiro[3.3]heptane (155-156); 2-(4-(5-isopropyl-6-(8-methyl-[1,2,4]triazolo[1,5-a]pyridin-6-yl)-1H-indazol-3-yl)cyclohexyl)-6-oxa-2-azaspiro[3.4]octane (157-158); 6-(4-(5-isopropyl-6-(8-methyl-[1,2,4]triazolo[1,5-a]pyridin-6-yl)-1H-indazol-3-yl)cyclohexyl)-2-oxa-6-azaspiro[3.4]octane (159-160); 6-(3-(4-(3-isopropoxyazetidin-1-yl)cyclohexyl)-5-isopropyl-1H-indazol-6-yl)-8-methyl-[1,2,4]triazolo[1,5-a]pyridine (161-162); 6-(3-(4-(3-fluoropyrrolidin-1-yl)cyclohexyl)-5-isopropyl-1H-indazol-6-yl)-8-methyl-[1,2,4]triazolo[1,5-a]pyridine (163-164); 1-(4-(5-isopropyl-6-(8-methyl-[1,2,4]triazolo[1,5-a]pyridin-6-yl)-1H-indazol-3-yl)cyclohexyl)-3-methylpyrrolidin-3-ol (165-166); 8-methyl-6-(5-methyl-3-(piperidin-4-yloxy)-1H-indazol-6-yl)-[1,2,4]triazolo[1,5-a]pyridine (167); 4-((4-ethyl-6-(8-methyl-[1,2,4]triazolo[1,5-a]pyridin-6-yl)-1H-indazol-3-yl)oxy)-N,N-dimethylcyclohexan-1-amine (168-169); 2-(dimethylamino)-1-(4-((5-methyl-6-(8-methyl-[1,2,4]triazolo[1,5-a]pyridin-6-yl)-1H-indazol-3-yl)oxy)piperidin-1-yl)ethan-1-one (170); 8-methyl-6-(5-methyl-3-((1-methylpiperidin-4-yl)oxy)-1H-indazol-6-yl)-[1,2,4]triazolo[1,5-a]pyridine (171); N,N-dimethyl-2-((5-methyl-6-(8-methyl-[1, 2,4]triazolo[1,5-a]pyridin-6-yl)-1H-indazol-3-yl)oxy)ethan-1-amine (172); N,N-dimethyl-2-((4-methyl-6-(8-methyl-[1,2,4]triazolo[1,5-a]pyridin-6-yl)-1H-indazol-3-yl)oxy)ethan-1-amine (173); 8-methyl-6-(4-methyl-3-(piperidin-4-yloxy)-1H-indazol-6-yl)-[1,2,4]triazolo[1,5-a]pyridine (174); 2-(dimethylamino)-1-(4-((4-methyl-6-(8-methyl-[1,2,4]triazolo[1,5-a]pyridin-6-yl)-1H-indazol-3-yl)oxy)piperidin-1-yl)ethan-1-one (175); N,N-dimethyl-2-(4-((4-methyl-6-(8-methyl-[1,2,4]triazolo[1,5-a]pyridin-6-yl)-1H-indazol-3-yl)oxy)piperidin-1-yl)acetamide (176); 8-methyl-6-(4-methyl-3-((1-methylpiperidin-4-yl)oxy)-1H-indazol-6-yl)-[1,2,4]triazolo[1,5-a]pyridine (177); 8-methyl-6-(4-methyl-3-((1-(tetrahydro-2H-pyran-4-yl) piperidin-4-yl)oxy)-1H-indazol-6-yl)-[1,2,4]triazolo[1,5-a]pyridine (178); N,N-dimethyl-4-((4-methyl-6-(8-methyl-[1,2,4]triazolo[1,5-a]pyridin-6-yl)-1H-indazol-3-yl)oxy)cyclohexan-1-amine (179-180); N,N-dimethyl-4-((5-methyl-6-(8-methyl-[1,2,4]triazolo[1,5-a]pyridin-6-yl)-1H-indazol-3-yl)oxy)cyclohexan-1-amine (181-182); 4-((6-(8-methoxy-[1,2,4]triazolo[1,5-a]pyridin-6-yl)-4-methyl-1H-indazol-3-yl)oxy)-N,N-dimethylcyclohexan-1-amine (183-184); N,N-dimethyl-2-((4-((4-methyl-6-(8-methyl-[1,2,4]triazolo[1,5-a]pyridin-6-yl)-1H-indazol-3-yl)oxy)cyclohexyl)amino)acetamide (185-186); 4-((4-methyl-6-(8-methyl-[1,2,4]triazolo[1,5-a]pyridin-6-yl)-1H-indazol-3-yl)oxy)-N-(2-(methylsulfonyl)ethyl)cyclohexan-1-amine (187-188); N-cyclopropyl-4-((4-methyl-6-(8-methyl-[1,2,4]triazolo[1,5-a]pyridin-6-yl)-1H-indazol-3-yl)oxy)cyclohexan-1-amine (189-190); 4-((5-ethyl-6-(8-methyl-[1,2,4] triazolo[1,5-a]pyridin-6-yl)-1H-indazol-3-yl)oxy)-N,N-dimethylcyclohexan-1-amine (191-192); 8-methyl-6-(4-methyl-3-((1-((1-methyl-1H-1,2,3-triazol-4-yl)methyl)piperidin-4-yl) oxy)-1H-indazol-6-yl)-[1,2,4]triazolo[1,5-a]pyridine (193); 2-(4-((4-methyl-6-(8-methyl-[1,2,4]triazolo[1,5-a]pyridin-6-yl)-1H-indazol-3-yl)oxy)piperidin-1-yl)acetonitrile (194); 6-(4-ethyl-3-(piperidin-4-yloxy)-1H-indazol-6-yl)-8-methyl-[1,2,4]triazolo[1,5-a]pyridine (195); 2-(4-((4-ethyl-6-(8-methyl-[1,2,4]triazolo[1,5-a]pyridin-6-yl)-1H-indazol-3-yl)oxy)piperidin-1-yl)-N,N-dimethylacetamide (196); 6-(8-methoxy-[1,2,4]triazolo[1,5-a]pyridin-6-yl)-N-(piperidin-4-yl)-1H-indole-3-carboxamide (197); 6-(8-methyl-[1,2,4]triazolo[1,5-a]pyridin-6-yl)-N-(piperidin-4-yl)-1H-indole-3-carboxamide (198); 6-(8-methyl-[1,2,4]triazolo[1,5-a]pyridin-6-yl)-N-(piperidin-4-yl)-1H-indazole-3-carboxamide (199); 6-(8-methyl-[1,2,4]triazolo[1,5-a]pyridin-6-yl)-N-(piperidin-4-yl)-1H-indazol-3-amine (200); 5-methyl-6-(8-methyl-[1,2,4]triazolo[1,5-a]pyridin-6-yl)-1H-indazol-3-amine (201); N-(5-methyl-6-(8-methyl-[1,2,4]triazolo[1,5-a]pyridin-6-yl)-1H-indazol-3-yl)piperidine-4-carboxamide (202); N-(5-methyl-6-(8-methyl-[1,2,4]triazolo[1,5-a]pyridin-6-yl)-1H-indazol-3-yl)piperidine-4-carboxamide (203); 5-methyl-6-(8-methyl-[1,2,4]triazolo[1,5-a]pyridin-6-yl)-N-(2-(pyrrolidin-1-yl)ethyl)-1H-indazol-3-amine (204); 8-methyl-6-(5-methyl-3-(piperazin-1-yl)-1H-indazol-6-yl)-[1,2,4]triazolo[1,5-a]pyridine (205); 6-(5-isopropyl-3-(piperazin-1-yl)-1H-indazol-6-yl)-8-methyl-[1,2,4]triazolo[1,5-a]pyridine (206); 6-(5-isopropyl-3-(piperazin-1-yl)-1H-indazol-6-yl)-8-methyl-[1,2,4]triazolo[1,5-a]pyridine (207); 6-(5-isopropyl-3-(4-isopropylpiperazin-1-yl)-1H-indazol-6-yl)-8-methyl-[1,2,4]triazolo[1,5-a]pyridine (208); 7-(4-(5-isopropyl-6-(8-methyl-[1,2,4]triazolo[1,5-a]pyridin-6-yl)-1H-indazol-3-yl)cyclohexyl)-2-oxa-7-azaspiro[4.4]nonane (209-210); or 6-(5-isopropyl-3-(4-(3-(methylsulfonyl) pyrrolidin-1-yl)cyclohexyl)-1H-indazol-6-yl)-8-methyl-[1,2,4]triazolo[1,5-a]pyridine (211-212).

The present invention may be embodied in other specific forms without departing from the spirit or essential attributes thereof. The invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phrase "compounds" refers to at least one compound. For example, a compound of Formula (I) includes a compound of Formula (I) and two or more compounds of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "cyano" refers to the group —CN.

The term "amino" refers to the group —NH$_2$.

The term "oxo" refers to the group =O.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$ alkyl" denotes straight and branched chain alkyl groups with one to six carbon atoms.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, —$CF_3$ and —$CH_2CF_3$.

The term "cyanoalkyl" includes both branched and straight-chain saturated alkyl groups substituted with one or more cyano groups. For example, "cyanoalkyl" includes —$CH_2CN$, —$CH_2CH_2CN$, and CM cyanoalkyl.

The term "aminoalkyl" includes both branched and straight-chain saturated alkyl groups substituted with one or more amine groups. For example, "aminoalkyl" includes —$CH_2NH_2$, —$CH_2CH_2NH_2$, and $C_{1-4}$ aminoalkyl.

The term "hydroxyalkyl" includes both branched and straight-chain saturated alkyl groups substituted with one or more hydroxyl groups. For example, "hydroxyalkyl" includes —$CH_2OH$, —$CH_2CH_2OH$, and CM hydroxyalkyl.

The term "hydroxy-fluoroalkyl" includes both branched and straight-chain saturated alkyl groups substituted with one or more hydroxyl groups and one or more fluorine atoms. For example, "hydroxy-fluoroalkyl" includes —$CHFCH_2OH$, —$CH_2CHFC(CH_3)_2OH$, and CM hydroxy-fluoroalkyl.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_3$-$C_6$ cycloalkyl" denotes cycloalkyl groups with three to six carbon atoms.

The term "alkoxy," as used herein, refers to an alkyl group attached to the parent molecular moiety through an oxygen atom, for example, methoxy group (—$OCH_3$). For example, "$C_{1-3}$ alkoxy" denotes alkoxy groups with one to three carbon atoms.

The term "alkoxyalkyl," as used herein, refers to an alkoxy group attached through its oxygen atom to an alkyl group, which is attached to the parent molecular moiety, for example, methoxymethyl group (—$CH_2OCH_3$). For example, "$C_{2-4}$ alkoxyalkyl" denotes alkoxyalkyl groups with two to four carbon atoms, such as —$CH_2OCH_3$, —$CH_2CH_2OCH_3$, —$CH_2OCH_2CH_3$, and —$CH_2CH_2OCH_2CH_3$.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as amorphous solids.

It should further be understood that solvates (e.g., hydrates) of the compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:
a) *The Practice of Medicinal Chemistry*, Camille G. Wermuth et al., Ch 31, (Academic Press, 1996);
b) *Design of Prodrugs*, edited by H. Bundgaard, (Elsevier, 1985);
c) *A Textbook of Drug Design and Development*, P. Krogsgaard-Larson and H. Bundgaard, eds. Ch 5, pgs 113-191 (Harwood Academic Publishers, 1991); and
d) *Hydrolysis in Drug and Prodrug Metabolism*, Bernard Testa and Joachim M. Mayer, (Wiley-VCH, 2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to TLR7/8/9, or effective to treat or prevent autoimmune and/or inflammatory disease states, such as SLE, IBD, multiple sclerosis (MS), and Sjögren's syndrome, and rheumatoid arthritis.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—CH$_3$) also includes deuterated methyl groups such as —CD$_3$.

Utility

The human immune system has evolved to defend the body from micro-organisms, viruses, and parasites that can cause infection, disease or death. Complex regulatory mechanisms ensure that the various cellular components of the immune system target the foreign substances or organisms, while not causing permanent or significant damage to the individual. While the initiating events are not well understood at this time, in autoimmune disease states the immune system directs its inflammatory response to target organs in the afflicted individual. Different autoimmune diseases are typically characterized by the predominate or initial target organ or tissues affected; such as the joint in the case of rheumatoid arthritis, the thyroid gland in the case of Hashimoto's thyroiditis, the central nervous system in the case of multiple sclerosis, the pancreas in the case of type I diabetes, and the bowel in the case of inflammatory bowel disease.

The compounds of the invention inhibit signaling through Toll-like receptor 7, or 8, or 9 (TLR7, TLR8, TLR9) or combinations thereof. Accordingly, compounds of Formula (I) have utility in treating conditions associated with the inhibition of signaling through one or more of TLR7, TLR8, or TLR9. Such conditions include TLR7, TLR8, or TLR9 receptor associated diseases in which cytokine levels are modulated as a consequence of intracellular signaling.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as selective inhibitors of TLR7, TLR8, or TLR9, compounds of Formula (I) are useful in treating TLR7, TLR8, or TLR9 family receptor associated diseases, but not limited to, inflammatory diseases such as Crohn's disease, ulcerative colitis, asthma, graft versus host disease, allograft rejection, chronic obstructive pulmonary disease; autoimmune diseases such as Graves' disease, rheumatoid arthritis, systemic lupus erythematosus, lupus nephritis, cutaneous lupus, psoriasis; auto-inflammatory diseases including Cryopyrin-Associated Periodic Syndromes (CAPS), TNF Receptor Associated Periodic Syndrome (TRAPS), Familial Mediterranean Fever (FMF), adult onset stills, systemic onset juvenile idiopathic arthritis, gout, gouty arthritis; metabolic diseases including type 2 diabetes, atherosclerosis, myocardial infarction; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovascularization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, keloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovascularization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hypoxia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Included in this embodiment are methods of treatment in which the condition is selected from lupus including lupus nephritis and systemic lupus erythematosus (SLE), Crohn's disease, ulcerative colitis, allograft rejection, rheumatoid arthritis, psoriasis, ankylosing spondylitis, psoriatic arthritis, and pemphigus vulgaris. Also included are methods of treatment in which the condition is selected from ischemia reperfusion injury, including cerebral ischemia reperfusions injury arising from stroke and cardiac ischemia reperfusion injury arising from myocardial infarction. Another method of treatment is one in which the condition is multiple myeloma.

In one embodiment, the compounds of Formula (I) are useful in treating cancer, including Waldenstrom's Macroglobulinemia (WM), diffuse large B cell lymphoma (DLBCL), chronic lymphocytic leukemia (CLL), cutaneous diffuse large B cell lymphoma, and primary CNS lymphoma.

In addition, the TLR7, TLR8, or TLR9 inhibitors of the present invention inhibit the expression of inducible pro-inflammatory proteins such as prostaglandin endoperoxide synthase-2 (PGHS-2), also referred to as cyclooxygenase-2 (COX-2), IL-1, IL-6, IL-18, chemokines. Accordingly, additional TLR7/8/9 associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retrovirus infections, including feline immunodeficiency virus, bovine immunodeficiency virus, and canine immunodeficiency virus.

The present invention thus provides methods for treating such conditions, comprising administering to a subject in need thereof a therapeutically-effective amount of at least one compound of Formula (I) or a salt thereof. "Therapeutically effective amount" is intended to include an amount of a compound of the present invention that is effective when administered alone or in combination to inhibit autoimmune disease or chronic inflammatory disease.

The methods of treating TLR7, TLR8, or TLR9 associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to inhibit TLR7, TLR8, or TLR9 and/or treat diseases associated with TLR7, TLR8, or TLR9.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal anti-inflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); anti-malarials such as hydroxychloroquine; cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating TLR7/8/9 receptor-associated conditions, including IL-1 family receptor-mediated diseases as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th Edition (1985), which is incorporated herein by reference in its entirety.

Compounds in accordance with Formula (I) can be administered by any means suitable for the condition to be treated, which can depend on the need for site-specific treatment or quantity of Formula (I) compound to be delivered.

Also embraced within this invention is a class of pharmaceutical compositions comprising a compound of Formula (I) and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parenterally including intravascularly, intravenously, intraperitoneally, subcutaneously, intramuscularly, and intrastemally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an antioxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride solution, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and (c) a package insert stating that the pharmaceutical composition can be used for the treatment of an inflammatory disorder and/or an autoimmune disease (as defined previously). In another embodiment, the package insert states that the pharmaceutical composition can be used in combination (as defined previously) with a second therapeutic agent to treat an inflammatory disorder and/or an autoimmune disease. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). In one embodiment, the package insert specifically recites the indications for which the pharmaceutical composition has been approved. The package insert may be made of any material on which a person can read information contained therein or thereon. For example, the package insert is a printable material (e.g., paper, plastic, cardboard, foil, adhesive-backed paper or plastic, etc.) on which the desired information has been formed (e.g, printed or applied).

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Third Edition, Wiley and Sons, 1999).

EXAMPLES

Preparation of compounds of Formula (I), and intermediates used in the preparation of compounds of Formula (I), can be prepared using procedures shown in the following Examples and related procedures. The methods and conditions used in these examples, and the actual compounds prepared in these Examples, are not meant to be limiting, but are meant to demonstrate how the compounds of Formula (I) can be prepared. Starting materials and reagents used in these examples, when not prepared by a procedure described herein, are generally either commercially available, or are reported in the chemical literature, or may be prepared by using procedures described in the chemical literature.

Abbreviations

Ac acetyl
ACN acetonitrile
anhyd. anhydrous
aq. aqueous
Bn benzyl
Boc-anhydride di-tert-butyl dicarbonate
Bu butyl
Boc tert-butoxy carbonyl
CV Column Volumes
DCE dichloroethane
DCM dichloromethane
DMAP dimethylaminopyridine
DMF dimethylformamide
DMSO dimethylsulfoxide
EtOAc ethyl acetate
Et ethyl
Et$_3$N triethylamine
H or H$_2$ hydrogen
h, hr or hrs hour(s)
hex hexane
i iso
HCl hydrochloric acid
HPLC high pressure liquid chromatography
LC liquid chromatography
LCMS liquid chromatography-mass spectroscopy
LiAlH$_4$ lithium aluminum hydride
M molar
mM millimolar
Me methyl
MeOH methanol
MHz megahertz
min. minute(s)
mins minute(s)
M$^{+1}$ (M+H)$^+$
MS mass spectrometry
n or N normal
NBS n-bromosuccinimide NCS n-chlorosuccinimide
nm nanometer
nM nanomolar
NMP N-methylpyrrolidinone
Pd/C palladium on carbon
PdCl$_2$(dppf) [1,1'-bis(diphenylphosphino)ferrocene]dichloropalladium(II)
Ph phenyl
Pr propyl
PSI pounds per square inch
Ret Time retention time
sat. saturated
SFC supercritical fluid chromatography
TEA triethylamine
TFA trifluoroacetic acid
THF tetrahydrofuran
XPhos Precatalyst chloro(2-dicyclohexylphosphino-2',4',6'-triisopropyl-1,1'-biphenyl)[2-(2'-amino-1,1'-biphenyl)]palladium(II)

Analytical HPLC Conditions:

QC-ACN-AA-XB: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm.

QC-ACN-TFA-XB: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

Method A1: L3 Acquity: Column: (LCMS) UPLC BEH C18, 2.1×50 mm, 1.7 μm particles; Mobile Phase: (A) water; (B) acetonitrile; Buffer: 0.05% TFA; Gradient Range: 2%-98% B (0 to 1 min) 98% B (to 1.5 min) 98%-2% B (to 1.6 min); Gradient Time: 1.6 min; Flow Rate: 0.8 mL/min; Analysis Time: 2.2 min; Detection: Detector 1: UV at 220 nm; Detector 2: MS (ESI$^+$).

Preparative HPLC Conditions:

Column: XBridge C18, 19×200 mm, 5 μm particles; Mobile Phase A: 5:95 acetonitrile: water with 10-mM ammonium acetate; Mobile Phase B: 95:5 acetonitrile: water with 10-mM ammonium acetate; Gradient: 10-50% B over 20 minutes, then a 5-minute hold at 100% B; Flow: 20 mL/min. Detection: UV at 220 nm.

Column: XBridge C18, 19×200 mm, 5 μm particles; Mobile Phase A: 5:95 acetonitrile: water with 0.1% trifluoroacetic acid; Mobile Phase B: 95:5 acetonitrile: water with 0.1% trifluoroacetic acid; Gradient: 6-46% B over 20 minutes, then a 4-minute hold at 100% B; Flow: 20 mL/min. Detection: UV at 220 nm.

Shimadzu prep HPLC, Luna® 0 8 30×100 mm, 5 μm (Phenomenex Inc.); 2 mL injection; Mobile Phase: 0.1% TFA in Water; Mobile Phase B: 0.1% TFA in MeOH; Temperature: 50° C.; Gradient: 20-100% B over 5 min, then a 10 min hold at 100% B, Flow: 30 mL/min; Detection: UV at 220 nm.

Intermediate 1

6-chloro-4-ethyl-1H-indazole

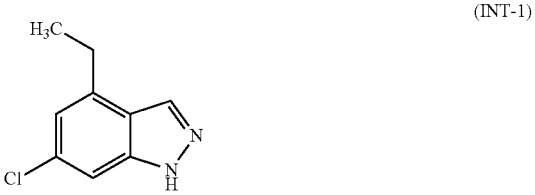

(INT-1)

Step 1:

To a mixture of 4-bromo-6-chloro-1H-indazole (1.5 g, 6.48 mmol), 4,4,5,5-tetramethyl-2-vinyl-1,3,2-dioxaborolane (1.193 mL, 7.13 mmol), and 2nd generation XPHOS precatalyst (0.153 g, 0.194 mmol) in dioxane (15 mL) was added 2 M K$_3$PO$_4$ (6.48 mL, 12.96 mmol). The reaction mixture was sparged with nitrogen for 5 minutes. The reactor was sealed and heated at 50° C. overnight. The reaction mixture was diluted with DCM then dried with MgSO$_4$, filtered and concentrated. The crude material was purified on a silica gel cartridge (40 g) using a MeOH/DCM gradient (0-10% MeOH over 15 min) to afford 6-chloro-4-vinyl-1H-indazole (1.0 g, 5.60 mmol, 86% yield). MS (M$^{+1}$) m/z: 179.0 (MH$^+$). LC retention time 0.87 min [A1].

Step 2:

To a mixture of 6-chloro-4-vinyl-1H-indazole (1.0 g, 5.60 mmol) in MeOH under a nitrogen atmosphere was added 10% platinum on Carbon (200 mg, 1.025 mmol). The reaction vessel was evacuated and then backfilled with hydrogen using a balloon. The hydrogenation reaction was allowed to proceed for 2 hours. The reaction was incomplete. Hydrogen was re-introduced to the reaction vessel and the reaction mixture was stirred overnight. The vessel was evacuated and then backfilled with nitrogen. The catalyst was removed by filtration. The reaction mass was concentrated and dried in vacuo to afford 6-chloro-4-ethyl-1H-indazole (1 g, 5.54 mmol, 99% yield). MS (M$^{+1}$) m/z: 181.0 (MH$^+$). LC retention time 0.90 min [A1].

Intermediate 2

1-(6-chloro-5-isopropyl-1H-indazol-1-yl)ethan-1-one

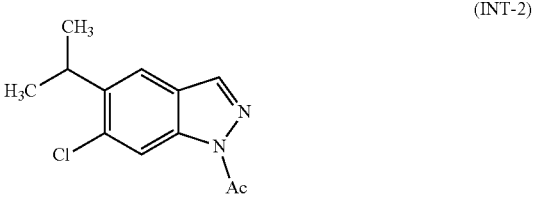 [SMILES: CC(=O)n1ncc2cc(C(C)C)c(Cl)cc21]

(INT-2)

Step 1:

To a mixture of 4-bromo-5-chloro-2-methylaniline (6 g, 27.2 mmol) in toluene (30 mL) was added acetic anhydride (2.82 mL, 29.9 mmol). The reaction mixture was heated at 110° C. for 4 hours. The reaction mixture was cooled and solvents were removed in vacuo to afford N-(4-bromo-5-chloro-2-methylphenyl)acetamide (7 g, 26.7 mmol, 98% yield) as an off-white solid. MS (M$^{+1}$) m/z: 264.0 (MH$^+$). LC retention time 0.83 min [A1].

Step 2:

To a mixture of N-(4-bromo-5-chloro-2-methylphenyl) acetamide (7.8 g, 29.7 mmol), 4,4,5,5-tetramethyl-2-(prop-1-en-2-yl)-1,3,2-dioxaborolane (5.58 mL, 29.7 mmol), and 2nd generation XPHOS precatalyst (0.701 g, 0.891 mmol) in dioxane (50 mL) was added 2 M K$_3$PO$_4$ (29.7 mL, 59.4 mmol). The reaction vessel was sparged with nitrogen for 5 minutes and then sealed. The reaction mixture stirred at 25° C. for 2 days. The reaction mixture was diluted with dichloromethane and washed with water. The organic layer was dried with MgSO$_4$, filtered and concentrated. The crude material was purified on a silica gel cartridge (80 g) using an EtOAc/Hex gradient (0-100% EtOAc over 25 min) to afford N-(5-chloro-2-methyl-4-(prop-1-en-2-yl)phenyl)acetamide (6.0 g, 26.8 mmol, 90% yield). MS (M$^{+1}$) m/z: 224.1 (MH$^+$). LC retention time 0.88 min [A1].

Step 3:

To a mixture of N-(5-chloro-2-methyl-4-(prop-1-en-2-yl) phenyl)acetamide (6.5 g, 29.1 mmol) in MeOH (50 mL) was added 10% platinum on carbon (500 mg). The MeOH was sparged with nitrogen before platinum was added. The reaction mixture was hydrogenated under a balloon of hydrogen overnight. The reaction vessel was evacuated and backfilled with nitrogen several times. The catalyst was removed by filtration. The reaction mixture was concentrated in vacuo to afford N-(5-chloro-4-isopropyl-2-methylphenyl) acetamide (6 g, 26.6 mmol). MS (M$^{+1}$) m/z: 226.3 (MH$^+$). LC retention time 0.91 min [A1].

Step 4

With ice-bath cooling, acetic anhydride (2.76 mL, 29.2 mmol) was added to a solution of N-(5-chloro-4-isopropyl-2-methylphenyl)acetamide (6 g, 26.6 mmol) in chloroform (10 mL). Potassium acetate (2.87 g, 29.2 mmol) and 18-crown-6 (1.405 g, 5.32 mmol) were added followed by the addition of t-butyl nitrite (2.282 mL, 17.29 mmol). The mixture was refluxed at 78° C. for 16 h. The reaction mixture was cooled and stirred (under ice bath cooling) with saturated aqueous sodium bicarbonate solution (20 mL), and then extracted with DCM (2×50 mL). The organics were combined, dried with MgSO$_4$ and concentrated in vacuo. The crude material was purified on a silica gel cartridge (80 g) using a MeOH/DCM gradient (0-10% MeOH over 25 min) to afford 1-(6-chloro-5-isopropyl-1H-indazol-1-yl) ethan-1-one (4.2 g, 17.74 mmol, 66.8% yield). MS (M$^{+1}$) m/z: 237.3 (MH$^+$). LC retention time 1.1 min [A1].

Intermediate 3

1,4-dioxaspiro[4.5]decan-8-yl 4-methylbenzenesulfonate (INT-3)

To a mixture of 1,4-dioxaspiro[4.5]decan-8-ol (10 g, 63.2 mmol), TEA (14 ml, 100 mmol), and DMAP (0.8 g, 6.55 mmol) in DCM (400 mL) was added toluenesulfonyl chloride (13.26 g, 69.5 mmol). The reaction mixture was stirred at room temperature overnight. The mixture was washed with 0.1 M HCl. The organic layer was dried with MgSO$_4$, filtered, and concentrated. The crude material was purified on a silica gel cartridge (120 g) using an EtOAc/Hex gradient (0-50% EtOAc over 30 min) to afford 1,4-dioxaspiro[4.5]decan-8-yl 4-methylbenzenesulfonate (14 g, 44.8 mmol, 70.9% yield) as a white solid. $^1$H NMR (499 MHz, CHLOROFORM-d) δ 7.88-7.78 (m, 1H), 7.82 (d, J=8.3 Hz, 1H), 7.35 (d, J=8.6 Hz, 2H), 4.66 (dt, J=6.3, 3.2 Hz, 1H), 4.01-3.82 (m, 4H), 2.47 (s, 3H), 1.97-1.69 (m, 6H), 1.59-1.50 (m, 2H).

SCHEME 1

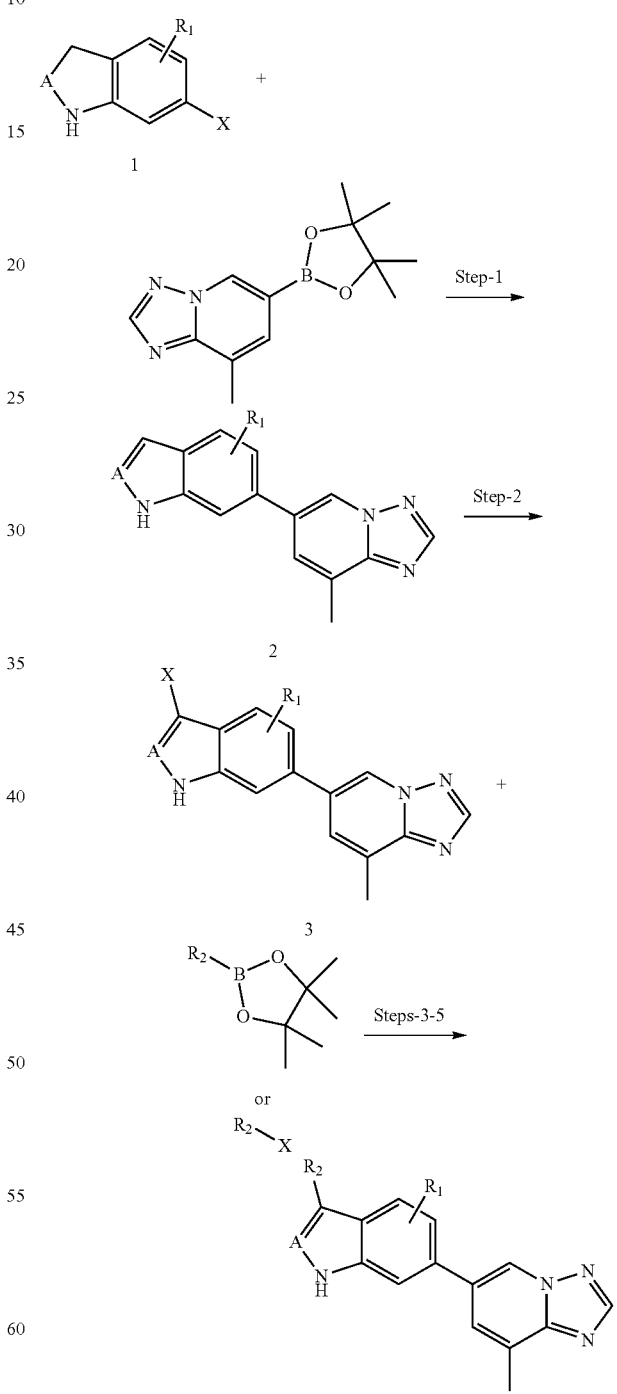

A = C or N  X = Cl, Br, or I  R$_1$ = H, Me, Et, iPr, OMe

Example 1

8-methyl-6-(5-methyl-3-(piperidin-4-yl)-1H-indol-6-yl)-[1,2,4]triazolo[1,5-a]pyridine

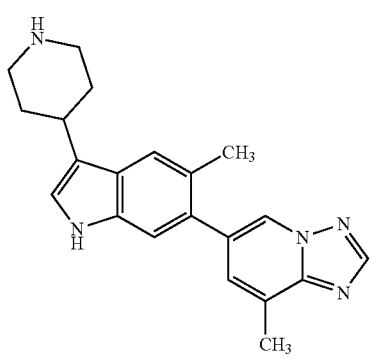

(1)

Step 1:

To a mixture of 6-bromo-5-methyl-1H-indole (50 mg, 0.238 mmol), 8-methyl-6-(4,4,5,5-tetramethyl-1,3,2-dioxaborolan-2-yl)-[1,2,4]triazolo[1,5-a]pyridine (74.0 mg, 0.286 mmol), and 2nd generation XPHOS precatalyst (9.36 mg, 0.012 mmol) in THF (2 mL) was added 3M $K_3PO_4$ (0.238 mL, 0.714 mmol). Reaction mixture was sparged with nitrogen for 5 minutes then sealed and heated at 85° C. overnight. The reaction mixture was diluted with ethyl acetate and washed with sat NaCl. The organic layer was dried with $MgSO_4$, filtered and concentrated to afford 8-methyl-6-(5-methyl-1H-indol-6-yl)-[1,2,4]triazolo[1,5-a]pyridine (53 mg, 0.202 mmol, 85% yield). MS ($M^{+1}$) m/z: 263.2 ($MH^+$). LC retention time 0.81 min [A1].

Step 2:

To a mixture of 8-methyl-6-(5-methyl-1H-indol-6-yl)-[1,2,4]triazolo[1,5-a]pyridine (62 mg, 0.236 mmol) in DCM (5 mL) was added NBS (42.1 mg, 0.236 mmol). The reaction mixture was stirred for 30 minutes. LCMS show complete conversion to brominated product. The reaction mixture was diluted with dichloromethane and washed with saturated NaCl. The organic layer was dried with $MgSO_4$, filtered and concentrated to afford 6-(3-bromo-5-methyl-1H-indol-6-yl)-8-methyl-[1,2,4]triazolo[1,5-a]pyridine (80 mg, 0.234 mmol, 99% yield). MS ($M^{+1}$) m/z: 341/343 ($MH^+$). LC retention time 0.89 min [A1].

Step 3:

To a mixture of 6-(3-bromo-5-methyl-1H-indol-6-yl)-8-methyl-[1,2,4]triazolo[1,5-a] pyridine (80 mg, 0.234 mmol), tert-butyl 4-(4,4,5,5-tetramethyl-1,3,2-dioxaborolan-2-yl)-3,6-dihydropyridine-1(2H)-carboxylate (94 mg, 0.305 mmol), and 2nd generation XPHOS precatalyst (9.22 mg, 0.012 mmol) in THF (2 mL) was added 3M $K_3PO_4$ (0.234 mL, 0.703 mmol). The reaction mixture was sparged with nitrogen for 5 minutes. The reaction vessel was sealed and heated at 65° C. overnight. The reaction mixture was diluted with dichloromethane and dried with $MgSO_4$, then filtered and concentrated. The crude material was purified on a silica gel cartridge (24 g) using an EtOAc/Hex gradient (20-100% EtOAc over 13 min) to afford tert-butyl 4-(5-methyl-6-(8-methyl-[1,2,4]triazolo[1,5-a]pyridin-6-yl)-1H-indol-3-yl)-3,6-dihydropyridine-1(2H)-carboxylate (45 mg, 0.101 mmol, 43.3% yield). MS ($M^{+1}$) m/z: 445.2 ($MH^+$). LC retention time 0.93 min [A1].

Step 4:

To a mixture of tert-butyl 4-(5-methyl-6-(8-methyl-[1,2,4]triazolo[1,5-a]pyridin-6-yl)-1H-indol-3-yl)-3,6-dihydropyridine-1(2H)-carboxylate (45 mg, 0.101 mmol) in MeOH (3 mL) was added 10% Pd—C (5.40 mg, 0.051 mmol). The reaction mixture was hydrogenated under a balloon of $H_2$ for 2 hours. The catalyst was removed by filtration and the residue was treated with TFA/DCM (1:1) for 30 minutes. Solvents were removed and the solid material was dissolved in DMF and purified by preparative HPLC afforded 8-methyl-6-(5-methyl-3-(piperidin-4-yl)-1H-indol-6-yl)-[1,2,4]triazolo[1,5-a]pyridine (13.2 mg, 0.038 mmol, 37.4% yield). MS ($M^{+1}$) m/z: 346.1 ($MH^+$). LC retention time 0.92 min [QC-ACN-AA-XB]. $^1$H NMR (500 MHz, DMSO-$d_6$) δ 8.68 (s, 1H), 8.45 (s, 1H), 7.53 (s, 1H), 7.49 (s, 1H), 7.28 (s, 1H), 7.10 (d, J=1.5 Hz, 1H), 2.92 (br d, J=9.8 Hz, 2H), 2.66-2.58 (m, 3H), 2.33 (s, 3H), 2.13-1.80 (m, 6H), 1.78-1.56 (m, 2H).

Example 2

8-methyl-6-(4-methyl-3-(piperidin-4-yl)-1H-indol-6-yl)-[1,2,4]triazolo[1,5-a]pyridine

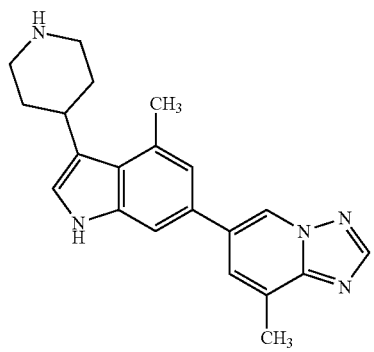

(2)

Step 1:

To a mixture of 6-bromo-4-methyl-1H-indole (100 mg, 0.476 mmol), 8-methyl-6-(4,4,5,5-tetramethyl-1,3,2-dioxaborolan-2-yl)-[1,2,4]triazolo[1,5-a]pyridine (185 mg, 0.714 mmol), and 2nd generation XPHOS precatalyst (18.73 mg, 0.024 mmol) in dioxane (4 mL) was added 3M $K_3PO_4$ (0.714 mL, 1.428 mmol). The reaction mixture was sparged with nitrogen for 5 minutes. The reaction vessel was sealed and heated at 85° C. overnight. The reaction mixture was diluted with dichloromethane and dried with $MgSO_4$, filtered and concentrated. The crude material was purified on a silica gel cartridge using a MeOH/DCM gradient (0-10% MeOH over 15 min) to afford 8-methyl-6-(4-methyl-1H-indol-6-yl)-[1,2,4]triazolo[1,5-a]pyridine (98 mg, 0.374 mmol, 78% yield). MS ($M^{+1}$) m/z: 263.4 ($MH^+$). LC retention time 0.82 min [A1].

Step 2:

To a mixture of 8-methyl-6-(4-methyl-1H-indol-6-yl)-[1,2,4]triazolo[1,5-a]pyridine (123 mg, 0.47 mmol) in DCM (10 mL) was added NBS (84 mg, 0.470 mmol). The reaction mixture was stirred for 1 hour, diluted with dichloromethane, and washed with saturated NaCl. The organic layer was dried with $MgSO_4$, filtered and concentrated to afford 6-(3-bromo-4-methyl-1H-indol-6-yl)-8-methyl-[1,2,4]triazolo[1, 5-a]pyridine (70 mg, 0.205 mmol). MS (M$^{+1}$) m/z: 341/343 (MH$^+$). LC retention time 0.94 min [A1].

Step 3:

To a mixture of 6-(3-bromo-4-methyl-1H-indol-6-yl)-8-methyl-[1,2,4]triazolo[1,5-a] pyridine (70 mg, 0.205 mmol), tert-butyl 4-(4,4,5,5-tetramethyl-1,3,2-dioxaborolan-2-yl)-3,6-dihydropyridine-1(2H)-carboxylate (95 mg, 0.308 mmol), and 2nd generation XPHOS precatalyst (8.07 mg, 10.26 µmol) in dioxane (10 mL) was added 3M K$_3$PO$_4$ (0.308 mL, 0.615 mmol). The reaction mixture was sparged with nitrogen for 5 minutes. The reaction vessel was sealed and heated at 85° C. overnight. The reaction mixture was diluted with ethyl acetate and washed with saturated NaCl. The organic layer was dried with MgSO$_4$, filtered and concentrated. The crude material was purified on a silica gel cartridge using a MeOH/DCM gradient (0-15% MeOH over 12 min) to afford tert-butyl 4-(4-methyl-6-(8-methyl-[1,2,4]triazolo[1,5-a]pyridin-6-yl)-1H-indol-3-yl)-3,6-dihydropyridine-1(2H)-carboxylate (72 mg, 0.162 mmol, 79% yield). MS (M$^{+1}$) m/z: 444.2 (MH$^+$). LC retention time 0.99 min [A1].

Step 4:

To a mixture of tert-butyl 4-(4-methyl-6-(8-methyl-[1,2,4]triazolo[1,5-a]pyridin-6-yl)-1H-indol-3-yl)-3,6-dihydropyridine-1(2H)-carboxylate (72 mg, 0.162 mmol) in MeOH (5 mL) was added Pd—C (17.27 mg, 0.162 mmol). The reaction mixture was hydrogenated under 50 psi hydrogen on a Parr apparatus for 8 hours. The hydrogen was replaced with nitrogen and the catalyst was removed by filtration. The mixture was concentrated in vacuo and the residue was treated with DCM/TFA (1:1) for 30 minutes. Solvents were removed. The residue was dissolved in DMF and purified by preparative HPLC to afford 8-methyl-6-(4-methyl-3-(piperidin-4-yl)-1H-indol-6-yl)-[1,2,4]triazolo[1,5-a]pyridine (7.3 mg, 0.020 mmol, 12.59% yield). MS (M$^{+1}$) m/z: 346.1 (MH$^+$). LC retention time 0.95 min [QC-ACN-AA-XB]. $^1$H NMR (500 MHz, DMSO-d$_6$) δ 9.01 (s, 1H), 8.46 (s, 1H), 7.86 (s, 1H), 7.55 (s, 1H), 7.17 (s, 2H), 3.27-3.09 (m, 2H), 2.81 (br t, J=11.9 Hz, 1H), 2.71 (s, 3H), 2.63 (s, 3H), 1.98 (br d, J=12.8 Hz, 2H), 1.84 (s, 3H), 1.63 (q, J=13.0 Hz, 2H).

Examples 3 and 4

N,N-dimethyl-4-(5-methyl-6-(8-methyl-[1,2,4]triazolo[1,5-a]pyridin-6-yl)-1H-indazol-3-yl) cyclohexan-1-amine (3, 4)

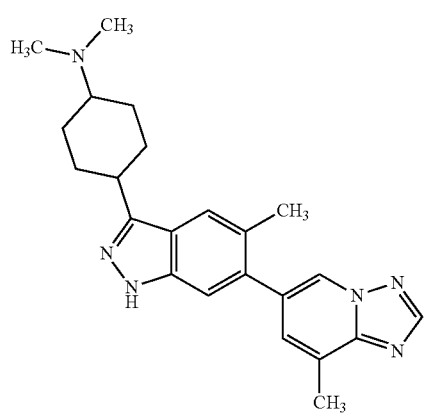

Step 1:

To a mixture of 6-bromo-5-methyl-1H-indazole (800 mg, 3.79 mmol), 8-methyl-6-(4,4,5,5-tetramethyl-1,3,2-dioxaborolan-2-yl)-[1,2,4]triazolo[1,5-a]pyridine (1179 mg, 4.55 mmol), and 2nd generation XPHOS precatalyst (149 mg, 0.190 mmol) in dioxane (2 mL) was added 3M K$_3$PO$_4$ (3.79 mL, 11.37 mmol). The reaction mixture was sparged with nitrogen for 5 minutes. The reaction vessel was sealed and heated at 85° C. overnight. LCMS showed the desired product mass and some remaining starting material. Additional 2nd generation XPHOS precatalyst (149 mg, 0.190 mmol) was added. The reaction mixture was re-sparged and heated an additional day. The reaction mixture was diluted with ethyl acetate and washed with saturated NaCl. The organic layer was dried with MgSO$_4$, filtered and concentrated. The crude material was purified on a silica gel cartridge (40 g) using a MeOH/DCM gradient (0-15% MeOH over min) to afford 8-methyl-6-(5-methyl-1H-indazol-6-yl)-[1,2,4]triazolo[1,5-a]pyridine (710 mg, 2.70 mmol, 71.1% yield). MS (M$^{+1}$) m/z: 264.1 (MH$^+$). LC retention time 0.74 min [A1].

Step 2:

To a solution of 8-methyl-6-(5-methyl-1H-indazol-6-yl)-[1,2,4]triazolo[1,5-a]pyridine (450 mg, 1.709 mmol) and sodium hydroxide (68.4 mg, 1.709 mmol) in methanol (25 mL) were added iodine (259 mg, 1.02 mmol) and an aqueous solution (5 mL) of potassium iodide (284 mg, 1.709 mmol). After stirring at room temperature for 12 h, the reaction mixture was diluted with dichloromethane and washed with saturated NaCl. The organic layer was dried with MgSO$_4$, filtered and concentrated. The crude material was purified on a silica gel cartridge using a MeOH/DCM gradient (0-10% MeOH) to afford 6-(3-iodo-5-methyl-1H-indazol-6-yl)-8-methyl-[1,2,4]triazolo[1,5-a]pyridine. MS (M$^{+1}$) m/z: 389.2 (MH$^+$). LC retention time 0.84 min [A1].

Step 3:

To a mixture of 6-(3-iodo-5-methyl-1H-indazol-6-yl)-8-methyl-[1,2,4]triazolo[1,5-a] pyridine (82 mg, 0.211 mmol), 4,4,5,5-tetramethyl-2-(1,4-dioxaspiro[4.5]dec-7-en-8-yl)-1,3,2-dioxaborolane (72.9 mg, 0.274 mmol), and 2nd generation XPHOS precatalyst (8.29 mg, 10.53 µmol) in THF (2 mL) was added 3M K$_3$PO$_4$ (0.211 mL, 0.632 mmol). The reaction mixture was sparged with nitrogen for 5 minutes. The reaction vessel was sealed and heated at 90° C. overnight. LCMS shows partial conversion. Additional 2nd generation XPHOS precatalyst (8.29 mg, 10.53 µmol) and 4,4,5,5-tetramethyl-2-(1,4-dioxaspiro[4.5]dec-7-en-8-yl)-1,3,2-dioxaborolane (72.9 mg, 0.274 mmol) were added. The reaction mixture was re-sparged and heated at 90° C. overnight. The reaction mixture was diluted with dichloromethane and dried with MgSO$_4$, then filtered and concentrated. The crude material was purified on a silica gel cartridge (24 g) using an EtOAc/Hex gradient (0-100% EtOAc over 11 min) to afford 8-methyl-6-(5-methyl-3-(1,4-dioxaspiro[4.5]dec-7-en-8-yl)-1H-indazol-6-yl)-[1,2,4]triazolo[1,5-a]pyridine (18 mg, 0.045 mmol, 21.28% yield). MS (M$^{+1}$) m/z: 389.2 (MH$^+$). LC retention time 0.84 min [A1].

Step 4:

To a mixture of 8-methyl-6-(5-methyl-3-(1,4-dioxaspiro[4.5]dec-7-en-8-yl)-1H-indazol-6-yl)-[1,2,4]triazolo[1,5-a]pyridine (18 mg, 0.045 mmol) in MeOH (3 mL) was added Pd—C (4.77 mg, 0.045 mmol). The reaction mixture was hydrogenated under a balloon of H$_2$ overnight. The catalyst was removed by filtration in vacuo. The crude product was treated with TFA (0.5 mL). After stirring 30 minutes, the mixture was concentrated in vacuo to afford 4-(5-methyl-6-(8-methyl-[1,2,4]triazolo[1,5-a]pyridin-6-yl)-1H-indazol-3- yl) cyclohexan-1-one (16 mg, 0.045 mmol). MS (M$^{+1}$) m/z: 360.2 (MH$^+$). LC retention time 0.77 min [A1].

Step 5:

4-(5-Methyl-6-(8-methyl-[1,2,4]triazolo[1,5-a]pyridin-6-yl)-1H-indazol-3-yl) cyclohexan-1-one (16 mg, 0.045 mmol) was dissolved in DMF (2 mL) and dimethylamine hydrochloride (18.15 mg, 0.223 mmol) and TEA (0.062 mL, 0.445 mmol) were added. The reaction mixture was stirred for 30 minutes. Sodium triacetoxyborohydride (47.2 mg, 0.223 mmol) was added along with a few drops of AcOH. The reaction mixture was stirred at room temperature overnight. MeOH (0.5 mL) was added and the mixture was filtered and purified by preparative HPLC to afford two isomers:

Example 3: Isomer 1: N,N-dimethyl-4-(5-methyl-6-(8-methyl-[1,2,4]triazolo[1,5-a] pyridin-6-yl)-1H-indazol-3-yl) cyclohexan-1-amine (5.6 mg, 0.014 mmol, 32.4% yield). MS (M$^{+1}$) m/z: 389.2 (MH$^+$). LC retention time 0.88 min [QC-ACN-AA-XB]. $^1$H NMR (500 MHz, DMSO-d$_6$) δ 8.82 (s, 1H), 8.51 (s, 1H), 7.76 (s, 1H), 7.54 (s, 1H), 7.42 (s, 1H), 3.24-3.12 (m, 1H), 3.13-2.99 (m, 1H), 2.85-2.74 (m, 6H), 2.67-2.59 (m, 3H), 2.37-2.26 (m, 3H), 2.24-2.08 (m, 4H), 1.88-1.73 (m, 2H), 1.75-1.58 (m, 1H), 1.01 (d, J=6.4 Hz, 1H).

Example 4: Isomer 2: N,N-dimethyl-4-(5-methyl-6-(8-methyl-[1,2,4]triazolo[1,5-a] pyridin-6-yl)-1H-indazol-3-yl) cyclohexan-1-amine (3.2 mg, 7.70 μmol, 17.30% yield). MS (M$^{+1}$) m/z: 389.2 (MH$^+$). LC retention time 1.04 min [QC-ACN-AA-XB]. $^1$H NMR (500 MHz, DMSO-d$_6$) δ 8.88-8.77 (m, 1H), 8.57-8.47 (m, 1H), 7.76-7.68 (m, 1H), 7.57-7.50 (m, 1H), 7.47-7.34 (m, 1H), 3.32-3.21 (m, 1H), 3.22-3.11 (m, 1H), 2.77-2.70 (m, 6H), 2.62 (s, 3H), 2.33 (s, 5H), 2.01-1.73 (m, 6H).

Example 5

2-(dimethylamino)-1-(3-(4-methyl-6-(8-methyl-[1,2,4]triazolo[1,5-a]pyridin-6-yl)-1H-indazol-3-yl)piperidin-1-yl)ethan-1-one (5)

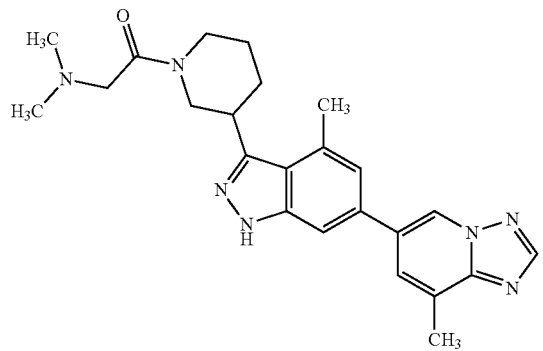

Step 1:

To a mixture of 6-bromo-4-methyl-1H-indazole (250 mg, 1.184 mmol), 8-methyl-6-(4,4,5,5-tetramethyl-1,3,2-dioxaborolan-2-yl)-[1,2,4]triazolo[1,5-a]pyridine (460 mg, 1.777 mmol), and 2nd generation XPHOS precatalyst (46.6 mg, 0.059 mmol) in dioxane (10 mL) was added 3M K$_3$PO$_4$ (1.184 mL, 3.55 mmol). The reaction mixture was sparged with nitrogen for 5 minutes. The reaction vessel was sealed and heated at 85° C. overnight. The reaction mixture was diluted with ethyl acetate and washed with saturated NaCl. The organic layer was dried with MgSO$_4$, filtered and concentrated to afford 8-methyl-6-(4-methyl-1H-indazol-6-yl)-[1,2,4]triazolo[1,5-a]pyridine (240 mg, 0.911 mmol, 77% yield). MS (M$^{+1}$) m/z: 263.2 (MH$^+$). LC retention time 0.74 min [A1].

Step 2:

To a mixture of 8-methyl-6-(4-methyl-1H-indazol-6-yl)-[1,2,4]triazolo[1,5-a]pyridine (240 mg, 0.911 mmol) in DCM (10 mL) was added NBS (162 mg, 0.911 mmol).

The reaction mixture was stirred at room temperature for 2 hours. The reaction mixture was diluted with dichloromethane and washed with water. The organic layer was dried with MgSO$_4$, filtered and concentrated to afford 6-(3-bromo-4-methyl-1H-indazol-6-yl)-8-methyl-[1,2,4]triazolo[1,5-a]pyridine (280 mg, 0.818 mmol, 90% yield). MS (M$^{+1}$) m/z: 342/344 (MH$^+$). LC retention time 0.82 min [A1].

Step 3:

To a mixture of 6-(3-bromo-4-methyl-1H-indazol-6-yl)-8-methyl-[1,2,4]triazolo[1,5-a]pyridine (85 mg, 0.248 mmol), tert-butyl 5-(4,4,5,5-tetramethyl-1,3,2-dioxaborolan-2-yl)-3,4-dihydropyridine-1(2H)-carboxylate (115 mg, 0.373 mmol), and 2nd generation XPHOS precatalyst (19.54 mg, 0.025 mmol) in dioxane (10 mL) was added 3M K$_3$PO$_4$ (0.166 mL, 0.497 mmol). The reaction mixture was sparged with nitrogen for 5 minutes. The reaction vessel was sealed and heated at 95° C. overnight. The reaction mixture was diluted with ethyl acetate and washed with saturated NaCl. The organic layer was dried with MgSO$_4$, filtered, concentrated, and purified on silica gel to afford tert-butyl 5-(4-methyl-6-(8-methyl-[1,2,4]triazolo[1,5-a]pyridin-6-yl)-1H-indazol-3-yl)-3,4-dihydropyridine-1(2H)-carboxylate (83 mg, 0.186 mmol, 75% yield). MS (M$^{+1}$) m/z: 445.5 (MH$^+$). LC retention time 0.98 min [A1].

Step 4:

To a mixture of tert-butyl 5-(4-methyl-6-(8-methyl-[1,2,4]triazolo[1,5-a]pyridin-6-yl)-1H-indazol-3-yl)-3,4-dihydropyridine-1(2H)-carboxylate (75 mg, 0.169 mmol) in DCM was added TFA (1 mL) followed by triethylsilane (0.5 ml, 3.13 mmol). The reaction mixture was stirred at room temperature for 1 hour. LCMS shows reduction to desired product. Solvents were removed in vacuo, chasing with MeOH and toluene (2×) to afford 8-methyl-6-(4-methyl-3-(piperidin-3-yl)-1H-indazol-6-yl)-[1,2,4]triazolo[1,5-a]pyridine (42 mg, 72% yield). MS (M$^{+1}$) m/z: 347.1 (MH$^+$). LC retention time 0.92 min [A1].

Step 5:

To a mixture of dimethylglycine (5 mg, 0.048 mmol), 8-methyl-6-(4-methyl-3-(piperidin-3-yl)-1H-indazol-6-yl)-[1,2,4]triazolo[1,5-a]pyridine (12 mg, 0.035 mmol), and TEA (15 μL, 0.108 mmol) in DMF (0.5 mL) was added HATU (18 mg, 0.047 mmol). The reaction mixture was stirred at room temperature for 2 hours. The mixture was filtered and purified by preparative HPLC to afford 2-(dimethylamino)-1-(3-(4-methyl-6-(8-methyl-[1,2,4]triazolo[1,5-a]pyridin-6-yl)-1H-indazol-3-yl)piperidin-1-yl)ethan-1-one (3.3 mg, 7.26 μmol, 20.97% yield). MS (M$^{+1}$) m/z: 432.0 (MH$^+$). LC retention time 1.1 min [QC-ACN-AA-XB]. $^1$H NMR (500 MHz, DMSO-d$_6$) δ 9.12 (br s, 1H), 8.49 (s, 1H), 7.93-7.84 (m, 1H), 7.68 (s, 1H), 7.30 (br d, J=4.3 Hz, 1H), 4.41-4.19 (m, 2H), 3.52-3.24 (m, 1H), 3.26-3.09 (m, 1H), 2.99-2.90 (m, 1H), 2.90-2.86 (m, 1H), 2.87-2.77 (m, 6H), 2.75-2.70 (m, 3H), 2.66-2.60 (m, 3H), 2.28-2.12 (m, 1H), 2.09-1.84 (m, 2H), 1.84-1.48 (m, 2H).

Examples 6 and 7

N,N-dimethyl-3-(5-methyl-6-(8-methyl-[1,2,4]triazolo[1,5-a]pyridin-6-yl)-1H-indazol-3-yl)cyclobutan-1-amine

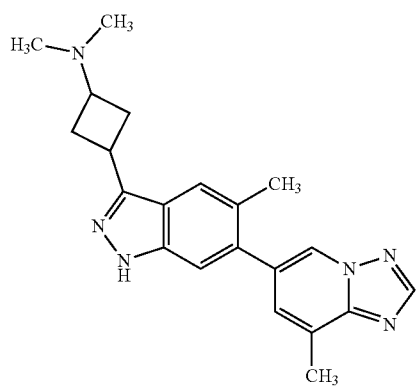

(6, 7)

Step 1:

To a mixture of 6-bromo-5-methyl-1H-indazole (800 mg, 3.79 mmol), 8-methyl-6-(4,4,5,5-tetramethyl-1,3,2-dioxaborolan-2-yl)-[1,2,4]triazolo[1,5-a]pyridine (1179 mg, 4.55 mmol), and 2nd generation XPHOS precatalyst (149 mg, 0.190 mmol) in dioxane (2 mL) was added 3M $K_3PO_4$ (3.79 mL, 11.37 mmol). The reaction mixture was sparged with nitrogen for 5 minutes. The reaction vessel was sealed and heated at 85° C. overnight. LCMS showed the desired product mass and some remaining starting material. Additional 2nd generation XPHOS precatalyst (149 mg, 0.190 mmol) was added. The reaction mixture was re-sparged and heated an additional day. The reaction mixture was diluted with ethyl acetate and washed with saturated NaCl. The organic layer was dried with $MgSO_4$, filtered and concentrated. The crude material was purified on a silica gel cartridge (40 g) using a MeOH/DCM gradient (0-15% MeOH over min) to afford 8-methyl-6-(5-methyl-1H-indazol-6-yl)-[1,2,4]triazolo[1,5-a]pyridine (710 mg, 2.70 mmol, 71.1% yield). MS ($M^+$) m/z: 264.1 ($MH^+$). LC retention time 0.74 min [A1].

Step 2:

To a mixture of 8-methyl-6-(5-methyl-1H-indazol-6-yl)-[1,2,4]triazolo[1,5-a]pyridine (500 mg, 1.899 mmol) in DCM (5 mL) was added NBS (338 mg, 1.899 mmol). The reaction mixture was stirred at room temperature for 1 hour. LCMS showed conversion to desired product by mass. The reaction mixture was diluted with dichloromethane and washed with saturated NaCl. The organic layer was dried with $MgSO_4$, filtered and concentrated. The crude material was purified on a silica gel cartridge (24 g) using a EtOAc/hexanes gradient (0-100% EtOAc over 13 min). Isolated fractions 34-40 were concentrated and dried in vacuo to afford 6-(3-bromo-5-methyl-1H-indazol-6-yl)-8-methyl-[1,2,4]triazolo[1,5-a]pyridine (300 mg, 0.877 mmol, 46.2% yield). MS ($M^{+1}$) m/z: 342 ($MH^+$). LC retention time 0.82 min [A1].

To a mixture of 6-(3-bromo-5-methyl-1H-indazol-6-yl)-8-methyl-[1,2,4]triazolo[1,5-a]pyridine (240 mg, 0.701 mmol) and TEA (0.147 mL, 1.052 mmol) in acetonitrile (10 mL) was added BOC-anhydride (0.525 mL, 0.736 mmol). After stirring 3 hours, LCMS showed partial reaction. Additional BOC-anhydride (0.525 mL, 0.736 mmol) was added. LCMS indicated consumption of the starting material. The reaction mixture was diluted with dichloromethane and washed with 0.1M HCl. The organic layer was dried with $MgSO_4$, filtered and concentrated to afford tert-butyl 3-bromo-5-methyl-6-(8-methyl-[1,2,4]triazolo[1,5-a]pyridin-6-yl)-1H-indazole-1-carboxylate (300 mg, 0.678 mmol, 97% yield). MS ($M^{+1}$) m/z: 442/444 ($MH^+$). LC retention time 1.02 min [A1].

Step 3:

tert-Butyl 3-bromo-5-methyl-6-(8-methyl-[1,2,4]triazolo[1,5-a]pyridin-6-yl)-1H-indazole-1-carboxylate (100 mg, 0.226 mmol), tert-butyl (3-iodocyclobutyl)carbamate (134 mg, 0.452 mmol), tris(trimethyl)silane (56.6 µL, 0.339 mmol), $Ir(dF(CF_3)ppy)_2(dtbbpy)PF_6$ (2.54 mg, 2.261 µmol), and $Na_2CO_3$ (96 mg, 0.904 mmol) were placed in a Teflon screw cap vial with a stir bar. 1,4-Dioxane (1884 µL) was added and the suspension was degassed (cap off) with nitrogen for 5 minutes. To a separate vial was added nickel (II) chloride ethylene glycol dimethyl ether complex (2.484 mg, 0.011 mmol) and 4,4'-di-tert-butyl-2,2'-bipyridine (3.64 mg, 0.014 mmol), which was evacuated and backfilled with nitrogen followed by 1,4-dioxane (377 µL). This solution was degassed (cap on) with nitrogen gas for 10 minutes and stirred. The resulting solution was added to the reaction mixture, which was further degassed with nitrogen gas for another 10 minutes (cap on). The resulting suspension was placed in a block with stirring and blue Kessil lamp irradiation. After stirring overnight (17 hours) in front of 2 Kessil lamps, the reaction mixture was diluted with DCM and then dried with $MgSO_4$. The mixture was filtered, concentrated and purified on silica (12 g silica gel, hexanes/EtOAc; 0-100% EtOAc over 12 min.) to afford tert-butyl 3-(3-((tert-butoxycarbonyl)amino)cyclobutyl)-5-methyl-6-(8-methyl-[1,2,4]triazolo[1,5-a]pyridin-6-yl)-1H-indazole-1-carboxylate (37 mg, 0.069 mmol, 30.7% yield) mixed with de-iodinated azetidine starting material in a 3:1 ratio favoring the desired product, carried forward as mixture. MS ($M^{+1}$) m/z: 533 ($MH^+$). LC retention time 1.04 min [A1].

Step 4:

tert-Butyl 3-(3-((tert-butoxycarbonyl)amino)cyclobutyl)-5-methyl-6-(8-methyl-[1,2,4]triazolo[1,5-a]pyridin-6-yl)-1H-indazole-1-carboxylate (32 mg, 0.060 mmol) was treated with TFA/DCM (1:1) for 1 hour. LCMS showed removal of both Boc groups. The mixture was concentrated in vacuo, chasing twice with DCM. The resulting product and $Et_3N$ (0.042 mL, 0.300 mmol) were mixed in DCM (1 mL). Formaldehyde (0.045 mL, 0.601 mmol) was added to the reaction vial followed by sodium triacetoxyborohydride (50.9 mg, 0.240 mmol). The reaction vial was sealed and the reaction mixture was stirred overnight. The reaction was quenched with MeOH. Next, 6 N HCl was added. The reaction mixture was heated to 80° C. for 2 hours. Solvents were removed in vacuo, and then taken up in MeOH and purified by preparative HPLC to afford two isomers:

Example 6: Isomer 1: N,N-dimethyl-3-(5-methyl-6-(8-methyl-[1,2,4]triazolo[1,5-a] pyridin-6-yl)-1H-indazol-3-yl)cyclobutan-1-amine (5.4 mg, 0.015 mmol, 24.94% yield). MS ($M^{+1}$) m/z: 361.1 ($MH^+$). LC retention time 0.92 min [QC-ACN-AA-XB]. $^1$H NMR (500 MHz, DMSO-$d_6$) δ 12.87 (s, 1H), 8.83 (s, 1H), 8.52 (s, 1H), 7.64 (s, 1H), 7.53 (s, 1H), 7.45 (s, 1H), 4.04-3.92 (m, 1H), 3.89 (br d, J=15.9 Hz, 1H), 2.75 (s, 7H), 2.65 (br s, 2H), 2.63-2.60 (m, 3H), 2.58-2.53 (m, 1H), 2.32 (s, 3H)

Example 7: Isomer 2: N,N-dimethyl-3-(5-methyl-6-(8-methyl-[1,2,4]triazolo[1,5-a] pyridin-6-yl)-1H-indazol-3-yl)cyclobutan-1-amine (1.6 mg, 4.30 µmol, 7.16% yield). MS ($M^{+1}$) m/z: 361.0 ($MH^+$). LC retention time 0.96 min [QC-ACN-AA-XB]. $^1$H NMR (500 MHz, DMSO-$d_6$) δ

12.87 (s, 1H), 8.83 (s, 1H), 8.52 (br s, 1H), 7.74 (s, 1H), 7.54 (s, 1H), 7.44 (s, 1H), 3.83-3.70 (m, 1H), 3.67-3.52 (m, 1H), 3.48-3.37 (m, 1H), 3.24-3.16 (m, 1H), 2.83-2.76 (m, 2H), 2.77-2.71 (m, 6H), 2.66-2.59 (m, 3H), 2.33 (s, 3H)

Example 8

2-(4-(4-ethyl-6-(8-methyl-[1,2,4]triazolo[1,5-a]pyridin-6-yl)-1H-indazol-3-yl)piperidin-1-yl)-N,N-dimethylacetamide (8)

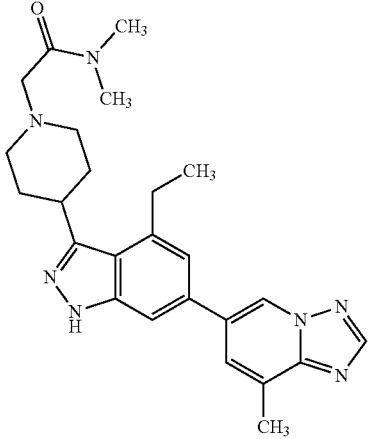

Step 1:
To a mixture of 6-chloro-4-vinyl-1H-indazole [INT-1], (365 mg, 2.043 mmol), 8-methyl-6-(4,4,5,5-tetramethyl-1,3,2-dioxaborolan-2-yl)-[1,2,4]triazolo[1,5-a]pyridine (794 mg, 3.07 mmol), and 2ND generation XPHOS precatalyst (80 mg, 0.102 mmol) in dioxane (14 mL) was added 2M $K_3PO_4$ (3.07 mL, 6.13 mmol). The reaction mixture was sparged with nitrogen for 5 minutes. The reaction vessel was sealed and heated at 95° C. overnight. The reaction mixture was diluted with DCM, then dried with $MgSO_4$, filtered and concentrated. The crude material was purified on a silica gel cartridge (40 g) using an MeOH/DCM gradient (0-10% MeOH over 15 min) to afford 8-methyl-6-(4-vinyl-1H-indazol-6-yl)-[1,2,4]triazolo[1,5-a]pyridine (430 mg, 1.562 mmol, 76% yield). MS ($M^{+1}$) m/z: 276.2 (MH$^+$). LC retention time 0.74 min [A1].

Step 2:
To a mixture of 8-methyl-6-(4-vinyl-1H-indazol-6-yl)-[1,2,4]triazolo[1,5-a]pyridine (430 mg, 1.562 mmol) in MeOH (15 mL) was added was added Pd/C (60 mg). The reaction mixture was hydrogenated under a balloon of $H_2$ overnight. The catalyst was removed by filtration. The residue was concentrated in vacuo. The crude product was dissolved in DCM (10 mL), and NBS (284 mg, 1 eq) was added. The mixture was stirred for one hour. The crude material was purified on a silica gel cartridge (12 g) using an EtOAc/Hex gradient (0-100% EtOAc over 13 min) to afford 6-(3-bromo-4-ethyl-1H-indazol-6-yl)-8-methyl-[1,2,4]triazolo[1,5-a] pyridine (520 mg, 1.460 mmol, 91% yield). MS ($M^{+1}$) m/z: 355.9 (MH$^+$). LC retention time 0.89 min [A1].

Step 3:
To a mixture of 6-(3-bromo-4-ethyl-1H-indazol-6-yl)-8-methyl-[1,2,4]triazolo[1,5-a] pyridine (220 mg, 0.618 mmol), tert-butyl 4-(4,4,5,5-tetramethyl-1,3,2-dioxaborolan-2-yl)-3,6-dihydropyridine-1(2H)-carboxylate (286 mg, 0.926 mmol), and 2ND generation XPHOS precatalyst (24.30 mg, 0.031 mmol) in dioxane (10 mL) was added 2M $K_3PO_4$ (0.926 mL, 1.853 mmol). The reaction mixture was sparged with nitrogen for 5 minutes. The reaction vessel was sealed and heated at 85° C. overnight. The reaction mixture was diluted with DCM, then dried with $MgSO_4$, filtered and concentrated. The crude material was purified on a silica gel cartridge (24 g) using an MeOH/DCM gradient (0-10% MeOH over 12 min) to afford tert-butyl 4-(4-ethyl-6-(8-methyl-[1,2,4]triazolo[1,5-a]pyridin-6-yl)-1H-indazol-3-yl)-3,6-dihydropyridine-1(2H)-carboxylate (265 mg, 0.578 mmol, 94% yield). MS ($M^{+1}$) m/z: 459.2 (MH$^+$). LC retention time 0.95 min [A1].

Step 4:
To a mixture of tert-butyl 4-(4-ethyl-6-(8-methyl-[1,2,4]triazolo[1,5-a]pyridin-6-yl)-1H-indazol-3-yl)-3,6-dihydropyridine-1(2H)-carboxylate (265 mg, 0.578 mmol) and ammonium formate (364 mg, 5.78 mmol) in MeOH (10 mL) was added Pd—C (61.5 mg, 0.578 mmol). The vial was sealed and heated at 60° C. After 2 hours, LCMS indicated that the reaction had occurred. The catalyst was removed by filtration. The reaction mixture was diluted with dichloromethane and washed with saturated NaCl. The organic layer was dried with $MgSO_4$, filtered and concentrated. This crude product was treated with TFA/DCM (1:1, 10 mL) for one hour. Solvents were removed in vacuo to afford 6-(4-ethyl-3-(piperidin-4-yl)-1H-indazol-6-yl)-8-methyl-[1,2,4]triazolo[1,5-a]pyridine, TFA (230 mg, 0.485 mmol, 84% yield). MS ($M^{+1}$) m/z: 361.6 (MH$^+$). LC retention time 0.75 min [A1].

Step 5:
To a mixture of 6-(4-ethyl-3-(piperidin-4-yl)-1H-indazol-6-yl)-8-methyl-[1,2,4]triazolo[1,5-a]pyridine, TFA (25 mg, 0.053 mmol) and potassium carbonate (14.56 mg, 0.105 mmol) in DMF was added 2-chloro-N,N-dimethylacetamide (9.61 mg, 0.079 mmol). The reaction mixture was stirred overnight. Solids were removed by filtration and the residue was purified by preparative HPLC to afford 2-(4-(4-ethyl-6-(8-methyl-[1,2,4]triazolo[1,5-a]pyridin-6-yl)-1H-indazol-3-yl)piperidin-1-yl)-N,N-dimethylacetamide (4 mg, 8.77 µmol, 16.65% yield). MS ($M^{+1}$) m/z: 446.4 (MH$^+$). LC retention time 1.22 min [QC-ACN-AA-XB]. $^1$H NMR (500 MHz, DMSO-d$_6$) δ 9.10 (s, 1H), 8.46 (s, 1H), 7.88 (s, 1H), 7.63 (s, 1H), 7.27 (s, 1H), 3.17-3.02 (m, 3H), 2.99 (br d, J=11.4 Hz, 2H), 2.85 (br s, 1H), 2.65 (s, 3H), 2.51-2.50 (m, 6H), 2.32-2.18 (m, 2H), 2.01-1.89 (m, 4H), 1.86 (s, 1H), 1.37 (t, J=7.5 Hz, 3H).

Example 9

6-(5-isopropyl-3-(1-propylpiperidin-4-yl)-1H-indazol-6-yl)-8-methyl-[1,2,4]triazolo[1,5-a] pyridine (9)

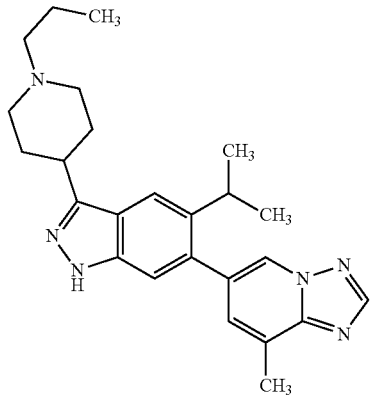

Step 1:

To a mixture of 1-(6-chloro-5-isopropyl-1H-indazol-1-yl)ethan-1-one [INT-2](700 mg, 2.96 mmol), 8-methyl-6-(4,4,5,5-tetramethyl-1,3,2-dioxaborolan-2-yl)-[1,2,4]triazolo[1,5-a]pyridine (920 mg, 3.55 mmol), and 2ND generation XPHOS precatalyst (116 mg, 0.148 mmol) in dioxane (10 mL) was added 2M $K_3PO_4$ (2.96 mL, 5.91 mmol). The reaction mixture was sparged with nitrogen for 5 minutes. The reaction vessel was sealed and heated at 95° C. overnight. LCMS showed some remaining starting material. Additional 2ND generation XPHOS precatalyst (50 mg) and 8-methyl-6-(4,4,5,5-tetramethyl-1,3,2-dioxaborolan-2-yl)-[1,2,4]triazolo[1,5-a]pyridine (200 mg) were added. The reaction vessel was re-sparged, sealed, and heated overnight. The reaction mixture was diluted with dichloromethane and the residue was dried with $MgSO_4$, filtered and concentrated. The crude material was purified on a silica gel cartridge (40 g) using a MeOH/DCM gradient (0-10% MeOH over 15 min) to afford 6-(5-isopropyl-1H-indazol-6-yl)-8-methyl-[1,2,4]triazolo[1,5-a]pyridine (860 mg, 2.95 mmol, 100% yield). MS ($M^{+1}$) m/z: 292.1 ($MH^+$). LC retention time 0.79 min [A1].

Step 2:

To a mixture of 6-(5-isopropyl-1H-indazol-6-yl)-8-methyl-[1,2,4]triazolo[1,5-a]pyridine (340 mg, 1.167 mmol) in DCM was added NBS (208 mg, 1.167 mmol). After stirring 1 hour, the crude material was purified on a silica gel cartridge (24 g) using a MeOH/DCM gradient (0-10% MeOH over 12 min) to afford 6-(3-bromo-5-isopropyl-1H-indazol-6-yl)-8-methyl-[1,2,4]triazolo[1,5-a]pyridine (300 mg, 0.810 mmol, 69.4% yield). MS ($M^{+1}$) m/z: 372.0 ($MH^+$). LC retention time 0.91 min [A1].

Step 3:

To a mixture of 6-(3-bromo-5-isopropyl-1H-indazol-6-yl)-8-methyl-[1,2,4]triazolo[1,5-a]pyridine (300 mg, 0.810 mmol), tert-butyl 4-(4,4,5,5-tetramethyl-1,3,2-dioxaborolan-2-yl)-3,6-dihydropyridine-1(2H)-carboxylate (376 mg, 1.215 mmol), and 2ND generation XPHOS precatalyst (31.9 mg, 0.041 mmol) in dioxane (15 mL) was added 2M $K_3PO_4$ (0.810 mL, 1.621 mmol). The reaction mixture was sparged with nitrogen for 5 minutes. The reaction vessel was sealed and heated at 95° C. overnight. The reaction mixture was diluted with dichloromethane, dried with $MgSO_4$, filtered and concentrated. The crude material was purified on a silica gel cartridge (40 g) using a MeOH/DCM gradient (0-10% MeOH over 15 min) to afford tert-butyl 4-(5-isopropyl-6-(8-methyl-[1,2,4]triazolo[1,5-a] pyridin-6-yl)-1H-indazol-3-yl)-3,6-dihydropyridine-1(2H)-carboxylate (270 mg, 0.571 mmol, 70.5% yield). MS ($M^{+1}$) m/z: 473.2 ($MH^+$). LC retention time 1.01 min [A1].

Step 4:

To a mixture of tert-butyl 4-(5-isopropyl-6-(8-methyl-[1,2,4]triazolo[1,5-a]pyridin-6-yl)-1H-indazol-3-yl)-3,6-dihydropyridine-1(2H)-carboxylate (270 mg, 0.571 mmol) in MeOH (10 mL) was added Pd—C (60.8 mg, 0.571 mmol). The reaction mixture was hydrogenated on a Parr apparatus at 45 psi overnight. LCMS showed partial reaction. Additional Pd—C (60.8 mg, 0.571 mmol) was added and the hydrogenation step was repeated as described above. After shaking overnight, LCMS shows complete reduction. The reaction vessel was evacuated and backfilled with nitrogen (3×). The catalyst was removed by filtration. The mixture was concentrated. The residue was treated with DCM/TFA (1:1) for 30 minutes and solvents were removed in vacuo. MS ($M^{+1}$) m/z: 375.1 ($MH^+$). LC retention time 0.62 min [A1].

Step 5:

To a mixture of 6-(5-isopropyl-3-(piperidin-4-yl)-1H-indazol-6-yl)-8-methyl-[1,2,4]triazolo[1,5-a]pyridine, TFA (50 mg, 0.102 mmol) and propionaldehyde (29.7 mg, 0.512 mmol) in DMF (1 mL) was added TEA (0.071 mL, 0.512 mmol). The reaction mixture was stirred for 30 minutes and sodium triacetoxyborohydride (108 mg, 0.512 mmol) was added. The reaction mixture was stirred overnight at room temperature. The reaction was quenched with MeOH (0.5 mL). The mixture was filtered and purified by preparative HPLC to afford 6-(5-isopropyl-3-(1-propylpiperidin-4-yl)-1H-indazol-6-yl)-8-methyl-[1,2,4]triazolo[1,5-a]pyridine (9.7 mg, 0.023 mmol, 22.64% yield). MS ($M^{+1}$) m/z: 417.4 ($MH^+$). LC retention time 1.2 min [QC-ACN-AA-XB]. $^1$H NMR (500 MHz, DMSO-$d_6$) δ 8.77 (s, 1H), 8.50 (s, 1H), 7.79 (s, 1H), 7.45 (s, 1H), 7.32 (s, 1H), 3.14-2.92 (m, 4H), 2.60 (s, 3H), 2.31 (br t, J=7.3 Hz, 2H), 2.18-2.05 (m, 2H), 1.99-1.91 (m, 4H), 1.59-1.43 (m, 2H), 1.17 (br d, J=6.4 Hz, 6H), 0.88 (br t, J=7.3 Hz, 3H).

Intermediate 4

2-bromo-1-ethyl-4-fluorobenzene

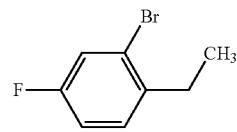

(INT-4)

Step 1:

To a mixture of methyltriphenylphosphonium iodide (5.97 g, 14.78 mmol) in THF (20 mL) at 0° C. was added BuLi (5.91 mL, 14.78 mmol) dropwise over 10 minutes. The reaction mixture was stirred for an additional 30 minutes, then 2-bromo-4-fluorobenzaldehyde (2.5 g, 12.31 mmol) was added dropwise. The reaction mixture was stirred for 15 minutes at 0° C., then allowed to warm to room temperature. The reaction mixture was stirred for 3 hours. The reaction was quenched with the addition of water. The reaction mixture was diluted with dichloromethane and washed with saturated NaCl. The organic layer was dried with $MgSO_4$, filtered and concentrated. The crude material was purified on a silica gel cartridge using DCM (100%) to afford 2-bromo-4-fluoro-1-vinylbenzene (1.5 g, 7.46 mmol, 60.6% yield). $^1$H NMR (499 MHz, CHLOROFORM-d) δ 7.55 (dd, J=8.7, 6.0 Hz, 1H), 7.32 (dd, J=8.3, 2.6 Hz, 1H), 7.08-6.95 (m, 2H), 5.66 (d, J=17.3 Hz, 1H), 5.37 (d, J=11.0 Hz, 1H).

Step 2:

To a mixture of 2-bromo-4-fluoro-1-vinylbenzene (600 mg, 2.98 mmol) and sodium acetate trihydrate (2031 mg, 14.92 mmol) in THF (10 mL) was added 4-methylbenzenesulfonhydrazide (2779 mg, 14.92 mmol). The reaction mixture was heated at 80° C. for 12 h, and then cooled to room temperature. The mixture was concentrated under reduced pressure to a volume of approximately 5 mL. Hexane (15 mL) was added to the reaction mixture, leading to precipitation of a solid. The solid was removed by filtration and washed with hexane (15 mL×3), followed by Et$_2$O (10 mL). The filtrate was concentrated under reduced pressure to give 2-bromo-1-ethyl-4-fluorobenzene (550 mg, 2.71 mmol, 91% yield). $^1$H NMR (499 MHz, CHLOROFORM-d) δ 7.32-7.28 (m, 2H), 7.21 (dd, J=8.5, 6.1 Hz, 1H), 6.99 (td, J=8.3, 2.7 Hz, 1H), 2.74 (q, J=7.5 Hz, 2H), 1.23 (t, J=7.5 Hz, 3H).

SCHEME 2

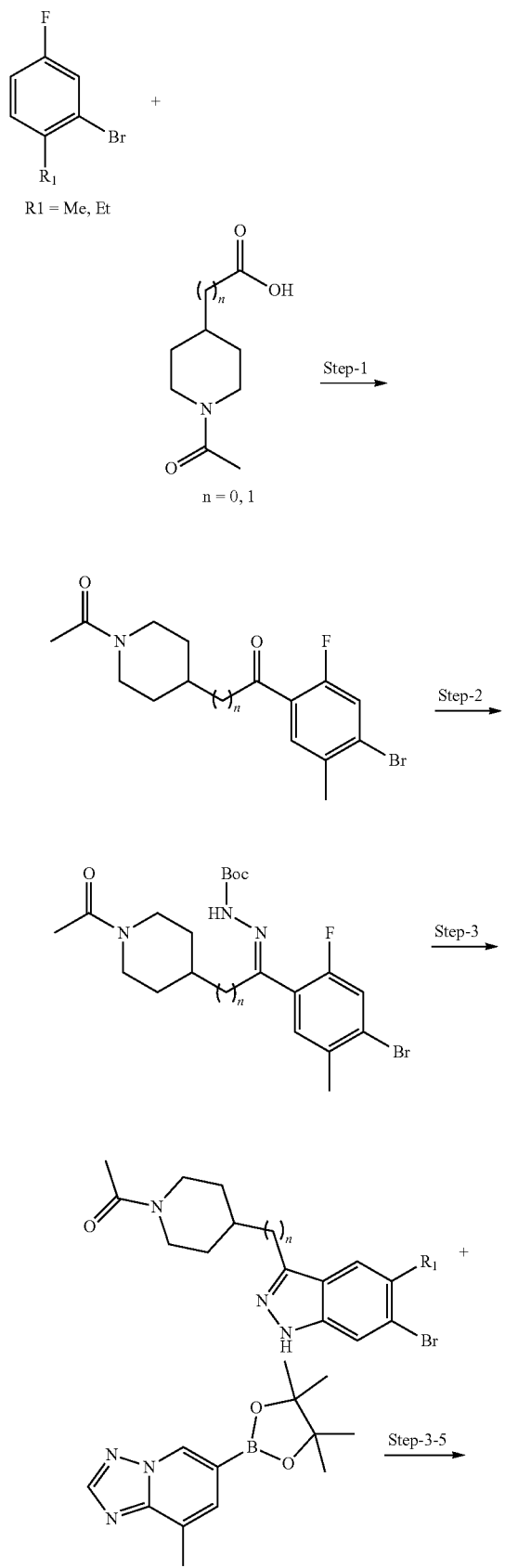

R1 = Me, Et n = 0, 1

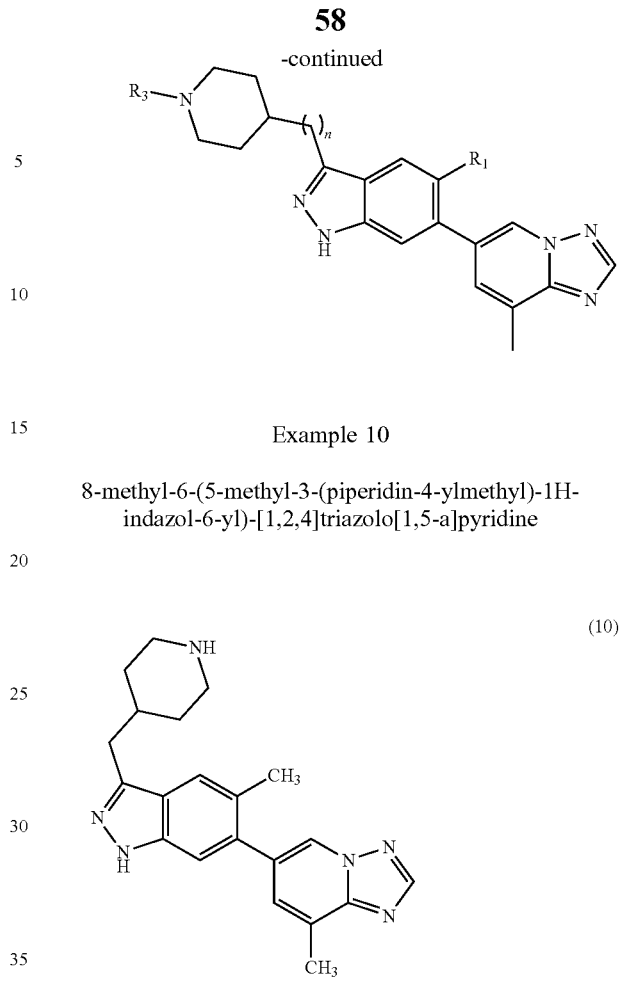

Example 10

8-methyl-6-(5-methyl-3-(piperidin-4-ylmethyl)-1H-indazol-6-yl)-[1,2,4]triazolo[1,5-a]pyridine (10)

Step 1:

Thionyl chloride (2.70 ml, 5.40 mmol) was added to 2-(1-acetylpiperidin-4-yl)acetic acid (1 g, 5.40 mmol). The reaction mixture was stirred overnight at room temperature. Thionyl chloride was removed in vacuo by chasing twice with CHCl$_3$. To this mixture was added 2-bromo-4-fluoro-1-methylbenzene (1.334 ml, 10.80 mmol) followed by the portion wise addition of aluminum chloride (1.440 g, 10.80 mmol) (5 portions over 30 min.). After the addition was complete, the reaction mixture was slowly warmed to 80° C. and heated for 2 hours. Next, the mixture was poured onto ice and then extracted with DCM. The residue was dried over MgSO$_4$, filtered and concentrated. The crude material was purified on a silica gel cartridge (80 g) using an EtOAc/Hex gradient (100% hexane for 5 minutes then 0-100% EtOAc over 15 min). Product fractions were isolated, concentrated, and dried in vacuo to afford 2-(1-acetylpiperidin-4-yl)-1-(4-bromo-2-fluoro-5-methylphenyl)ethan-1-one (1.7 g, 4.77 mmol, 88% yield). $^1$H NMR (499 MHz, CDCl$_3$) δ 7.72 (d, J=7.8 Hz, 1H), 7.39 (d, J=10.3 Hz, 1H), 4.62 (dt, J=13.2, 1.9 Hz, 1H), 3.90-3.74 (m, 1H), 3.11 (td, J=13.0, 2.7 Hz, 1H), 2.89 (td, J=6.2, 3.0 Hz, 2H), 2.62 (td, J=12.8, 2.8 Hz, 1H), 2.42 (s, 3H), 2.34-2.17 (m, 1H), 2.10 (s, 3H), 1.93-1.73 (m, 2H), 1.40-1.13 (m, 2H).

Step 2:

To a mixture of 2-(1-acetylpiperidin-4-yl)-1-(4-bromo-2-fluoro-5-methylphenyl) ethan-1-one (1.7 g, 4.77 mmol) in ethanol (20 mL) was added tert-butyl hydrazinecarboxylate (1.261 g, 9.54 mmol). The reaction vessel was sealed and heated at 85° C. overnight. Next, the reaction mixture was cooled and solvent was removed. The crude material was purified on a silica gel cartridge (40 g) using an EtOAc/Hex gradient (0-100% EtOAc over 15 min) to afford tert-butyl (E)-2-(2-(1-acetylpiperidin-4-yl)-1-(4-bromo-2-fluoro-5-methylphenyl)ethylidene)hydrazine-1-carboxylate (1.8 g, 3.83 mmol, 80% yield). MS (M+1) m/z: 470/472 (MH+). LC retention time 1.01 min [A1].

Step 3:

To a mixture of tert-butyl (E)-2-(2-(1-acetylpiperidin-4-yl)-1-(4-bromo-2-fluoro-5-methylphenyl)ethylidene)hydrazine-1-carboxylate (800 mg, 1.701 mmol) in DCM (10 mL) was added TFA (5 mL). The reaction mixture was stirred for one hour. Solvents were removed in vacuo. Ethylene glycol (5 mL) was added to the residue. Next, the reaction mixture was heated in a sealed vessel at 130° C. overnight. The mixture was cooled and the crude material was purified on a silica gel cartridge (40 g) using a MeOH/DCM gradient (0-15% MeOH over 18 min) to afford 1-(4-((6-bromo-5-methyl-1H-indazol-3-yl)methyl) piperidin-1-yl)ethan-1-one (210 mg, 0.600 mmol, 35.3% yield). MS (M+1) m/z: 350/352 (MH+). LC retention time 0.86 min [A1].

Step 4:

To a mixture of 1-(4-((6-bromo-5-methyl-1H-indazol-3-yl)methyl)piperidin-1-yl) ethan-1-one (28.0 mg, 0.080 mmol), 8-methyl-6-(4,4,5,5-tetramethyl-1,3,2-dioxaborolan-2-yl)-[1,2,4]triazolo[1,5-a]pyridine (31.1 mg, 0.120 mmol), and 2nd generation XPHOS precatalyst (3.14 mg, 4.00 μmol) in dioxane (2 mL) was added 2M $K_3PO_4$ (0.120 mL, 0.240 mmol). The reaction mixture was sparged with nitrogen for 5 minutes. The reaction vessel was sealed and heated at 85° C. over the weekend. LCMS shows desired product mass and no remaining starting material. Next, 6 N HCl (1 mL) was heated and the mixture was heated at 85° C. for 2 hours. Solvents were removed under a stream of nitrogen and then dissolved in DMF, filtered and purified by preparative HPLC to afford 8-methyl-6-(5-methyl-3-(piperidin-4-ylmethyl)-1H-indazol-6-yl)-[1,2,4]triazolo[1,5-a]pyridine (9.4 mg, 0.025 mmol, 31.6% yield). MS (M+1) m/z: 361.4 (MH+). LC retention time 0.91 min [QC-ACN-AA-XB]. $^1$H NMR (500 MHz, DMSO-$d_6$) δ 8.79 (s, 1H), 8.50 (s, 1H), 7.68 (s, 1H), 7.53 (s, 1H), 7.42 (s, 1H), 3.17 (s, 2H), 2.87 (br d, J=7.0 Hz, 2H), 2.72-2.63 (m, 2H), 2.60 (s, 3H), 2.31 (s, 3H), 2.04-1.90 (m, 1H), 1.75-1.64 (m, 2H), 1.33 (br d, J=11.6 Hz, 2H).

The following examples were prepared according to the general procedures for Examples 1-10.

TABLE 1

| Ex. No. | Obs. MS Ion | Ret time (min) | HPLC |
|---|---|---|---|
| 1 | 346.2 | 0.92 | QC-ACN-AA-XB |

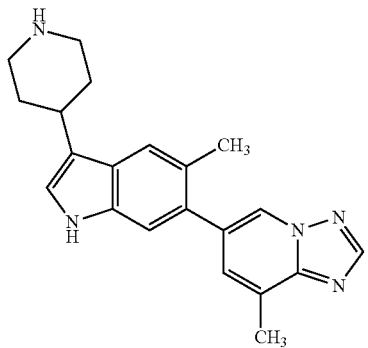 [SMILES: Cc1cc2c(C3CCNCC3)c[nH]c2cc1-c1cc(C)c2ncnn2c1]

| 2 | 346.1 | 0.95 | QC-ACN-AA-XB |

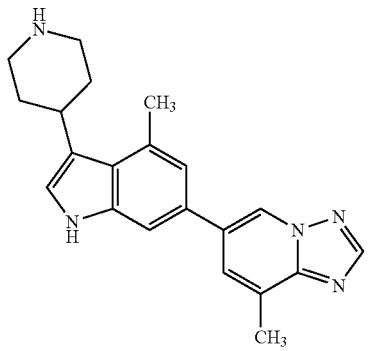 [SMILES: Cc1cc(-c2cc(C)c3ncnn3c2)cc2[nH]cc(C3CCNCC3)c12]

TABLE 1-continued
| Ex. No. | | Obs. MS Ion | Ret time (min) | HPLC |
|---|---|---|---|---|
| 3 | 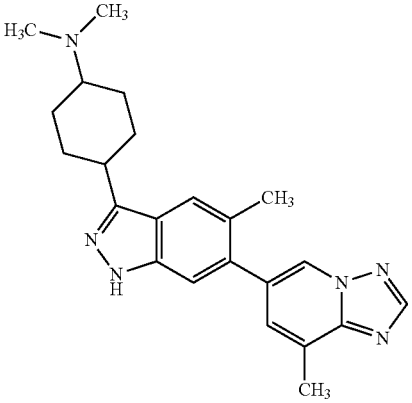 [SMILES: Cc1cc2c(C3CCC(N(C)C)CC3)n[nH]c2cc1-c1cc(C)c2ncnn2c1] | 389.2 | 0.88 | QC-ACN-TFA-XB |
| 4 | 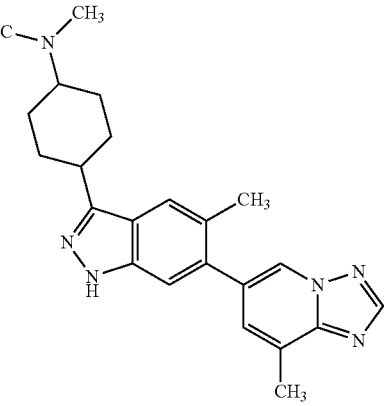 | 389.2 | 1 | QC-ACN-TFA-XB |
| 5 | 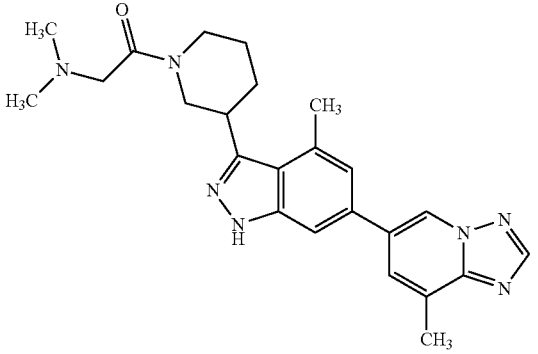 [SMILES: Cc1cc(-c2cc(C)c3ncnn3c2)cc2[nH]nc(C3CCCN(C(=O)CN(C)C)C3)c12] | 432.3 | 1 | QC-ACN-TFA-XB |
| 6 | 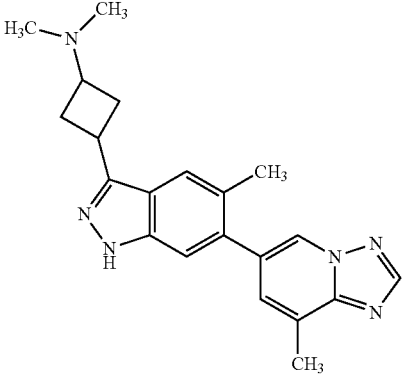 [SMILES: Cc1cc2c(C3CC(N(C)C)C3)n[nH]c2cc1-c1cc(C)c2ncnn2c1] | 363.3 | 0.85 | QC-ACN-TFA-XB |

TABLE 1-continued

| Ex. No. | Obs. MS Ion | Ret time (min) | HPLC |
|---|---|---|---|
| 7 | 361.1 | 0.96 | QC-ACN-AA-XB |
| 8 | 446.3 | 0.99 | QC-ACN-TFA-XB |
| 9 | 417.4 | 1.2 | QC-ACN-TFA-XB |
| 10 | 361.4 | 0.91 | QC-ACN-AA-XB |

TABLE 1-continued

| Ex. No. | Structure | Obs. MS Ion | Ret time (min) | HPLC |
|---|---|---|---|---|
| 11 | | 348.1 | 0.80 | QC-ACN-AA-XB |
| 12 | | 332.1 | 0.93 | QC-ACN-AA-XB |
| 13 | | 375.2 | 0.76 | QC-ACN-AA-XB |
| 14 | | 374.1 | 1.09 | QC-ACN-AA-XB |

TABLE 1-continued
| Ex. No. | | Obs. MS Ion | Ret time (min) | HPLC |
|---|---|---|---|---|
| 15 | 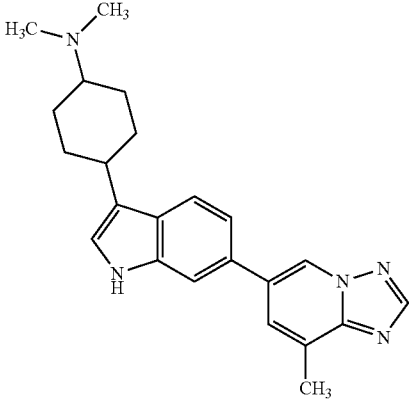 [SMILES: Cc1cc(-c2ccc3c(C4CCC(N(C)C)CC4)c[nH]c3c2)cn2ncnc12] | 374.1 | 1.0 | QC-ACN-AA-XB |
| 16 | 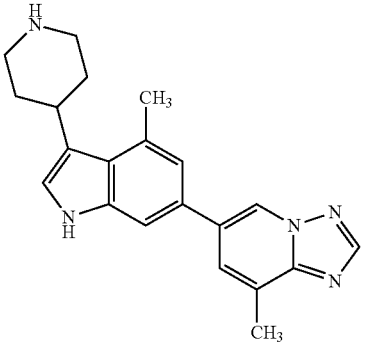 [SMILES: Cc1cc(-c2cc(C)c3ncnn3c2)cc2[nH]cc(C3CCNCC3)c12] | 346.2 | 1.08 | QC-ACN-AA-XB |
| 17 | 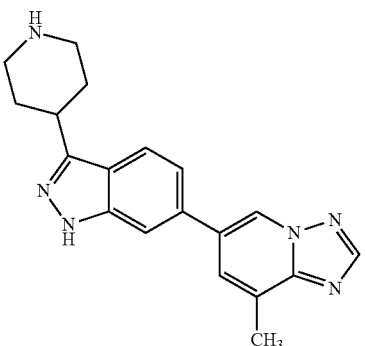 | 333.1 | 0.77 | QC-ACN-AA-XB |
| 18 | 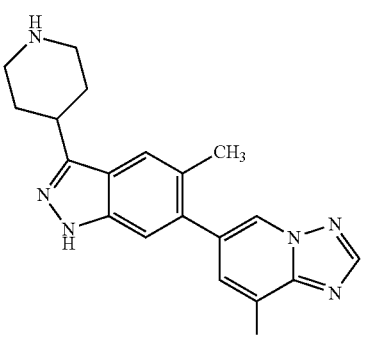 | 347.2 | 0.81 | QC-ACN-TFA-XB |

TABLE 1-continued
| Ex. No. | | Obs. MS Ion | Ret time (min) | HPLC |
|---|---|---|---|---|
| 19 | 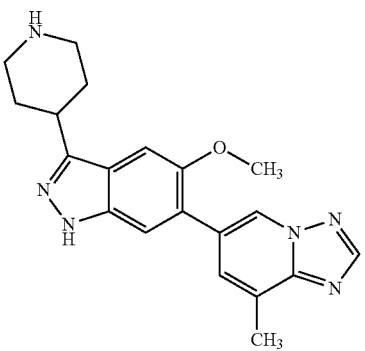 | 363.1 | 1.16 | QC-ACN-AA-XB |
| 20 | 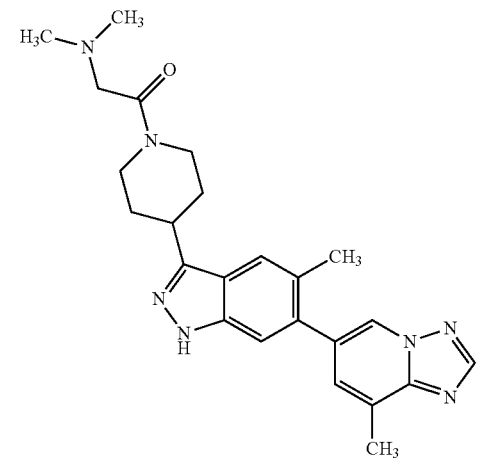 [SMILES: Cc1cc2c(C3CCN(C(=O)CN(C)C)CC3)n[nH]c2cc1-c1cc(C)c2ncnn2c1] | 432.1 | 0.96 | QC-ACN-TFA-XB |
| 21 | 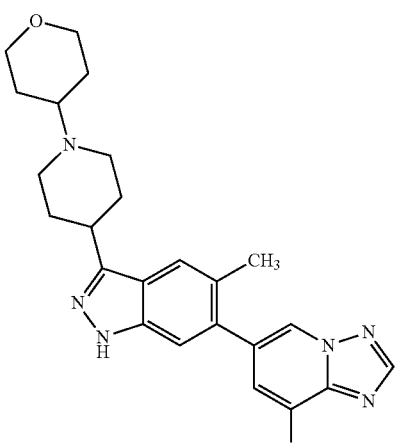 | 431.4 | 0.96 | QC-ACN-AA-XB |

TABLE 1-continued

| Ex. No. | Structure | Obs. MS Ion | Ret time (min) | HPLC |
|---|---|---|---|---|
| 22 | | 389.1 | 1.14 | QC-ACN-AA-XB |
| 23 | | 432.1 | 0.96 | QC-ACN-AA-XB |
| 24 | | 347.4 | 0.88 | QC-ACN-TFA-XB |
| 25 | | 337.2 | 0.73 | QC-ACN-AA-XB |

TABLE 1-continued
| Ex. No. | | Obs. MS Ion | Ret time (min) | HPLC |
|---|---|---|---|---|
| 26 | 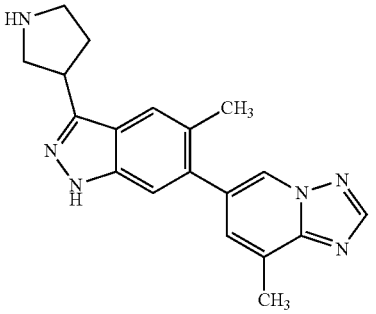 [SMILES: Cc1cc2c(C3CCNC3)n[nH]c2cc1-c1cc(C)c2ncnn2c1] | 333.1 | 0.75 | QC-ACN-AA-XB |
| 27 | 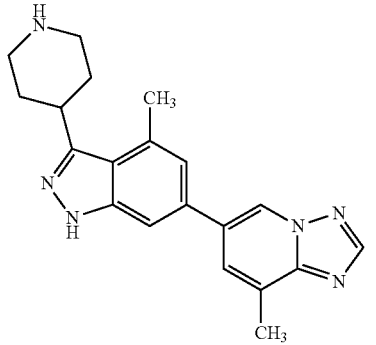 [SMILES: Cc1cc(-c2cc(C)c3ncnn3c2)cc2[nH]nc(C3CCNCC3)c12] | 347.2 | 0.88 | QC-ACN-AA-XB |
| 28 | 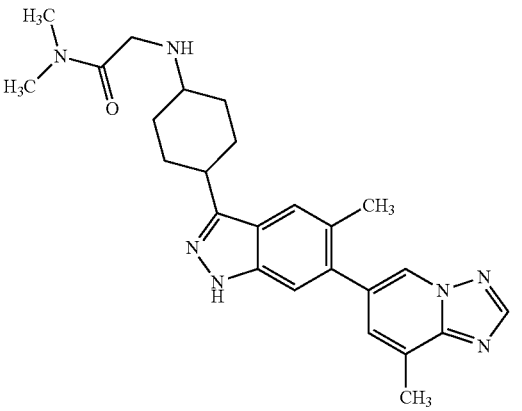 [SMILES: Cc1cc2c(C3CCC(NCC(=O)N(C)C)CC3)n[nH]c2cc1-c1cc(C)c2ncnn2c1] | 446.2 | 0.92 | QC-ACN-TFA-XB |
| 29 | 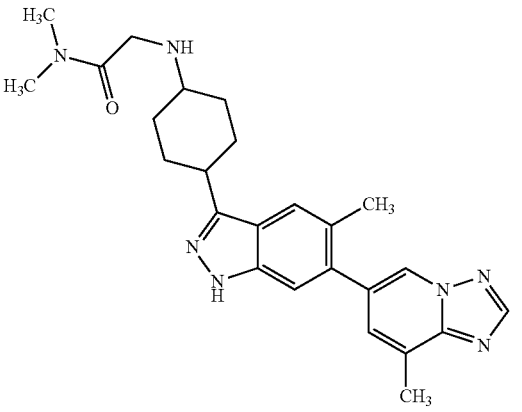 [SMILES: Cc1cc2c(C3CCC(NCC(=O)N(C)C)CC3)n[nH]c2cc1-c1cc(C)c2ncnn2c1] | 446.3 | 1.13 | QC-ACN-AA-XB |

TABLE 1-continued
| Ex. No. | | Obs. MS Ion | Ret time (min) | HPLC |
|---|---|---|---|---|
| 30 | 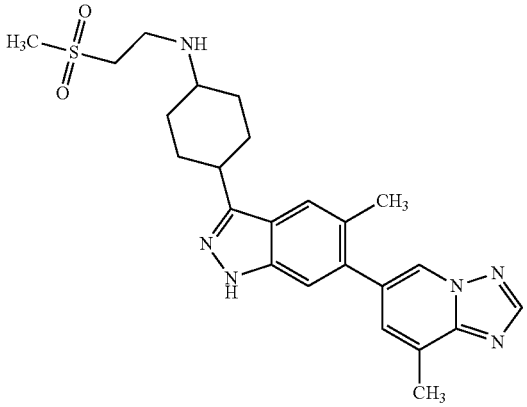 [SMILES: Cc1cc2c(C3CCC(NCCS(C)(=O)=O)CC3)n[nH]c2cc1-c1cc(C)c2ncnn2c1] | 467.1 | 0.96 | QC-ACN-AA-XB |
| 31 | 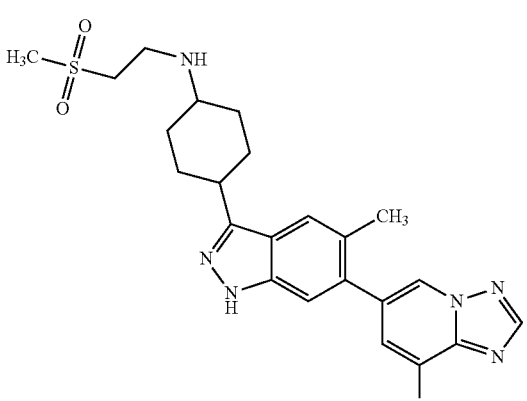 | 467 | 1.2 | QC-ACN-AA-XB |
| 32 | 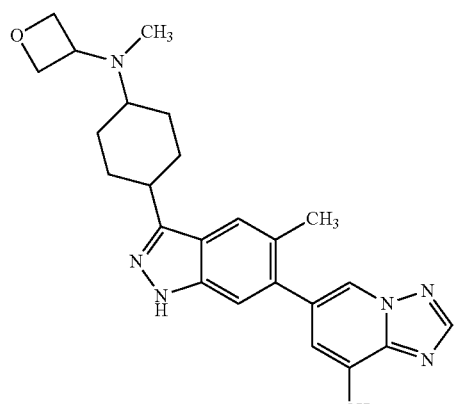 | 430.9 | 1.09 | QC-ACN-TFA-XB |

TABLE 1-continued

| Ex. No. | | Obs. MS Ion | Ret time (min) | HPLC |
|---|---|---|---|---|
| 33 | | 431.2 | 1.19 | QC-ACN-AA-XB |
| 34 | | 416.9 | 1.05 | QC-ACN-AA-XB |
| 35 | | 417.1 | 1.24 | QC-ACN-AA-XB |

TABLE 1-continued
| Ex. No. | | Obs. MS Ion | Ret time (min) | HPLC |
|---|---|---|---|---|
| 36 | 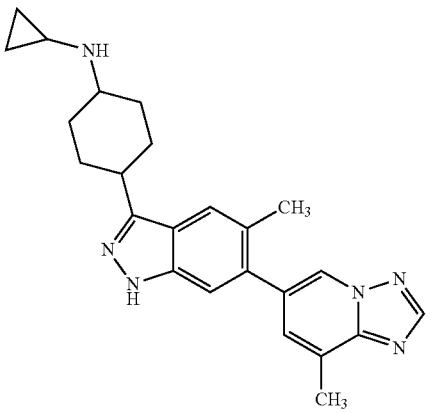 [SMILES: Cc1cc2c(C3CCC(NC4CC4)CC3)n[nH]c2cc1-c1cc(C)c2ncnn2c1] | 401.2 | 0.95 | QC-ACN-TFA-XB |
| 37 | 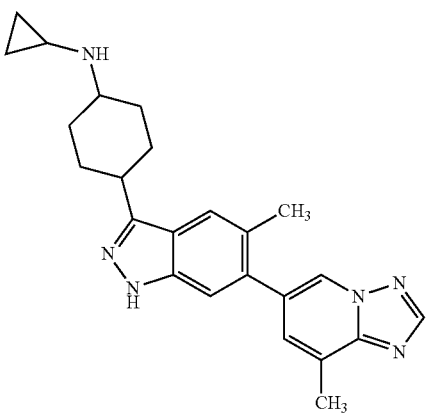 [SMILES: Cc1cc2c(C3CCC(NC4CC4)CC3)n[nH]c2cc1-c1cc(C)c2ncnn2c1] | 401 | 1.18 | QC-ACN-AA-XB |
| 38 | 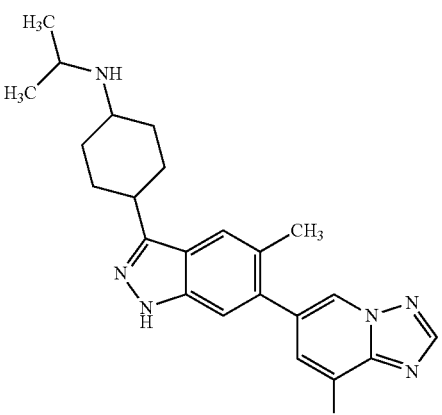 | 403.2 | 0.96 | QC-ACN-AA-XB |

TABLE 1-continued
| Ex. No. | | Obs. MS Ion | Ret time (min) | HPLC |
|---|---|---|---|---|
| 39 | 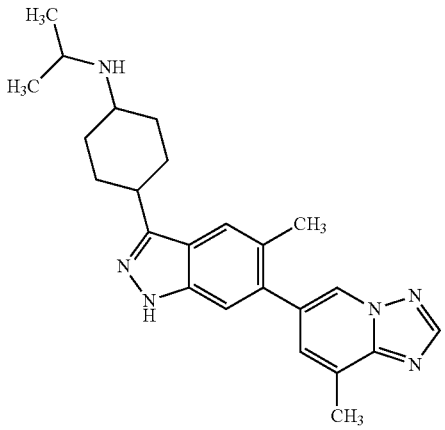 [SMILES: Cc1cc2c(C3CCC(NC(C)C)CC3)n[nH]c2cc1-c1cc(C)c2ncnn2c1] | 403.2 | 1.13 | QC-ACN-TFA-XB |
| 40 | 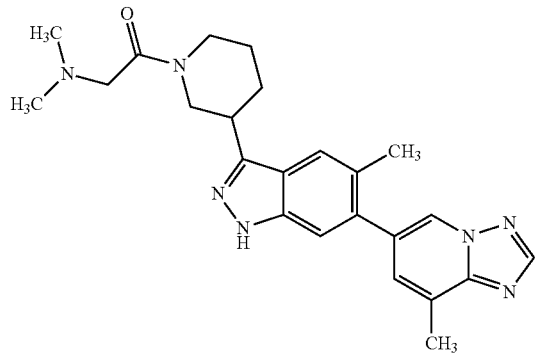 [SMILES: Cc1cc2c(C3CCCN(C(=O)CN(C)C)C3)n[nH]c2cc1-c1cc(C)c2ncnn2c1] | 432.3 | 1.03 | QC-ACN-AA-XB |
| 41 | 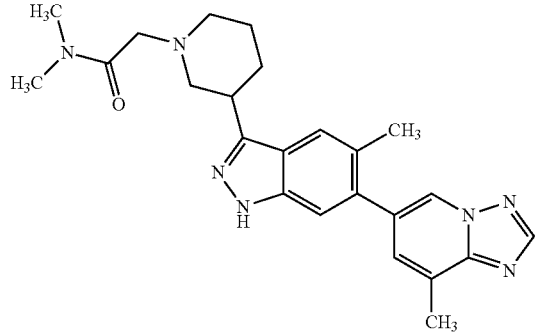 [SMILES: Cc1cc2c(C3CCCN(CC(=O)N(C)C)C3)n[nH]c2cc1-c1cc(C)c2ncnn2c1] | 431.9 | 1.2 | QC-ACN-AA-XB |
| 42 | 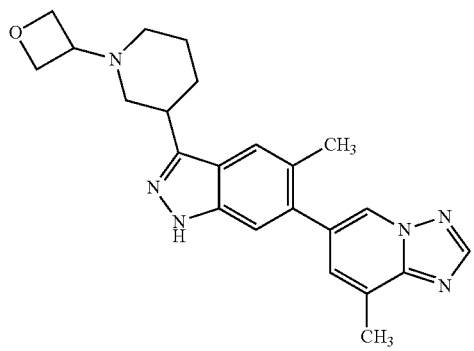 [SMILES: Cc1cc2c(C3CCCN(C4COC4)C3)n[nH]c2cc1-c1cc(C)c2ncnn2c1] | 403.1 | 0.88 | QC-ACN-TFA-XB |

TABLE 1-continued

| Ex. No. | | Obs. MS Ion | Ret time (min) | HPLC |
|---|---|---|---|---|
| 43 | | 431 | 0.95 | QC-ACN-TFA-XB |
| 44 | | 375.2 | 0.86 | QC-ACN-AA-XB |
| 45 | | 363.3 | 0.85 | QC-ACN-TFA-XB |
| 46 | | 337.2 | 0.8 | QC-ACN-AA-XB |

TABLE 1-continued

| Ex. No. | Structure | Obs. MS Ion | Ret time (min) | HPLC |
|---|---|---|---|---|
| 47 | | 346.1 | 0.84 | QC-ACN-TFA-XB |
| 48 | | 361.1 | 0.85 | QC-ACN-TFA-XB |
| 49 | | 319.2 | 0.78 | QC-ACN-AA-XB |
| 50 | | 321.2 | 0.97 | QC-ACN-AA-XB |

TABLE 1-continued

| Ex. No. | Obs. MS Ion | Ret time (min) | HPLC |
|---|---|---|---|
| 51 | 347.1 | 0.92 | QC-ACN-AA-XB |
| 52 | 431 | 0.95 | QC-ACN-TFA-XB |
| 53 | 431.9 | 0.94 | QC-ACN-TFA-XB |
| 54 | 432.1 | 0.99 | QC-ACN-TFA-XB |

TABLE 1-continued

| Ex. No. | Structure | Obs. MS Ion | Ret time (min) | HPLC |
|---|---|---|---|---|
| 55 | (structure) | 431.3 | 0.95 | QC-ACN-TFA-XB |
| 56 | (structure) | 432.1 | 0.99 | QC-ACN-TFA-XB |
| 57 | (structure) | 432.2 | 1.15 | QC-ACN-AA-XB |
| 58 | (structure) | 333.2 | 0.82 | QC-ACN-TFA-XB |

TABLE 1-continued
| Ex. No. | | Obs. MS Ion | Ret time (min) | HPLC |
|---|---|---|---|---|
| 59 | 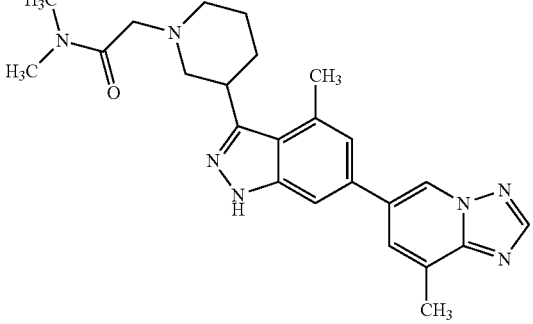 | 432.3 | 1.12 | QC-ACN-AA-XB |
| 60 | 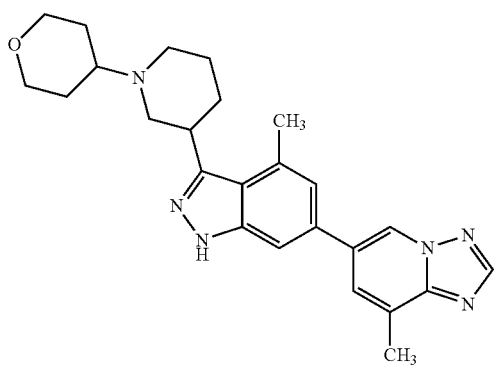 [SMILES: Cc1cc(-c2cc(C)c3ncnn3c2)cc2[nH]nc(C3CCCN(C4CCOCC4)C3)c12] | 431.3 | 0.96 | QC-ACN-TFA-XB |
| 61 | 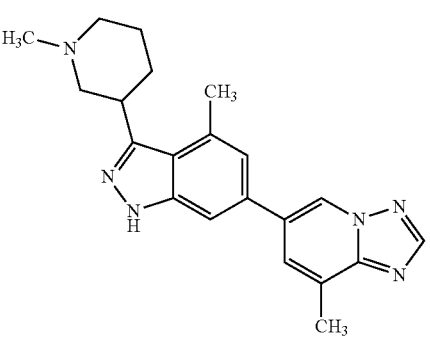 [SMILES: Cc1cc(-c2cc(C)c3ncnn3c2)cc2[nH]nc(C3CCCN(C)C3)c12] | 361.1 | 0.92 | QC-ACN-TFA-XB |
| 62 | 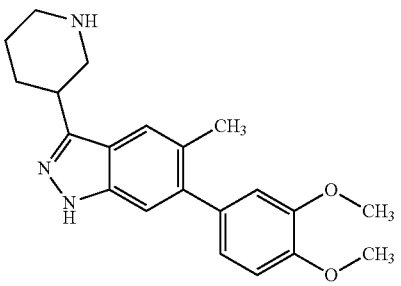 [SMILES: COc1ccc(-c2cc3[nH]nc(C4CCCNC4)c3cc2C)cc1OC] | 352.2 | 1.29 | QC-ACN-AA-XB |
| 63 | 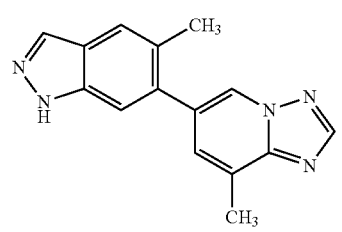 [SMILES: Cc1cc2cn[nH]c2cc1-c1cc(C)c2ncnn2c1] | 264.2 | 1.31 | QC-ACN-AA-XB |

TABLE 1-continued

| Ex. No. | Structure | Obs. MS Ion | Ret time (min) | HPLC |
|---|---|---|---|---|
| 64 | | 280.2 | 1.25 | QC-ACN-AA-XB |
| 65 | | 264.2 | 1.17 | QC-ACN-TFA-XB |
| 66 | | 280 | 1.11 | QC-ACN-TFA-XB |
| 67 | | 419.3 | 1.08 | QC-ACN-AA-XB |

TABLE 1-continued
| Ex. No. | | Obs. MS Ion | Ret time (min) | HPLC |
|---|---|---|---|---|
| 68 | | 453.2 | 0.91 | QC-ACN-TFA-XB |
| | 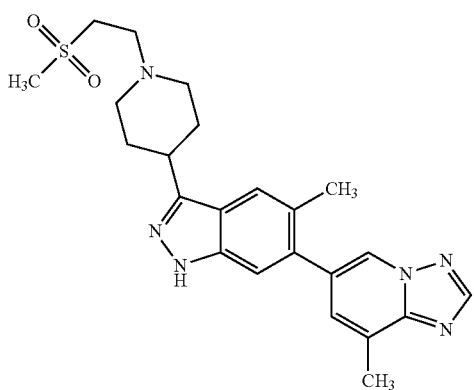 [SMILES: Cc1cc2c(C3CCN(CCS(C)(=O)=O)CC3)n[nH]c2cc1-c1cc(C)c2ncnn2c1] | | | |
| 69 | | 468.1 | 1.01 | QC-ACN-AA-XB |
| | 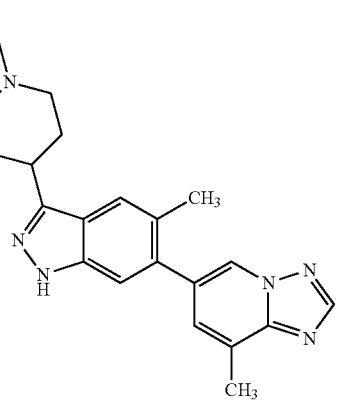 | | | |
| 70 | | 404.1 | 1.08 | QC-ACN-AA-XB |
| | 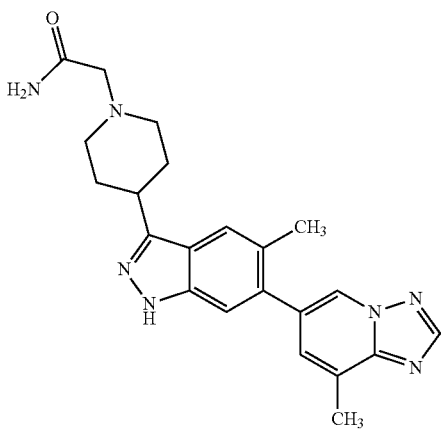 [SMILES: Cc1cc2c(C3CCN(CC(N)=O)CC3)n[nH]c2cc1-c1cc(C)c2ncnn2c1] | | | |

TABLE 1-continued
| Ex. No. | | Obs. MS Ion | Ret time (min) | HPLC |
|---|---|---|---|---|
| 71 | 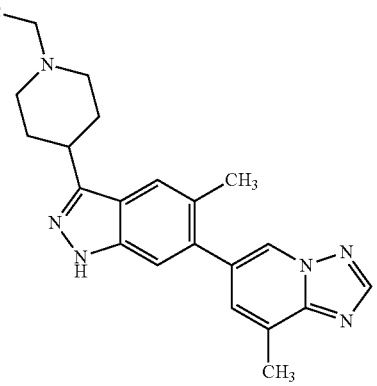 | 386.2 | 1 | QC-ACN-TFA-XB |
| 72 | 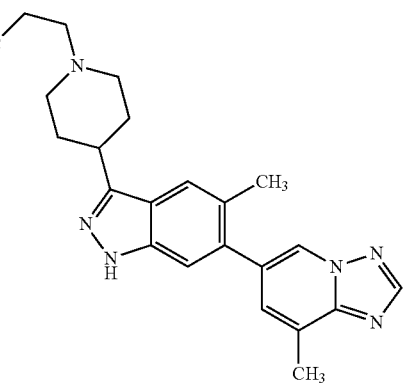 | 400.2 | 0.91 | QC-ACN-TFA-XB |
| 73 | 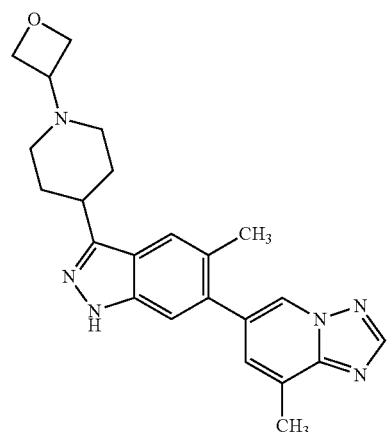 | 403 | 0.84 | QC-ACN-TFA-XB |
| 74 | 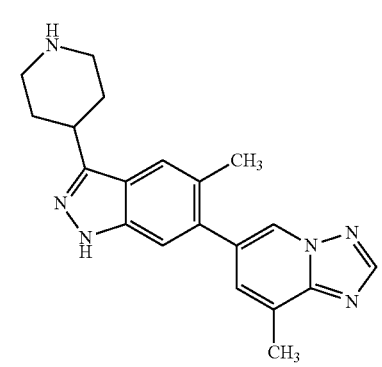 [SMILES: Cc1cc2c(C3CCNCC3)n[nH]c2cc1-c1cc(C)c2ncnn2c1] | 348.2 | 1.05 | QC-ACN-TFA-XB |

TABLE 1-continued

| Ex. No. | | Obs. MS Ion | Ret time (min) | HPLC |
|---|---|---|---|---|
| 75 | [structure] | 432.3 | 1.03 | QC-ACN-AA-XB |
| 76 | [structure] | 432.3 | 0.87 | QC-ACN-TFA-XB |
| 77 | [structure] | 419.3 | 1.02 | QC-ACN-AA-XB |

TABLE 1-continued
| Ex. No. | | Obs. MS Ion | Ret time (min) | HPLC |
|---|---|---|---|---|
| 78 | 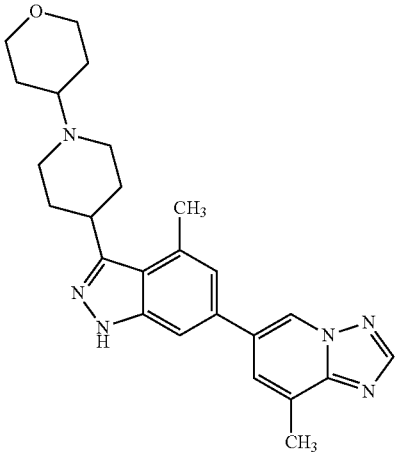 [SMILES: Cc1cc(-c2cc(C)c3ncnn3c2)cc2[nH]nc(C3CCN(C4CCOCC4)CC3)c12] | 431.2 | 0.9 | QC-ACN-TFA-XB |
| 79 | 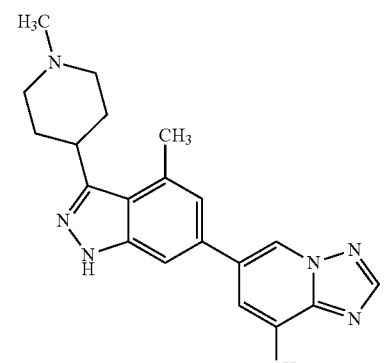 | 361.2 | 1.14 | QC-ACN-AA-XB |
| 80 | 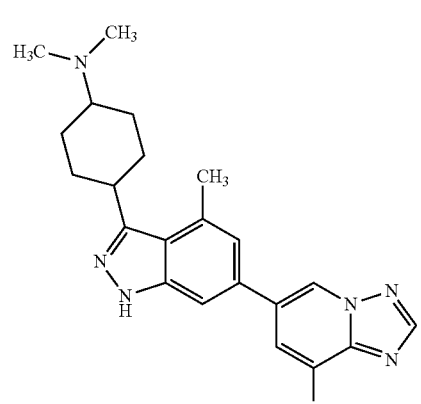 | 388.9 | 1.13 | QC-ACN-AA-XB |

TABLE 1-continued

| Ex. No. | Structure | Obs. MS Ion | Ret time (min) | HPLC |
|---|---|---|---|---|
| 81 | | 389.3 | 1.26 | QC-ACN-AA-XB |
| 82 | | 361.2 | 1 | QC-ACN-TFA-XB |
| 83 | | 361.3 | 0.89 | QC-ACN-AA-XB |
| 84 | | 358.2 | 0.85 | QC-ACN-AA-XB |

TABLE 1-continued
| Ex. No. | | Obs. MS Ion | Ret time (min) | HPLC |
|---|---|---|---|---|
| 85 | | 411.2 | 0.83 | QC-ACN-AA-XB |
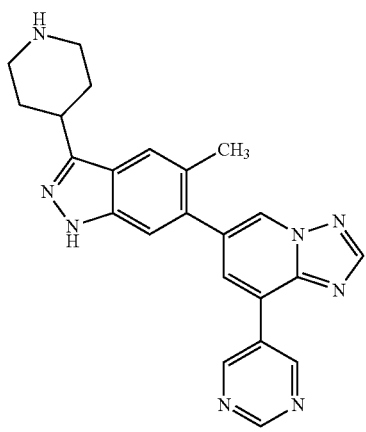 [SMILES: Cc1cc2c(C3CCNCC3)n[nH]c2cc1-c1cc(-c2cncnc2)c2ncnn2c1]
| 86 | | 363.2 | 0.84 | QC-ACN-AA-XB |
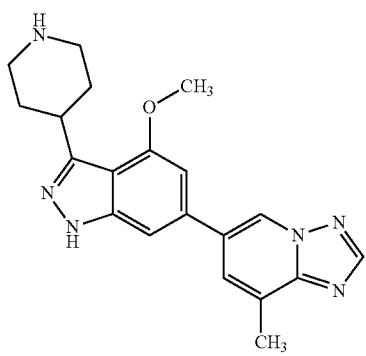 [SMILES: COc1cc(-c2cc(C)c3ncnn3c2)cc2[nH]nc(C3CCNCC3)c12]
| 87 | | 446.3 | 1.05 | QC-ACN-TFA-XB |
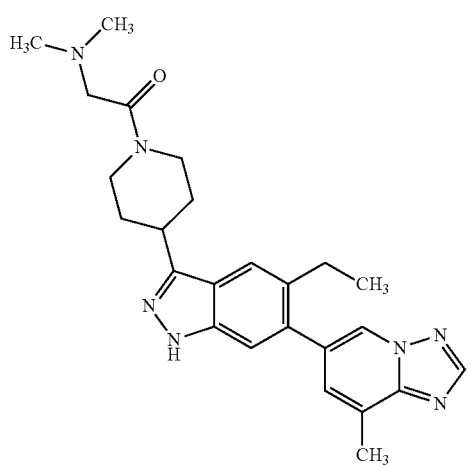 [SMILES: CCc1cc2c(C3CCN(C(=O)CN(C)C)CC3)n[nH]c2cc1-c1cc(C)c2ncnn2c1]

TABLE 1-continued
| Ex. No. | | Obs. MS Ion | Ret time (min) | HPLC |
|---|---|---|---|---|
| 88 | 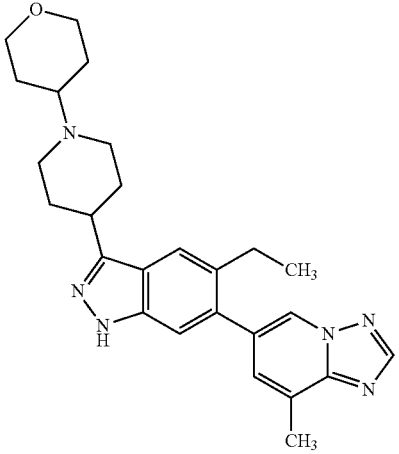 [SMILES: CCc1cc2c(C3CCN(C4CCOCC4)CC3)n[nH]c2cc1-c1cc(C)c2ncnn2c1] | 445.3 | 1.11 | QC-ACN-AA-XB |
| 89 | 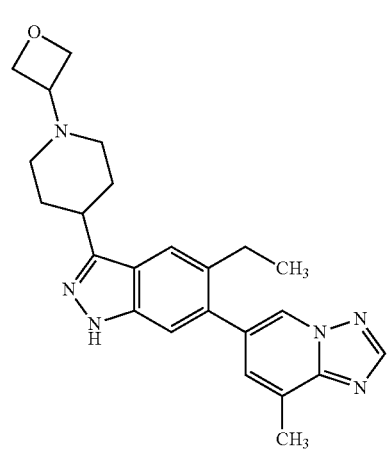 [SMILES: CCc1cc2c(C3CCN(C4COC4)CC3)n[nH]c2cc1-c1cc(C)c2ncnn2c1] | 417.2 | 1.27 | QC-ACN-AA-XB |
| 90 | 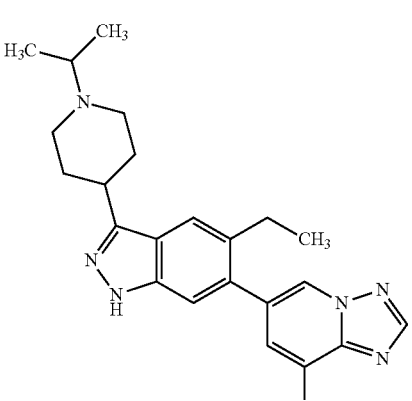 | 403.4 | 1.14 | QC-ACN-AA-XB |

TABLE 1-continued
| Ex. No. | | Obs. MS Ion | Ret time (min) | HPLC |
|---|---|---|---|---|
| 91 | 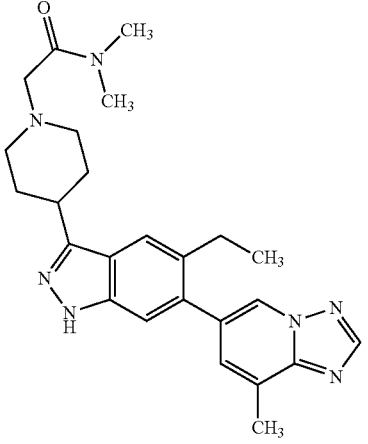 [SMILES: CCc1cc2c(C3CCN(CC(=O)N(C)C)CC3)n[nH]c2cc1-c1cc(C)c2ncnn2c1] | 446.4 | 1.15 | QC-ACN-AA-XB |
| 92 | 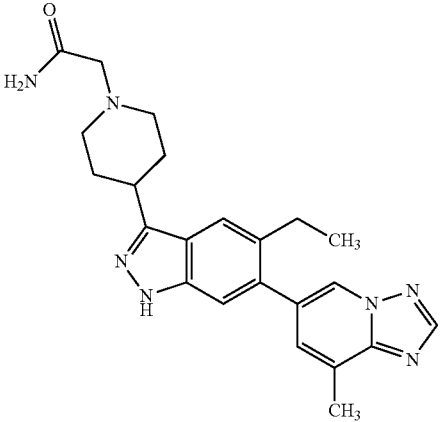 [SMILES: CCc1cc2c(C3CCN(CC(N)=O)CC3)n[nH]c2cc1-c1cc(C)c2ncnn2c1] | 418.3 | 1.17 | QC-ACN-AA-XB |
| 93 | 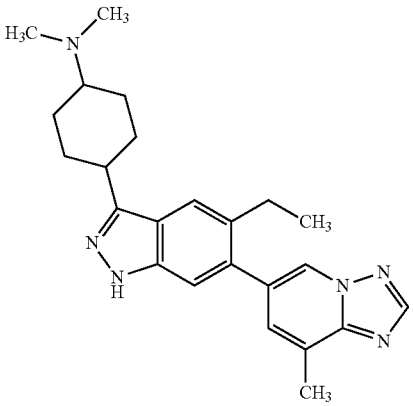 [SMILES: CCc1cc2c(C3CCC(N(C)C)CC3)n[nH]c2cc1-c1cc(C)c2ncnn2c1] | 403.4 | 1.07 | QC-ACN-AA-XB |

TABLE 1-continued
| Ex. No. | | Obs. MS Ion | Ret time (min) | HPLC |
|---|---|---|---|---|
| 94 | 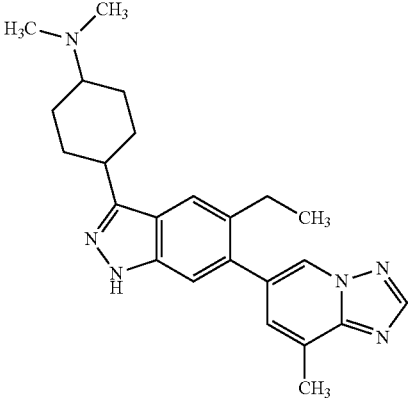 [SMILES: CCc1cc2c(C3CCC(N(C)C)CC3)n[nH]c2cc1-c1cc(C)c2ncnn2c1] | 403.3 | 1.19 | QC-ACN-TFA-XB |
| 95 | 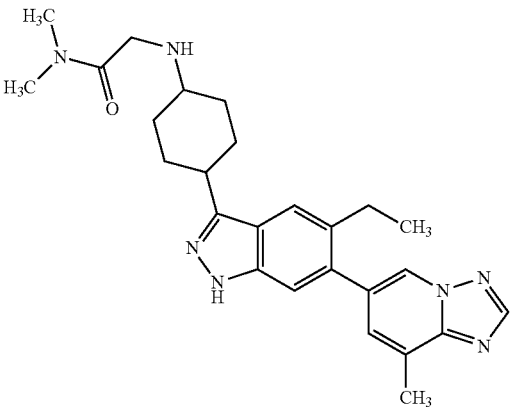 [SMILES: CCc1cc2c(C3CCC(NCC(=O)N(C)C)CC3)n[nH]c2cc1-c1cc(C)c2ncnn2c1] | 460.4 | 1.26 | QC-ACN-AA-XB |
| 96 | 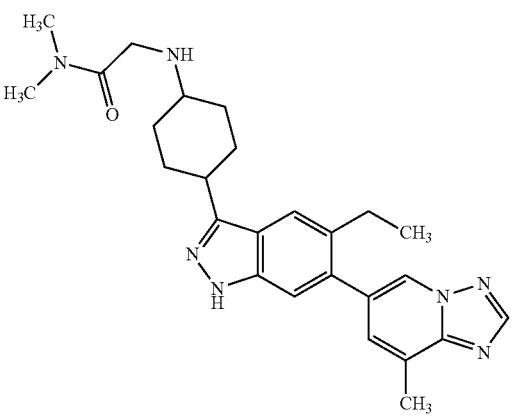 [SMILES: CCc1cc2c(C3CCC(NCC(=O)N(C)C)CC3)n[nH]c2cc1-c1cc(C)c2ncnn2c1] | 460.4 | 1.09 | QC-ACN-AA-XB |

TABLE 1-continued

| Ex. No. | Structure | Obs. MS Ion | Ret time (min) | HPLC |
|---|---|---|---|---|
| 97 | | 415.4 | 1.1 | QC-ACN-TFA-XB |
| 98 | | 415.4 | 1.25 | QC-ACN-TFA-XB |
| 99 | | 481.4 | 1.17 | QC-ACN-AA-XB |

TABLE 1-continued
| Ex. No. | | Obs. MS Ion | Ret time (min) | HPLC |
|---|---|---|---|---|
| 100 | 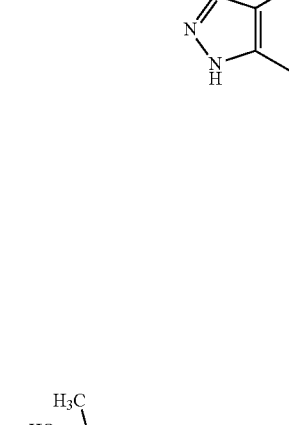 | 481.2 | 1.29 | QC-ACN-AA-XB |
| 101 | 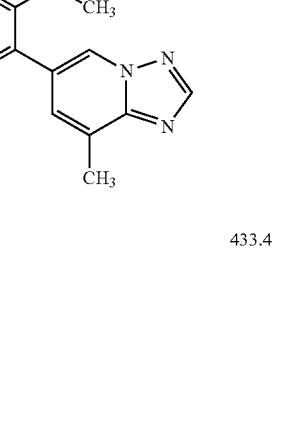 | 433.4 | 1.11 | QC-ACN-AA-XB |
| 102 | 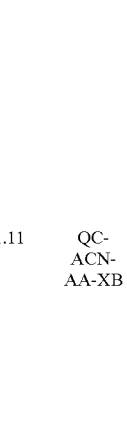 | 375.1 | 1.18 | QC-ACN-AA-XB |

TABLE 1-continued
| Ex. No. | | Obs. MS Ion | Ret time (min) | HPLC |
|---|---|---|---|---|
| 103 | 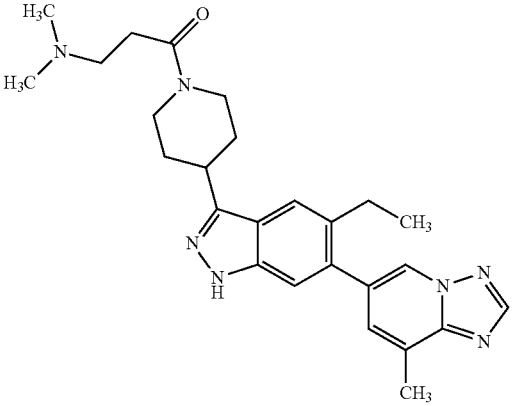 [SMILES: CCc1cc2c(C3CCN(C(=O)CCN(C)C)CC3)n[nH]c2cc1-c1cc(C)c2ncnn2c1] | 460.1 | 1.23 | QC-ACN-AA-XB |
| 104 | 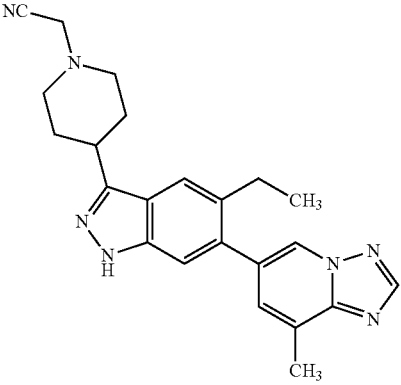 [SMILES: CCc1cc2c(C3CCN(CC#N)CC3)n[nH]c2cc1-c1cc(C)c2ncnn2c1] | 400.3 | 1.55 | QC-ACN-AA-XB |
| 105 | 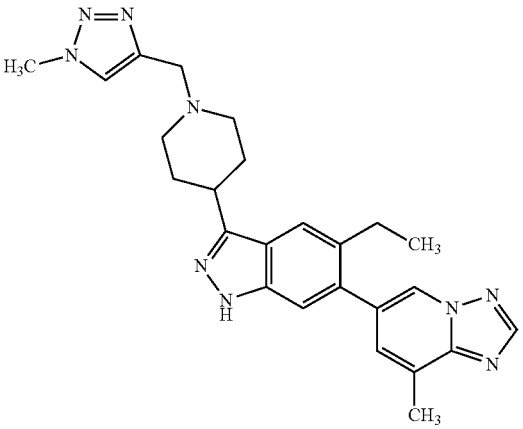 [SMILES: CCc1cc2c(C3CCN(Cc4cn(C)nn4)CC3)n[nH]c2cc1-c1cc(C)c2ncnn2c1] | 456.4 | 0.99 | QC-ACN-TFA-XB |

TABLE 1-continued

| Ex. No. | Structure | Obs. MS Ion | Ret time (min) | HPLC |
|---|---|---|---|---|
| 106 | | 414.4 | 1.43 | QC-ACN-AA-XB |
| 107 | | 474.5 | 1.1 | QC-ACN-TFA-XB |
| 108 | | 457 | 1.39 | QC-ACN-TFA-XB |
| 109 | | 361.1 | 1.14 | QC-ACN-TFA-XB |

TABLE 1-continued
| Ex. No. | | Obs. MS Ion | Ret time (min) | HPLC |
|---|---|---|---|---|
| 110 | 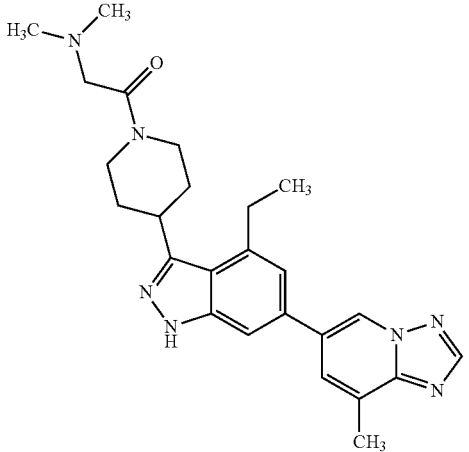 [SMILES: CCc1cc(-c2cc(C)c3ncnn3c2)cc2[nH]nc(C3CCN(C(=O)CN(C)C)CC3)c12] | 446.1 | 1.38 | QC-ACN-AA-XB |
| 111 | | 460.2 | 1.27 | QC-ACN-AA-XB |
| 112 | 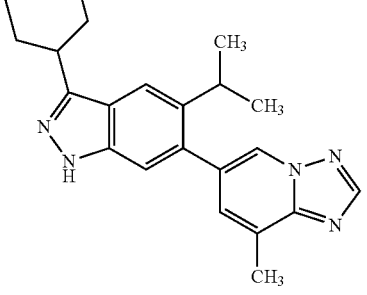 | 460.2 | 1.41 | QC-ACN-AA-XB |

TABLE 1-continued
| Ex. No. | | Obs. MS Ion | Ret time (min) | HPLC |
|---|---|---|---|---|
| 113 | 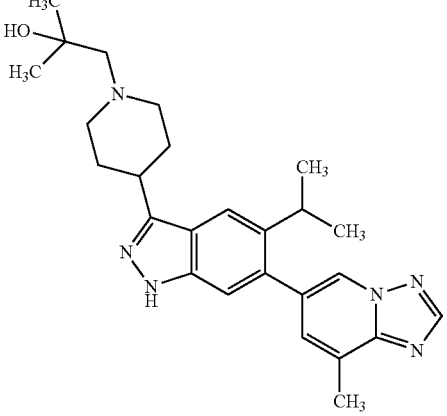 [SMILES: Cc1cc(-c2cc3[nH]nc(C4CCN(CC(C)(C)O)CC4)c3cc2C(C)C)cn2ncnc12] | 446.9 | 1.34 | QC-ACN-AA-XB |
| 114 | 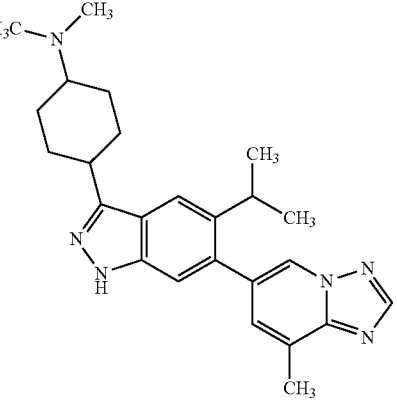 | 417.1 | 1.2 | QC-ACN-TFA-XB |
| 115 | 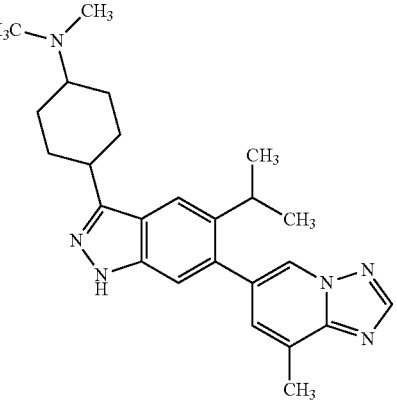 | 417.5 | 1.3 | QC-ACN-AA-XB |

TABLE 1-continued
| Ex. No. | | Obs. MS Ion | Ret time (min) | HPLC |
|---|---|---|---|---|
| 116 | 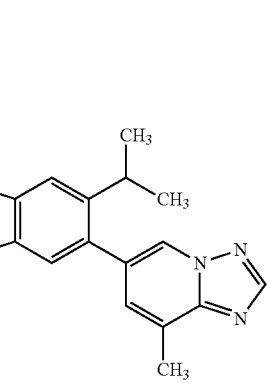 | 459.5 | 1.13 | QC-ACN-TFA-XB |
| 117 |  | 476.2 | 1.33 | QC-ACN-TFA-XB |
| 118 | 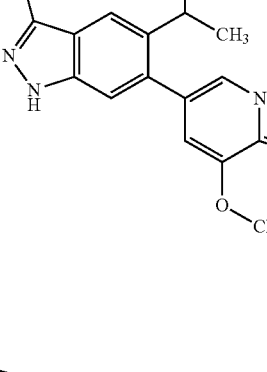 | 429 | 1.41 | QC-ACN-AA-XB |

TABLE 1-continued

| Ex. No. | | Obs. MS Ion | Ret time (min) | HPLC |
|---|---|---|---|---|
| 119 | | 428.9 | 1.55 | QC-ACN-AA-XB |
| 120 | | 431.3 | 1.48 | QC-ACN-AA-XB |
| 121 | | 428.4 | 1.63 | QC-ACN-AA-XB |

TABLE 1-continued
| Ex. No. | | Obs. MS Ion | Ret time (min) | HPLC |
|---|---|---|---|---|
| 122 | 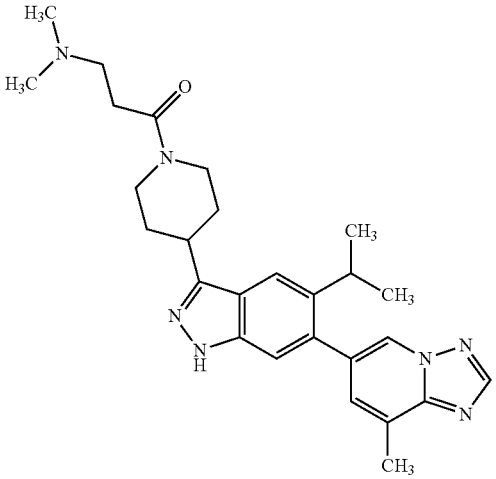 [SMILES: Cc1cc(-c2cc3[nH]nc(C4CCN(C(=O)CCN(C)C)CC4)c3cc2C(C)C)cn2ncnc12] | 474.2 | 1.32 | QC-ACN-AA-XB |
| 123 | 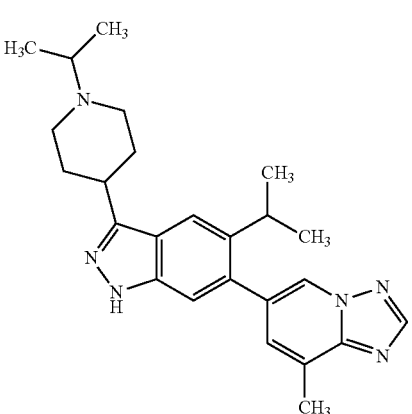 | 417.5 | 1.22 | QC-ACN-AA-XB |
| 124 | 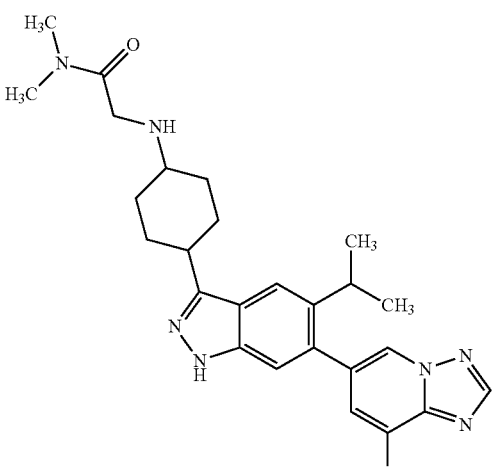 | 474 | 1.36 | QC-ACN-AA-XB |

TABLE 1-continued
| Ex. No. | | Obs. MS Ion | Ret time (min) | HPLC |
|---|---|---|---|---|
| 125 | 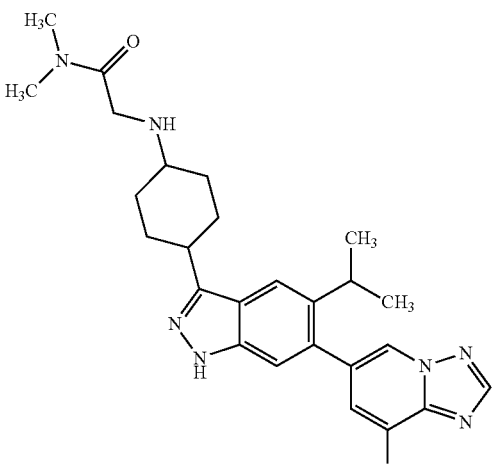 | 474 | 1.54 | QC-ACN-AA-XB |
| 126 | | 495.1 | 1.24 | QC-ACN-AA-XB |
| 127 | 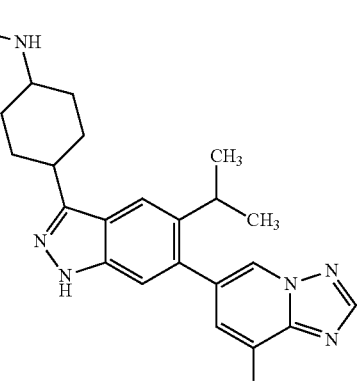 | 495.2 | 1.64 | QC-ACN-AA-XB |

TABLE 1-continued
| Ex. No. | | Obs. MS Ion | Ret time (min) | HPLC |
|---|---|---|---|---|
| 128 | 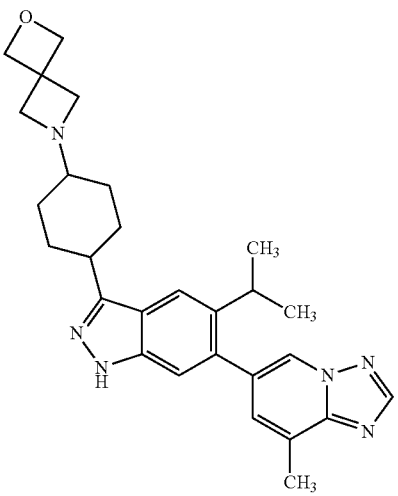 [SMILES: Cc1cc(-c2cc3[nH]nc(C4CCC(N5CC6(COC6)C5)CC4)c3cc2C(C)C)cn2ncnc12] | 470.9 | 1.4 | QC-ACN-AA-XB |
| 129 | 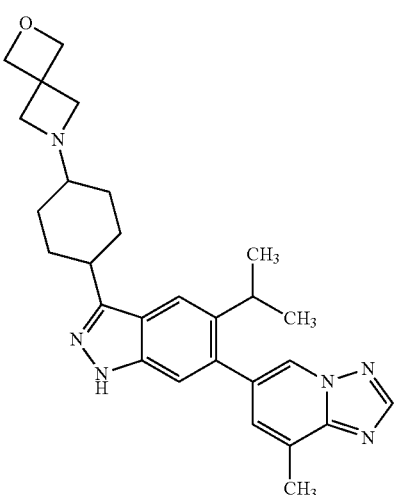 | 471.3 | 1.24 | QC-ACN-TFA-XB |
| 130 | 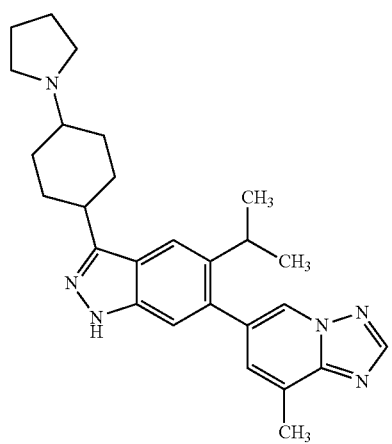 [SMILES: Cc1cc(-c2cc3[nH]nc(C4CCC(N5CCCC5)CC4)c3cc2C(C)C)cn2ncnc12] | 443.2 | 1.23 | QC-ACN-AA-XB |

TABLE 1-continued

| Ex. No. | Structure | Obs. MS Ion | Ret time (min) | HPLC |
|---|---|---|---|---|
| 131 | | 443.3 | 1.35 | QC-ACN-AA-XB |
| 132 | | 459.3 | 1.14 | QC-ACN-TFA-XB |
| 133 | | 459.3 | 1.26 | QC-ACN-TFA-XB |

TABLE 1-continued
| Ex. No. | | Obs. MS Ion | Ret time (min) | HPLC |
|---|---|---|---|---|
| 134 | 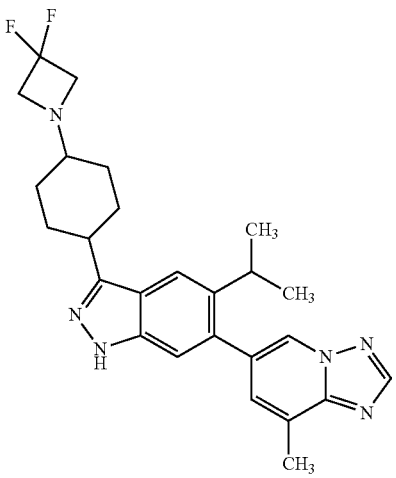 [SMILES: Cc1cc(-c2cc3[nH]nc(C4CCC(N5CC(F)(F)C5)CC4)c3cc2C(C)C)cn2ncnc12] | 464.9 | 1.95 | QC-ACN-AA-XB |
| 135 | 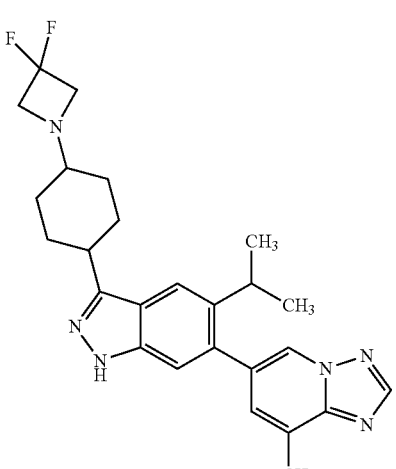 | 465.2 | 2.23 | QC-ACN-AA-XB |
| 136 | 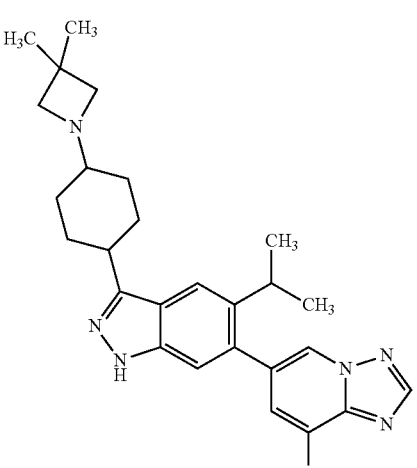 | 457.2 | 1.54 | QC-ACN-AA-XB |

TABLE 1-continued

| Ex. No. | Structure | Obs. MS Ion | Ret time (min) | HPLC |
|---|---|---|---|---|
| 137 | (3,3-dimethylazetidinyl-cyclohexyl-isopropyl-methyl-[1,2,4]triazolo[1,5-a]pyridinyl-indazole) | 457.4 | 1.51 | QC-ACN-AA-XB |
| 138 | (azetidinyl-cyclohexyl-isopropyl-methyl-[1,2,4]triazolo[1,5-a]pyridinyl-indazole) | 428.9 | 1.26 | QC-ACN-TFA-XB |
| 139 | (azetidinyl-cyclohexyl-isopropyl-methyl-[1,2,4]triazolo[1,5-a]pyridinyl-indazole) | 428.9 | 1.54 | QC-ACN-AA-XB |

TABLE 1-continued

| Ex. No. | | Obs. MS Ion | Ret time (min) | HPLC |
|---|---|---|---|---|
| 140 | (structure) | 433.2 | 1.09 | QC-ACN-TFA-XB |
| 141 | (structure) | 433.2 | 1.22 | QC-ACN-TFA-XB |
| 142 | (structure) | 519 | 1.43 | QC-ACN-AA-XB |

TABLE 1-continued
| Ex. No. | | Obs. MS Ion | Ret time (min) | HPLC |
|---|---|---|---|---|
| 143 | 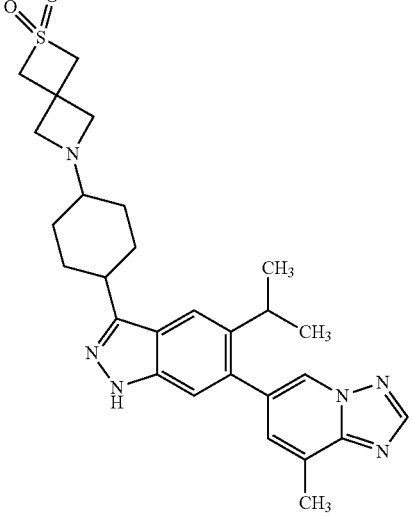 | 519.2 | 1.25 | QC-ACN-TFA-XB |
| 144 | 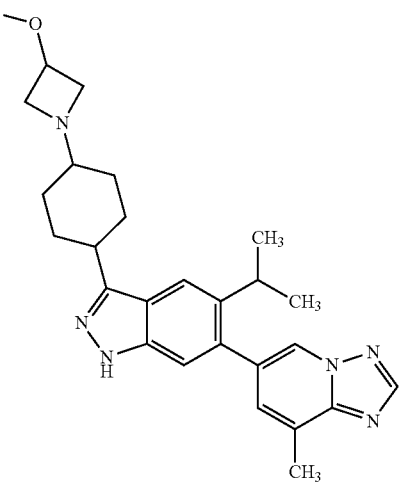 | 459.3 | 1.25 | QC-ACN-TFA-XB |
| 145 | 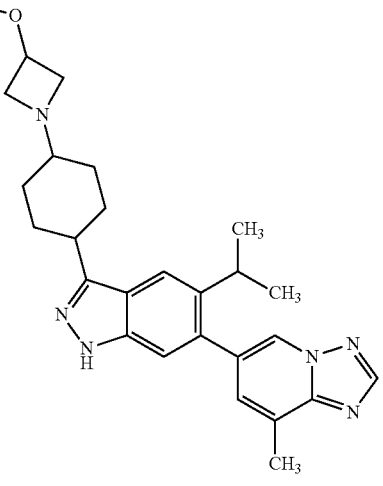 | 459.1 | 1.38 | QC-ACN-TFA-XB |

TABLE 1-continued

| Ex. No. | Structure | Obs. MS Ion | Ret time (min) | HPLC |
|---|---|---|---|---|
| 146 | | 489.3 | 1.15 | QC-ACN-AA-XB |
| 147 | | 476.3 | 1.26 | QC-ACN-AA-XB |
| 148 | | 476.3 | 1.39 | QC-ACN-AA-XB |

TABLE 1-continued
| Ex. No. | | Obs. MS Ion | Ret time (min) | HPLC |
|---|---|---|---|---|
| 149 | 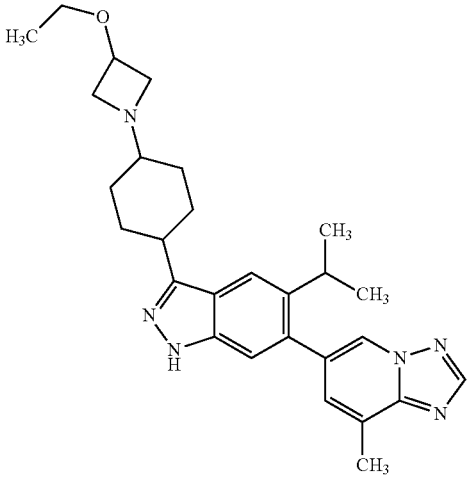 [SMILES: CCOC1CN(C2CCC(c3n[nH]c4cc(-c5cc(C)c6ncnn6c5)c(C(C)C)cc34)CC2)C1] | 473.5 | 1.43 | QC-ACN-AA-XB |
| 150 | 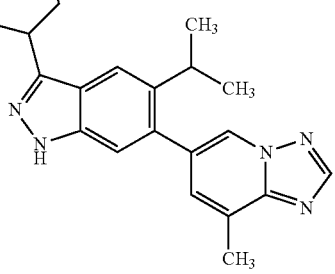 | 473.4 | 1.53 | QC-ACN-AA-XB |
| 151 | 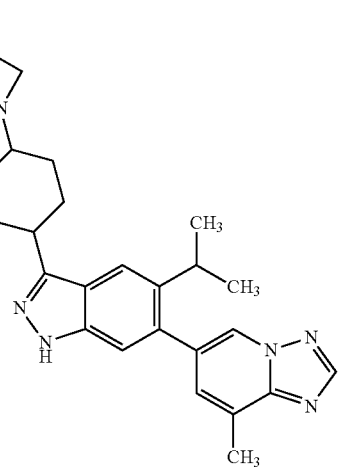 | 447.4 | 1.63 | QC-ACN-AA-XB |

TABLE 1-continued
| Ex. No. | | Obs. MS Ion | Ret time (min) | HPLC |
|---|---|---|---|---|
| 152 | 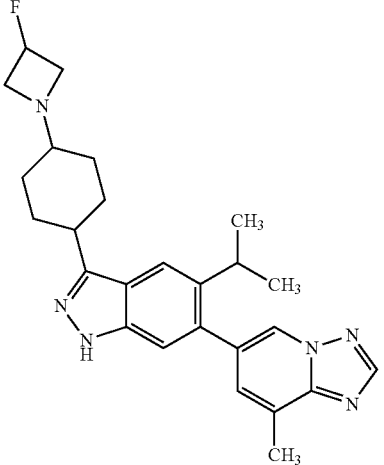 [SMILES: Cc1cc(-c2cc3[nH]nc(C4CCC(N5CC(F)C5)CC4)c3cc2C(C)C)cn2ncnc12] | 447.2 | 1.41 | QC-ACN-AA-XB |
| 153 | 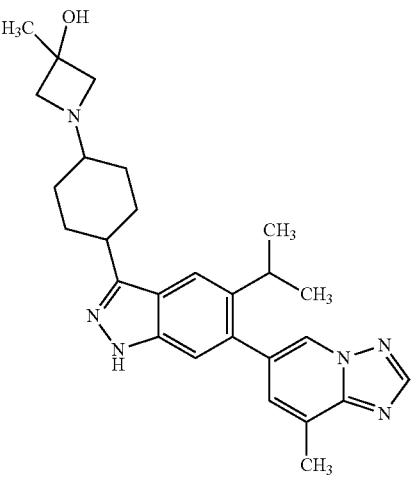 | 459.2 | 1.36 | QC-ACN-AA-XB |
| 154 | 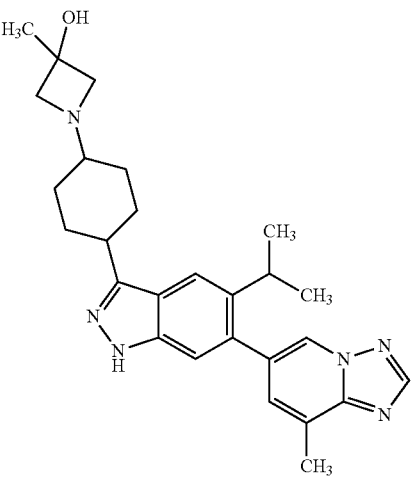 | 459.3 | 1.12 | QC-ACN-TFA-XB |

TABLE 1-continued
| Ex. No. | | Obs. MS Ion | Ret time (min) | HPLC |
|---|---|---|---|---|
| 155 | 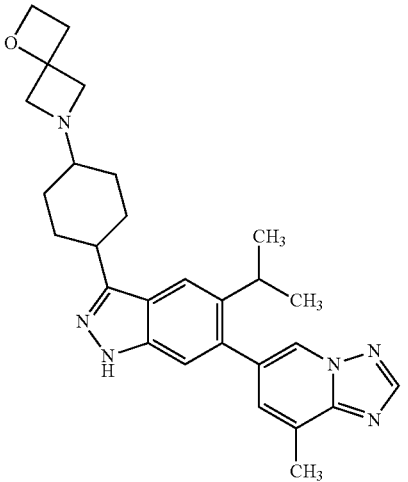 [SMILES: Cc1cc(-c2cc3[nH]nc(C4CCC(N5CC6(CCO6)C5)CC4)c3cc2C(C)C)cn2ncnc12] | 471.3 | 1.3 | QC-ACN-TFA-XB |
| 156 | 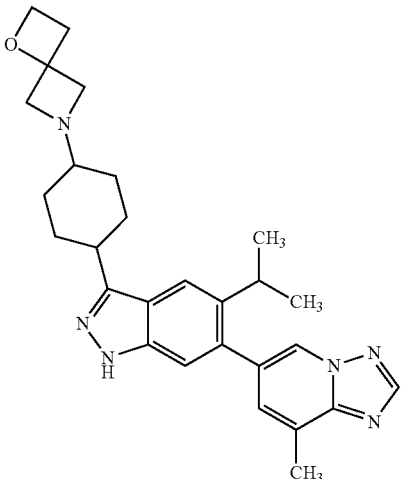 | 471.3 | 1.25 | QC-ACN-AA-XB |
| 157 | 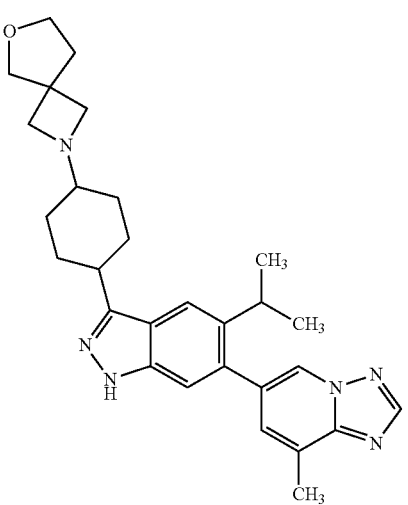 [SMILES: Cc1cc(-c2cc3[nH]nc(C4CCC(N5CC6(CCOC6)C5)CC4)c3cc2C(C)C)cn2ncnc12] | 485.5 | 1.42 | QC-ACN-AA-XB |

TABLE 1-continued

| Ex. No. | | Obs. MS Ion | Ret time (min) | HPLC |
|---|---|---|---|---|
| 158 | | 485.4 | 1.16 | QC-ACN-TFA-XB |
| 159 | | 485.3 | 1.09 | QC-ACN-TFA-XB |
| 160 | | 485.5 | 1.56 | QC-ACN-AA-XB |

TABLE 1-continued
| Ex. No. | | Obs. MS Ion | Ret time (min) | HPLC |
|---|---|---|---|---|
| 161 | 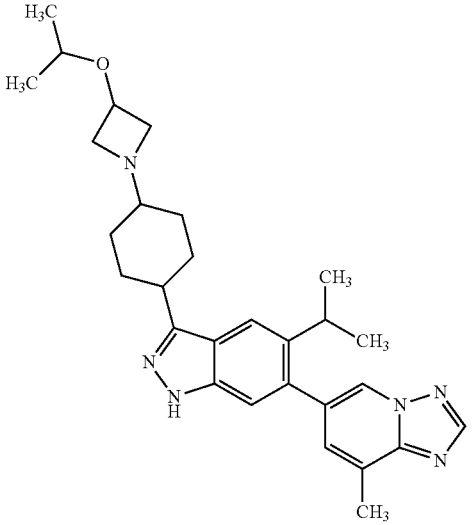 [SMILES: Cc1cc(-c2cc3[nH]nc(C4CCC(N5CC(OC(C)C)C5)CC4)c3cc2C(C)C)cn2ncnc12] | 487.3 | 1.64 | QC-ACN-AA-XB |
| 162 | 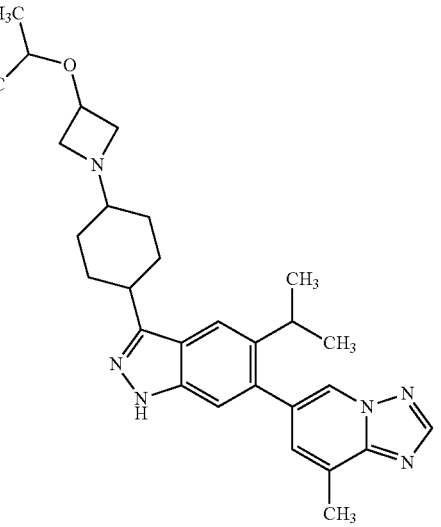 | 487.3 | 1.29 | QC-ACN-TFA-XB |
| 163 | 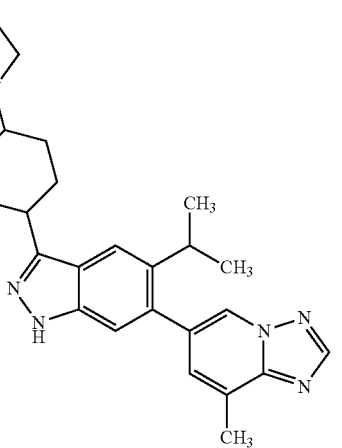 | 461 | 1.48 | QC-ACN-AA-XB |

TABLE 1-continued
| Ex. No. | | Obs. MS Ion | Ret time (min) | HPLC |
|---|---|---|---|---|
| 164 | 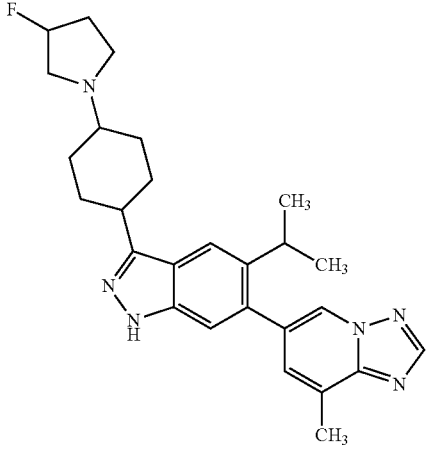 [SMILES: Cc1cc(-c2cc3[nH]nc(C4CCC(N5CCC(F)C5)CC4)c3cc2C(C)C)cn2ncnc12] | 461 | 1.61 | QC-ACN-AA-XB |
| 165 | 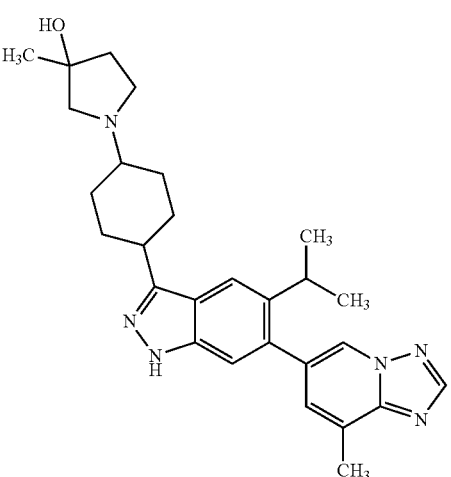 | 473.2 | 1.11 | QC-ACN-TFA-XB |
| 166 | 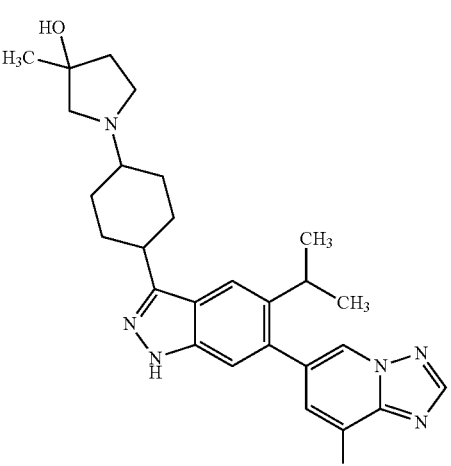 | 473.4 | 1.32 | QC-ACN-TFA-XB |

SCHEME 3

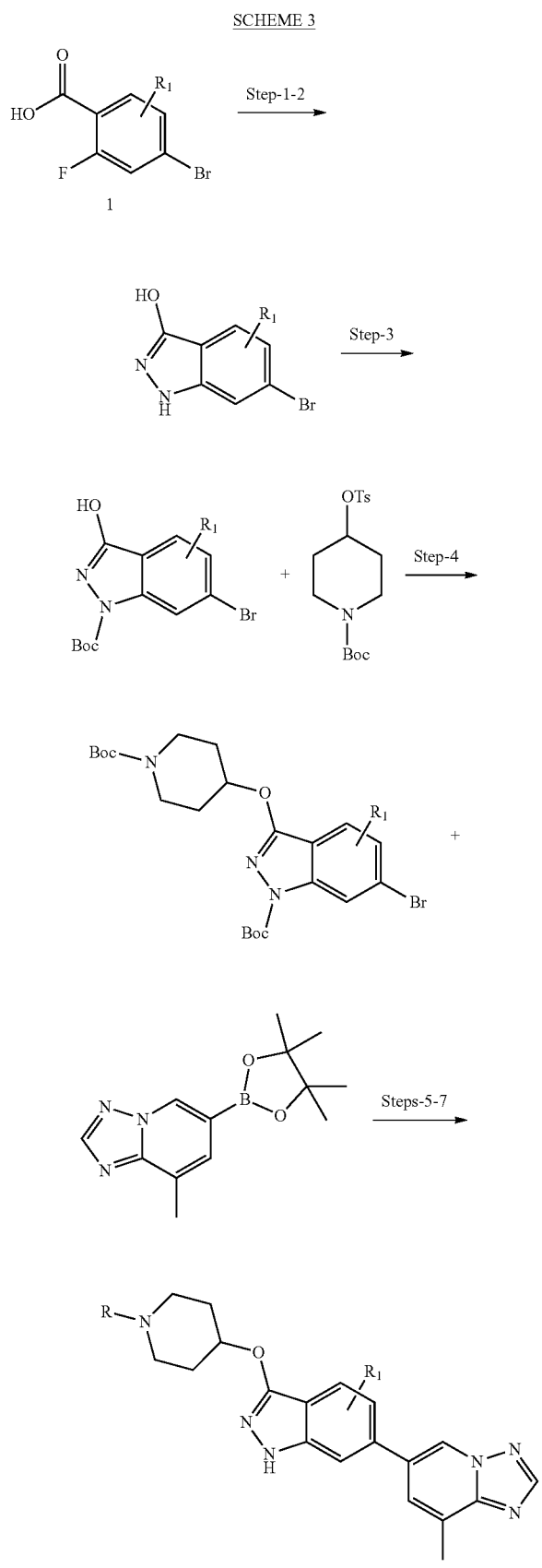

Example 167

8-methyl-6-(5-methyl-3-(piperidin-4-yloxy)-1H-indazol-6-yl)-[1,2,4]triazolo[1,5-a]pyridine

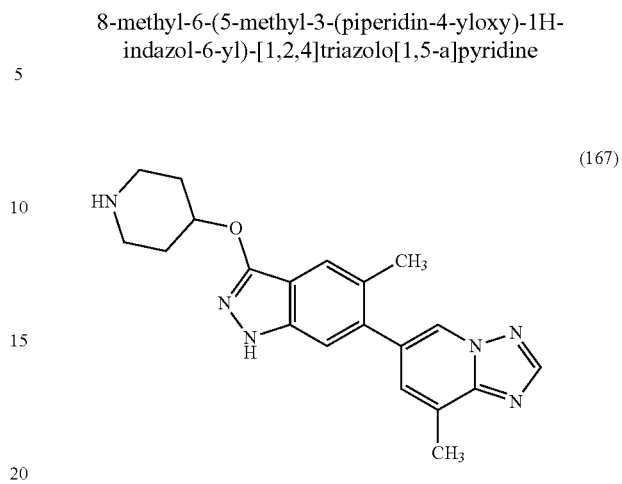

(167)

Step 1:

To a mixture of 4-bromo-2-fluoro-5-methylbenzoic acid (1 g, 4.29 mmol) in MeOH (20 mL) at 0° C. was added thionyl chloride (3.13 mL, 42.9 mmol) dropwise over 15 minutes. The reaction mixture was slowly warmed to room temperature and stirred for 1 hour. The mixture was concentrated in vacuo to afford methyl 4-bromo-2-fluoro-5-methylbenzoate (1 g, 4.05 mmol, 94% yield). MS ($M^{+1}$) m/z: 247.0 ($MH^+$). LC retention time 0.93 min [A1].

Step 2:

To a mixture of methyl 4-bromo-2-fluoro-5-methylbenzoate (500 mg, 2.024 mmol) in EtOH (2 mL) was added hydrazine hydrate (0.757 mL, 10.12 mmol). The reaction vessel was sealed and heated at 80° C. for two days. The reaction mixture was diluted with dichloromethane and washed with $H_2O$. The organic layer was dried with $MgSO_4$, filtered and concentrated to afford 6-bromo-5-methyl-1H-indazol-3-ol (406 mg, 1.788 mmol, 88% yield). MS ($M^{+1}$) m/z: 227/229.3 ($MH^+$). LC retention time 0.71 min [A1].

Step 3:

To a mixture of 6-bromo-5-methyl-1H-indazol-3-ol (200 mg, 0.881 mmol) and DMAP (10.76 mg, 0.088 mmol) in acetonitrile (10 mL) was added BOC-anhydride (384 mg, 1.762 mmol). The reaction mixture was stirred at room temperature for 4 days. The reaction mixture was concentrated in vacuo then 7 M $NH_3$ in MeOH was added (10 mL). The reaction mixture was stirred at room temperature overnight and then concentrated in vacuo. The crude material was purified on a silica gel cartridge (24 g) using an MeOH/DCM gradient (0-10% MeOH over 12 min) to afford tert-butyl 6-bromo-3-hydroxy-5-methyl-1H-indazole-1-carboxylate (135 mg, 0.413 mmol, 46.8% yield). $^1$H NMR (499 MHz, $CDCl_3$) δ 8.01 (d, J=8.4 Hz, 1H), 7.39 (d, J=11.1 Hz, 1H), 2.53 (s, 1H), 2.43 (s, 3H), 1.51-1.48 (m, 9H).

Step 4:

To a mixture of 4-(toluene-4-sulfonyloxy-piperidine-1-carboxylic acid tert-butyl ester (183 mg, 0.513 mmol) and tert-butyl 6-bromo-3-hydroxy-5-methyl-1H-indazole-1-carboxylate (120 mg, 0.367 mmol) in DMF (1 mL) was added cesium carbonate (215 mg, 0.660 mmol). The reaction vessel was sealed and heated at 80° C. After stirring overnight, the reaction mixture was diluted with ethyl acetate and washed with saturated NaCl. The organic layer was dried with $MgSO_4$, filtered, and concentrated. The crude material was purified on a silica gel cartridge (24 g) using an EtOAc/Hex gradient (0-100% EtOAc over 12) to afford tert-butyl 6-bromo-3-((1-(tert-butoxycarbonyl)piperidin-4-yl)oxy)-5-methyl-1H-indazole-1-carboxylate (37 mg, 0.072 mmol, 19.76% yield). MS (M+1) m/z: 510/512.3 (MH+). LC retention time 1.2 min [A1].

Step 5:

To a mixture of tert-butyl 6-bromo-3-((1-(tert-butoxycarbonyl)piperidin-4-yl)oxy)-5-methyl-1H-indazole-1-carboxylate (37 mg, 0.072 mmol), 8-methyl-6-(4,4,5,5-tetramethyl-1,3,2-dioxaborolan-2-yl)-[1,2,4]triazolo[1,5-a]pyridine (37.6 mg, 0.145 mmol), and 2nd generation XPHOS precatalyst (5.70 mg, 7.25 μmol) in dioxane (1 mL) was added 2 M $K_3PO_4$ (0.109 mL, 0.217 mmol). The reaction mixture was sparged with nitrogen for 5 minutes. The reaction vessel was sealed and heated at 95° C. for 12 hours. Solvents were removed under a stream of nitrogen and the residue was treated with TFA/DCM (1:1) for 30 minutes. The solvents were removed. The residue was dissolved in DMF and purified by preparative HPLC to afford 8-methyl-6-(5-methyl-3-(piperidin-4-yloxy)-1H-indazol-6-yl)-[1,2,4]triazolo[1,5-a]pyridine (19.3 mg, 0.052 mmol, 71.6% yield). MS (M+1) m/z: 363.4 (MH+). LC retention time 0.91 min [QC-ACN-AA-XB]. $^1$H NMR (500 MHz, DMSO-$d_6$) δ 8.81-8.74 (m, 1H), 8.51-8.44 (m, 1H), 7.57 (s, 1H), 7.54-7.46 (m, 1H), 7.33 (s, 1H), 5.17-4.91 (m, 1H), 3.58-3.27 (m, 2H), 3.18 (br d, J=6.6 Hz, 2H), 2.62 (s, 3H), 2.30 (s, 3H), 2.28-2.19 (m, 2H), 2.10-1.94 (m, 2H).

SCHEME 4

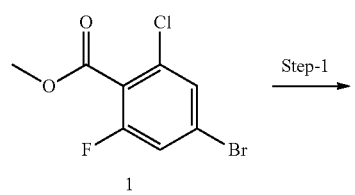

1

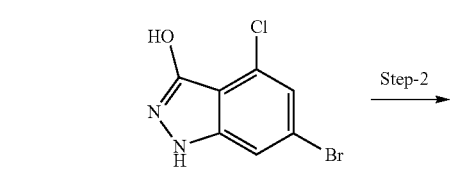

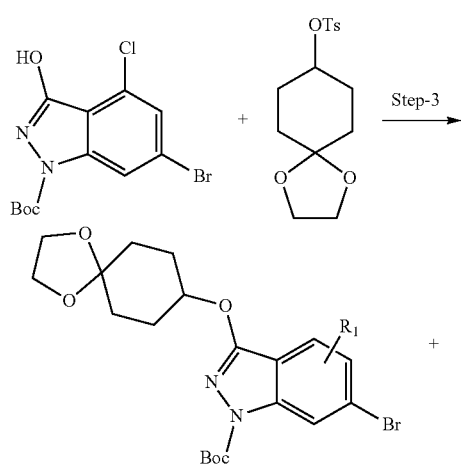

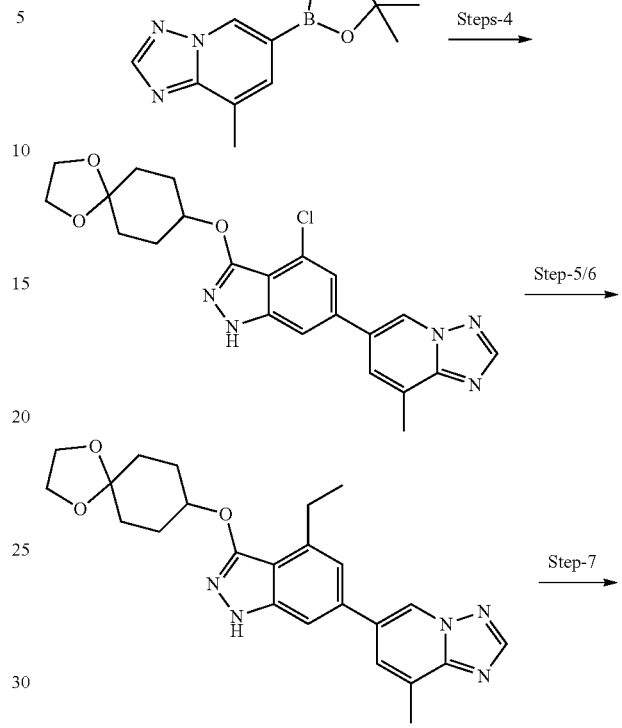

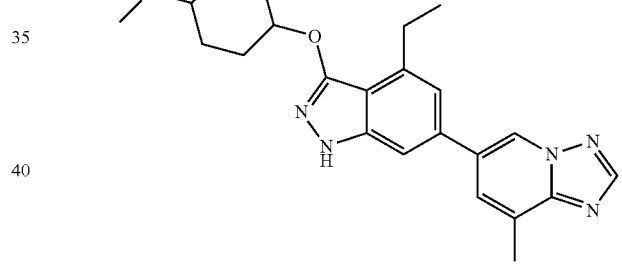

Examples 168 and 169

4-((4-ethyl-6-(8-methyl-[1,2,4]triazolo[1,5-a]pyridin-6-yl)-1H-indazol-3-yl)oxy)-N,N-dimethylcyclohexan-1-amine (168-169)

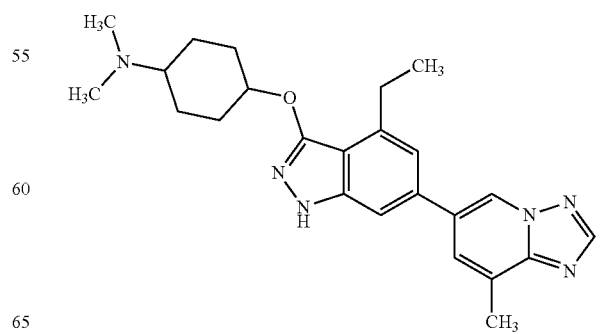

Step 1:

To a mixture of 4-bromo-2-chloro-6-fluoro-N-methylbenzamide (1000 mg, 3.75 mmol) in EtOH (2 mL) was added hydrazine hydrate (2.81 mL, 37.5 mmol). The reaction mixture was heated at 80° C. for 3 days. The reaction mixture was diluted with dichloromethane and washed with water. The organic layer was dried with MgSO$_4$, filtered and concentrated to afford 6-bromo-4-chloro-1H-indazol-3-ol (840 mg, 3.39 mmol, 90% yield). MS (M$^{+1}$) m/z: 248.8 (MH$^+$). LC retention time 0.75 min [A1].

Step 2:

To a mixture of 6-bromo-4-chloro-1H-indazol-3-ol (600 mg, 2.424 mmol) and DMAP (29.6 mg, 0.242 mmol) in acetonitrile (40 mL) was added BOC-anhydride (1.295 mL, 5.58 mmol). The reaction mixture was stirred overnight. Solvents were removed in vacuo and the residue was dissolved in MeOH (20 mL). Next, 7 N NH$_3$ in MeOH (10 mL) was added. The reaction mixture was stirred overnight and solvents were removed in vacuo. The reaction mixture was diluted with ethyl acetate and washed with 0.1M HCl. The organic layer was dried with MgSO$_4$, filtered and concentrated to afford tert-butyl 6-bromo-4-chloro-3-hydroxy-1H-indazole-1-carboxylate (782 mg, 2.250 mmol, 93% yield). MS (M$^{+1}$) m/z: 348.9 (MH$^+$). LC retention time 1.05 min [A1].

Step 3:

To a mixture of 1,4-dioxaspiro[4.5]decan-8-yl 4-methylbenzenesulfonate [INT-3](755 mg, 2.417 mmol) and tert-butyl 6-bromo-4-chloro-3-hydroxy-1H-indazole-1-carboxylate (420 mg, 1.208 mmol) in DMF (2 mL) was added potassium carbonate (501 mg, 3.62 mmol). The reaction vessel was sealed and heated at 95° C. overnight. The reaction mixture was diluted with ethyl acetate and washed with saturated NaCl. The organic layer was dried with MgSO$_4$, filtered and concentrated. The crude material was purified on a silica gel cartridge (40 g) using an DCM/MeOH gradient to afford 3-((1,4-dioxaspiro[4.5]decan-8-yl)oxy)-6-bromo-4-chloro-1H-indazole (187 mg, 0.482 mmol, 39.9% yield). MS (M$^{+1}$) m/z: 389.0 (MH$^+$). LC retention time 1.05 min [A1].

Step 4:

To a mixture of 3-((1,4-dioxaspiro[4.5]decan-8-yl)oxy)-6-bromo-4-chloro-1H-indazole (187 mg, 0.482 mmol), 8-methyl-6-(4,4,5,5-tetramethyl-1,3,2-dioxaborolan-2-yl)-[1,2,4]triazolo[1,5-a]pyridine (137 mg, 0.531 mmol), and 2nd generation XPHOS precatalyst (18.98 mg, 0.024 mmol) in dioxane (10 mL) was added 2M K$_3$PO$_4$ (0.724 mL, 1.447 mmol). The reaction mixture was sparged with nitrogen for 5 minutes. The reaction vessel was sealed and heated at 85° C. for 5 days. The reaction mixture was diluted with DCM, then dried with MgSO$_4$, filtered, and concentrated. The crude material was purified on a silica gel cartridge (24 g) using a MeOH/DCM gradient (0-10% MeOH over 12 min) to afford 6-(3-((1,4-dioxaspiro[4.5]decan-8-yl)oxy)-4-chloro-1H-indazol-6-yl)-8-methyl-[1,2,4]triazolo[1,5-a] pyridine (166 mg, 0.377 mmol, 78% yield). MS (M$^{+1}$) m/z: 440.2 (MH$^+$). LC retention time 0.89 min [A1].

Step 5:

To a mixture of 6-(3-((1,4-dioxaspiro[4.5]decan-8-yl)oxy)-4-chloro-1H-indazol-6-yl)-8-methyl-[1,2,4]triazolo[1,5-a]pyridine (166 mg, 0.377 mmol), 4,4,5,5-tetramethyl-2-vinyl-1,3,2-dioxaborolane (0.098 mL, 0.566 mmol), and 2nd generation XPHOS precatalyst (14.85 mg, 0.019 mmol) in dioxane (10 mL) was added 2M K$_3$PO$_4$ (0.566 mL, 1.132 mmol). The reaction mixture was sparged with nitrogen for 5 minutes. The reaction vessel was sealed and heated at 85° C. overnight. The reaction mixture was diluted with DCM then dried with MgSO$_4$, filtered, and concentrated. The crude material was purified on a silica gel cartridge (24 g) using an MeOH/DCM gradient (0-10% MeOH over 12 min) to afford 6-(3-((1,4-dioxaspiro[4.5]decan-8-yl)oxy)-4-vinyl-1H-indazol-6-yl)-8-methyl-[1,2,4]triazolo[1,5-a] pyridine (150 mg, 0.348 mmol, 92% yield). MS (M$^{+1}$) m/z: 432.0 (MH$^+$). LC retention time 0.89 min [A1].

Step 6:

To a mixture of 6-(3-((1,4-dioxaspiro[4.5]decan-8-yl)oxy)-4-vinyl-1H-indazol-6-yl)-8-methyl-[1,2,4]triazolo[1,5-a]pyridine (150 mg, 0.348 mmol) in MeOH (10 mL) was added Pd—C (37.0 mg, 0.348 mmol). The reaction mixture was hydrogenated under a balloon of H$_2$ overnight. The hydrogen was removed and the reaction vessel was backfilled with nitrogen. The catalyst was removed by filtration. The mixture was concentrated in vacuo. This material was then treated with TFA (2 mL) overnight. LCMS show conversion of ketal to ketone by mass. The solvents were removed in vacuo to afford 4-((4-ethyl-6-(8-methyl-[1,2,4]triazolo[1,5-a]pyridin-6-yl)-1H-indazol-3-yl)oxy)cyclohexan-1-one (130 mg, 0.334 mmol, 96% yield). MS (M$^{+1}$) m/z: 390.1 (MH$^+$). LC retention time 0.83 min [A1].

Step 7:

To a mixture of 4-((4-ethyl-6-(8-methyl-[1,2,4]triazolo[1,5-a]pyridin-6-yl)-1H-indazol-3-yl)oxy)cyclohexan-1-one (45 mg, 0.116 mmol) and dimethylamine, HCl (94 mg, 1.155 mmol) in DMF (1 mL) was added TEA (0.161 mL, 1.155 mmol). The reaction mixture was stirred for 30 minutes and then sodium triacetoxyborohydride (245 mg, 1.155 mmol) was added. The reaction mixture was stirred overnight. The reaction was quenched with MeOH (0.5 mL). The reaction mixture was filtered and purified by preparative HPLC to afford two isomers:

Ex. 168 Isomer 1: 4-((4-ethyl-6-(8-methyl-[1,2,4]triazolo[1,5-a]pyridin-6-yl)-1H-indazol-3-yl)oxy)-N,N-dimethylcyclohexan-1-amine (1.7 mg, 3.92 µmol, 3.40% yield). MS (M$^{+1}$) m/z: 419.2 (MH$^+$). LC retention time 1.27 min [QC-ACN-AA-XB]. $^1$H NMR (500 MHz, DMSO-d$_6$) δ 9.14 (s, 1H), 8.49 (s, 1H), 7.90 (s, 1H), 7.50 (s, 1H), 7.20 (s, 1H), 5.02 (br s, 1H), 3.05 (q, J=7.3 Hz, 2H), 2.64 (s, 3H), 2.23 (s, 6H), 1.91 (s, 3H), 1.65 (br d, J=4.9 Hz, 6H), 1.34 (br t, J=7.5 Hz, 3H)

Ex. 169 Isomer 2: 4-((4-ethyl-6-(8-methyl-[1,2,4]triazolo[1,5-a]pyridin-6-yl)-1H-indazol-3-yl)oxy)-N,N-dimethylcyclohexan-1-amine (1.1 mg, 2.55 µmol, 2.206% yield). MS (M$^{+1}$) m/z: 419.2 (MH$^+$). LC retention time 1.39 min [QC-ACN-AA-XB]. $^1$H NMR (500 MHz, DMSO-d$_6$) δ 9.14 (s, 1H), 8.49 (s, 1H), 7.89 (s, 1H), 7.49 (s, 1H), 7.19 (s, 1H), 4.84-4.65 (m, 1H), 2.99 (q, J=7.3 Hz, 2H), 2.64 (s, 3H), 2.40-2.29 (m, 2H), 2.27 (br s, 6H), 2.02-1.80 (m, 3H), 1.63-1.38 (m, 4H), 1.30 (t, J=7.5 Hz, 3H)

The following examples were prepared according to the general procedures for Examples 167-169.

TABLE 2

| Ex. No. | Structure | Obs. MS Ion | Ret time (min) | HPLC |
|---|---|---|---|---|
| 167 | 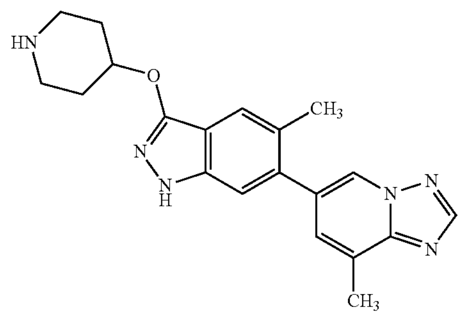 [SMILES: Cc1cc2c(OC3CCNCC3)n[nH]c2cc1-c1cc(C)c2ncnn2c1] | 363.2 | 0.91 | QC-ACN-TFA-XB |
| 168 | 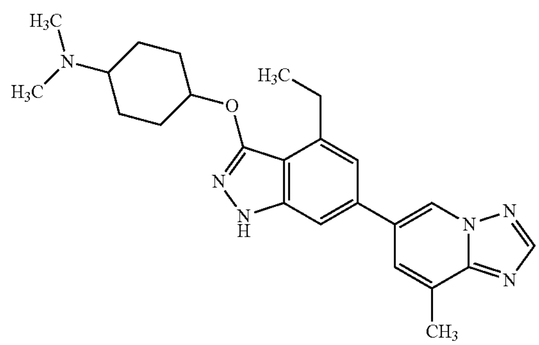 [SMILES: CCc1cc(-c2cc(C)c3ncnn3c2)cc2[nH]nc(OC3CCC(N(C)C)CC3)c12] | 419.2 | 1.27 | QC-ACN-AA-XB |
| 169 | 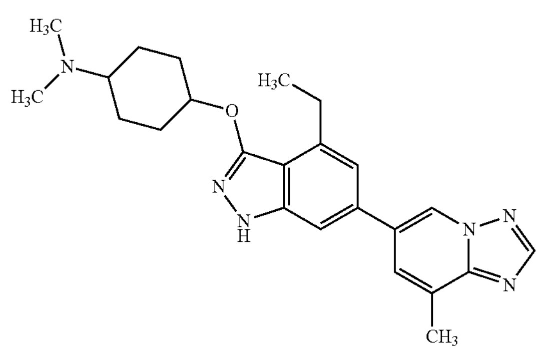 [SMILES: CCc1cc(-c2cc(C)c3ncnn3c2)cc2[nH]nc(OC3CCC(N(C)C)CC3)c12] | 419.1 | 1.39 | QC-ACN-AA-XB |
| 170 | 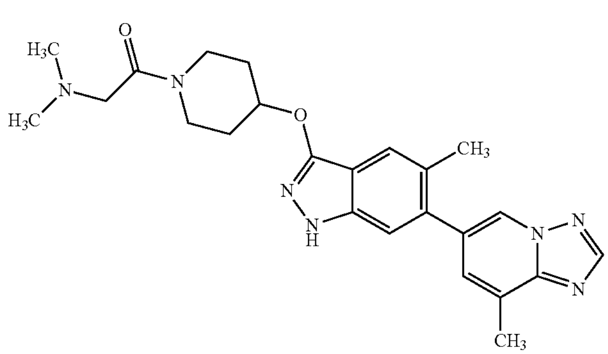 [SMILES: Cc1cc2c(OC3CCN(C(=O)CN(C)C)CC3)n[nH]c2cc1-c1cc(C)c2ncnn2c1] | 448.2 | 1.13 | QC-ACN-AA-XB |

TABLE 2-continued

| Ex. No. | Structure | Obs. MS Ion | Ret time (min) | HPLC |
|---|---|---|---|---|
| 171 | 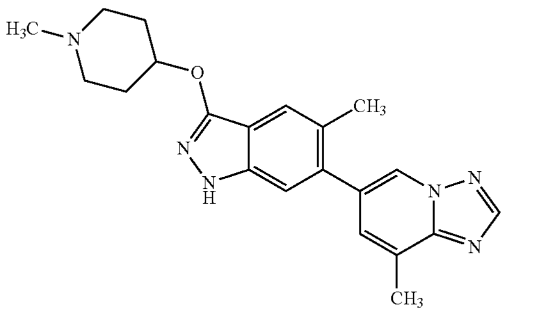 [SMILES: Cc1cc2c(OC3CCN(C)CC3)n[nH]c2cc1-c1cc(C)c2ncnn2c1] | 377.3 | 1.03 | QC-ACN-AA-XB |
| 172 | 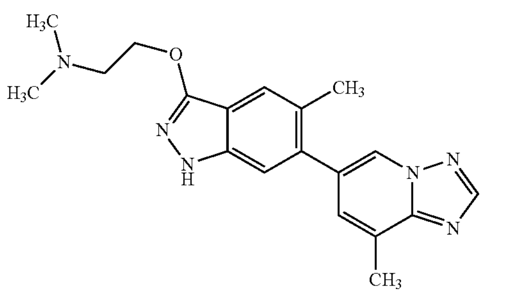 [SMILES: Cc1cc2c(OCCN(C)C)n[nH]c2cc1-c1cc(C)c2ncnn2c1] | 351.1 | 0.87 | QC-ACN-TFA-XB |
| 173 | 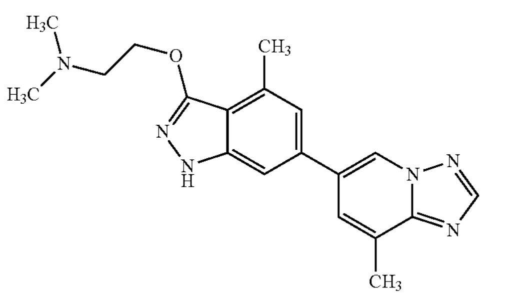 [SMILES: Cc1cc(-c2cc(C)c3ncnn3c2)cc2[nH]nc(OCCN(C)C)c12] | 351.2 | 0.95 | QC-ACN-AA-XB |
| 174 | 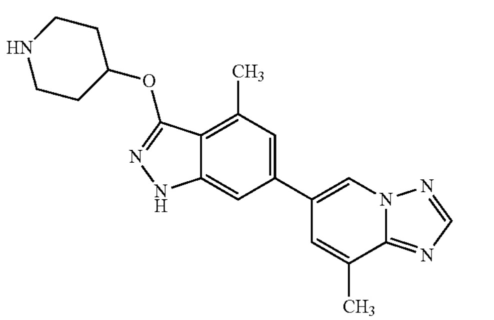 [SMILES: Cc1cc(-c2cc(C)c3ncnn3c2)cc2[nH]nc(OC3CCNCC3)c12] | 363.2 | 1.03 | QC-ACN-AA-XB |
| 175 | 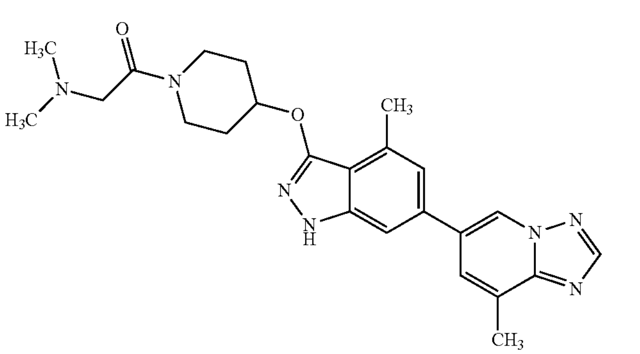 [SMILES: Cc1cc(-c2cc(C)c3ncnn3c2)cc2[nH]nc(OC3CCN(C(=O)CN(C)C)CC3)c12] | 448.3 | 1.04 | QC-ACN-TFA-XB |

TABLE 2-continued

| Ex. No. | Structure | Obs. MS Ion | Ret time (min) | HPLC |
|---|---|---|---|---|
| 176 | 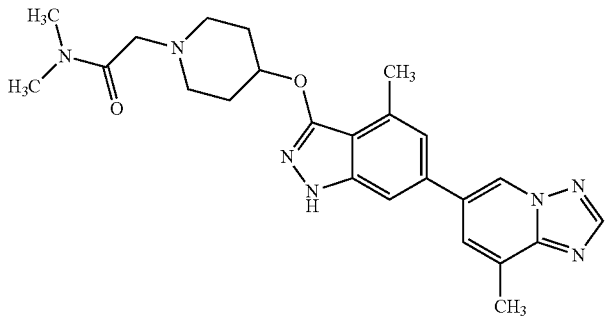 [SMILES: Cc1cc(-c2cc(C)c3ncnn3c2)cc2[nH]nc(OC3CCN(CC(=O)N(C)C)CC3)c12] | 448.3 | 0.95 | QC-ACN-TFA-XB |
| 177 | 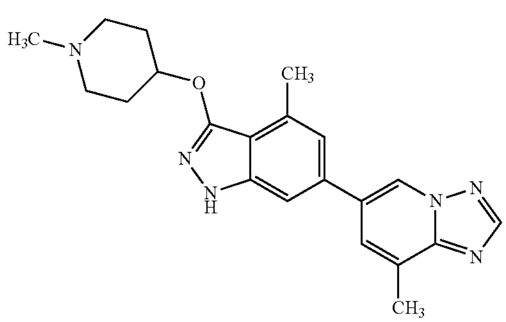 [SMILES: Cc1cc(-c2cc(C)c3ncnn3c2)cc2[nH]nc(OC3CCN(C)CC3)c12] | 377.2 | 1.04 | QC-ACN-TFA-XB |
| 178 | 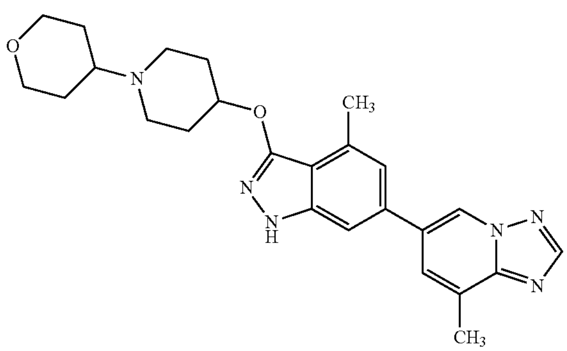 [SMILES: Cc1cc(-c2cc(C)c3ncnn3c2)cc2[nH]nc(OC3CCN(C4CCOCC4)CC3)c12] | 447.3 | 1.03 | QC-ACN-TFA-XB |
| 179 | 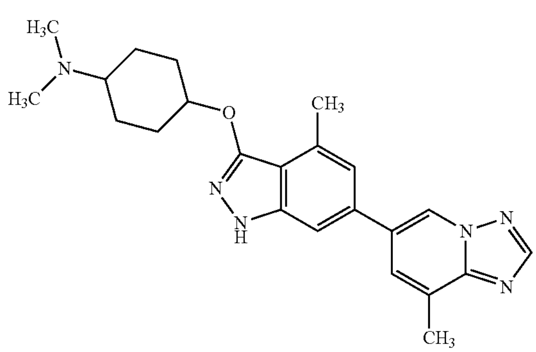 [SMILES: Cc1cc(-c2cc(C)c3ncnn3c2)cc2[nH]nc(OC3CCC(N(C)C)CC3)c12] | 405.2 | 1.01 | QC-ACN-TFA-XB |

TABLE 2-continued
| Ex. No. | Structure | Obs. MS Ion | Ret time (min) | HPLC |
|---|---|---|---|---|
| 180 | 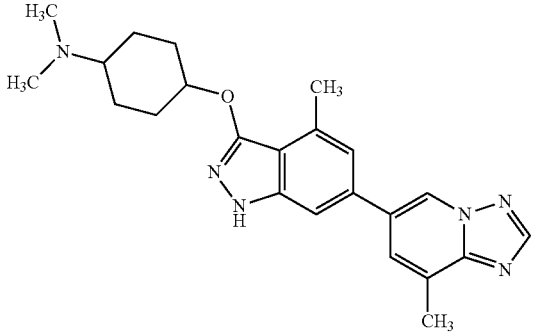 [SMILES: Cc1cc(-c2cc(C)c3ncnn3c2)cc2[nH]nc(OC3CCC(N(C)C)CC3)c12] | 405.2 | 1.14 | QC-ACN-AA-XB |
| 181 | 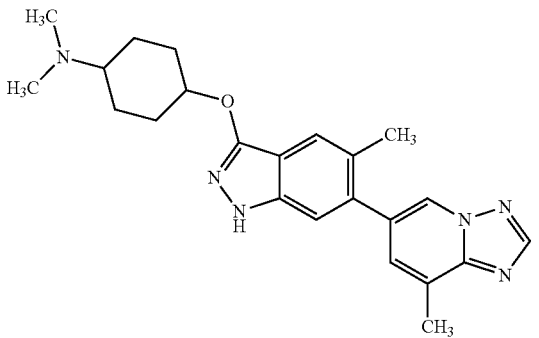 [SMILES: Cc1cc2c(OC3CCC(N(C)C)CC3)n[nH]c2cc1-c1cc(C)c2ncnn2c1] | 405.3 | 1.02 | QC-ACN-AA-XB |
| 182 | 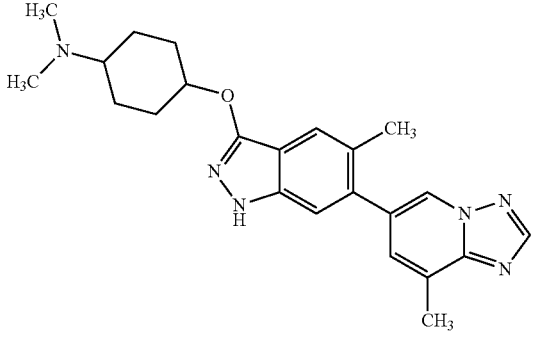 [SMILES: Cc1cc2c(OC3CCC(N(C)C)CC3)n[nH]c2cc1-c1cc(C)c2ncnn2c1] | 405.1 | 1.15 | QC-ACN-TFA-XB |
| 183 | 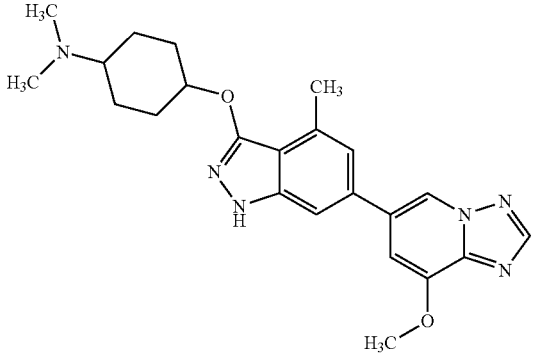 [SMILES: COc1cc(-c2cc(C)c3c(OC4CCC(N(C)C)CC4)n[nH]c3c2)cn2ncnc12] | 421.3 | 0.95 | QC-ACN-AA-XB |

TABLE 2-continued

| Ex. No. | Structure | Obs. MS Ion | Ret time (min) | HPLC |
|---|---|---|---|---|
| 184 | 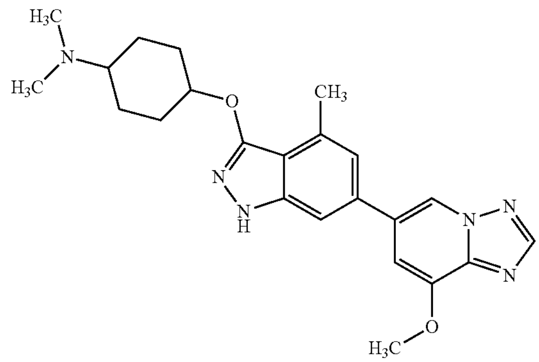 [SMILES: COc1cc(-c2cc(C)c3c(OC4CCC(N(C)C)CC4)n[nH]c3c2)cn2ncnc12] | 421.2 | 1.08 | QC-ACN_TFA-XB |
| 185 | 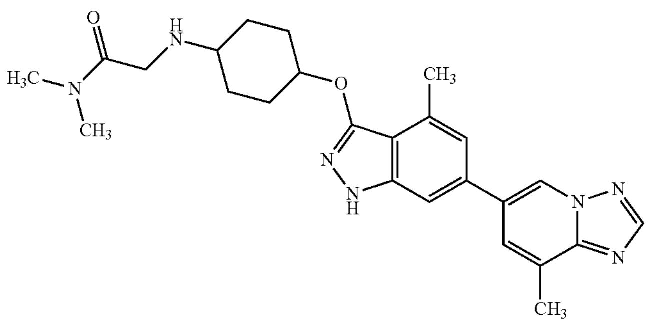 [SMILES: Cc1cc(-c2cc(C)c3ncnn3c2)cc2[nH]nc(OC3CCC(NCC(=O)N(C)C)CC3)c12] | 462.4 | 1.02 | QC-ACN-TFA-XB |
| 186 | 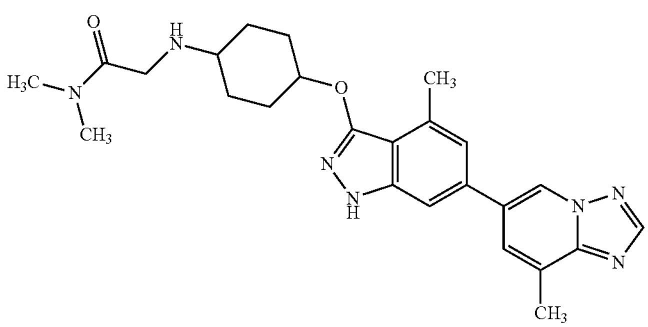 [SMILES: Cc1cc(-c2cc(C)c3ncnn3c2)cc2[nH]nc(OC3CCC(NCC(=O)N(C)C)CC3)c12] | 462.4 | 1.13 | QC-ACN-TFA-XB |
| 187 | 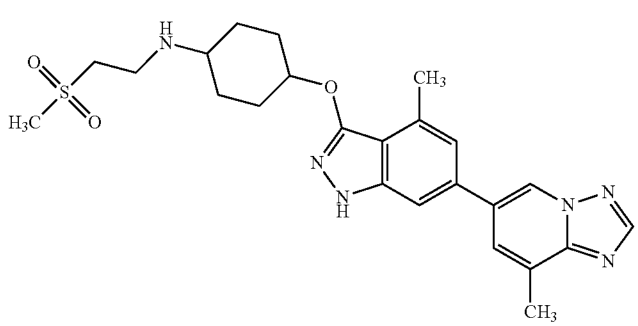 [SMILES: Cc1cc(-c2cc(C)c3ncnn3c2)cc2[nH]nc(OC3CCC(NCCS(C)(=O)=O)CC3)c12] | 483.2 | 1.18 | QC-ACN-AA-XB |

TABLE 2-continued
| Ex. No. | Structure | Obs. MS Ion | Ret time (min) | HPLC |
|---|---|---|---|---|
| 188 | 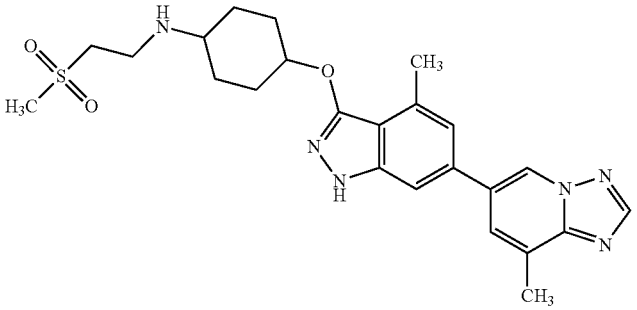 [SMILES: Cc1cc(-c2cc(C)c3ncnn3c2)cc2[nH]nc(OC3CCC(NCCS(C)(=O)=O)CC3)c12] | 483.3 | 1.12 | QC-ACN-TFA-XB |
| 189 | 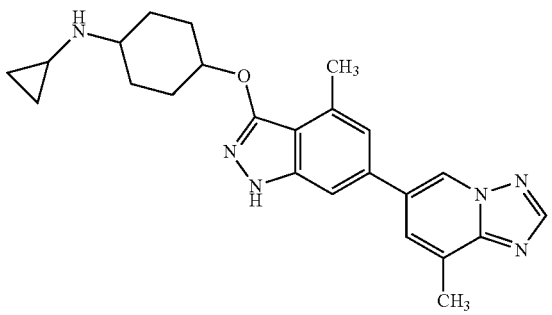 [SMILES: Cc1cc(-c2cc(C)c3ncnn3c2)cc2[nH]nc(OC3CCC(NC4CC4)CC3)c12] | 417.3 | 1.18 | QC-ACN-AA-XB |
| 190 | 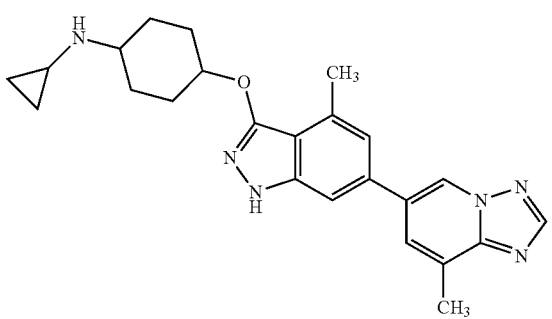 [SMILES: Cc1cc(-c2cc(C)c3ncnn3c2)cc2[nH]nc(OC3CCC(NC4CC4)CC3)c12] | 417.3 | 1.19 | QC-ACN-TFA-XB |
| 191 | 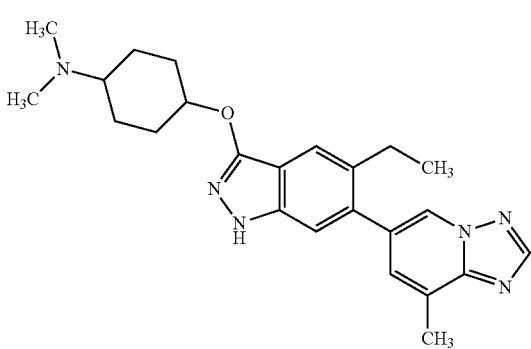 [SMILES: CCc1cc2c(OC3CCC(N(C)C)CC3)n[nH]c2cc1-c1cc(C)c2ncnn2c1] | 419.4 | 1.15 | QC-ACN-TFA-XB |

TABLE 2-continued

| Ex. No. | Structure | Obs. MS Ion | Ret time (min) | HPLC |
|---|---|---|---|---|
| 192 | 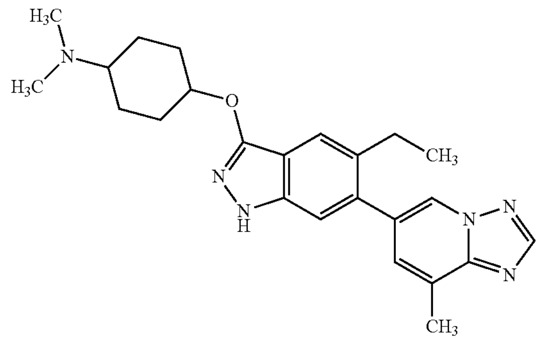 [SMILES: CCc1cc2c(OC3CCC(N(C)C)CC3)n[nH]c2cc1-c1cc(C)c2ncnn2c1] | 419.04 | | QC-ACN-AA-XB |
| 193 | 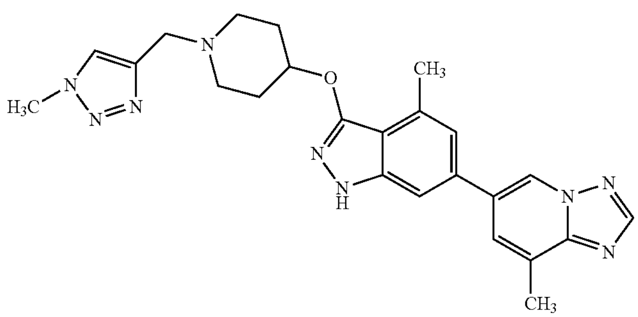 [SMILES: Cc1cc(-c2cc(C)c3ncnn3c2)cc2[nH]nc(OC3CCN(Cc4cn(C)nn4)CC3)c12] | 458.4 | 1.14 | QC-ACN-AA-XB |
| 194 | 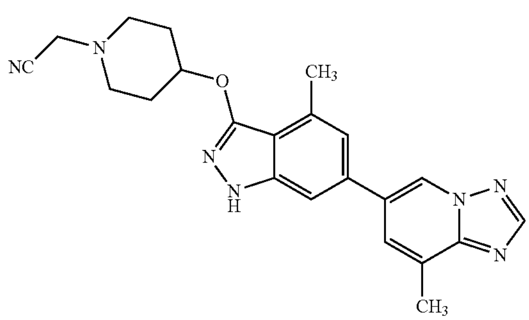 [SMILES: Cc1cc(-c2cc(C)c3ncnn3c2)cc2[nH]nc(OC3CCN(CC#N)CC3)c12] | 402 | 1.15 | QC-ACN-TFA-XB |
| 195 | 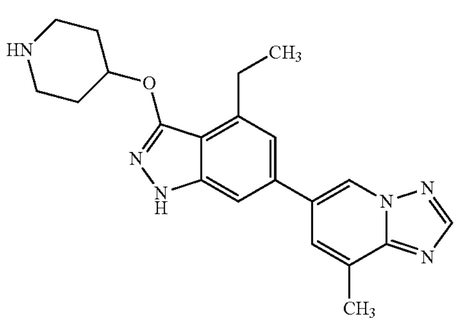 [SMILES: CCc1cc(-c2cc(C)c3ncnn3c2)cc2[nH]nc(OC3CCNCC3)c12] | 377.3 | 1.27 | QC-ACN-AA-XB |

TABLE 2-continued

| Ex. No. | Structure | Obs. MS Ion | Ret time (min) | HPLC |
|---|---|---|---|---|
| 196 | 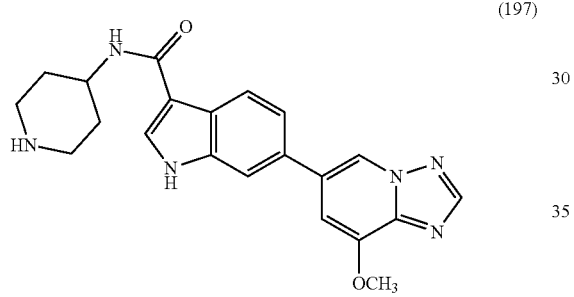 | 462.1 | 1.09 | QC-ACN-TFA-XB |

Example 197

6-(8-methoxy-[1,2,4]triazolo[1,5-a]pyridin-6-yl)-N-(piperidin-4-yl)-1H-indole-3-carboxamide (197)

Step 1:
To a mixture of 6-bromo-1H-indole-3-carboxylic acid (200 mg, 0.833 mmol), tert-butyl 4-aminopiperidine-1-carboxylate (167 mg, 0.833 mmol), and HATU (380 mg, 1.000 mmol) in DCM was added TEA (232 µl, 1.666 mmol). The reaction mixture was stirred at room temperature for 30 minutes. The reaction mixture was diluted with DCM and washed with 0.1 M HCl, saturated NaCl, and 1 N NaOH. The organic layer was dried with MgSO$_4$, filtered, and concentrated to afford tert-butyl 4-(6-bromo-1H-indole-3-carboxamido) piperidine-1-carboxylate (303 mg, 0.717 mmol, 86% yield). MS (M$^{+1}$) m/z: 422/424 (MH$^+$). LC retention time 0.92 min [A1].

Step 2:
To a mixture of 8-methoxy-6-(4,4,5,5-tetramethyl-1,3,2-dioxaborolan-2-yl)-[1,2,4]triazolo[1,5-a]pyridine (23.45 mg, 0.085 mmol), tert-butyl 4-(6-bromo-1H-indole-3-carboxamido)piperidine-1-carboxylate (30 mg, 0.071 mmol), and 2ND generation XPHOS precatalyst (5.59 mg, 7.10 µmol) in THF (2 mL) was added 3M K$_3$PO$_4$ (0.071 mL, 0.213 mmol). The reaction mixture was sparged with nitrogen for 5 minutes. The reaction vessel was sealed and heated at 85° C. overnight. LCMS shows formation of desired product mass and no remaining starting material. The reaction mixture was concentrated to dryness and then treated with TFA/DCM (1:1) for 1 hour. Solvents were removed and the residue was dissolved in DMF. The mixture was filtered and purified by preparative HPLC to afford 6-(8-methoxy-[1,2,4]triazolo[1,5-a]pyridin-6-yl)-N-(piperidin-4-yl)-1H-indole-3-carboxamide (5.7 mg, 0.015 mmol, 20.55% yield). MS (M$^{+1}$) m/z: 391.2 (MH$^+$). LC retention time 0.7 min [QC-ACN-AA-XB]. $^1$H NMR in DMSO-d$_6$ is consistent with desired product Example 198

6-(8-methyl-[1,2,4]triazolo[1,5-a]pyridin-6-yl)-N-(piperidin-4-yl)-1H-indole-3-carboxamide

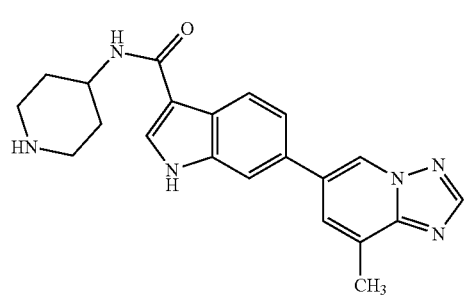

(198)

To a mixture of 8-methyl-6-(4,4,5,5-tetramethyl-1,3,2-dioxaborolan-2-yl)-[1,2,4]triazolo[1,5-a]pyridine (22.09 mg, 0.085 mmol), tert-butyl 4-(6-bromo-1H-indole-3-carboxamido)piperidine-1-carboxylate (30 mg, 0.071 mmol), and 2ND generation XPHOS precatalyst (5.59 mg, 7.10 µmol) in THF (2 mL) was added 2M K$_3$PO$_4$ (0.071 mL, 0.213 mmol). The reaction mixture was sparged with nitrogen for 5 minutes. The reaction vessel was sealed and heated at 70° C. overnight. Solvents were removed in vacuo. The residue was treated with TFA/DCM for 10 minutes and the solvents were removed. The residue was dissolved in DMF and purified by preparative HPLC to afford 6-(8-methyl-[1,2,4]triazolo[1,5-a]pyridin-6-yl)-N-(piperidin-4-yl)-1H-indole-3-carboxamide (5.8 mg, 0.015 mmol, 21.59% yield). MS (M$^{+1}$) m/z: 374.9 (MH$^+$). LC retention time 0.73 min [QC-ACN-AA-XB].

Example 199

6-(8-methyl-[1,2,4]triazolo[1,5-a]pyridin-6-yl)-N-(piperidin-4-yl)-1H-indazole-3-carboxamide

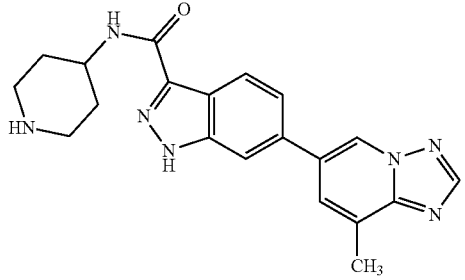

(199)

Step 1:
To a mixture of 6-bromo-1H-indazole-3-carboxylic acid (100 mg, 0.415 mmol), tert-butyl 4-aminopiperidine-1-carboxylate (91 mg, 0.456 mmol), and TEA (116 µl, 0.830 mmol) in DCM was added HATU (189 mg, 0.498 mmol). The reaction mixture was stirred at room temperature overnight. The reaction mixture was diluted with DCM and washed with 0.1 M HCl, saturated NaCl, and 1 N NaOH. The organic layer was dried with MgSO$_4$, filtered and concentrated to afford tert-butyl 4-(6-bromo-1H-indazole-3-carboxamido)piperidine-1-carboxylate (145 mg, 0.343 mmol, 83% yield). MS (M$^{+1}$) m/z: 423/425 (MH$^+$). LC retention time 0.93 min [A1].

Step 2:
To a mixture of 8-methyl-6-(4,4,5,5-tetramethyl-1,3,2-dioxaborolan-2-yl)-[1,2,4]triazolo[1,5-a]pyridine (25.5 mg, 0.098 mmol), tert-butyl 4-(6-bromo-1H-indazole-3-carboxamido)piperidine-1-carboxylate (26 mg, 0.061 mmol), and 2ND generation XPHOS precatalyst (4.83 mg, 6.14 µmol) in THF (2 mL) was added 2M K$_3$PO$_4$ (0.061 mL, 0.184 mmol). The reaction mixture was sparged with nitrogen for 5 minutes. The reaction vessel was sealed and heated at 85° C. overnight. The reaction mixture was diluted with dichloromethane and dried with MgSO$_4$, then filtered and concentrated. The residue was treated with TFA for 1 hour. Solvent was removed. The residue was dissolved in DMF and purified by preparative HPLC to afford 6-(8-methyl-[1,2,4]triazolo[1,5-a]pyridin-6-yl)-N-(piperidin-4-yl)-1H-indazole-3-carboxamide (4.5 mg, 0.012 mmol, 19.51% yield). MS (M$^{+1}$) m/z: 376.1 (MH$^+$). LC retention time 0.84 min [QC-ACN-AA-XB].

Example 200

6-(8-methyl-[1,2,4]triazolo[1,5-a]pyridin-6-yl)-N-(piperidin-4-yl)-1H-indazol-3-amine

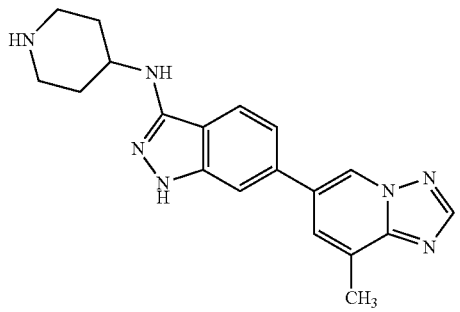

(200)

Step 1:
To a mixture of 6-bromo-1H-indazol-3-amine (140 mg, 0.660 mmol) in DMF (5 mL) was added tert-butyl 4-oxopiperidine-1-carboxylate (263 mg, 1.320 mmol). The reaction mixture was stirred at room temperature for 30 minutes, then sodium triacetoxyborohydride (420 mg, 1.981 mmol) was added along with a few drops of AcOH. The reaction mixture was stirred for 2 hours. The reaction mixture was diluted with ethyl acetate and washed with saturated NaCl. The organic layer was dried with MgSO$_4$, filtered and concentrated to afford tert-butyl 4-((6-bromo-1H-indazol-3-yl)amino)piperidine-1-carboxylate (220 mg, 0.557 mmol, 84% yield). MS (M$^{+1}$) m/z: 395/397 (MH$^+$). LC retention time 0.85 min [A1].

Step 2:
To a mixture of tert-butyl 4-((6-bromo-1H-indazol-3-yl)amino)piperidine-1-carboxylate (40 mg, 0.101 mmol), 8-methyl-6-(4,4,5,5-tetramethyl-1,3,2-dioxaborolan-2-yl)-[1,2,4]triazolo[1,5-a]pyridine (31.5 mg, 0.121 mmol), and 2ND generation XPHOS precatalyst (7.96 mg, 10.12 µmol) in THF (2 mL) was added 3M K$_3$PO$_4$ (0.101 mL, 0.304 mmol). The reaction mixture was sparged with nitrogen for 5 minutes. The reaction vessel was sealed and heated at 85° C. for 3 days. The solvent was removed and DCM and TFA (1 mL each) were added. The reaction mixture was stirred for one hour and solvents were removed. The residue was dissolved in DMF, filtered, and purified by preparative HPLC to afford 6-(8-methyl-[1,2,4]triazolo[1,5-a]pyridin-6-yl)-N-(piperidin-4-yl)-1H-indazol-3-amine (6.6 mg, 0.019 mmol, 18.60% yield). MS (M$^{+1}$) m/z: 348.1 (MH$^+$). LC retention time 0.74 min [QC-ACN-AA-XB].

Example 201

5-methyl-6-(8-methyl-[1,2,4]triazolo[1,5-a]pyridin-6-yl)-1H-indazol-3-amine

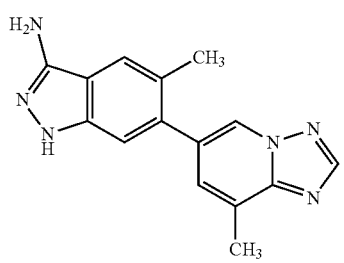

(201)

Step 1:
To a mixture of 4-bromo-2-fluoro-5-methylbenzonitrile (260 mg, 1.215 mmol) in ethanol (5 mL) was added hydrazine hydrate (0.089 mL, 12.15 mmol). The reaction vessel was sealed and heated at 90° C. overnight. The reaction mixture was poured into water (50 mL) and then placed in a refrigerator for 1 hour. The solid material was collected by filtration, washed with water, and dried in vacuo for 12 hours to afford 6-bromo-5-methyl-1H-indazol-3-amine (210 mg, 0.929 mmol, 76% yield). NMR was consistent with desired product. MS (M$^{+1}$) m/z: 228.0 (MH$^+$). LC retention time 0.65 min [A1].

183

Step 2:

To a mixture of 6-bromo-5-methyl-1H-indazol-3-amine (20 mg, 0.088 mmol), 8-methyl-6-(4,4,5,5-tetramethyl-1,3,2-dioxaborolan-2-yl)-[1,2,4]triazolo[1,5-a]pyridine (30 mg, 0.116 mmol), and 2ND generation XPHOS precatalyst (7 mg, 8.90 µmol) in dioxane (10 mL) was added 2M $K_3PO_4$ (0.133 mL, 0.265 mmol). The reaction mixture was sparged with nitrogen for 5 minutes. The reaction vessel was sealed and heated at 95° C. overnight. The reaction mixture was concentrated then dissolved in DMF, filtered and purified by preparative HPLC to afford 5-methyl-6-(8-methyl-[1,2,4]triazolo[1,5-a]pyridin-6-yl)-1H-indazol-3-amine (14.2 mg, 0.050 mmol, 56.0% yield). MS ($M^{+1}$) m/z: 279.1 ($MH^+$). LC retention time 0.91 min [QC-ACN-AA-XB].

Example 202

N-(5-methyl-6-(8-methyl-[1,2,4]triazolo[1,5-a]pyridin-6-yl)-1H-indazol-3-yl)piperidine-4-carboxamide

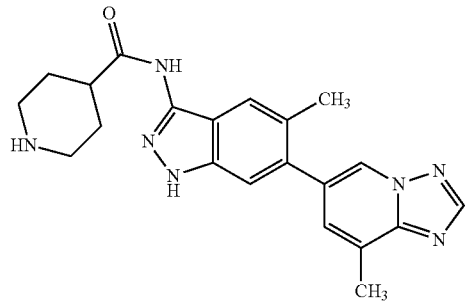

(202)

Step 1:

To a mixture of 1-(tert-butoxycarbonyl)piperidine-4-carboxylic acid (50.4 mg, 0.22 mmol) and TEA (0.061 mL, 0.440 mmol) in DCM (3 mL) was added thionyl chloride in DCM (0.440 mL, 0.440 mmol). The reaction mixture was stirred at room temperature for two hours. The solvents were removed in vacuo to provide the acid chloride. In a separate vial, 5-methyl-6-(8-methyl-[1,2,4]triazolo[1,5-a]pyridin-6-yl)-1H-indazol-3-amine (61.2 mg, 0.220 mmol) was dissolved in pyridine (0.089 mL, 1.100 mmol). The acid chloride from was dissolved in DCM and added dropwise via a pipette. The reaction mixture was stirred at room temperature overnight. The reaction mixture was diluted with dichloromethane and washed with water. The organic layer was dried with $MgSO_4$, filtered and concentrated. This residue was treated with DCM/TFA (1:1) for 30 minutes. Solvents were removed in vacuo. The residue was dissolved in DMF and purified by preparative HPLC to afford 3-amino-5-methyl-6-(8-methyl-[1,2,4]triazolo[1,5-a]pyridin-6-yl)-1H-indazol-1-yl)(piperidin-4-yl) methanone (1 mg, 2.406 µmol, 1.094% yield). MS ($M^{+1}$) m/z: 390.1 ($MH^+$). LC retention time 0.76 min [QC-ACN-AA-XB].

184

Example 203

N-(5-methyl-6-(8-methyl-[1,2,4]triazolo[1,5-a]pyridin-6-yl)-1H-indazol-3-yl)piperidine-4-carboxamide

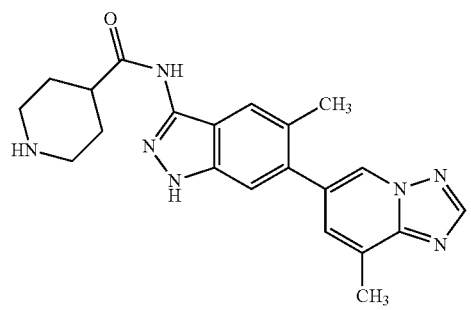

(203)

Step 1:

To a mixture of 6-(3-bromo-5-methyl-1H-indazol-6-yl)-8-methyl-[1,2,4]triazolo[1,5-a]pyridine (120 mg, 0.351 mmol) and TEA (0.073 mL, 0.526 mmol) in acetonitrile (10 mL) was added BOC-anhydride (0.263 mL, 0.368 mmol) along with a catalytic amount of DMAP. The reaction mixture was stirred overnight at room temperature. LCMS indicated that the reaction was almost complete. Additional BOC-anhydride (0.263 mL, 0.368 mmol) was added. After stirring one more hour, the reaction mixture was diluted with ethyl acetate and washed with saturated NaCl. The organic layer was dried with $MgSO_4$, filtered and concentrated to afford tert-butyl 3-bromo-5-methyl-6-(8-methyl-[1,2,4]triazolo[1,5-a] pyridin-6-yl)-1H-indazole-1-carboxylate (155 mg, 0.350 mmol, 100% yield). MS ($M^{+1}$) m/z: 442/444 ($MH^+$). LC retention time 0.85 min [A1].

Step 2:

A mixture of tert-butyl 3-bromo-5-methyl-6-(8-methyl-[1,2,4]triazolo[1,5-a]pyridin-6-yl)-1H-indazole-1-carboxylate (30 mg, 0.068 mmol), tert-butyl 4-aminopiperidine-1-carboxylate (20.38 mg, 0.102 mmol), cesium carbonate (44.2 mg, 0.136 mmol), XANTPHOS (5.89 mg, 10.17 µmol) and $Pd_2dba_3$ (6.21 mg, 6.78 µmol) in 1,4-dioxane (2 mL) was placed in a red capped pressure vessel, and sparged with nitrogen for 5 minutes. The reaction vessel was sealed and heated at 100° C. for 3 hours. The reaction mixture was diluted with dichloromethane and dried with $MgSO_4$, then filtered, and concentrated. The crude residue was treated with TFA/DCM for 1 hour. The reaction mixture was concentrated, then dissolved in DMF, filtered, and purified by preparative HPLC to afford 5-methyl-6-(8-methyl-[1,2,4]triazolo[1,5-a]pyridin-6-yl)-N-(piperidin-4-yl)-1H-indazol-3-amine (3.4 mg, 9.13 µmol, 13.47% yield). MS ($M^{+1}$) m/z: 362.2 ($MH^+$). LC retention time 0.77 min [QC-ACN-TFA-XB].

Example 204

5-methyl-6-(8-methyl-[1,2,4]triazolo[1,5-a]pyridin-6-yl)-N-(2-(pyrrolidin-1-yl)ethyl)-1H-indazol-3-amine

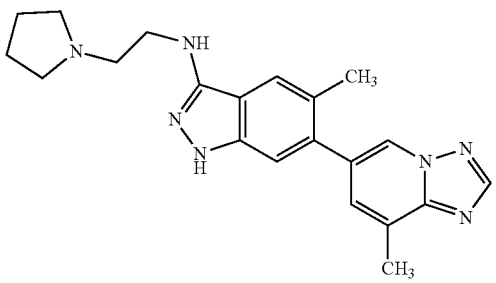

(204)

Step 1:

A mixture of 6-bromo-5-methyl-1H-indazole (200 mg, 0.948 mmol) in AcOH (2 mL) was added to a mixture of acetic anhydride (1 mL, 10.60 mmol) and nitric acid (0.042 mL, 0.948 mmol) at 0° C. After stirring 5 minutes the reaction mixture was poured onto ice. The mixture was stirred for 30 minutes allowing ice to melt. The solids were collected by filtration and dried in vacuo for 2 hours.

Step 2:

To a mixture of 6-bromo-5-methyl-2-nitro-2H-indazole (100 mg, 0.391 mmol) in THF (2 mL) was added 2-(pyrrolidin-1-yl)ethan-1-amine (0.099 mL, 0.781 mmol). The reaction mixture was stirred at room temperature overnight. The reaction mixture was diluted with dichloromethane and washed with water. The organic layer was dried with $MgSO_4$, filtered and concentrated. The crude material was purified on a silica gel cartridge (24 g) using a DCM/MeOH gradient (0-20% EtOAc over 15 min) to afford 6-bromo-5-methyl-N-(2-(pyrrolidin-1-yl)ethyl)-1H-indazol-3-amine (13 mg, 0.040 mmol, 10.30% yield). MS ($M^{+1}$) m/z: 325.4 ($M2H^+$). LC retention time 0.64 min [A1].

Step 3:

To a mixture of 6-bromo-5-methyl-N-(2-(pyrrolidin-1-yl)ethyl)-1H-indazol-3-amine (13 mg, 0.040 mmol), 8-methyl-6-(4,4,5,5-tetramethyl-1,3,2-dioxaborolan-2-yl)-[1,2,4]triazolo[1,5-a]pyridine (20.84 mg, 0.080 mmol), and 2ND generation XPHOS precatalyst (3.16 mg, 4.02 µmol) in dioxane (1 mL) was added 2 M $K_3PO_4$ (0.060 mL, 0.121 mmol). The reaction mixture was sparged with nitrogen for 5 minutes. The reaction vessel was sealed and heated at 95° C. for 12 hours. The reaction mixture was filtered and purified by preparative HPLC to afford 5-methyl-6-(8-methyl-[1,2,4]triazolo[1,5-a]pyridin-6-yl)-N-(2-(pyrrolidin-1-yl)ethyl)-1H-indazol-3-amine (2.2 mg, 5.79 µmol, 14.41% yield). MS ($M^{+1}$) m/z: 376.1 ($MH^+$). LC retention time 0.85 min [QC-ACN-AA-XB].

Example 205

8-methyl-6-(5-methyl-3-(piperazin-1-yl)-1H-indazol-6-yl)-[1,2,4]triazolo[1,5-a]pyridine

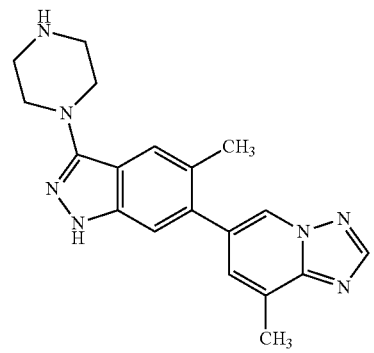

(205)

6-(3-bromo-5-methyl-1H-indazol-6-yl)-8-methyl-[1,2,4]triazolo[1,5-a]pyridine (75 mg, 0.219 mmol) and piperazine (944 mg, 10.96 mmol) were placed in a Teflon screw cap vial with a stir bar. The reaction vessel was sealed and placed in a heating block at 160° C. After 24 h, the desired product formed partially as detected by LCMS (RT=0.54, M+1=348). The reaction vessel was resealed and heated for 3 more days.

The reaction mixture was cooled and MeOH was added. The residue was purified by preparative HPLC to afford 8-methyl-6-(5-methyl-3-(piperazin-1-yl)-1H-indazol-6-yl)-[1,2,4]triazolo[1,5-a]pyridine (2 mg, 5.33 µmol, 2.432% yield). MS ($M^{+1}$) m/z: 348.2 ($MH^+$). LC retention time 0.85 min [QC-ACN-AA-XB].

Example 206

6-(5-isopropyl-3-(piperazin-1-yl)-1H-indazol-6-yl)-8-methyl-[1,2,4]triazolo[1,5-a]pyridine

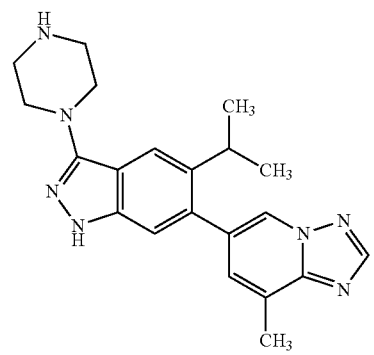

(206)

To a mixture of tert-butyl 3-bromo-5-isopropyl-6-(8-methyl-[1,2,4]triazolo[1,5-a]pyridin-6-yl)-1H-indazole-1-carboxylate (500 mg, 1.063 mmol), tert-butyl piperazine-1-carboxylate (594 mg, 3.19 mmol), and DABCO (215 mg, 1.913 mmol) in DMA (10 mL) were added nickel(II) bromide ethylene glycol dimethyl ether complex (16.40 mg, 0.053 mmol) and $(Ir[DF(CF_3)PPY]_2(DTBPY))PF_6$ (0.298 mg, 0.266 μmol). The reaction mixture was sparged for 5 minutes with nitrogen. The resulting solution was sealed and placed in a rack with stirring and irradiation with 34 W Kessil KSH 150B blue grow lamps and a cooling fan for 18 hours. LCMS shows partial reaction. Additional (Ir[DF (CF$_3$)PPY]$_2$(DTBPY))PF$_6$ (0.298 mg, 0.266 μmol) was added. Re-sparged and irradiated for an additional 18 hours. The reaction mixture was diluted with ethyl acetate and washed with saturated NaCl. The organic layer was dried with MgSO$_4$, filtered and concentrated. The crude material was purified on a silica gel cartridge (40 g) using an EtOAc/Hex gradient (0-100% EtOAc over 13 min). The product fractions were isolated, concentrated, and dried in vacuo to afford tert-butyl 3-(4-(tert-butoxycarbonyl)piperazin-1-yl)-5-isopropyl-6-(8-methyl-[1,2,4]triazolo[1,5-a]pyridin-6-yl)-1H-indazole-1-carboxylate (150 mg, 0.261 mmol, 24.51% yield).

tert-Butyl 3-(4-(tert-butoxycarbonyl)piperazin-1-yl)-5-isopropyl-6-(8-methyl-[1,2,4]triazolo[1,5-a]pyridin-6-yl)-1H-indazole-1-carboxylate (150 mg, 0.261 mmol) was stirred in TFA (5 mL) for 30 minutes. A drop of water was added and the reaction mixture was stirred for an additional 30 minutes. Solvent was removed in vacuo and dried. The residue was dissolved with CHCl$_3$/IPA (9:1) and washed with saturated NaHCO$_3$. The organic layer was dried with MgSO$_4$, filtered and concentrated. The crude product was purified by preparative HPLC to afford 6-(5-isopropyl-3-(piperazin-1-yl)-1H-indazol-6-yl)-8-methyl-[1,2,4]triazolo[1,5-a]pyridine (80 mg, 0.213 mmol, 82% yield). MS (M$^{+1}$) m/z: 376.3 (MH$^+$). LC retention time 1.08 min [QC-ACN-AA-XB].

Example 207

6-(5-isopropyl-3-(4-(tetrahydro-2H-pyran-4-yl)piperazin-1-yl)-1H-indazol-6-yl)-8-methyl-[1,2,4]triazolo[1,5-a]pyridine

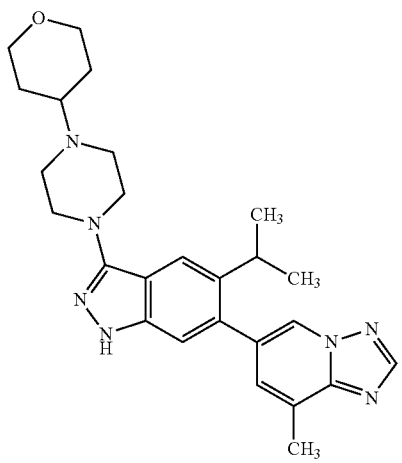

(207)

To a mixture of 6-(5-isopropyl-3-(piperazin-1-yl)-1H-indazol-6-yl)-8-methyl-[1,2,4] triazolo[1,5-a]pyridine (20 mg, 0.053 mmol), tetrahydro-4H-pyran-4-one (160 mg, 1.598 mmol), and TEA (0.074 mL, 0.533 mmol) in DCM (1 mL) was added sodium triacetoxyborohydride (33.9 mg, 0.160 mmol). A drop of acetic acid was added and the reaction mixture was stirred at room temperature overnight. The reaction was incomplete by LCMS. Additional tetrahydro-4H-pyran-4-one (160 mg, 1.598 mmol) and sodium triacetoxyborohydride (33.9 mg, 0.160 mmol) were added and the reaction mixture was stirred over the weekend. The reaction was quenched with MeOH. The reaction mixture was filtered and purified by preparative HPLC to afford 6-(5-isopropyl-3-(4-(tetrahydro-2H-pyran-4-yl)piperazin-1-yl)-1H-indazol-6-yl)-8-methyl-[1,2,4]triazolo[1,5-a]pyridine (5.2 mg, 10.81 μmol, 20.29% yield). MS (M$^{+1}$) m/z: 460.2 (MH$^+$). LC retention time 1.45 min [QC-ACN-AA-XB].

Example 208

6-(5-isopropyl-3-(4-isopropylpiperazin-1-yl)-1H-indazol-6-yl)-8-methyl-[1,2,4]triazolo[1,5-a]pyridine

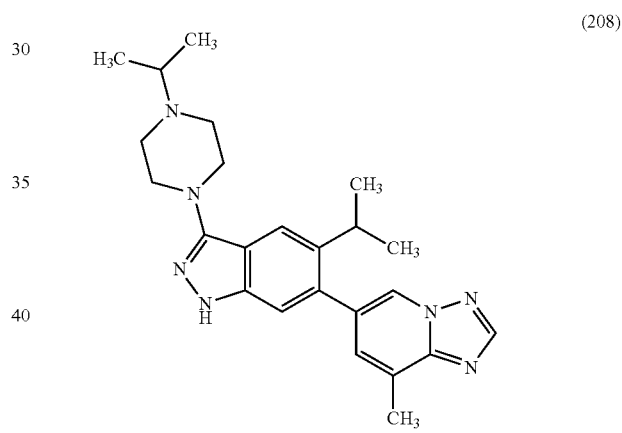

(208)

To a mixture of 6-(5-isopropyl-3-(piperazin-1-yl)-1H-indazol-6-yl)-8-methyl-[1,2,4]triazolo[1,5-a]pyridine (20 mg, 0.053 mmol) and acetone (0.039 mL, 0.533 mmol) in DCM (1 mL) was added sodium triacetoxyborohydride (33.9 mg, 0.160 mmol). The reaction mixture was stirred for 4 hours. LCMS show incomplete reaction. Additional acetone (0.039 mL, 0.533 mmol) and sodium triacetoxyborohydride (33.9 mg, 0.160 mmol) were added and the reaction mixture was stirred overnight. The reaction was still incomplete. Additional acetone (0.039 mL, 0.533 mmol) and sodium triacetoxyborohydride (33.9 mg, 0.160 mmol) were added. The reaction mixture was stirred over the weekend. The reaction was quenched with MeOH. The reaction mixture was filtered and purified by preparative HPLC to afford 6-(5-isopropyl-3-(4-isopropylpiperazin-1-yl)-1H-indazol-6-yl)-8-methyl-[1,2,4]triazolo[1,5-a]pyridine (6.5 mg, 0.015 mmol, 28.0% yield). MS (M$^{+1}$) m/z: 418.4 (MH$^+$). LC retention time 1.34 min [QC-ACN-AA-XB].

The following examples were prepared according to the general procedures for Examples 1-10.

TABLE 3

| Ex. No. | Structure | Obs. MS Ion | Ret time (min) | HPLC |
|---|---|---|---|---|
| 209 | | 499.4 | 1.25 | QC-ACN-AA-XB |
| 210 | | 499.4 | 1.44 | QC-ACN-AA-XB |
| 211 | | 521.4 | 1.28 | QC-ACN-AA-XB |
| 212 | | 521.2 | 1.74 | QC-ACN-AA-XB |

BIOLOGICAL ASSAYS

The pharmacological properties of the compounds of this invention may be confirmed by a number of biological assays. The exemplified biological assays, which follow, have been carried out with compounds of the invention.

TLR7/8/9 Inhibition Reporter Assays

HEK-Blue™-cells (Invivogen) overexpressing human TLR7, TLR8 or TLR9 receptors were used for screening inhibitors of these receptors using an inducible SEAP (secreted embryonic alkaline phosphatase) reporter gene under the control of the IFN-β minimal promoter fused to five NF-κB and AP-1-binding sites. Briefly, cells are seeded into Greiner 384 well plates (15000 cells per well for TLR7, 20,000 for TLR8 and 25,000 for TLR9) and then treated with test compounds in DMSO to yield a final dose response concentration range of 0.05 nM to 50 μM. After a 30 minute compound pre-treatment at room temperature, the cells are then stimulated with a TLR7 ligand (gardiquimod at a final concentration of 7.5 μM), TLR8 ligand (R848 at a final concentration of 15.9 μM) or TLR9 ligand (ODN2006 at a final concentration of 5 nM) to activate NF-κB and AP-1 which induce the production of SEAP. After a 22 hour incubation at 37° C., 5% $CO_2$, SEAP levels are determined with the addition of HEK-Blue™ Detection reagent (Invivogen), a cell culture medium that allows for detection of SEAP, according to manufacturer's specifications. The percent inhibition is determined as the % reduction in the HEK-Blue signal present in wells treated with agonist plus DMSO alone compared to wells treated with a known inhibitor.

TABLE 4

TLR7/8/9 Reporter Assay Data

| Ex. No. | TLR7 $IC_{50}$ (nM) | TLR8 $IC_{50}$ (nM) | TLR9 $IC_{50}$ (nM) |
|---|---|---|---|
| 1 | 4.1 | 3.9 | 657 |
| 2 | 0.9 | 19.9 | 1037 |
| 3 | 10.2 | 0.4 | 1122 |
| 4 | 19.9 | 0.7 | 2817 |

TABLE 4-continued

TLR7/8/9 Reporter Assay Data

| Ex. No. | TLR7 IC$_{50}$ (nM) | TLR8 IC$_{50}$ (nM) | TLR9 IC$_{50}$ (nM) |
|---|---|---|---|
| 5 | 4.9 | 13.5 | 1565 |
| 6 | 9.3 | 0.3 | 3210 |
| 7 | 21.6 | 1.3 | 4477 |
| 8 | 4.0 | 4.5 | 6072 |
| 9 | 0.5 | 0.1 | 6199 |
| 10 | 68.9 | 3.8 | 1008 |
| 11 | 64.4 | 244.6 | 363 |
| 12 | 16.9 | 31.2 | 192 |
| 13 | 1687.6 | 269.3 | 605 |
| 14 | 80.6 | 114.8 | 3431 |
| 15 | 29.4 | 25.9 | 1129 |
| 16 | 3.3 | 35.2 | 1425 |
| 17 | 388.0 | 327.6 | 3189 |
| 18 | 12.9 | 3.3 | 1501 |
| 19 | 31.8 | 11.2 | 1778 |
| 20 | 24.6 | 3.8 | 4419 |
| 21 | 26.2 | 0.7 | 4544 |
| 22 | 17.7 | 0.8 | 3129 |
| 23 | 43.4 | 2.9 | 6626 |
| 24 | 15.8 | 1.1 | 862 |
| 25 | 262.8 | 10.4 | 2236 |
| 26 | 18.8 | 1.5 | 1319 |
| 27 | 6.6 | 25.9 | 650 |
| 28 | 12.4 | 0.4 | 4405 |
| 29 | 39.0 | 0.9 | 6341 |
| 30 | 15.3 | 0.4 | 6739 |
| 31 | 39.8 | 0.6 | 6121 |
| 32 | 18.3 | 0.3 | 4437 |
| 33 | 96.7 | 3.0 | 9009 |
| 34 | 8.1 | 0.2 | 3950 |
| 35 | 29.7 | 0.8 | 3102 |
| 36 | 7.0 | 0.2 | 3343 |
| 37 | 12.4 | 0.4 | 5144 |
| 38 | 6.0 | 0.1 | 50000 |
| 39 | 22.6 | 0.9 | 4118 |
| 40 | 23.4 | 4.6 | 13038 |
| 41 | 20.0 | 1.9 | 7303 |
| 42 | 83.6 | 0.9 | 14526 |
| 43 | 46.7 | 0.2 | 2436 |
| 44 | 46.3 | 1.9 | 5488 |
| 45 | 19.2 | 0.7 | 50000 |
| 46 | 124.2 | 2.1 | 1037 |
| 47 | 22.9 | 0.2 | 2884 |
| 48 | 47.6 | 2.5 | 2306 |
| 49 | 173.9 | 15.3 | 1887 |
| 50 | 63.4 | 1.5 | 404 |
| 51 | 4.7 | 19.6 | 287 |
| 52 | 27.2 | 4.6 | 4262 |
| 53 | 44.2 | 1.2 | 5826 |
| 54 | 41.0 | 6.4 | 5268 |
| 55 | 53.9 | 0.1 | 2186 |
| 56 | 12.2 | 1.7 | 4942 |
| 57 | 19.9 | 4.5 | 6899 |
| 58 | 76.2 | 2.8 | 661 |
| 59 | 10.5 | 43.9 | 3212 |
| 60 | 79.3 | 62.2 | 4252 |
| 61 | 13.5 | 19.5 | 3340 |
| 62 | 823.7 | 5.2 | 3202 |
| 63 | 561.9 | 32.4 | — |
| 64 | 905.2 | 41.8 | 9037 |
| 65 | 219.4 | 47.0 | 50000 |
| 66 | 217.8 | 45.4 | 8837 |
| 67 | 23.8 | 0.9 | 3956 |
| 68 | 68.0 | 2.5 | 13024 |
| 69 | 18.0 | 1.4 | 1314 |
| 70 | 18.3 | 1.4 | 6210 |
| 71 | 9.8 | 3.3 | 1369 |
| 72 | 50.8 | 2.3 | 11247 |
| 73 | 52.3 | 4.3 | 9072 |
| 74 | 49.3 | 15.5 | 4944 |
| 75 | 7.2 | 14.1 | 1919 |
| 76 | 6.9 | 37.8 | 2115 |
| 77 | 11.1 | 10.9 | 2195 |
| 78 | 92.2 | 252.4 | 24526 |
| 79 | 10.3 | 53.8 | 6051 |
| 80 | 3.8 | 2.5 | 2839 |
| 81 | 1.3 | 5.3 | 1827 |
| 82 | 1.6 | 0.4 | 2196 |
| 83 | 45.0 | 5.5 | 8006 |
| 84 | 33.4 | 15.7 | 5612 |
| 85 | 33.0 | 1.5 | 3935 |
| 86 | 5.8 | 21.8 | 1292 |
| 87 | 6.3 | 0.6 | 11615 |
| 88 | 3.7 | 0.2 | 14198 |
| 89 | 8.3 | 0.7 | — |
| 90 | 2.6 | 0.1 | 7943 |
| 91 | 3.7 | 0.4 | 14464 |
| 92 | 2.7 | 0.2 | 17158 |
| 93 | 0.8 | 0.1 | 6125 |
| 94 | 3.0 | 0.5 | 10337 |
| 95 | 5.4 | 0.2 | 10845 |
| 96 | 3.0 | 0.2 | 15996 |
| 97 | 0.6 | 0.1 | 5455 |
| 98 | 2.5 | 0.2 | 6574 |
| 99 | 0.9 | 0.1 | 14020 |
| 100 | 7.5 | 0.2 | 17491 |
| 101 | 5.6 | 0.2 | 12152 |
| 102 | 1.0 | 0.4 | 10911 |
| 103 | 11.0 | 0.9 | 12220 |
| 104 | 6.9 | 0.8 | 13617 |
| 105 | 5.1 | 0.1 | 8779 |
| 106 | 7.2 | 0.2 | 39780 |
| 107 | 10.3 | 1.7 | 16690 |
| 108 | 5.6 | 0.2 | 23470 |
| 109 | 2.0 | 2.6 | 1631 |
| 110 | 2.4 | 1.8 | 3863 |
| 111 | 1.8 | 0.5 | 18600 |
| 112 | 1.5 | 0.3 | 20886 |
| 113 | 1.5 | 0.1 | 20266 |
| 114 | 0.2 | 0.0 | 6667 |
| 115 | 0.6 | 0.1 | 6699 |
| 116 | 0.6 | 0.1 | 6550 |
| 117 | 3.4 | 0.5 | 11235 |
| 118 | 0.3 | 0.1 | 4129 |
| 119 | 1.0 | 0.1 | 4916 |
| 120 | 7.4 | 1.1 | 50000 |
| 121 | 1.9 | 0.1 | — |
| 122 | 3.2 | 0.8 | 13681 |
| 123 | 0.5 | 0.1 | 5657 |
| 124 | 0.3 | 0.0 | 11005 |
| 125 | 2.5 | 0.3 | 12117 |
| 126 | 1.1 | 0.1 | 10804 |
| 127 | 1.9 | 0.1 | 8467 |
| 128 | 0.6 | 0.2 | 9564 |
| 129 | 4.1 | 0.5 | 7546 |
| 130 | 0.2 | 0.1 | 4203 |
| 131 | 2.0 | 0.3 | 4571 |
| 132 | 0.9 | 0.1 | 5431 |
| 133 | 1.4 | 0.2 | 9191 |
| 134 | 2.5 | 0.2 | 15938 |
| 135 | 15.5 | 9.4 | 18929 |
| 136 | 26.3 | 3.9 | 4903 |
| 137 | 5.5 | 0.6 | 8678 |
| 138 | 1.0 | 0.5 | 5872 |
| 139 | 1.2 | 0.1 | 6250 |
| 140 | 0.2 | 0.1 | 3433 |
| 141 | 5.3 | 2.9 | 3722 |
| 142 | 1.3 | 0.2 | 9706 |
| 143 | 3.5 | 1.5 | 6711 |
| 144 | 0.8 | 0.5 | 13146 |
| 145 | 1.5 | 0.8 | 8691 |
| 146 | 4.7 | 2.6 | 50000 |
| 147 | 0.4 | 0.2 | 13085 |
| 148 | 1.3 | 31.3 | 6452 |
| 149 | 0.8 | 0.4 | 7476 |
| 150 | 1.7 | 0.1 | 6910 |
| 151 | 1.4 | 0.6 | 8365 |
| 152 | 1.3 | 0.3 | 12984 |

TABLE 4-continued
TLR7/8/9 Reporter Assay Data
| Ex. No. | TLR7 IC$_{50}$ (nM) | TLR8 IC$_{50}$ (nM) | TLR9 IC$_{50}$ (nM) |
|---|---|---|---|
| 153 | 1.1 | 0.6 | 7454 |
| 154 | 0.5 | 0.2 | 15878 |
| 155 | 1.8 | 0.2 | 7558 |
| 156 | 0.8 | 0.1 | 6111 |
| 157 | 0.5 | 0.4 | 6729 |
| 158 | 0.5 | 0.2 | 9848 |
| 159 | 0.3 | 0.1 | 7434 |
| 160 | 5.3 | 0.4 | 7305 |
| 161 | 6.4 | 0.5 | 8395 |
| 162 | 1.5 | 0.7 | 8544 |
| 163 | 0.9 | 0.1 | 6227 |
| 164 | 1.5 | 0.1 | 6449 |
| 165 | 0.5 | 0.0 | 13296 |
| 166 | 4.2 | 0.2 | 8897 |
| 167 | 5.4 | 0.2 | 631 |
| 168 | 1.9 | 1.6 | 2572 |
| 169 | 1.2 | 0.5 | 1832 |
| 170 | 13.3 | 3.0 | 5726 |
| 171 | 8.2 | 0.1 | 2769 |
| 172 | 37.2 | 1.4 | 5072 |
| 173 | 18.9 | 8.0 | 1848 |
| 174 | 1.8 | 1.4 | 438 |
| 175 | 5.1 | 10.6 | 1629 |
| 176 | 12.5 | 3.8 | 4915 |
| 177 | 2.7 | 0.5 | 928 |
| 178 | 6.1 | 0.5 | 1624 |
| 179 | 3.3 | 8.5 | 2078 |
| 180 | 2.6 | 2.3 | 3258 |
| 181 | 71.7 | 19.9 | 50000 |
| 182 | 25.9 | 5.8 | 27383 |
| 183 | 4.9 | 8.1 | 2313 |
| 184 | 1.8 | 1.8 | 1190 |
| 185 | 20.9 | 9.5 | 2771 |
| 186 | 2.4 | 1.9 | 2550 |
| 187 | 11.3 | 4.9 | 1819 |
| 188 | 4.0 | 2.3 | 4341 |
| 189 | 12.2 | 8.2 | 2342 |
| 190 | 1.6 | 1.9 | 4510 |
| 191 | 2.6 | 0.5 | 14624 |
| 192 | 0.7 | 0.1 | 7893 |
| 193 | 13.2 | 1.6 | 3732 |
| 194 | 7.2 | 1.9 | 1658 |
| 195 | 3.7 | 0.8 | 6185 |
| 196 | 4.9 | 1.0 | 5759 |
| 197 | 319.4 | 2357.4 | 28230 |
| 198 | 492.8 | 590.4 | 9210 |
| 199 | 226.5 | 217.8 | 4367 |
| 200 | 289.2 | 149.4 | 1892 |
| 201 | 856.6 | 55.7 | 50000 |
| 202 | 266.1 | 15.3 | 9920 |
| 203 | 51.7 | 2.1 | 1423 |
| 204 | 85.9 | 1.9 | 2526 |
| 205 | 14.1 | 0.7 | 6097 |
| 206 | 3.2 | 16.4 | 21946 |
| 207 | 6.5 | 0.15 | 33280 |
| 208 | 5.8 | 0.12 | 11877 |
| 209 | 0.62 | 0.05 | 7997 |
| 210 | 2.1 | 0.37 | 5907 |
| 211 | 2.5 | 0.15 | 32313 |
| 212 | 8.2 | 0.36 | 24098 |
The invention claimed is:
1. A compound of Formula (I)
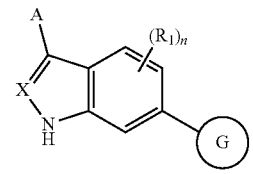
N-oxide, or a salt thereof, wherein:
X is CR$_1$ or N;
each R$_1$ is independently H, F, Cl, —CN, C$_{1-3}$ alkyl, C$_{1-2}$ fluoroalkyl, —OCH$_3$, or —S(O)$_2$(C$_{1-3}$ alkyl);
G is
a 9-membered heterocyclic ring selected from:
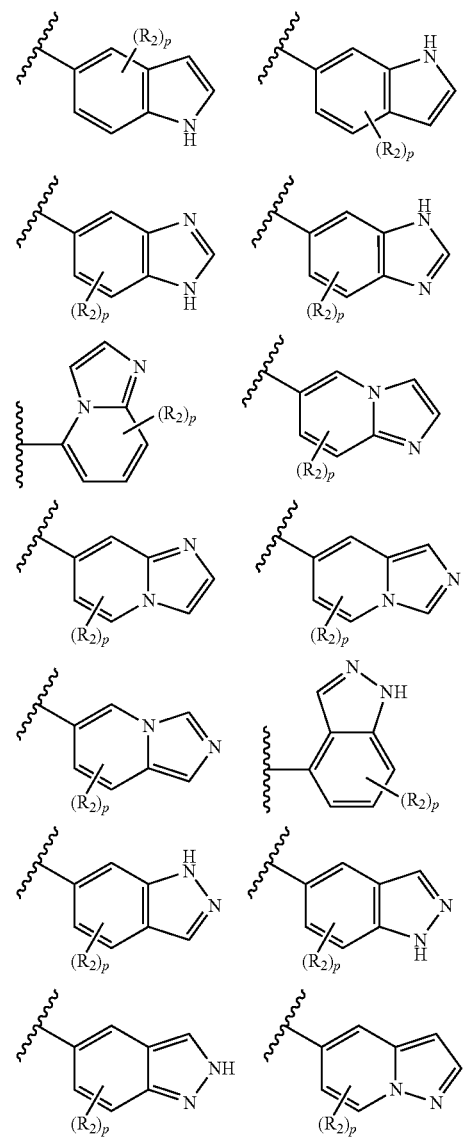

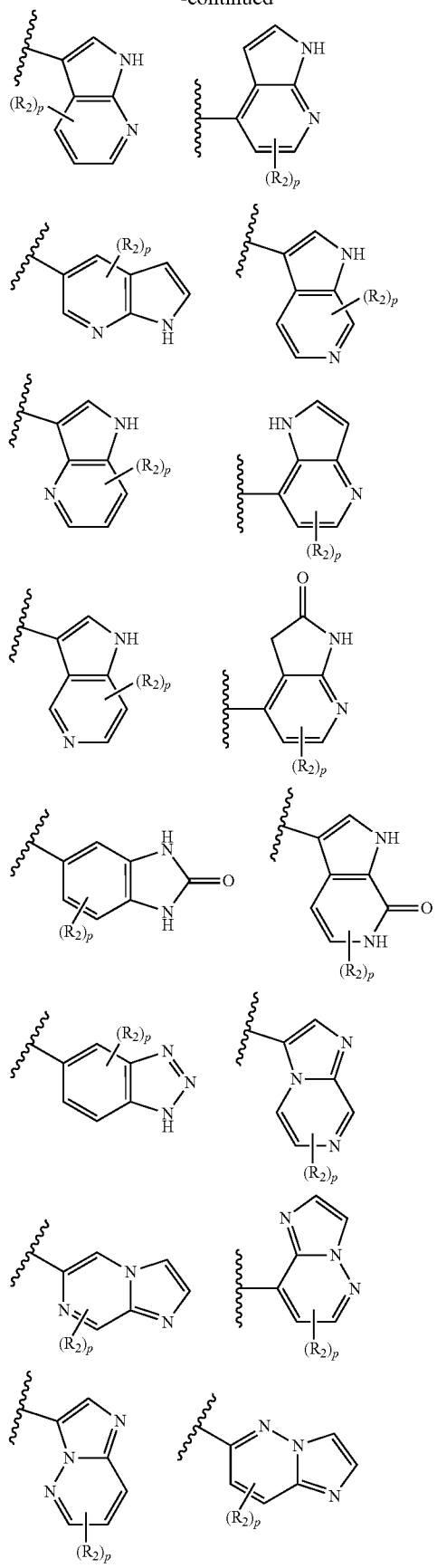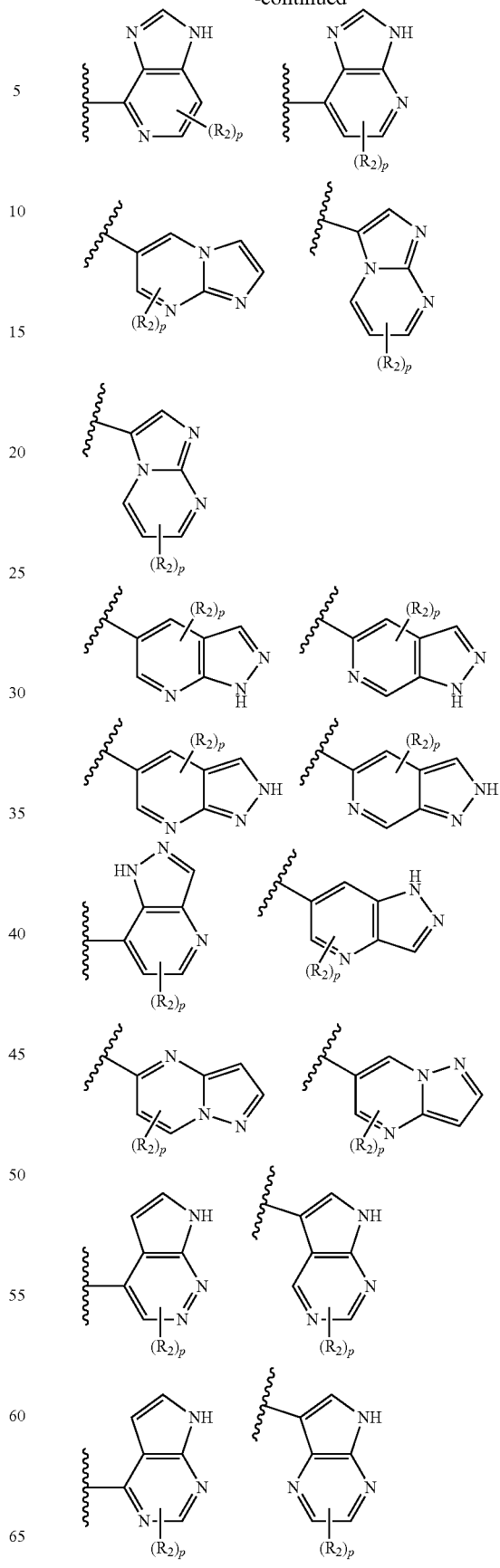

-continued
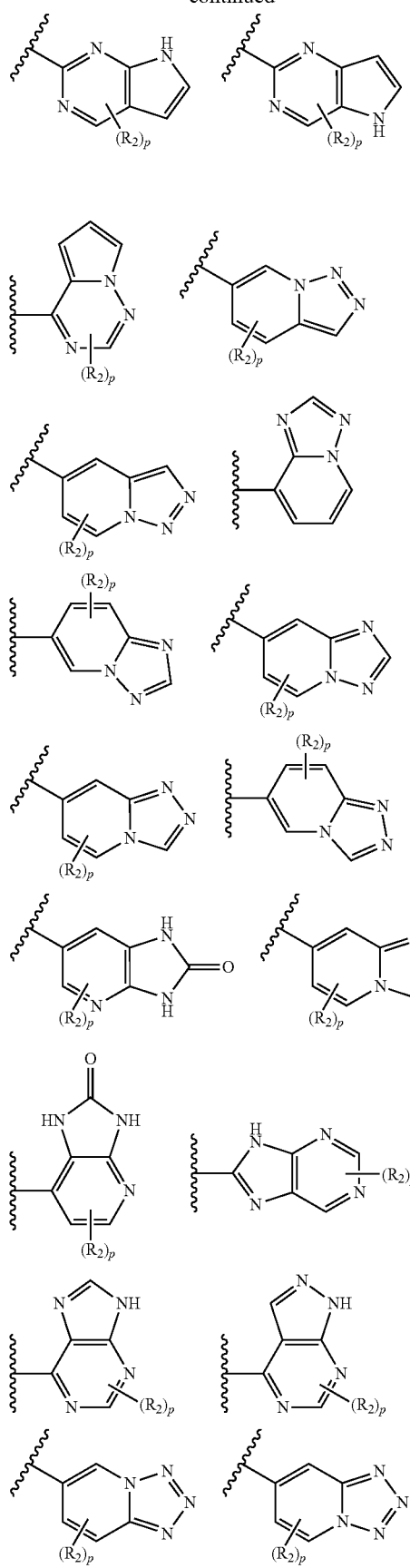
-continued
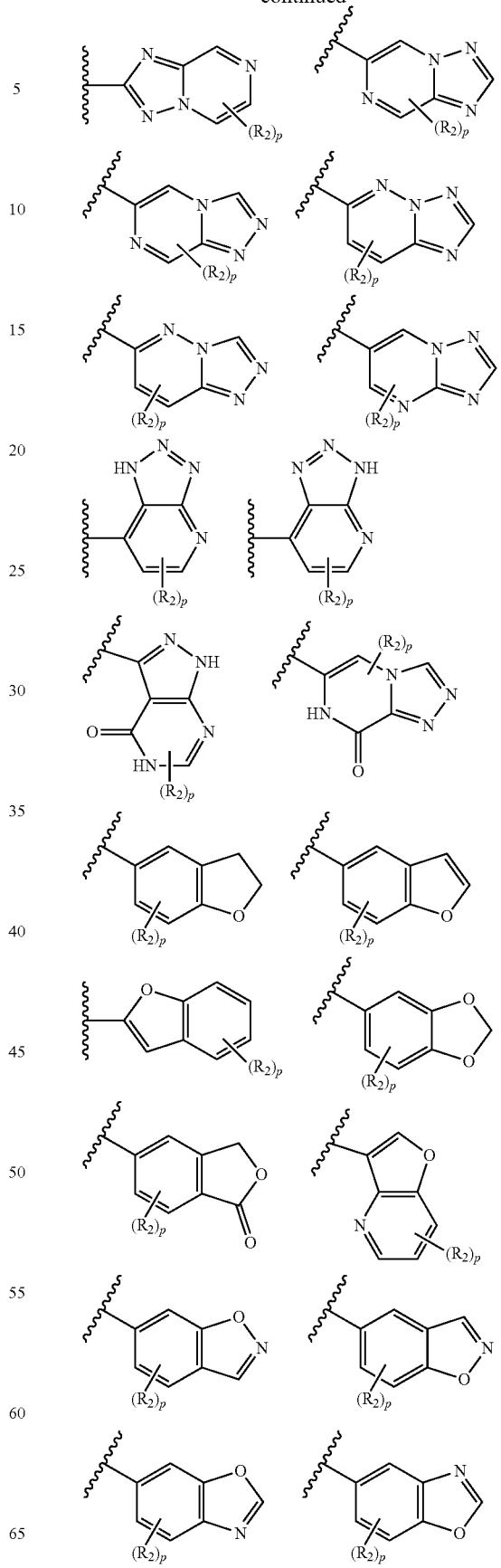

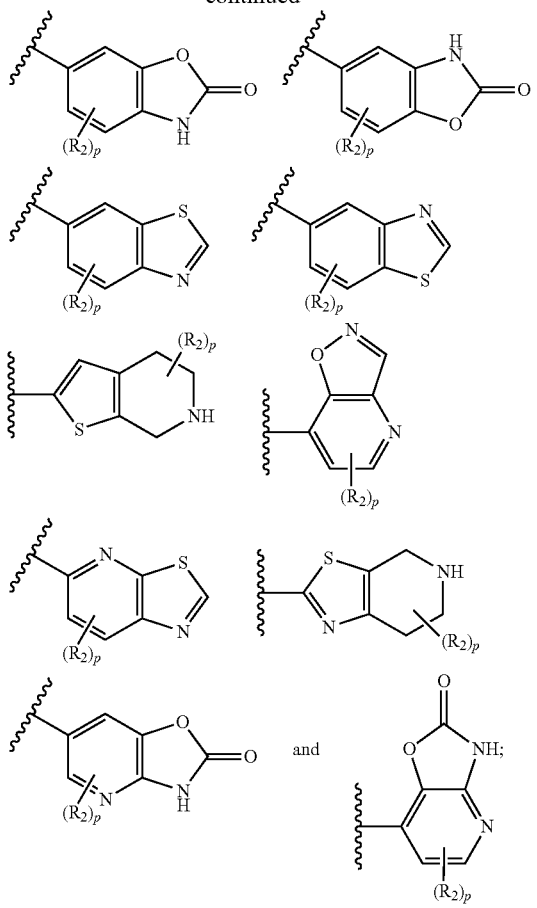

each R₂ is independently F, Cl, —CN, —OH, $C_{1-3}$ alkyl, $C_{1-2}$ fluoroalkyl, $C_{1-2}$ cyanoalkyl, $C_{1-3}$ hydroxyalkyl, $C_{1-2}$ aminoalkyl, —(CH₂)₀₋₂ O($C_{1-3}$ alkyl), $C_{3-6}$ cycloalkyl, —NR$_x$R$_x$, —(CH₂)₀₋₂C(O)NR$_x$R$_x$, —(CH₂)₀₋₂S(O)₂($C_{1-3}$ alkyl), —CH₂($C_{3-6}$ cycloalkyl), —CH₂(phenyl), phenyl, pyrimidinyl, or triazolyl;

A is:
(i) —OCH₂CH₂NR$_y$R$_y$;
(ii) —CR$_x$R$_x$R₃, —CH₂CH₂NR$_x$R₃, —C(O)NR$_x$R₃, —NR$_x$R₃, —NR$_x$CH₂CH₂R₃, or —OR₃; or
(iii) R₃;

R₃ is $C_{3-6}$ cycloalkyl, azetidinyl, morpholinyl, piperazinyl, piperidinyl, or pyrrolidinyl, each substituted with zero to 2 R$_{3a}$;

each R$_{3a}$ is independently $C_{1-4}$ alkyl, $C_{1-3}$ cyanoalkyl, $C_{1-3}$ fluoroalkyl, $C_{1-4}$ hydroxyalkyl, —CH₂C(O)NR$_x$R$_x$, —C(O)(CH₂)₁₋₃NR$_x$R$_x$, —NR$_y$R$_y$, (CH₂)₁₋₂S(O)₂($C_{1-2}$ alkyl), —(CH₂)₁₋₂NR$_x$S(O)₂($C_{1-2}$ alkyl), —NR$_x$CH₂C(O)NR$_y$R$_y$, —NR$_x$CH₂CH₂S(O)₂($C_{1-2}$ alkyl), —NR$_x$($C_{3-6}$ cycloalkyl), —NR$_x$(oxetanyl), —CH₂(methyltriazolyl), morpholinyl, oxetanyl, pyrrolidinyl, fluoropyrrolidinyl, hydroxy-methylpyrrolidinyl, tetrahydropyranyl, 1-oxa-6-azaspiro[3.3]heptanyl, 2-oxa-6-azaspiro[3.3]heptanyl, 2-oxa-6-azaspiro[3.4]octanyl, 6-oxa-2-azaspiro[3.4]octanyl, 2,2-dioxo-2-thia-6-azaspiro[3.3]heptanyl, 2-oxa-7-azaspiro[4.4]nonanyl, or azetidinyl substituted with zero to 3 substituents independently selected from F, Cl, —OH, —CN, $C_{1-2}$ alkyl, $C_{1-2}$ hydroxyalkyl, $C_{1-2}$ fluoroalkyl, and $C_{1-3}$ alkoxy;

each R$_x$ is independently H or —CH₃;

each R$_y$ is independently H or $C_{1-6}$ alkyl;

n is zero, 1, or 2; and p is zero, 1, or 2.

2. The compound according to claim 1, N-oxide, or a salt thereof,
wherein:
each R₁ is independently H, —CH₃, —CH₂CH₃, —CH(CH₃)₂, —OCH₃, or —S(O)₂CH₃;

G is:

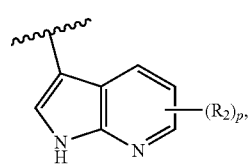

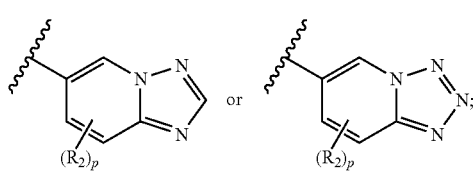

each R₂ is independently —CN, —CH₃, —OCH₃, or pyrimidinyl;

A is:
(i) —OCH₂CH₂N(CH₃)₂;
(ii) —CH₂R₃, —CH₂CH₂NHR₃, —C(O)NHR₃, —NHR₃, —NHCH₂CH₂R₃, or —OR₃; or
(iii) R₃;

R₃ is azetidinyl, cyclobutyl, cyclohexyl, piperazinyl, piperidinyl, or pyrrolidinyl, each substituted with zero to 1 R$_{3a}$;

R$_{3a}$ is —CH₃, —CH₂CH₂CH₃, —CH(CH₃)₂, —CH₂CN, —CH₂CH₂CN, —CH₂CH₂CF₃, —CH₂C(CH₃)₂OH, —CH₂C(O)NH₂, —CH₂C(O)N(CH₃)₂, —C(O)CH₂N(CH₃)₂, —C(O)CH₂CH₂N(CH₃)₂, —C(O)CH₂CH₂CH₂N(CH₃)₂, —NH(CH₃), —N(CH₃)₂, —NH(CH(CH₃)₂), —CH₂CH₂S(O)₂CH₃, —CH₂CH₂NHS(O)₂CH₃, —NHCH₂C(O)N(CH₃)₂, —NHCH₂CH₂S(O)₂CH₃, —NH(cyclopropyl), —NH(oxetanyl), —N(CH₃) (oxetanyl), —CH₂(methyltriazolyl), morpholinyl, oxetanyl, pyrrolidinyl, fluoropyrrolidinyl, hydroxy-methylpyrrolidinyl, tetrahydropyranyl, 1-oxa-6-azaspiro[3.3]heptanyl, 2-oxa-6-azaspiro[3.3]heptanyl, 2-oxa-6-azaspiro[3.4]octanyl, 6-oxa-2-azaspiro[3.4]octanyl, 2,2-dioxo-2-thia-6-azaspiro[3.3]heptanyl, 2-oxa-7-azaspiro[4.4]nonanyl, or azetidinyl substituted with zero to 2 substituents independently selected from F, —OH, —CH₃, —CH₂OH, —OCH₃, —OCH₂CH₃, and —OCH(CH₃)₂;

n is zero or 1; and p is zero, 1, or 2.

3. The compound according to claim 1, N-oxide, or a salt thereof, wherein:
each $R_1$ is independently H, —$CH_3$, —$CH_2CH_3$, —CH($CH_3$)$_2$, —$OCH_3$, or —$S(O)_2CH_3$;
G is:

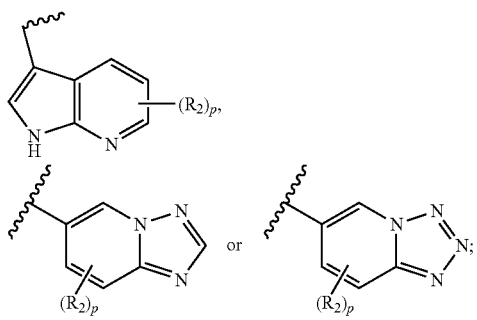

each $R_2$ is independently —CN, —$CH_3$, —$OCH_3$, or pyrimidinyl;
A is:
(i) —$CH_2R_3$, —$CH_2CH_2NHR_3$, —$C(O)NHR_3$, —$NHR_3$, —$NHCH_2CH_2R_3$, or —$OR_3$; or
(ii) $R_3$;
$R_3$ is azetidinyl, cyclobutyl, cyclohexyl, piperazinyl, piperidinyl, or pyrrolidinyl, each substituted with zero to 1 $R_{3a}$;
$R_{3a}$ is —$CH_3$, —$CH_2CH_2CH_3$, —$CH(CH_3)_2$, —$CH_2CN$, —$CH_2CH_2CN$, —$CH_2CH_2CF_3$, —$CH_2C(CH_3)_2OH$, —$CH_2C(O)NH_2$, —$CH_2C(O)N(CH_3)_2$, —$C(O)CH_2N(CH_3)_2$, —$C(O)CH_2CH_2N(CH_3)_2$, —$C(O)CH_2CH_2CH_2N(CH_3)_2$, —$NH(CH_3)$, —$N(CH_3)_2$, —$NH(CH(CH_3)_2)$, —$CH_2CH_2S(O)_2CH_3$, —$CH_2CH_2NHS(O)_2CH_3$, —$NHCH_2C(O)N(CH_3)_2$, —$NH(CH_2CH_2S(O)_2CH_3)$, —NH(cyclopropyl), —NH(oxetanyl), —$N(CH_3)$(oxetanyl), —$CH_2$(methyl-triazolyl), morpholinyl, oxetanyl, pyrrolidinyl, fluoro-pyrrolidinyl, hydroxy-methylpyrrolidinyl, tetrahydro-pyranyl, 1-oxa-6-azaspiro[3.3]heptanyl, 2-oxa-6-azaspiro[3.3]heptanyl, 2-oxa-6-azaspiro[3.4]octanyl, 6-oxa-2-azaspiro[3.4]octanyl, 2,2-dioxo-2-thia-6-azaspiro[3.3]heptanyl, 2-oxa-7-azaspiro[4.4]nonanyl, or azetidinyl substituted with zero to 2 substituents independently selected from F, —OH, —$CH_3$, —$CH_2OH$, —$OCH_3$, —$OCH_2CH_3$, and —$OCH(CH_3)_2$;
n is zero or 1; and
p is zero, 1, or 2.

4. The compound according to claim 1, N-oxide, or a salt thereof, wherein X is N.

5. The compound according to claim 1 or a salt thereof, wherein
X is CH or N;
G is:

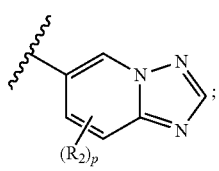

$R_2$ is —$CH_3$ or —$OCH_3$;
A is: —$OR_3$ or $R_3$;
$R_3$ is cyclobutyl, cyclohexyl, piperazinyl, piperidinyl, or pyrrolidinyl, each substituted with zero to 1 $R_{3a}$;
n is zero or 1; and
p is zero or 1.

6. The compound according to claim 1 or a salt thereof, wherein
X is N;
G is:

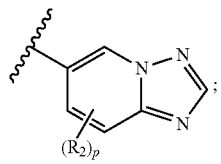

$R_2$ is —$CH_3$ or —$OCH_3$.

7. The compound according to claim 1, N-oxide, or a salt thereof, wherein said compound is:
8-methyl-6-(5-methyl-3-(piperidin-4-yl)-1H-indol-6-yl)-[1,2,4]triazolo[1,5-a]pyridine (1);
8-methyl-6-(4-methyl-3-(piperidin-4-yl)-1H-indol-6-yl)-[1,2,4]triazolo[1,5-a]pyridine (2);
N,N-dimethyl-4-(5-methyl-6-(8-methyl-[1,2,4]triazolo[1,5-a]pyridin-6-yl)-1H-indazol-3-yl)cyclohexan-1-amine (3-4);
2-(dimethylamino)-1-(3-(4-methyl-6-(8-methyl-[1,2,4]triazolo[1,5-a]pyridin-6-yl)-1H-indazol-3-yl) piperidin-1-yl) ethan-1-one (5);
N,N-dimethyl-3-(5-methyl-6-(8-methyl-[1,2,4]triazolo[1,5-a]pyridin-6-yl)-1H-indazol-3-yl) cyclobutan-1-amine (6-7);
2-(4-(4-ethyl-6-(8-methyl-[1,2,4]triazolo[1,5-a]pyridin-6-yl)-1H-indazol-3-yl) piperidin-1-yl)-N,N-dimethyl-acetamide (8);
6-(5-isopropyl-3-(1-propylpiperidin-4-yl)-1H-indazol-6-yl)-8-methyl-[1,2,4]triazolo[1,5-a]pyridine (9);
8-methyl-6-(5-methyl-3-(piperidin-4-ylmethyl)-1H-indazol-6-yl)-[1,2,4]triazolo[1,5-a]pyridine (10);
8-methoxy-6-(3-(piperidin-4-yl)-1H-indol-6-yl)-[1,2,4]triazolo[1,5-a]pyridine (11);
8-methyl-6-(3-(piperidin-4-yl)-1H-indol-6-yl)-[1,2,4]triazolo[1,5-a] pyridine (12);
N-(2-(6-(8-methyl-[1,2,4]triazolo[1,5-a] pyridin-6-yl)-1H-indol-3-yl) ethyl) piperidin-4-amine (13);
N,N-dimethyl-4-(6-(8-methyl-[1,2,4]triazolo[1,5-a]pyridin-6-yl)-1H-indol-3-yl) cyclohexan-1-amine (14);
N,N-dimethyl-4-(6-(8-methyl-[1,2,4]triazolo[1,5-a]pyridin-6-yl)-1H-indol-3-yl) cyclohexan-1-amine (15);
8-methyl-6-(4-methyl-3-(piperidin-4-yl)-1H-indol-6-yl)-[1,2,4]triazolo[1,5-a]pyridine (16);
8-methyl-6-(3-(piperidin-4-yl)-1H-indazol-6-yl)-[1,2,4]triazolo[1,5-a]pyridine (17);
8-methyl-6-(5-methyl-3-(piperidin-4-yl)-1H-indazol-6-yl)-[1,2,4]triazolo[1,5-a]pyridine (18);
6-(5-methoxy-3-(piperidin-4-yl)-1H-indazol-6-yl)-8-methyl-[1,2,4]triazolo[1,5-a]pyridine (19);
2-(dimethylamino)-1-(4-(5-methyl-6-(8-methyl-[1,2,4]triazolo[1,5-a]pyridin-6-yl)-1H-indazol-3-yl) piperidin-1-yl) ethan-1-one (20);
8-methyl-6-(5-methyl-3-(1-(tetrahydro-2H-pyran-4-yl) piperidin-4-yl)-1H-indazol-6-yl)-[1,2,4]triazolo[1,5-a] pyridine (21);

8-methyl-6-(5-methyl-3-(1-propylpiperidin-4-yl)-1H-indazol-6-yl)-[1,2,4]triazolo[1,5-a]pyridine (22);

N,N-dimethyl-2-(4-(5-methyl-6-(8-methyl-[1,2,4]triazolo[1,5-a]pyridin-6-yl)-1H-indazol-3-yl) piperidin-1-yl) acetamide (23);

8-methyl-6-(5-methyl-3-(piperidin-3-yl)-1H-indazol-6-yl)-[1,2,4]triazolo[1,5-a]pyridine (24);

8-methyl-6-(5-methyl-3-(pyrrolidin-3-yl)-1H-indazol-6-yl)-[1,2,4]triazolo[1,5-a]pyridine (26);

8-methyl-6-(4-methyl-3-(piperidin-4-yl)-1H-indazol-6-yl)-[1,2,4]triazolo[1,5-a] pyridine (27);

N,N-dimethyl-2-((4-(5-methyl-6-(8-methyl-[1,2,4] triazolo[1,5-a] pyridin-6-yl)-1H-indazol-3-yl) cyclohexyl) amino) acetamide (28);

N,N-dimethyl-2-((4-(5-methyl-6-(8-methyl-[1,2,4]triazolo[1,5-a]pyridin-6-yl)-1H-indazol-3-yl) cyclohexyl) amino) acetamide (29);

4-(5-methyl-6-(8-methyl-[1,2,4]triazolo[1,5-a]pyridin-6-yl)-1H-indazol-3-yl)-N-(2-(methylsulfonyl) ethyl) cyclohexan-1-amine (30);

4-(5-methyl-6-(8-methyl-[1,2,4]triazolo[1,5-a]pyridin-6-yl)-1H-indazol-3-yl)-N-(2-(methylsulfonyl) ethyl) cyclohexan-1-amine (31);

N-methyl-N-(4-(5-methyl-6-(8-methyl-[1,2,4]triazolo[1,5-a] pyridin-6-yl)-1H-indazol-3-yl) cyclohexyl) oxetan-3-amine (32);

N-methyl-N-(4-(5-methyl-6-(8-methyl-[1,2,4]triazolo[1,5-a]pyridin-6-yl)-1H-indazol-3-yl) cyclohexyl) oxetan-3-amine (33);

N-(4-(5-methyl-6-(8-methyl-[1,2,4]triazolo[1,5-a]pyridin-6-yl)-1H-indazol-3-yl) cyclohexyl) oxetan-3-amine (34);

N-(4-(5-methyl-6-(8-methyl-[1,2,4]triazolo[1,5-a]pyridin-6-yl)-1H-indazol-3-yl) cyclohexyl) oxetan-3-amine (35);

N-cyclopropyl-4-(5-methyl-6-(8-methyl-[1,2,4]triazolo[1,5-a]pyridin-6-yl)-1H-indazol-3-yl) cyclohexan-1-amine (36);

N-cyclopropyl-4-(5-methyl-6-(8-methyl-[1,2,4]triazolo[1,5-a]pyridin-6-yl)-1H-indazol-3-yl) cyclohexan-1-amine (37);

N-isopropyl-4-(5-methyl-6-(8-methyl-[1,2,4]triazolo[1,5-a] pyridin-6-yl)-1H-indazol-3-yl) cyclohexan-1-amine (38);

N-isopropyl-4-(5-methyl-6-(8-methyl-[1,2,4]triazolo[1,5-a]pyridin-6-yl)-1H-indazol-3-yl) cyclohexan-1-amine (39);

2-(dimethylamino)-1-(3-(5-methyl-6-(8-methyl-[1,2,4]triazolo[1,5-a]pyridin-6-yl)-1H-indazol-3-yl) piperidin-1-yl) ethan-1-one (40);

N,N-dimethyl-2-(3-(5-methyl-6-(8-methyl-[1,2,4]triazolo[1,5-a]pyridin-6-yl)-1H-indazol-3-yl) piperidin-1-yl) acetamide (41);

8-methyl-6-(5-methyl-3-(1-(oxetan-3-yl) piperidin-3-yl)-1H-indazol-6-yl)-[1,2,4]triazolo[1,5-a]pyridine (42);

8-methyl-6-(5-methyl-3-(1-(tetrahydro-2H-pyran-4-yl) piperidin-3-yl)-1H-indazol-6-yl)-[1,2,4]triazolo[1,5-a] pyridine (43);

N-methyl-4-(5-methyl-6-(8-methyl-[1,2,4]triazolo[1,5-a] pyridin-6-yl)-1H-indazol-3-yl) cyclohexan-1-amine (44);

8-methoxy-6-(5-methyl-3-(piperidin-3-yl)-1H-indazol-6-yl)-[1,2,4]triazolo[1,5-a]pyridine (45);

5-methyl-6-(1-methyl-1H-pyrrolo[2,3-b]pyridin-3-yl)-3-(piperidin-3-yl)-1H-indazole (47);

7,8-dimethyl-6-(5-methyl-3-(piperidin-3-yl)-1H-indazol-6-yl)-[1,2,4]triazolo[1,5-a]pyridine (48);

6-(3-(azetidin-3-yl)-5-methyl-1H-indazol-6-yl)-8-methyl-[1,2,4]triazolo[1,5-a]pyridine (49);

8-methyl-6-(4-methyl-3-(piperidin-3-yl)-1H-indazol-6-yl)-[1,2,4]triazolo[1,5-a]pyridine (51);

8-methyl-6-(5-methyl-3-(1-(tetrahydro-2H-pyran-4-yl) piperidin-3-yl)-1H-indazol-6-yl)-[1,2,4]triazolo [1,5-a] pyridine (52);

N,N-dimethyl-2-(3-(5-methyl-6-(8-methyl-[1,2,4]triazolo[1,5-a]pyridin-6-yl)-1H-indazol-3-yl) piperidin-1-yl) acetamide (53);

2-(dimethylamino)-1-(3-(5-methyl-6-(8-methyl-[1,2,4] triazolo[1,5-a]pyridin-6-yl)-1H-indazol-3-yl) piperidin-1-yl) ethan-1-one (54);

8-methyl-6-(5-methyl-3-(1-(tetrahydro-2H-pyran-4-yl) piperidin-3-yl)-1H-indazol-6-yl)-[1,2,4]triazolo[1,5-a] pyridine (55);

2-(dimethylamino)-1-(3-(5-methyl-6-(8-methyl-[1,2,4] triazolo[1,5-a]pyridin-6-yl)-1H-indazol-3-yl) piperidin-1-yl) ethan-1-one (56);

N,N-dimethyl-2-(3-(5-methyl-6-(8-methyl-[1,2,4] triazolo[1,5-a]pyridin-6-yl)-1H-indazol-3-yl) piperidin-1-yl) acetamide (57);

6-(5-methyl-3-(piperidin-3-yl)-1H-indazol-6-yl)-[1,2,4] triazolo[1,5-a] pyridine (58);

N,N-dimethyl-2-(3-(4-methyl-6-(8-methyl-[1,2,4]triazolo[1,5-a]pyridin-6-yl)-1H-indazol-3-yl) piperidin-1-yl) acetamide (59);

8-methyl-6-(4-methyl-3-(1-(tetrahydro-2H-pyran-4-yl) piperidin-3-yl)-1H-indazol-6-yl)-[1,2,4]triazolo[1,5-a] pyridine (60);

8-methyl-6-(4-methyl-3-(1-methylpiperidin-3-yl)-1H-indazol-6-yl)-[1,2,4]triazolo[1,5-a]pyridine (61);

8-methyl-6-(5-methyl-1H-indazol-6-yl)-[1,2,4]triazolo[1,5-a]pyridine (63);

8-methoxy-6-(5-methyl-1H-indazol-6-yl)-[1,2,4]triazolo [1,5-a]pyridine (64);

8-methyl-6-(4-methyl-1H-indazol-6-yl)-[1,2,4] triazolo [1,5-a]pyridine (65);

8-methoxy-6-(4-methyl-1H-indazol-6-yl)-[1,2,4]triazolo [1,5-a] pyridine (66);

2-methyl-1-(4-(5-methyl-6-(8-methyl-[1,2,4]triazolo[1,5-a]pyridin-6-yl)-1H-indazol-3-yl) piperidin-1-yl) propan-2-ol (67);

8-methyl-6-(5-methyl-3-(1-(2-(methylsulfonyl) ethyl) piperidin-4-yl)-1H-indazol-6-yl)-[1,2,4]triazolo[1,5-a] pyridine (68);

N-(2-(4-(5-methyl-6-(8-methyl-[1,2,4]triazolo[1,5-a] pyridin-6-yl)-1H-indazol-3-yl) piperidin-1-yl) ethyl) methanesulfonamide (69);

2-(4-(5-methyl-6-(8-methyl-[1,2,4]triazolo[1,5-a]pyridin-6-yl)-1H-indazol-3-yl) piperidin-1-yl) acetamide (70);

2-(4-(5-methyl-6-(8-methyl-[1,2,4]triazolo[1,5-a]pyridin-6-yl)-1H-indazol-3-yl) piperidin-1-yl) acetonitrile (71);

3-(4-(5-methyl-6-(8-methyl-[1,2,4]triazolo[1,5-a]pyridin-6-yl)-1H-indazol-3-yl) piperidin-1-yl) propanenitrile (72);

8-methyl-6-(5-methyl-3-(1-(oxetan-3-yl) piperidin-4-yl)-1H-indazol-6-yl)-[1,2,4]triazolo[1,5-a]pyridine (73);

8-methyl-6-(5-methyl-3-(piperidin-4-yl)-1H-indazol-6-yl) tetrazolo[1,5-a]pyridine (74);

2-(dimethylamino)-1-(4-(4-methyl-6-(8-methyl-[1,2,4] triazolo[1,5-a]pyridin-6-yl)-1H-indazol-3-yl) piperidin-1-yl) ethan-1-one (75);

N,N-dimethyl-2-(4-(4-methyl-6-(8-methyl-[1,2,4]triazolo[1,5-a]pyridin-6-yl)-1H-indazol-3-yl) piperidin-1-yl) acetamide (76);

2-methyl-1-(4-(4-methyl-6-(8-methyl-[1,2,4]triazolo[1,5-a]pyridin-6-yl)-1H-indazol-3-yl) piperidin-1-yl) propan-2-ol (77);

8-methyl-6-(4-methyl-3-(1-(tetrahydro-2H-pyran-4-yl) piperidin-4-yl)-1H-indazol-6-yl)-[1,2,4]triazolo[1,5-a]pyridine (78);

8-methyl-6-(4-methyl-3-(1-methylpiperidin-4-yl)-1H-indazol-6-yl)-[1,2,4]triazolo[1,5-a]pyridine (79);

N,N-dimethyl-4-(4-methyl-6-(8-methyl-[1,2,4]triazolo[1,5-a]pyridin-6-yl)-1H-indazol-3-yl) cyclohexan-1-amine (80);

N,N-dimethyl-4-(4-methyl-6-(8-methyl-[1,2,4]triazolo[1,5-a]pyridin-6-yl)-1H-indazol-3-yl) cyclohexan-1-amine (81);

6-(5-ethyl-3-(piperidin-4-yl)-1H-indazol-6-yl)-8-methyl-[1,2,4]triazolo[1,5-a]pyridine (82);

5,8-dimethyl-6-(5-methyl-3-(piperidin-4-yl)-1H-indazol-6-yl)-[1,2,4] triazolo[1,5-a] pyridine (83);

6-(5-methyl-3-(piperidin-4-yl)-1H-indazol-6-yl)-[1,2,4]triazolo[1,5-a]pyridine-8-carbonitrile (84);

6-(5-methyl-3-(piperidin-4-yl)-1H-indazol-6-yl)-8-(pyrimidin-5-yl)-[1,2,4]triazolo[1,5-a]pyridine (85);

6-(4-methoxy-3-(piperidin-4-yl)-1H-indazol-6-yl)-8-methyl-[1,2,4]triazolo[1,5-a]pyridine (86);

2-(dimethylamino)-1-(4-(5-ethyl-6-(8-methyl-[1,2,4]triazolo[1,5-a]pyridin-6-yl)-1H-indazol-3-yl) piperidin-1-yl) ethan-1-one (87);

6-(5-ethyl-3-(1-(tetrahydro-2H-pyran-4-yl) piperidin-4-yl)-1H-indazol-6-yl)-8-methyl-[1,2,4]triazolo[1,5-a] pyridine (88);

6-(5-ethyl-3-(1-(oxetan-3-yl) piperidin-4-yl)-1H-indazol-6-yl)-8-methyl-[1,2,4]triazolo[1,5-a]pyridine (89);

6-(5-ethyl-3-(1-isopropylpiperidin-4-yl)-1H-indazol-6-yl)-8-methyl-[1,2,4]triazolo[1,5-a]pyridine (90);

2-(4-(5-ethyl-6-(8-methyl-[1,2,4]triazolo[1,5-a]pyridin-6-yl)-1H-indazol-3-yl) piperidin-1-yl)-N,N-dimethylacetamide (91);

2-(4-(5-ethyl-6-(8-methyl-[1,2,4]triazolo[1,5-a]pyridin-6-yl)-1H-indazol-3-yl) piperidin-1-yl) acetamide (92);

4-(5-ethyl-6-(8-methyl-[1,2,4]triazolo[1,5-a]pyridin-6-yl)-1H-indazol-3-yl)-N,N-dimethylcyclohexan-1-amine (93-94);

2-((4-(5-ethyl-6-(8-methyl-[1,2,4]triazolo[1,5-a]pyridin-6-yl)-1H-indazol-3-yl) cyclohexyl) amino)-N,N-dimethylacetamide (95-96);

N-cyclopropyl-4-(5-ethyl-6-(8-methyl-[1,2,4]triazolo[1,5-a]pyridin-6-yl)-1H-indazol-3-yl) cyclohexan-1-amine (97-98);

4-(5-ethyl-6-(8-methyl-[1,2,4] triazolo[1,5-a]pyridin-6-yl)-1H-indazol-3-yl)-N-(2-(methylsulfonyl) ethyl) cyclohexan-1-amine (99-100);

1-(4-(5-ethyl-6-(8-methyl-[1,2,4]triazolo[1,5-a]pyridin-6-yl)-1H-indazol-3-yl) piperidin-1-yl)-2-methylpropan-2-ol (101);

6-(5-isopropyl-3-(piperidin-4-yl)-1H-indazol-6-yl)-8-methyl-[1,2,4]triazolo[1,5-a]pyridine (102);

3-(dimethylamino)-1-(4-(5-ethyl-6-(8-methyl-[1,2,4]triazolo[1,5-a]pyridin-6-yl)-1H-indazol-3-yl) piperidin-1-yl) propan-1-one (103);

2-(4-(5-ethyl-6-(8-methyl-[1,2,4]triazolo[1,5-a]pyridin-6-yl)-1H-indazol-3-yl) piperidin-1-yl) acetonitrile (104);

6-(5-ethyl-3-(1-((1-methyl-1H-1,2,3-triazol-4-yl) methyl) piperidin-4-yl)-1H-indazol-6-yl)-8-methyl-[1,2,4]triazolo[1,5-a]pyridine (105);

3-(4-(5-ethyl-6-(8-methyl-[1,2,4]triazolo[1,5-a]pyridin-6-yl)-1H-indazol-3-yl) piperidin-1-yl) propanenitrile (106);

4-(dimethylamino)-1-(4-(5-ethyl-6-(8-methyl-[1,2,4]triazolo[1,5-a]pyridin-6-yl)-1H-indazol-3-yl) piperidin-1-yl) butan-1-one (107);

6-(5-ethyl-3-(1-(3,3,3-trifluoropropyl) piperidin-4-yl)-1H-indazol-6-yl)-8-methyl-[1,2,4]triazolo[1,5-a]pyridine (108);

6-(4-ethyl-3-(piperidin-4-yl)-1H-indazol-6-yl)-8-methyl-[1,2,4]triazolo[1,5-a]pyridine (109);

2-(dimethylamino)-1-(4-(4-ethyl-6-(8-methyl-[1,2,4]triazolo[1,5-a]pyridin-6-yl)-1H-indazol-3-yl) piperidin-1-yl) ethan-1-one (110);

2-(dimethylamino)-1-(4-(5-isopropyl-6-(8-methyl-[1,2,4]triazolo[1,5-a]pyridin-6-yl)-1H-indazol-3-yl) piperidin-1-yl) ethan-1-one (111);

2-(4-(5-isopropyl-6-(8-methyl-[1,2,4]triazolo[1,5-a]pyridin-6-yl)-1H-indazol-3-yl) piperidin-1-yl)-N,N-dimethylacetamide (112);

1-(4-(5-isopropyl-6-(8-methyl-[1,2,4]triazolo[1,5-a]pyridin-6-yl)-1H-indazol-3-yl) piperidin-1-yl)-2-methylpropan-2-ol (113);

4-(5-isopropyl-6-(8-methyl-[1,2,4]triazolo[1,5-a]pyridin-6-yl)-1H-indazol-3-yl)-N,N-dimethylcyclohexan-1-amine (114-115);

6-(5-isopropyl-3-(1-(tetrahydro-2H-pyran-4-yl) piperidin-4-yl)-1H-indazol-6-yl)-8-methyl-[1,2,4]triazolo[1,5-a]pyridine (116);

2-(dimethylamino)-1-(4-(5-isopropyl-6-(8-methoxy-[1,2,4]triazolo[1,5-a]pyridin-6-yl)-1H-indazol-3-yl) piperidin-1-yl) ethan-1-one (117);

N-cyclopropyl-4-(5-isopropyl-6-(8-methyl-[1,2,4]triazolo[1,5-a]pyridin-6-yl)-1H-indazol-3-yl) cyclohexan-1-amine (118-119);

6-(5-isopropyl-3-(1-(oxetan-3-yl) piperidin-4-yl)-1H-indazol-6-yl)-8-methyl-[1,2,4]triazolo[1,5-a]pyridine (120);

3-(4-(5-isopropyl-6-(8-methyl-[1,2,4]triazolo[1,5-a]pyridin-6-yl)-1H-indazol-3-yl) piperidin-1-yl) propanenitrile (121);

3-(dimethylamino)-1-(4-(5-isopropyl-6-(8-methyl-[1,2,4]triazolo[1,5-a]pyridin-6-yl)-1H-indazol-3-yl) piperidin-1-yl) propan-1-one (122);

6-(5-isopropyl-3-(1-isopropylpiperidin-4-yl)-1H-indazol-6-yl)-8-methyl-[1,2,4]triazolo[1,5-a]pyridine (123);

2-((4-(5-isopropyl-6-(8-methyl-[1,2,4]triazolo[1,5-a]pyridin-6-yl)-1H-indazol-3-yl) cyclohexyl) amino)-N,N-dimethylacetamide (124-125);

4-(5-isopropyl-6-(8-methyl-[1,2,4]triazolo[1,5-a]pyridin-6-yl)-1H-indazol-3-yl)-N-(2-(methylsulfonyl) ethyl) cyclohexan-1-amine (126-127);

6-(4-(5-isopropyl-6-(8-methyl-[1,2,4]triazolo[1,5-a]pyridin-6-yl)-1H-indazol-3-yl) cyclohexyl)-2-oxa-6-azaspiro[3.3]heptane (128-129);

6-(5-isopropyl-3-(4-(pyrrolidin-1-yl) cyclohexyl)-1H-indazol-6-yl)-8-methyl-[1,2,4]triazolo[1,5-a]pyridine (130-131);

4-(4-(5-isopropyl-6-(8-methyl-[1,2,4]triazolo[1,5-a]pyridin-6-yl)-1H-indazol-3-yl) cyclohexyl) morpholine (132-133);

6-(3-(4-(3,3-difluoroazetidin-1-yl) cyclohexyl)-5-isopropyl-1H-indazol-6-yl)-8-methyl-[1,2,4]triazolo[1,5-a]pyridine (134-135);

6-(3-(4-(3,3-dimethylazetidin-1-yl) cyclohexyl)-5-isopropyl-1H-indazol-6-yl)-8-methyl-[1,2,4]triazolo[1,5-a]pyridine (136-137);

6-(3-(4-(azetidin-1-yl) cyclohexyl)-5-isopropyl-1H-indazol-6-yl)-8-methyl-[1,2,4]triazolo[1,5-a]pyridine (138-139);

4-(5-isopropyl-6-(8-methoxy-[1,2,4]triazolo[1,5-a]pyridin-6-yl)-1H-indazol-3-yl)-N,N-dimethylcyclohexan-1-amine (140-141);

6-(4-(5-isopropyl-6-(8-methyl-[1,2,4]triazolo[1,5-a]pyridin-6-yl)-1H-indazol-3-yl) cyclohexyl)-2-thia-6-azaspiro[3.3] heptane 2,2-dioxide (142-143);

6-(5-isopropyl-3-(4-(3-methoxyazetidin-1-yl) cyclohexyl)-1H-indazol-6-yl)-8-methyl-[1,2,4]triazolo[1,5-a]pyridine (144-145);

(1-(4-(5-isopropyl-6-(8-methyl-[1,2,4]triazolo[1,5-a]pyridin-6-yl)-1H-indazol-3-yl) cyclohexyl) azetidine-3,3-diyl) dimethanol (146);

6-(5-isopropyl-3-(4-(3-methoxyazetidin-1-yl) cyclohexyl)-1H-indazol-6-yl)-8-methoxy-[1,2,4]triazolo[1,5-a]pyridine (147-148);

6-(3-(4-(3-ethoxyazetidin-1-yl) cyclohexyl)-5-isopropyl-1H-indazol-6-yl)-8-methyl-[1,2,4]triazolo[1,5-a]pyridine (149-150);

6-(3-(4-(3-fluoroazetidin-1-yl) cyclohexyl)-5-isopropyl-1H-indazol-6-yl)-8-methyl-[1,2,4] triazolo[1,5-a]pyridine (151-152);

1-(4-(5-isopropyl-6-(8-methyl-[1,2,4]triazolo[1,5-a] pyridin-6-yl)-1H-indazol-3-yl) cyclohexyl)-3-methylazetidin-3-ol (153-154);

6-(4-(5-isopropyl-6-(8-methyl-[1,2,4]triazolo[1,5-a]pyridin-6-yl)-1H-indazol-3-yl) cyclohexyl)-1-oxa-6-azaspiro[3.3]heptane (155-156);

2-(4-(5-isopropyl-6-(8-methyl-[1,2,4]triazolo[1,5-a] pyridin-6-yl)-1H-indazol-3-yl) cyclohexyl)-6-oxa-2-azaspiro[3.4]octane (157-158);

6-(4-(5-isopropyl-6-(8-methyl-[1,2,4]triazolo[1,5-a]pyridin-6-yl)-1H-indazol-3-yl) cyclohexyl)-2-oxa-6-azaspiro[3.4]octane (159-160);

6-(3-(4-(3-isopropoxyazetidin-1-yl) cyclohexyl)-5-isopropyl-1H-indazol-6-yl)-8-methyl-[1,2,4]triazolo[1,5-a]pyridine (161-162);

6-(3-(4-(3-fluoropyrrolidin-1-yl) cyclohexyl)-5-isopropyl-1H-indazol-6-yl)-8-methyl-[1,2,4]triazolo[1,5-a] pyridine (163-164);

1-(4-(5-isopropyl-6-(8-methyl-[1,2,4]triazolo[1,5-a]pyridin-6-yl)-1H-indazol-3-yl) cyclohexyl)-3-methylpyrrolidin-3-ol (165-166);

8-methyl-6-(5-methyl-3-(piperidin-4-yloxy)-1H-indazol-6-yl)-[1,2,4]triazolo[1,5-a]pyridine (167);

4-((4-ethyl-6-(8-methyl-[1,2,4]triazolo[1,5-a]pyridin-6-yl)-1H-indazol-3-yl) oxy)-N,N-dimethylcyclohexan-1-amine (168-169);

2-(dimethylamino)-1-(4-((5-methyl-6-(8-methyl-[1,2,4] triazolo[1,5-a] pyridin-6-yl)-1H-indazol-3-yl) oxy) piperidin-1-yl) ethan-1-one (170);

8-methyl-6-(5-methyl-3-((1-methylpiperidin-4-yl) oxy)-1H-indazol-6-yl)-[1,2,4]triazolo[1,5-a]pyridine (171);

N,N-dimethyl-2-((5-methyl-6-(8-methyl-[1,2,4]triazolo[1,5-a]pyridin-6-yl)-1H-indazol-3-yl) oxy) ethan-1-amine (172);

N,N-dimethyl-2-((4-methyl-6-(8-methyl-[1,2,4]triazolo[1,5-a]pyridin-6-yl)-1H-indazol-3-yl) oxy) ethan-1-amine (173);

8-methyl-6-(4-methyl-3-(piperidin-4-yloxy)-1H-indazol-6-yl)-[1,2,4]triazolo[1,5-a]pyridine (174);

2-(dimethylamino)-1-(4-((4-methyl-6-(8-methyl-[1,2,4] triazolo[1,5-a]pyridin-6-yl)-1H-indazol-3-yl) oxy) piperidin-1-yl) ethan-1-one (175);

N,N-dimethyl-2-(4-((4-methyl-6-(8-methyl-[1,2,4]triazolo[1,5-a]pyridin-6-yl)-1H-indazol-3-yl) oxy) piperidin-1-yl) acetamide (176);

8-methyl-6-(4-methyl-3-((1-methylpiperidin-4-yl) oxy)-1H-indazol-6-yl)-[1,2,4]triazolo[1,5-a]pyridine (177);

8-methyl-6-(4-methyl-3-((1-(tetrahydro-2H-pyran-4-yl) piperidin-4-yl) oxy)-1H-indazol-6-yl)-[1,2,4] triazolo [1,5-a]pyridine (178);

N,N-dimethyl-4-((4-methyl-6-(8-methyl-[1,2,4]triazolo [1,5-a] pyridin-6-yl)-1H-indazol-3-yl) oxy) cyclohexan-1-amine (179-180);

N,N-dimethyl-4-((5-methyl-6-(8-methyl-[1,2,4]triazolo [1,5-a]pyridin-6-yl)-1H-indazol-3-yl) oxy) cyclohexan-1-amine (181-182);

4-((6-(8-methoxy-[1,2,4]triazolo[1,5-a]pyridin-6-yl)-4-methyl-1H-indazol-3-yl) oxy)-N,N-dimethylcyclohexan-1-amine (183-184);

N,N-dimethyl-2-((4-((4-methyl-6-(8-methyl-[1,2,4]triazolo[1,5-a]pyridin-6-yl)-1H-indazol-3-yl) oxy) cyclohexyl) amino) acetamide (185-186);

4-((4-methyl-6-(8-methyl-[1,2,4]triazolo[1,5-a]pyridin-6-yl)-1H-indazol-3-yl) oxy)-N-(2-(methylsulfonyl) ethyl) cyclohexan-1-amine (187-188);

N-cyclopropyl-4-((4-methyl-6-(8-methyl-[1,2,4]triazolo [1,5-a]pyridin-6-yl)-1H-indazol-3-yl) oxy) cyclohexan-1-amine (189-190);

4-((5-ethyl-6-(8-methyl-[1,2,4]triazolo[1,5-a]pyridin-6-yl)-1H-indazol-3-yl) oxy)-N,N-dimethylcyclohexan-1-amine (191-192);

8-methyl-6-(4-methyl-3-((1-((1-methyl-1H-1,2,3-triazol-4-yl) methyl) piperidin-4-yl) oxy)-1H-indazol-6-yl)-[1,2,4]triazolo[1,5-a]pyridine (193);

2-(4-((4-methyl-6-(8-methyl-[1,2,4]triazolo[1,5-a]pyridin-6-yl)-1H-indazol-3-yl) oxy) piperidin-1-yl) acetonitrile (194);

6-(4-ethyl-3-(piperidin-4-yloxy)-1H-indazol-6-yl)-8-methyl-[1,2,4]triazolo[1,5-a]pyridine (195);

2-(4-((4-ethyl-6-(8-methyl-[1,2,4]triazolo[1,5-a]pyridin-6-yl)-1H-indazol-3-yl) oxy) piperidin-1-yl)-N,N-dimethylacetamide (196);

6-(8-methoxy-[1,2,4]triazolo[1,5-a]pyridin-6-yl)-N-(piperidin-4-yl)-1H-indole-3-carboxamide (197);

6-(8-methyl-[1,2,4]triazolo[1,5-a]pyridin-6-yl)-N-(piperidin-4-yl)-1H-indole-3-carboxamide (198);

6-(8-methyl-[1,2,4]triazolo[1,5-a]pyridin-6-yl)-N-(piperidin-4-yl)-1H-indazole-3-carboxamide (199);

6-(8-methyl-[1,2,4]triazolo[1,5-a] pyridin-6-yl)-N-(piperidin-4-yl)-1H-indazol-3-amine (200);

5-methyl-6-(8-methyl-[1,2,4] triazolo[1,5-a]pyridin-6-yl)-1H-indazol-3-amine (201);

5-methyl-6-(8-methyl-[1,2,4]triazolo[1,5-a]pyridin-6-yl)-N-(2-(pyrrolidin-1-yl) ethyl)-1H-indazol-3-amine (204);

8-methyl-6-(5-methyl-3-(piperazin-1-yl)-1H-indazol-6-yl)-[1,2,4]triazolo[1,5-a]pyridine (205);

6-(5-isopropyl-3-(piperazin-1-yl)-1H-indazol-6-yl)-8-methyl-[1,2,4]triazolo[1,5-a]pyridine (206);

6-(5-isopropyl-3-(piperazin-1-yl)-1H-indazol-6-yl)-8-methyl-[1,2,4]triazolo[1,5-a]pyridine (207);

6-(5-isopropyl-3-(4-isopropylpiperazin-1-yl)-1H-indazol-6-yl)-8-methyl-[1,2,4]triazolo[1,5-a]pyridine (208);

7-(4-(5-isopropyl-6-(8-methyl-[1,2,4]triazolo[1,5-a]pyridin-6-yl)-1H-indazol-3-yl) cyclohexyl)-2-oxa-7-azaspiro[4.4] nonane (209-210); or 6-(5-isopropyl-3-(4-(3-(methylsulfonyl) pyrrolidin-1-yl) cyclohexyl)-1H-indazol-6-yl)-8-methyl-[1,2,4]triazolo [1,5-a]pyridine (211-212).

8. A pharmaceutical composition comprising a compound according to claim 1 or a pharmaceutically-acceptable salt thereof; and a pharmaceutically acceptable carrier.

9. A method of treating an autoimmune disease or a chronic inflammatory disease, comprising administering to a mammalian patent a compound according to claim 1 or a pharmaceutically acceptable salt thereof, wherein said autoimmune disease or chronic inflammatory disease is selected from systemic lupus erythematosus (SLE), rheumatoid arthritis, multiple sclerosis (MS), and Sjögren's syndrome.

\* \* \* \* \*